United States Patent
Chern et al.

(10) Patent No.: US 8,946,282 B2
(45) Date of Patent: Feb. 3, 2015

(54) INDOLIN-2-ONE DERIVATIVES AS PROTEIN KINASE INHIBITORS

(71) Applicant: Annji Pharmaceutical Co., Ltd., Taipei (TW)

(72) Inventors: Ji-Wang Chern, Taipei (TW); Ajit Dhananjay Jagtap, Taipei (TW); Hsiao-Chun Wang, Taipei (TW); Grace Shiahuy Chen, Taipei (TW)

(73) Assignee: Annji Pharmaceutical Co., Ltd., Taipei (TW)

( * ) Notice: Subject to any disclaimer, the term of this patent is extended or adjusted under 35 U.S.C. 154(b) by 0 days.

(21) Appl. No.: 13/855,916

(22) Filed: Apr. 3, 2013

(65) Prior Publication Data

US 2013/0281451 A1    Oct. 24, 2013

Related U.S. Application Data

(60) Provisional application No. 61/635,931, filed on Apr. 20, 2012.

(51) Int. Cl.
*C07D 209/34* (2006.01)
*C07D 403/06* (2006.01)
(Continued)

(52) U.S. Cl.
CPC ............ *C07D 209/34* (2013.01); *C07D 403/06* (2013.01); *C07D 401/06* (2013.01);
(Continued)

(58) Field of Classification Search
USPC .............................. 546/277.7; 548/324.5, 465
See application file for complete search history.

(56) References Cited

U.S. PATENT DOCUMENTS

| 6,573,293 | B2 | 6/2003 | Tang et al. |
| 2005/0090541 | A1 | 4/2005 | Arnaiz et al. |

(Continued)

FOREIGN PATENT DOCUMENTS

| WO | 2006/052936 | 5/2006 |
| WO | 2007/038251 | 4/2007 |

(Continued)

OTHER PUBLICATIONS

Chiang, et al. J. Med. Chem. 2010, 53, 5929-5941.*

(Continued)

*Primary Examiner* — Shawquia Jackson
(74) *Attorney, Agent, or Firm* — Hsiu-Ming Saunders; Intellectual Property Connections, Inc.

(57) ABSTRACT

A novel class of indoline-2-one derivatives are disclosed. These compounds are protein kinase inhibitors which are useful for treating hyperproliferative diseases such as cancer.

In one aspect, the invention relates to a compound a compound of Formula A:

Formula A or a pharmaceutically acceptable salt thereof, wherein:
$R^a$ is hydrogen, $(C_6-C_{18})$aryl, halo$(C_6-C_{18})$aryl, or $(C_1-C_6)$alkoxy$(C_6-C_{18})$aryl;

$R^b$ is hydrogen, $(C_3-C_{18})$heteroaryl, $(C_1-C_6)$alkoxy$(C_3-C_{18})$heteroaryl; $(C_1-C_6)$alkyl$(C_3-C_{18})$heteroaryl, $(C_1-C_6)$alkyl$(C_1-C_6)$alkoxy$(C_3-C_{18})$heteroaryl, $(C_1-C_6)$alkyl$(C_1-C_6)$carboxyalkyl$(C_3-C_{18})$heteroaryl; $(C_1-C_6)$alkyl$(C_1-C_6)$alkylamino$(C_1-C_6)$alkylcarbamoyl)$(C_3-C_{18})$heteroaryl, $(C_1-C_6)$alkyl$(C_1-C_{18})$aryl$(C_3-C_{18})$heteroaryl, $(C_1-C_6)$alkyl$(C_1-C_6)$alkoxycarbonyl)$(C_3-C_{18})$heteroaryl, $(C_1-C_6)$alkyl$(C_1-C_6)$alkoxy$(C_1-C_6)$oxyalkyl$(C_3-C_{18})$heteroaryl, $(C_1-C_6)$alkyl$(C_3-C_6)$heterocyclylcarbonyl$(C_3-C_{18})$heteroaryl, $(C_1-C_6)$alkyl$(C_3-C_6)$heterocyclyl$(C_1-C_6)$oxyalkyl$(C_3-C_{18})$heteroaryl, or $(C_1-C_6)$alkyl$((C_3-C_6)$heterocyclyl$(C_1-C_6)$alkylcarbamoyl)$(C_3-C_{18})$heteroaryl;

$R^c$ is hydrogen, $(C_1-C_6)$alkoxybenzoylureido, or halo$(C_6-C_{18})$aryl$(C_3-C_{18})$heteroarylamido;

$R^d$ is hydrogen, halogen, $(C_1-C_6)$alkoxybenzoylureido, or halo$(C_6-C_{18})$aryl$(C_3-C_{18})$heteroarylamido;

$R^e$ is-hydrogen, benzoylureido, halobenzoylureido, halo$(C_1-C_6)$alkoxybenzoylureido, $(C_1-C_6)$alkoxybenzoylureido, $(C_1-C_6)$alkylaminobenzoylureido, $(C_1-C_6)$alkylbenzoylureido, nitrobenzoylureido, $(C_1-C_6)$haloalkylbenzoylureido, $(C_1-C_6)$haloalkylhalobenzoylureido, halo$(C_6-C_{18})$arylcarbomylacetamido, $(C_1-C_6)$alkoxy$(C_6-C_{18})$arylcarbomylacetamido, $(C_1-C_6)$alkoxy$(C_6-C_{18})$arylcarbamoyl$(C_3-C_6)$cycloalkylamido, halo$(C_6-C_{18})$aryl$(C_3-C_{18})$heteroarylcarbonylamino, $(C_3-C_6)$cycloalkyl$(C_3-C_{18})$heteroarylcarbonylamino, $(C_1-C_6)$alkylamino$(C_6-C_{18})$aryl$(C_3-C_{18})$heteroarylcarbonylamino, halo$(C_1-C_6)$alkoxy$(C_6-C_{18})$aryl$(C_3-C_{18})$ heteroarylcarbonylamino, $(C_1-C_6)$alkoxy$(C_6-C_{18})$aryl$(C_3-C_{18})$heteroarylcarbonylamino, $(C_1-C_6)$alkyl$(C_3-C_{18})$heteroarylcarbonylamino, aryl$(C_3-C_{18})$heteroarylcarbonylamino, $(C_1-C_6)$haloalkylhalo$(C_6-C_{18})$aryl$(C_3-C_6)$heterocyclylcarbonylamino, $(C_1-C_6)$haloalkyl$(C_6-C_{18})$aryl$(C_3-C_{18})$heteroarylcarbonylamino, halo$(C_6-C_{18})$aryl$(C_3-C_{18})$heteroarylamido, $(C_1-C_6)$oxyalkyl$(C_3-C_6)$heterocyclylamido, $(C_1-C_6)$alkoxy$(C_1-C_6)$alkyl$(C_3-C_{18})$heteroarylamido, $(C_6-C_{18})$aryl$(C_3-C_{18})$heteroarylamido, $(C_1-C_6)$alkyl$(C_1-C_{18})$aryl$(C_3-C_{18})$heteroarylamido, $(C_1-C_6)$haloalkyl$(C_6-C_{18})$aryl$(C_3-C_{18})$heteroarylamido, $(C_1-C_6)$alkyl$(C_3-C_{18})$heteroarylamido, or $(C_1-C_6)$alkoxy$(C_6-C_{18})$aryl$(C_3-C_{18})$heteroarylamido; and $R^f$ is hydrogen, $(C_1-C_6)$alkoxybenzoylureido, or halo$(C_6-C_{18})$aryl$(C_3-C_{18})$heteroarylamido.

18 Claims, 1 Drawing Sheet

(51) Int. Cl.
  *C07D 401/06* (2006.01)
  *A61K 38/45* (2006.01)
  *C07D 401/14* (2006.01)
  *C07D 409/06* (2006.01)
  *C07D 405/06* (2006.01)
  *C07D 403/14* (2006.01)
  *A61K 31/522* (2006.01)
  *C07D 473/32* (2006.01)
  *C07D 209/00* (2006.01)

(52) U.S. Cl.
  CPC ............ *C07D401/14* (2013.01); *C07D 409/06* (2013.01); *C07D 405/06* (2013.01); *C07D 403/14* (2013.01); *A61K 31/522* (2013.01); *A61K 38/45* (2013.01); *C07D 473/32* (2013.01); *C07D 209/00* (2013.01)
  USPC .................... 514/414; 546/277.7; 548/324.5; 548/465

(56) References Cited

U.S. PATENT DOCUMENTS

2008/0221192 A1   9/2008   Wan et al.
2010/0298376 A1   11/2010  D'Mello et al.
2012/0270859 A1   10/2012  Treu et al.

FOREIGN PATENT DOCUMENTS

WO    2008/073480      6/2008
WO    2012025726 A1   3/2012

OTHER PUBLICATIONS

Registry No. 557795-19-4, retrieved from Registry, Jul. 31, 2003.*
Registry No. 356069-35-7, retrieved from Registry, Sep. 12, 2001.*
Registry No. 356068-94-5, retrieved from Registry, Sep. 12, 2001.*
Registry No. 252916-29-3, retrieved from Registry, Jan. 14, 2000.*
Registry No. 215543-92-3, retrieved from Registry, Dec. 13, 1998.*
Registry No. 204005-46-9, retrieved from Registry, Apr. 12, 1998.*
Registry No. 186611-56-3, retrieved from Registry, Feb. 27, 1997.*
Registry No. 91822-51-4, retrieved from Registry, Nov. 16, 1984.*
Registry No. 627908-92-3, retrieved from Registry, Dec. 19, 2003.*
Bhaskar, et al. Document No. 157:45000, retrieved from STN, May 23, 2012.*
Henschke, et al. Document No. 156:613297, retrieved from STN, May 11, 2012.*
Kozlowski, et al. Document No. 157:177496, retrieved from STN, Jun. 28, 2012.*
Park, et al. Document No. 158:140653, retrieved from CAPLUS, Jan. 3, 2013.*
PCT International Search Report for PCT/US2013/035177.

* cited by examiner

INDOLIN-2-ONE DERIVATIVES AS PROTEIN KINASE INHIBITORS

REFERENCE TO RELATED APPLICATION

The present application claims the priority to U.S. Provisional Application Ser. No. 61/635,931, filed Apr. 20, 2012, which is herein incorporated by reference in its entirety.

FIELD OF THE INVENTION

The invention relates generally to novel indoline-2-one derivatives as protein kinase inhibitors, especially Aurora-B and FLT-3 inhibitors, useful for treating hyperproliferative diseases such as cancer.

BACKGROUND OF THE INVENTION

U.S. Pat. No. 6,573,293 discloses pyrrole substituted 2-indolinone protein kinase inhibitors. US patent publication No. 20050090541 and 20120270859 disclose indolinone derivatives and their use in treating disease-states such as cancer. US patent publication No. 20080221192, WO/2008/073480 and WO2006052936 disclose compounds and compositions as kinase inhibitors. WO/2007/038251 discloses alkoxy indolinone based protein kinase inhibitors.

SUMMARY OF THE INVENTION

In one aspect, the invention relates to a compound of Formula A:

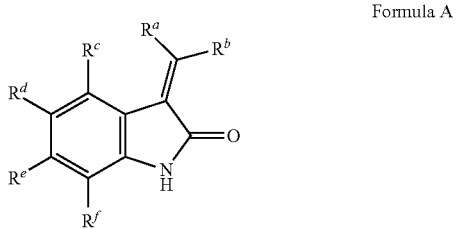

Formula A or a pharmaceutically acceptable salt, a solvate or hydrate, a prodrug, or a metabolite thereof, wherein
  $R_a$ is hydrogen, $(C_6-C_{18})$aryl, halo$(C_6-C_{18})$aryl, or $(C_1-C_6)$alkoxy$(C_6-C_{18})$aryl;
  $R^b$ is hydrogen, $(C_3-C_{18})$heteroaryl, $(C_1-C_6)$alkoxy$(C_3-C_{18})$heteroaryl; $(C_1-C_6)$alkyl$(C_3-C_{18})$heteroaryl, $(C_1-C_6)$alkyl$(C_1-C_6)$alkoxy$(C_3-C_{18})$heteroaryl, $(C_1-C_6)$alkyl$(C_1-C_6)$carboxyalkyl$(C_3-C_{18})$heteroaryl; $C_1-C_6)$alkyl$((C_1-C_6)$alkylamino$(C_1-C_6)$alkylcarbamoyl)$(C_3-C_{18})$heteroaryl, $(C_1-C_6)$alkyl$(C_6-C_{18})$aryl$(C_3-C_{18})$heteroaryl, $(C_1-C_6)$alkyl$(C_1-C_6)$alkoxycarbonyl$(C_3-C_{18})$heteroaryl, $(C_1-C_6)$alkyl$(C_1-C_6)$alkoxy$(C_1-C_6)$oxyalkyl$(C_3-C_{18})$heteroaryl, $(C_1-C_6)$alkyl$(C_1-C_6)$heterocyclylcarbonyl$(C_3-C_{18})$heteroaryl, $(C_1-C_6)$alkyl$(C_3-C_6)$heterocyclyl$(C_1-C_6)$oxyalkyl$(C_3-C_{18})$heteroaryl, or $(C_1-C_6)$alkyl$((C_3-C_6)$heterocyclyl$(C_1-C_6)$alkylcarbamoyl)$(C_3-C_{18})$heteroaryl;
  $R^c$ is hydrogen, $(C_1-C_6)$alkoxybenzoylureido, or halo$(C_6-C_{18})$aryl$(C_3-C_{18})$heteroarylamido;
  $R^d$ is hydrogen, halogen, $(C_1-C_6)$alkoxybenzoylureido, or halo$(C_6-C_{18})$aryl$(C_3-C_{18})$heteroarylamido;
  $R_e$ is hydrogen, benzoylureido, halobenzoylureido, halo$(C_1-C_6)$alkoxybenzoylureido, $(C_1-C_6)$alkoxybenzoylureido, $(C_1-C_6)$alkylaminobenzoylureido, $(C_1-C_6)$alkylbenzoylureido, nitrobenzoylureido, $(C_1-C_6)$haloalkylbenzoylureido, $(C_1-C_6)$haloalkylhalobenzoylureido, halo$(C_6-C_{18})$arylcarbomylacetamido, $(C_1-C_6)$alkoxy$(C_6-C_{18})$arylcarbomylacetamido, $(C_1-C_6)$alkoxy$(C_6-C_{18})$arylcarbamoyl$(C_3-C_6)$cycloalkylamido, halo$(C_6-C_{18})$aryl$(C_3-C_{18})$heteroarylcarbonylamino, $(C_3-C_6)$cycloalkyl$(C_3-C_{18})$heteroarylcarbonylamino, $(C_1-C_6)$alkylamino$(C_6-C_{18})$aryl$(C_3-C_{18})$heteroarylcarbonylamino, halo$(C_1-C_6)$alkoxy$(C_6-C_{18})$aryl$(C_3-C_{18})$heteroarylcarbonylamino, $(C_1-C_6)$alkoxy$(C_6-C_{18})$aryl$(C_3-C_{18})$heteroarylcarbonylamino, $(C_1-C_6)$alkyl$(C_3-C_{18})$heteroarylcarbonylamino, aryl$(C_3-C_{18})$heteroarylcarbonylamino, $(C_1-C_6)$haloalkylhalo$(C_3-C_{18})$aryl$(C_3-C_6)$heterocyclylcarbonylamino, $(C_1-C_6)$haloalkyl$(C_6-C_{18})$aryl$(C_3-C_{18})$heteroarylcarbonylamino, halo$(C_6-C_{18})$aryl$(C_3-C_{18})$heteroarylamido, $(C_1-C_6)$oxyalkyl$(C_3-C_6)$heterocyclylamido, $(C_1-C_6)$alkoxy$(C_1-C_6)$alkyl$(C_3-C_{18})$heteroarylamido, $(C_6-C_{18})$aryl$(C_3-C_{18})$heteroarylamido, $(C_1-C_6)$alkyl$(C_6-C_{18})$aryl$(C_3-C_{18})$heteroarylamido, $(C_1-C_6)$haloalkyl$(C_6-C_{18})$aryl$(C_3-C_{18})$heteroarylamido, $(C_1-C_6)$alkyl$(C_3-C_{18})$heteroarylamido, or $(C_1-C_6)$alkoxy$(C_6-C_{18})$aryl$(C_3-C_{18})$heteroarylamido:
  $R^f$ is hydrogen, $(C_1-C_6)$alkoxybenzoylureido, or halo$(C_6-C_{18})$aryl$(C_3-C_{18})$heteroarylamido, and
wherein acetamido, amido, amino, benzoylureido, carbamoyl, $(C_1-C_6)$alkyl, $(C_1-C_6)$alkylamino, $(C_1-C_6)$alkoxy, $(C_6-C_{18})$aryl, $(C_1-C_6)$carboxyalkyl, $(C_3-C_6)$cycloalkyl, $(C_3-C_{18})$heteroaryl, $(C_3-C_6)$heterocyclylcarbonyl, or $(C_1-C_6)$oxyalkyl are each independently optionally substituted on carbon or nitrogen with one or more alkyl, hydroxyalkyl, arylalkyl, heteroarylalkyl, aryl, heterocyclyl, oxo, hydroxy, halogen, nitro, alkoxy, or trifluoromethyl.

In one embodiment of the invention, $R^a$, $R^b$, $R^c$, $R^d$, $R^e$, and $R^f$ are as follows:
  $R^a$ is selected from hydrogen, phenyl, 4-chlorophenyL or 4-methoxyphenyl;
  $R^b$ is selected from hydrogen, furan-2-yl, 1H-pyrrol-2-yl, 5-carboxy-1H-pyrrol-2-yl, 3,3-dimethyl-1H-pyrrol-2-yl, 3,5-dimethyl-4-carboxy-1H-pyrrol-2-yl, 3,5-dimethyl-4-(2-carboxyethyl)-1H-pyrrol-2-yl, 3,5-dimethyl-4-carboxymethyl-1H-pyrrol-2-yl, 3,5-dimethyl-4-([2-(dimethylamino)ethyl]carbamoyl)-1H-pyrrol-2-yl, 3,5-dimethyl-4-phenyl-1H-pyrrol-2-yl, 3,5-dimethyl-4-ethoxycarbonyl-1H-pyrrol-2-yl, 3,5-dimethyl-4-(3-ethoxy-3-oxopropyl)-1H-pyrrol-2-yl, 3,5-dimethyl-4-(4-methylpiperazino-1-carbonyl)-1H-pyrrol-2-yl, 3,5-dimethyl-4-(3-(4-methylpiperazino-3-oxopropyl))-1H-pyrrol-2-yl, 3,5-dimethyl-4-(3-(4-methylpiperazino-2-oxoethyl))-1H-pyrrol-2-yl, 3,5-dimethyl-4-(3-methoxy-3-oxopropyl)-1H-pyrrol-2-yl, 3,5-dimethyl-4-(morpholine-1-carbonyl)-1H-pyrrol-2-yl, 3,5-dimethyl-4-(3-morpholino-2-oxoethyl)-1H-pyrrol-2-yl, 3,5-dimethyl-4-(3-morpholino-3-oxopropyl)-1H-pyrrol-2-yl, 3,5-dimethyl-4-([2-(pyrrolidin-1-yl)ethyl]carbomyl)-1H-pyrrol-2-yl, 3,5-dimethyl-4-([2-(pyrrolidin-1-yl)ethyl]carbomyl)-1H-pyrrol-2-yl; pyrid-2-yl, pyrid-4-yl, or thiphen-2-yl;
  $R^c$ is selected from hydrogen, $N^3$-(4-methoxybenzoyl)ureido, or 1-(4-fluorophenyl)-2-oxopyridine-3-amido;
  $R^d$ is selected from hydrogen, fluoro, $N^3$-(4-methoxybenzoyl)ureido, or 1-(4-fluorophenyl)-2-oxopyridine-3-amido;

$R^e$ is selected from hydrogen, $N^3$-benzoylureido, $N^3$-(4-chlorobenzoyl)ureido, $N^3$-(3,4-dichlorobenzoyl)ureido, $N^3$-(2,4-difluorobenzoyl)ureido, $N^3$-(2,6-difluoro-4-methoxybenzoyl)ureido, $N^3$-(2,6-difluoro-4-methoxybenzoyl)ureido, $N^3$-(3,5-dimethoxybenzoyl)ureido, $N^3$-((4-dimethylaminobenzoyl)ureido, $N^3$-(2-fluorobenzoyl)ureido, $N^3$-(4-fluorobenzoyl)ureido, $N^3$-(2-fluoro-4-methoxybenzoyl)ureido, $N^3$-(3-methylbenzoyl)ureido, $N^3$-(4-methylbenzoyl)ureido, $N^3$-(4-methoxybenzoyl)ureido, $N^3$-(4-nitrobenzoyl)ureido, $N^3$-(4-trifluoromethylbenzoyl)ureido, $N^3$-(3-trifluoromethyl-4-chlorobenzoyl)ureido, 2-[(4-fluorophenyl)carbamoyl]acetamido, 2-[(4-methoxypehnyl)carbomyl]acetamido, 1-{(4-methoxyphenyl)carbamoyl]cyclopropaneamido}, 3-(4-chlorophenyl)-2-oxoimidazolidine-1-carbonylamino, 3-(3-chlorophenyl)-2-oxoimidazolidine-1-carbonylamino, 3-cyclopropyl-2-oxoimidazolidine-1-carbonylamino, 3-(3,4-dichlorophenyl)-2-oxoimidazolidine-1-carbonylamino, 3-(4-dimethylaminophenyl)-2-oxoimidazolidine-1-carbonylamino, 3-(2-fluorophenyl)-2-oxoimidazolidine-1-carbonylamino, 3-(4-fluorophenyl)-2-oxoimidazolidine-1-carbonylamino, 3-(2-fluoro-4-methoxyphenyl)-2-oxoimidazolidine-1-carbonylamino, 3-(4-methoxyphenyl)-2-oxoimidazolidine-1-carbonylamino, 3-(4-methylphenyl)-2-oxoimidazolidine-1-carbonylamino, 3-methyl-2-oxoimidazolidine-1-carbonylamino, 3-phenyl-2-oxoimidazolidine-1-carbonylamino, 3-(3-trifluoromethyl-4-chlorophenyl)-2-oxoimidazolidine-1-carbonylamino, 3-(4-trifluoromethylphenyl)-2-oxoimidazolidine-1-carbonylamino, 1-(4-chlorophenyl)-2-oxopyridine-3-amido, 1-(3-chlorophenyl)-2-oxopyridine-3-amido, 1-(3,4-dichlorophenyl)-2-oxopyridine-3-amido, 1-(2-fluorophenyl)-2-oxopyridine-3-amido, 1-(4-fluoropehnyl)-2-oxopyridine-3-amido, 1-(2-hydroxyethyl)-2-oxopyridine-3-amido, 1-(4-methoxyphenyl)-2-oxopyridine-3-amido, 1-methyl-2-oxopyridine-3-amido, 1-(4-methylphenyl)-2-oxopyridine-3-amido, 1-phenyl-2-oxopyridine-3-amido, 1-(3-trifluoromethyl-4-chlorophenyl)-2-oxopyridine-3-amido, 1-(3-trifluoromethylphenyl)-2-oxopyridine-3-amido, 1-(4-trifluoromethylphenyl)-2-oxopyridine-3-amido, 5-(3-chlorophenyl)-4-oxopyridine-3-amido, 5-(4-chlorophenyl)-4-oxopyridine-3-amido, 5-(2,4-difluorophenyl)-4-oxopyridine-3-amido, 5-(3,5-difluorophenyl)-4-oxopyridine-3-amido; 5-(2-fluorophenyl)-4-oxopyridine-3-amido, 5-(4-fluorophenyl)-4-oxopyridine-3-amido, 1-methyl-5-(4-fluorophenyl)-4-oxopyridine-3-amido, 5-methyl-4-oxopyridine-3-amido, 5-(4-methylphenyl)-4-oxopyridine-3-amido, 5-(4-methoxyophenyl)-4-oxopyridine-3-amido, 5-phenyl-4-oxopyridine-3-amido, or 5-(4-trifluoromethylphenyl)-4-oxopyridine-3-amido; and $R^f$ is selected from hydrogen, $N^3$-(4-methoxybenzoyl)ureido, or 1-(4-fluorophenyl)-2-oxopyridine-3-amido.

In another embodiment of the invention, $R^a$, $R^b$, $R^c$, $R^d$, $R^e$, and $R^f$ are as follows:

$R^a$ is selected from hydrogen, phenyl 4-chlorophenyl, or 4-methoxyphenyl;

$R^b$ is selected from hydrogen, furan-2-yl, 1H-pyrrol-2-yl, 5-carboxy-1H-pyrrol-2-yl, 3,5-dimethyl-1H-pyrrol-2-yl, 3,5-dimethyl-4-carboxy-1H-pyrrol-2-yl, 3,5-dimethyl-4-(2-carboxyethyl)-1H-pyrrol-2-yl, 3,5-dimethyl-4-carboxymethyl-1H-pyrrol-2-yl, 3,5-dimethyl-4-([2-(dimethylamino)ethyl]carbamoyl)-1H-pyrrol-2-yl, 3,5-dimethyl-4-phenyl-1H-pyrrol-2-yl, 3,5-dimethyl-4-ethoxycarbonyl-1H-pyrrol-2-yl, 3,5-dimethyl-4-(3-ethoxy-3-oxopropyl)-1H-pyrrol-2-yl, 3,5-dimethyl-4-(4-methylpiperazino-1-carbonyl)-1H-pyrrol-2-yl, 3,5-dimethyl-4-(3-(4-methylpiperazino-3-oxopropyl))-1H-pyrrol-2-yl, 3,5-dimethyl-4-(3-(4-methylpiperazino-2-oxoethyl))-1H-pyrrol-2-yl, 3,5-dimethyl-4-(morpholine-1-carbonyl)-1H-pyrrol-2-yl, 3,5-dimethyl-4-(3-morpholino-2-oxoethyl)-1H-pyrrol-2-yl, 3,5-dimethyl-4-(3-morpholino-3-oxopropyl)-1H-pyrrol-2-yl, 3,5-dimethyl-4-([2-(pyrrolidin-2-yl)ethyl]carbonyl)-1H-pyrrol-2-yl, 3,5-dimethyl-4-([2-(pyrrolidin-1-yl)ethyl]carbomyl)-1H-pyrrol-2-yl; pyrid-2-yl, pyrid-4-yl, or thiophen-2-yl;

$R^c$ is selected from hydrogen or $N^3$-(4-methoxybenzoyl)ureido;

$R^d$ is selected from hydrogen, fluoro, or $N^3$-(4-methoxybenzoyl)ureido;

$R^e$ is selected from hydrogen, $N^3$-benzoylureido, $N^3$-(4-chlorobenzoyl)ureido, $N^3$-(3,4-dichlorobenzoyl)ureido, $N^3$-(2,4-difluorobenzoyl)ureido, $N^3$-(2,6-difluoro-4-methoxybenzol)ureido, $N^3$-(2,6-difluoro-4-methoxybenzoyl)ureido, $N^3$-(3,5-dimethoxybenzyl)ureido, $N^3$-((4-dimethylaminobenzayl)ureido, $N^3$-(2-fluorobenzoyl)ureido, $N^3$-(4-fluorobenzoyl)ureido, $N^3$-(2-fluoro-4-methoxybenzoyl)ureido, $N^3$-(3-methylbenzoyl)ureido, $N^3$-(4-methylbenzoyl)ureido, $N^3$-(4-methoxybenzoyl)ureido, $N^3$-(4-nitrobenzoyl)ureido, $N^3$-(4-trifluoromethylbenzoyl)ureido, or $N^3$-(3-trifluoromethyl-4-chlorobenzoyl)ureido; and $R^f$ is hydrogen or $N^3$-(4-methoxybenzoyl)ureido.

In another embodiment of the invention, $R^a$, $R^b$, $R^c$, $R^d$, $R^e$, and $R^f$ are as follows:

$R^a$, $R^c$, $R^d$ and $R^f$ are each independently hydrogen;

$R^b$ is 1H-pyrrol-2-yl; and $R^e$ is 2-[(4-methoxyphenyl)carbomyl]acetamido or 1-{(4-methoxyphenyl)carbamoyl]cyclopropaneamido}.

Further in another embodiment of the invention, $R^a$, $R^b$, $R^c$, $R^d$, $R^e$ and $R^f$ are as follows:

$R^a$, $R^c$, $R^d$ and $R^f$ are each independently hydrogen;

$R^b$ is 1H-pyrrol-2-yl, 3,5-dimethyl-4-carboxy-1H-pyrrol-2-yl, 3,5-dimethyl-4-carboxymethyl-1H-pyrrol-2-yl, or 3,5-dimethyl-4-(2-carboxyethyl)-1H-pyrrol-2-yl; and $R^e$ is 3-methyl-2-oxoimidazolidine-1-carbonylamino, 3-cyclopropyl-2-oxoimidazolidine-1-carbonylamino, 3-phenyl-2-oxoimidazolidine-1-carbonylamino, 3-(4-chlorophenyl)-2-oxoimidazolidine-1-carbonylamino, 3-(3-chlorophenyl)-2-oxoimidazolidine-1-carbonylamino, 3-(3,4-dichlorophenyl)-2-oxoimidazolidine-1-carbonylamino, 3-(3-trifluoromethyl-4-chlorophenyl)-2-oxoimaidazolidine-1-carbonylamino, 3-(4-trifluoromethylphenyl)-2-oxoimidazolidine-1-carbonylamino, 3-(4-fluorophenyl)-2-oxoimidazolidine-1-carbonylamino, 3-(2-fluorophenyl)-2-oxoimidazolidine-1-carbonylamino, 3-(4-methoxyphenyl)-2-oxoimidazolidine-1-carbonylamino, 3-(4-methylphenyl)-2-oxoimidazolidine-1-carbonylamino, 3-(4-dimethylaminophenyl)-2-oxoimidazolidine-1-carbonylamino, 3-(2-fluoro-4-methoxyphenyl)-2-oxoimidazolidine-1-carbonylamino, 3-(4-methoxyphenyl)-2-oxoimidazolidine-1-carbonylamino, 3-cyclopropyl-2-oxoimidazolidine-1-carbonylamino, 3-(2-fluorophenyl)-2-oxoimidaxolidine-1-carbonylamino, or 3-(2-fluoro-4-methoxyphenyl)-2-oxoimidazolidine-1-carbonylamino.

In another embodiment of the invention, wherein;
R$^a$ is hydrogen;
R$^b$ is 1H-pyrrol-2-yl, 3,5-dimethyl-1H-pyrrol-2-yl, 3,5-dimethyl-4-carboxy-1H-pyrrol-2-yl, 3,5-dimethyl-4-carboxymethyl-1H-pyrrol-2-yl, 3,5-dimethyl-4-(2-carboxyethyl)-1H-pyrrol-2-yl, 3,5-dimethyl-4-(3-methoxy-3-oxopropyl)-1H-pyrrol-2-yl, or 3,5-dimethyl-4-carboxy-1H-pyrrol-2-yl;
R$^c$ and R$^d$ are each independently hydrogen or 1-(4-fluorophenyl)-2-oxopyridine-3-amido;
R$^e$ is hydrogen, 1-phenyl-2-oxopyridine-3-amido, 1-(4-methoxyphenyl)-2-oxopyridine-3-amido, 1-(4-fluorophenyl)-2-oxopyridine-3-amido, 1-(4-chlorophenyl)-2-oxopyridine-3-amido, 1-(3-trifluoromethyl-4-chlorophenyl)-2-oxopyridine-3-amido, 1-(3,4-dichlorophenyl)-2-oxopyridine-3-amido, 1-(4-methylphenyl)-2-oxopyridine-3-amido, 1-(4-trifluoromethylphenyl)-2-oxopyridine-3-amido, 1-(3-trifluoromethylphenyl)-2-oxopyridine-3-amido, 1-(3-chlorophenyl)-2-oxopyridine-3-amido, 1-(2-fluorophenyl)-2-oxopyridine-3-amido, 1-methyl-2-oxopyridine-3-amido, 1-(2-hydroxyethyl)-2-oxopyridine-3-amido, 1-(4-fluorophenyl)-2-oxopyridine-3-amido, or 1-methyl-2-oxopyridine-3-amido; and
R$^f$ is hydrogen or 1-(4-fluorophenyl)-2-oxopyridine-3-amido.

Further in another embodiment of the invention, wherein;
R$^a$, R$^a$, R$^c$, R$^d$ and R$^f$ are each independently hydrogen;
R$^b$ is 1H-pyrrol-2-yl, 3,5-dimethyl-1H-pyrrol-2-yl, 3,5-dimethyl-4-carboxy-1H-pyrrol-2-yl, 3,5-dimethyl-4-carboxymethyl-1H-pyrrol-2-yl, 3,5-dimethyl-4-(2-carboxyethyl)-1H-pyrrol-2-yl, 3-methyl-5-carboxy-1H-pyrrol-2-yl, 3,5-dimethyl-4-(4-methylpiperazino-1-carbonyl)-1H-pyrrol-2-yl, 3,5-dimethyl-4-(3-(4-methylpiperazino-2-oxoethyl))-1H-pyrrol-2-yl, 3,5-dimethyl-4-(3-(4-methylpiperazino-3-oxopropyl))-1H-pyrrol-2-yl, 3,5-dimethyl-4-(morpholino-1-carbonyl)-1H-pyrrol-2-yl, 3,5-dimethyl-4-(3-morpholino-2-oxoethyl)-1H-pyrrol-2-yl, 3,5-dimethyl-4-(4-methylpiperazino-1-carbonyl)-1H-pyrrol-2-yl, or 3,5-dimethyl-4-([2-(pyrrolidin-1-yl)ethyl]carbonyl)-1H-pyrrol-2-yl; and
R$^e$ is 5-methyl-4-oxopyridine-3-amido, 5-phenyl-4-oxopyridine-3-amido, 5-(4-methoxyphenyl)-4-oxopyridine-3-amido, 5-(4-fluorophenyl)-4-oxopyridine-3-amido, 5-(4-chlorophenyl)-4-oxopyridine-3-amido, 5-(4-methylphenyl)-4-oxopyridine-3-amido, 5-(3-chlorophenyl)-4-oxopyridine-3-amido, 5-(4-trifluoromethylphenyl)-4-oxopyridine-3-amido, 5-(2-fluorophenyl)-4)-4-oxopyridine-3-amido, 5-(2,4-difluorophenyl)-4-oxopyridine-3-amido, 5-(3,5-difluorophenyl)-4-oxopyridine-3-amido, or 1-methyl-5-(4-fluorophenyl)-4-oxopyridine-3-amido.

In another embodiment of the invention, the compound is selected from the group consisting of (Z)—N-(3-((1H-pyrrol-2-yl)methylene)-2-oxoindolin-4-ylcarbamoyl)-4-methoxybenzamide, (Z)—N-(3-((1H-pyrrol-2-yl)methylene-2-oxoindolin-5-ylcarbamoyl)-4-methoxybenzamide, (Z)—N-(3-((1H-pyrrol-2-yl)methylene)-2-oxoindolin-6-ylcarbamoyl)-4-methoxybenzamide, (Z)—N-(3-((1H-pyrrol-2-yl)methylene)-2-oxoindolin-7-ylcarbamoyl)-4-methoxybenzamide, (E)-N-(3-benzylidene-2-oxoindolin-6-ylcarbamoyl)-4-methoxybenzamide, (E)-N-(3-(4-chlorobenzylidene)-2-oxoindolin-6-ylcarbamoyl)-4-methoxybenzamide, (E)-4-methoxy-N-(3-(4-methoxybenzylidene)-2-oxoindolin-6-yl-carbamoyl) benzamide, (Z)-4-methoxy-N-(2-oxo-3-(pyridin-2-ylmethylene)indolin-6-ylcarbamoyl)benzamide, (Z)-4-methoxy-N-(2-oxo-3-(pyridin-4-ylmethylme)indolin-6-ylcarbamoyl)benzamide, (Z)-4-methoxy-N-(2-oxo-3-(thiophen-2-ylmethylene)indolin-6-ylcarbamoyl) benzamide, (E)-N-(3-(furan-2-ylmethylene)-2-oxoindolin-6-ylcarbanoyl)-4-methoxybenzamide, (Z)—N-(3-((1H-pyrrol-2-yl)methylene)-2-oxoindolin-6-ylcarbamoyl) benzamide, (Z)—N-(3-((1H-pyrrol-2-yl)methylene)-2-oxoindolin-6-ylcarbamoyl)-4-chlorobenzamide, (Z)—N-(3-((1H-pyrrol-2-yl)methylene)-2-oxoindolin-6-ylcarbamoyl)-3,4-dichlorobenzamide, (Z)—N-(3-((1H-pyrrol-2-yl)methylene)-2-oxoindolin-6-ylcarbamoyl)-4-(trifluoromethyl)-benzamide, (Z)—N-(3-((1H-pyrrol-2-yl)methylene)-2-oxoindolin-6-ylcarbamoyl)-4-chloro-3-(trifluoromethyl)-benzamide, (Z)—N-(3-((1H-pyrrol-2-yl)methylene)-2-oxoindolin-6-ylcarbamoyl)-4-methylbenzamide, (Z)—N-(3-((1H-pyrrol-2-yl)methylene)-2-oxoindolin-6-ylcarbamoyl)-3,5-dimethoxybenzamide, (Z)—N-(3-((1H-pyrrol-2-yl)methylene)-2-oxoindolin-6-yl-carbamoyl)-4-(dimethylamino)-benzamide, (Z)-5-((6-(3-benzoylureido)-2-oxoindolin-3-ylidene)methyl)-2,4-dimethyl-1H-pyrrole-3-carboxylic acid, (Z)-5-((6-(3-(4-chlorobenzoyl)ureido)-2-oxoindolin-3-ylidene)-methyl)-2,4-dimethyl-1H-pyrrole-3-carboxylic acid, (Z)-5-((6-(3-(3,4-dichlorobenzoyl)ureido)-2-oxoindolin-3-ylidene)methyl)-2,4-dimethyl-1H-pyrrole-3-carboxylic acid, (Z)-2,4-dimethyl-5-(2-oxo-6-(3-(4-(trifluoromethyl)benzoyl)ureido)indolin-3-ylidene)methyl)-1H-pyrrole-3-carboxylic acid, (Z)-5-((6-(3-(4-chloro-3-(trifluoromethyl)benzoyl)ureido)-2-oxoindolin-3-ylid-ene)methyl)-2,4-dimethyl-1H-pyrrole-3-carboxylic acid, (Z)-3-(5-((6-(3-(4-chloro-3-(trifluoromethyl)benzoyl)ureido)-2-oxo-indolin-3-yl-indene)methyl)-2,4-dimethyl-1H-pyrrol-3-yl)propanoic acid, (Z)-2,4-diimethyl-5-((6-(3-(4-nitrobenzoyl)ureido)-2-oxoindolin-3-ylidene)methyl)-1H-pyrrole-3-carboxylic acid, (Z)-2,4-dimemthyl-5-((6-(3-(4-methylbenzoyl)ureido)-2-oxoindolin-3-ylidene)-methy)-1H-pyrrole-3-carboxylic acid, (Z)-3-(2,4-dimethyl-5-((6-(3-(3-methylbenzoyl)ureido)-2-oxoindolin-3-ylidene)-methyl)-1H-pyrrol-3-yl)propanoic acid, (Z)-5-((6-(3-(4-methoxybenzoyl)ureido)-2-oxomdolin-3-ylidene)-methyl)-2,4-di-methyl-1H-pyrrole-3-carboxylic acid, (Z)-5-((6-(3-(3,5-dimethoxybenzoyl)ureido)-2-oxoindolin-3-ylidene)methyl)-2,4-dimethyl-1H-pyrrole-3-carboxylic acid, (Z)—N-(3-((3,5-dimethyl-4-phenyl-1H-pyrrol-2-yl)methylene)-2-oxolindolin-6-ylcarbamoyl)-4-methoxybenzamide, (Z)—N-(3-((3,5-dimethyl-1H-pyrrol-2-yl)methylene)-2-oxoindolin-6-ylcarbamoyl)-4-methoxybenzamide, (Z)-5-((6-(3-(4-methoxybenzoyl)ureido)-2-oxoindolin-3-ylidene)methyl)-1H-pyrrole-2-carboxylic acid, (Z)-2-(5-((6-(3-(4-methoxybenzoyl)ureido)-2-oxoindolin-3-ylidene)methyl)-2,4-dimethy-1H-pyrrol-3-yl)acetic acid, (Z)-3-(5-((6-(3-(4-methoxybenzoyl)ureido)-2-oxoindolin-3-ylidene)methyl)-2,4-dimethyl-1H-pyrrol-3-yl)propanoic acid, (Z)—N-(3-(1H-pyrrol-2-yl)methylene)-5-fluoro-2-oxoindolin-6-ylcarbamoyl)-4-methoxybenzamide, (Z)-5-(5-fluoro-6-(3-(4-methoxybenzoyl)ureido)-2-oxoindolin-3-ylidene) methyl)-2,4-dimethyl-1H-pyrrole-3-carboxlic acid, (Z)-2-(5-((5-fluoro-6-(3-(4-methoxybenzoyl)ureido)-2-oxoindolin-3-ylidene)-methyl)-2,4-dimethyl, 1H-pyrrol-3-yl)acetic acid, (Z)-3-(5-((5-fluoro-(6-(3-(4-methoxybenzoyl)ureido)-2-oxoindolin-3-ylidene)-methyl)-2,4-dimethyl-1H-pyrrol-3-yl)propanoic acid, (Z)—N-(3-((1H-pyrrol-2-yl)methylene)-2-oxoindolin-6-ylcarbamoyl)-2-fluorobenzamide, (Z)-5-((6-(3-(2-fluorobenzoyl)ureido)-2-oxoindolin-3-ylidene)methyl)-2,4-dimethyl-1H-pyrrol-3- carboxylic acid, (Z)-3-(5-((6-(3-(2-fluorobenzoyl)ureido)-2-oxoindolin-3-ylidene)methyl)-2,4-dimethyl-1H-pyrrole-3-yl)propanoic acid, (Z)-3-(5-((6-(3-(4-fluorobenzoyl)ureido)-2-oxoindolin-3-ylidene)methyl)-2,4-dimethyl-1H-pyrrol-3-yl)propanoic acid, (Z)-3-(5-((6-(3-(2,4-difluorobenzoyl)ureido]-2-oxoindolin-3-ylidene)methyl)-2,4-dimethyl-1H-pyrrol-3-yl)propanoic acid, (Z)-5-((6-(3-(2-fluoro-4-methoxybenzoyl)ureido)-2-oxoindolin-3-ylidene)methyl)-2,4-dimethyl-1H-pyrrole-3-carboxylic acid, (Z)-3-(5-((6-(3-(2-fluoro-4-methoxybenzoyl)ureido)-2-oxoindolin-3-ylidene)methyl)-2,4-dimethyl-1H-pyrrol-3-yl)propanoic acid, (Z)-5-((5-fluoro-6-(3-(2-fluoro-4-methoxybenzoyl)ureido)-2-oxoindolin-3-ylidene)methyl)-2,4-dimethyl-1H-pyrrole-3-carboxylic acid, (Z)-3-(5-((5-fluoro-6-(3-(2-fluoro-4-methoxybenzoyl)ureido)-2-oxoindolin-3-ylidene)methyl)-2,4-dimethyl-1H-pyrrol-3-yl)propanoic acid, (Z)-5-((6-(3-(2,6-difluoro-4-methoxybenzoyl)ureido)-5-fluoro-2-oxoindolin-3-ylidene)methyl)-2,4-dimethyl-1H-pyrrole-3-carboxylic acid, (Z)-ethyl-5-((6-(3-(2-fluoro-4-methoxybenzoyl)ureido)-2-oxoindolin-3-ylidene)methyl)-2,4-dimethyl-1H-pyrrole-3-carboxylate, (Z)-ethyl-3-(5-((6-(3-(2-fluoro-4-methoxybenzoyl)ureido)-2-oxoindolin-3-ylidene)methyl)-2,4-dimethyl-1H-pyrrol-3-yl)propanoate, (Z)—N-(3-((3,5-dimethyl-4-(4-methylpiperazine-1-carbonyl)-1H-pyrrol-2-yl)methylene)-2-oxoindolin-6-ylcarbamoyl)-2-fluoro-4-methoxybenzamide, (Z)—N-(3-((3,5-dimethyl-4-(3-(4-methylpiperazin-1-yl)-3-oxopropyl)-1H-pyrrol-2-yl)methylene)-2-oxoindolin-6-ylcarbamoyl)-2-fluoro-4-methoxybenzamide, (Z)—N-((3,5-dimethyl-4-(morpholine-4-carbonyl)-1H-pyrrol-2-yl)methylene)-2-oxoindolin-6-ylcarbamoyl)-2-fluoro-4-methoxybenzamide, (Z)—N-(3-((3,5-dimethyl-4-(3-morpholino-3-oxopropyl)-1H-pyrrol-2-yl)methylene)-2-oxoindolin-6-ylcarbamoyl)-2-fluoro-4-methoxybenzamide, (Z)—N-(2-(dimethylamino)ethyl)-5-((6-(3-(2-fluoro-4-methoxybenzoyl)-ureido)-2-oxoindolin-3-ylidene)methyl)-2,4-dimethyl-1H-pyrrole-3-carboxamide, (Z)—N-(2-(diethylamino)ethyl)-5-((6-(3-(2-fluoro-4-methoxybenzoyl)ureido)-2-oxoindolin-3-ylidene)methyl)-2,4-dimethyl-1H-pyrrole-3-carboxamide, (Z)-5-((6-(3-(2-fluoro-4-methoxybenzoyl)ureido)-2-oxoindolin-3-ylidene)methyl)-2,4-dimethyl-N-(2-pyrrolidin-1-yl)ethyl)-1H-pyrrole-3-carboxamide, and Malic acid salt of (Z)-5-((6-(3-(2-fluoro-4-methoxybenzoyl)ureido)-2-oxoindolin-3-ylidene)methyl)-2,4-dimethyl-N-(2-(pyrrolidin-1-yl)ethyl)-1H-pyrrole-3-carboxamide.

In another embodiment of the invention, the compound is selected from the group consisting of (Z)—N$^1$-(3-((1H-pyrrol-2-yl)methylene)-2-oxoindolin-6-yl)-N$^3$-(4-fluorophenyl)malonamide, (Z)—N$^1$-(3-((1H-pyrrol-2-yl)methylene)-2-oxoindolin-6-yl)-N$^3$-(4-methoxyphenyl)malonamide, and (Z)—N-(3-((1H-pyrrol-2-yl)methylene)-2-oxoindolin-6-yl)-N-(4-methoxyphenyl)cyclopropane-1,1-dicarboxamide. (3-((1H-pyrrol-2-yl)methylene)-2-oxoindolin-6-yl)-N-(4-methoxyphenyl)cyclopropane-1,1-dicarboxamide.

In another embodiment of the invention, the compound is selected from the group consisting of (Z)—N-(3-((1H-pyrrol-2-yl)methylene)-2-oxoindolin-6-yl)-3-methyl-2-oxoimidazolidine-1-carboxamide, (Z)—N-(3-((1H-pyrrol-2-yl)methylene)-2-oxoindolin-6-yl)-3-cyclopropyl-2-oxoimidazolidine-1-carboxamide, (Z)—N-(3-((1H-pyrrol-2-yl)methylene)-5-fluoro-2-oxoindolin-6-pyrrol-3-cyclopropyl-2-oxoimidazolidine-1-carboxamide, (Z)—N-(3-((1H-pyrrol-2-yl)methylene)-2-oxoindolin-6-yl)-2-oxo-3-phenylimidazolidine-1-carboxamide, (Z)—N-(3-((1H-pyrrol-2-yl)methylene)-2-oxoindolin-6-yl)-3-(4-chlorophenyl)-2-oxoimidazolidine-1-carboxamide, (Z)—N-(3-((1H-pyrrol-2-yl)methylene)-2-oxoindolin-6-yl)-3-(3-chlorophenyl)-2-oxoimidazolidine-1-carboxamide, (Z)—N-(3-((1H-pyrrol-2-yl)methylene)-2-oxoindolin-6-yl)-3-(3,4-dichlorophenyl)-2-oxoimidazolidine-1-carboxamide, (Z)—N-(3-((1H-pyrrol-2-yl)methylene)-2-oxoindolin-6-yl)-3-(4-chloro-3-(trifluoro-methyl)phenyl)-2-oxoimidazolidine-1-carboxamide, (Z)—N-(3-((1H-pyrrol-2-yl)methylene)-2-oxoindolin-6-yl)-2-oxo-3-(4-(trifluoro-methyl)phenyl)imidazolidine-1-carboxamide, (Z)—N-(3-((1H-pyrrol-2-yl)methylene)-2-oxoindolin-6-yl)-3-(4-fluorophenyl)-2-oxoimidazolidine-1-carboxamide, (Z)—N-(3-((1H-pyrrol-2-yl)methylene)-2-oxoindolin-6-yl)-3-(2-fluorophenyl)-2-oxoimidazolidine-1-carboxamide, (Z)—N-(3-((1H-pyrrol-2-yl)methylene)-2-oxoindolin-6-yl)-3-(4-methoxyphenyl)-2-oxoimidazolidine-1-carboxamide, (Z)—N-(3-((1H-pyrrol-2-yl)methylene)-2-oxoindolin-6-yl)-2-oxo-3-p-tolylimida-zolidine-1-carboxamide, (Z)—N-(3-((1H-pyrrol-2-yl)methylene)-2-oxoindolin-6-yl)-3-(4-(dimethylamino)phenyl)-2-oxoimidaxolidine-1-carboxamide, (Z)—N-(3-((1H-pyrrol-2-yl)methylene)-2-oxoindolin-6-yl)-3-(2-fluoro-4-methoxyphenyl)-2-oxoimidazolidine-1-carboxamide, (Z)-5-((6-(3-(4-methoxyphenyl)-2-oxoimidazolidine-1-carboxamido)-2-oxoindolin-3-ylidene)methyl)-2,4-dimethyl-1H-pyrrole-3-carboxylic acid, (Z)-5-((6-(3-cyclopropyl-2-oxoimidazolidine-1-carboxamido)-2-oxoindolin-3-ylidene)methyl)-2,4-dimethyl-1H-pyrrole-3-carboxylic acid, (Z)-2-(5-((6-(3-cyclopropyl-2-oxoimidazolidine-1-carboxamido)-2-oxoindolin-3-ylidene)methyl)-2,4-dimethyl-1H-pyrrol-3-yl)acetic acid, (Z)-3-(5-((6-(3-cyclopropyl-2-oxoimidazolidine-1-carboxamido)-2-oxoindolin-3-ylidene)methyl)-2,4-dimethyl-1H-pyrrol-3-yl)propanoic acid, (Z)-5-((6-(3-(2-fluorophenyl)-2-oxoimidazolidine-1-carboxamido)-2-oxoindolin-3-ylidene)methyl)-2,4-dimethyl-1H-pyrrole-3-carboxylic acid, and (Z)-5-((6-(3-(2-fluoro-4-methoxyphenyl)-2-oxoimidazolidine-1-carboxamido)-2-oxoindolin-3-ylidene)methyl)-2,4-dimethyl-1H-pyrrole-3-carboxylic acid.

In another embodiment of the invention, the compound is selected from the group consisting of (Z)—N-(3-((1H-pyrrol-2-yl)methylene)-2-oxoindolin-4-yl)-1-(4-fluorophenyl)-2-oxo-1,2-dihydropyridine-3-carboxamide, (Z)—N-(3-((1H-pyrrol-2-yl)methylene)-2-oxomdolin-5-yl)-1-(4-fluorophenyl)-2-oxo-1,2-dihydropyridine-3-carboxamide, (Z)—N-(3-((1H-pyrrol-2-yl)methylene)-2-oxoindolin-6-yl)-2-oxo-1-phenyl-1,2-dihydropyridine-3-carboxamide, (Z)—N-(3-((1H-pyrrol-2-yl)methylene)-2-oxoindolin-6-yl)-1-(4-methoxyphenyl)-2-oxo-1,2-dihydropyridine-3-carboxamide, (Z)—N-(3-((1H-pyrrol-2-yl)methylene)-2-oxoindolin-6-yl)-1-(4-fluorophenyl)-2-oxo-1,2-dihydropyridine-3-carboxamide, (Z)—N-(3-((1H-pyrrol-2-yl)methylene)-2-oxoindolin-6-yl)-1-(4-chlorophenyl)-2-oxo-1,2-dihydropyridine-3-carboxamide, (Z)—N-(3-((1H-pyrrol-2-yl)methylene)-2-oxoindolin-6-yl)-1-(4-chloro-(3-trifluoromethyl)phenyl)-2-oxo-1,2-dihydropyridine-3-carboxamide, (Z)—N-(3-((1H-pyrrol-2-yl)methylene)-2-oxoindolin-6-yl)-1-(3,4-dichlorophenyl)-2-oxo-1,2-dihydropyridine-3-carboxamide, (Z)—N-(3-(1H-pyrrol-2-yl)methylene-2-oxoindolin-6-yl)-2-oxo-1-(p-tolyl)-1,2-dihydropyridine-3-carboxamide, (Z)—N-(3-((1H-pyrrol-2-yl)methylene)-2-oxoindolin-6-yl)-1-(4-(trifluoromethyl)phenyl)-2-oxo-1,2-dihydropyridine-3-carboxamide, (Z)—N-(3-((1H-pyrrol-2-yl)methylene)-2-oxoindolin-6-yl)-1-(3-(trifluoromethyl)phenyl-2-oxo-1,2-dihydropyridine-3-carboxamide, (Z)—N-(3-((1H-pyrrol-2-yl)methylene)-2-oxoindolin-6-yl)-1-(3-chlorophenyl)-2-oxo-1,2-dihydropyridine-3-carboxamide, (Z)—N-(3-((1H-pyrrol-2-yl)methylene)-2-oxoindolin-6-yl)-1-(2-fluorophenyl)-2-oxo-1,2-dihydropyridine-3-carboxamide, (Z)—N-(3-((1H- pyrrol-2-yl)methylene)-2-oxoindolin-6-yl)-1-methyl-2-oxo-1,2-dihydropyridine-3-carboxamide, (Z)—N-(3-((1H-pyrrol-2-yl)methylene)-2-oxoindolin-6-yl)-1-(2-hydroxyethyl)-2-oxo-1,2-dihydropyridine-3-carboxamide, (Z)—N-(3-((1H-pyrrol-2-yl)methylene)-2-oxoindolin-7-yl)-1-(4-fluorophenyl)-2-oxo-1,2-dihydropyridine-3-carboxamide, (Z)—N-(3-((3,5-dimethyl-1H-pyrrol-2-yl)methylene)-2-oxoindolin-6-yl)-1-(4-fluorophenyl)-2-oxo-1,2-dihydropyridine-3-carboxamide, (Z)-5-((6-(1-(4-fluorophenyl)-2-oxo-1,2-dihydropyridine-3-carboxamido)-2-oxoindolin-3-ylidene)methyl)-2,4-dimethyl-1H-pyrrole-3-carboxylic acid, (Z)-2-(5-((6-(1-(4-fluorophenyl)-2-oxo-1,2-dihydropyridine-3-carboxamido)-2-oxoindolin-3-ylidene)methyl)-2,4-dimethyl-1H-pyrrol-3-yl)acetic acid, (Z)-3-(5-((6-(1-(4-fluorophenyl)-2-oxo-1,2-dihydropyridine-3-carboxamido)-2-oxoindolin-3-ylidene)methyl)-2,4-dimethyl-1H-pyrrol-3-yl)propanoic acid, (Z)-methyl-3-(5-((6-(1-(4-fluorophenyl)-2-oxo-1,2-dihydropyridine-3-carboxamido)-2-oxoindolin-3-ylidene)methyl)-2,4-dimethyl-1H-pyrrol-3-yl)propanoate, and (Z)-2,4-dimethyl-5-((6-(1-methyl-2-oxo-1,2-dihydropyridine-3-carboxamido)-2-oxoindolin-3-ylidene)methyl)-1H-pyrrole-3-carboxylic acid.

In another embodiment of the invention, the compound is selected from the group consisting of (Z)—N-(3-((1H-pyrrol-2-yl)methylene)-2-oxoindolin-6-yl)-4-oxo-5-phenyl-1,4-dihydropyridine-3-carboxamide, (Z)—N-(3-((1H-pyrrol-2-yl)methylene)-2-oxoindolin-6-yl)-5-(4-methoxyphenyl)-4-oxo-1,4-dihydropyridine-3-carboxamide, (Z)—N-(3-((1H-pyrrol-2-yl)methylene)-2-oxoindolin-6-yl)-5-(4-fluorophenyl)-4-oxo-1,4-dihydropyridine-3-carboxamide, (Z)—N-(3-((1H-pyrrol-2-yl)methylene)-2-oxoindolin-6-yl)-5-(4-chlorophenyl)-4-oxo-1,4-dihydropyridine-3-carboxamide, (Z)—N-(3-((1H-pyrrol-2-yl)methylene)-2-oxoindolin-6-yl)-5-p-tolyl-4-oxo-1,4-dihydropyridine-3-carboxamide, (Z)—N-(3-((1H-pyrrol-2-yl)methylene)-2-oxoindolin-6-yl)-5-(3-chlorophenyl)-4-oxo-1,4-dihydropyridine-3-carboxamide, (Z)—N-(3-((1H-pyrrol-2-yl)methylene)-2-oxoindolin-6-yl)-4-oxo-5-(4-(trifluoromethyl)phenyl)-1,4-dihydropyndine-3-carboxamide, (Z)—N-(3-((1H-pyrrol-2-yl)methylene)-2-oxoindolin-6-yl)-4-oxo-5-(2-fluorophenyl)-1,4-dihydropyridine-3-carboxamide, (Z)—N-(3-((1H-pyrrol-2-yl)methylene)-2-oxoindolin-6-yl)-4-oxo-5-(2,4-difluorophenyl)-1,4-dihydropyridine-3-carboxamide, (Z)—N-(3-((1H-pyrrol-2-yl)methylene)-2-oxoindolin-6-yl)-4-oxo-5-(3,5-difluorophenyl)-1,4-dihydropyridine-3-carboxamide, (Z)—N-(3-((1H-pyrrol-2-yl)methylene)-5-fluoro-2-oxoindolin-6-yl)-5-(4-fluorophenyl)-4-oxo-1,4-dihydropyridine-3-carboxamide, (Z)—N-(3-((1H-pyrrol-2-yl)methylene)-2-oxoindolin-6-yl)-5-(4-fluorophenyl)-1-methyl-4-oxo-1,4-dihydropyridine-3-carboxamide, (Z)—N-(3-((1H-pyrrol-2-yl)methylene)-2-oxoindolin-6-yl)-5-methyl-4-oxo-1,4-dihydropyridine-3-carboxamide, (Z)—N-(3-((3,5-dimethyl-1H-pyrrol-2-yl)methylene)-2-oxoindolin-6-yl)-5-(4-fluorophenyl)-4-oxo-1,4-dihydropyridine-3-carboxamide, (Z)-5-((6-(5-(4-fluorophenyl)-4-oxo-1,4-dihydropyridine-3-carboxamido)-2-oxoindolin-3-ylidene)methyl)-2,4-dimethyl-1 H-pyrrole-3-carboxylic acid, (Z)-5-((6-(5-(4-methoxyphenyl)-4-oxo-1,4-dihydropyridine-3-carboxamido)-2-oxoindolin-3-ylidene)methyl)-2,4-dimethyl-1H-pyrrole-3-carboxylic acid, (Z)-2,4-dimethyl-5-((6-(5-methy-4-oxo-1,4-dihydropyridine-3-carboxamide)-2-oxoindolin-3-ylidene)methyl)-1H-pyrrole-3-carboxylic acid, (Z)-2-(5-((6-(5-(4-fluorophenyl)-4-oxo-1,4-dihydropyridine-3-carboxamido)-2-oxoindolin-3-ylidene)methyl)-2,4-dimethyl-1H-pyrrol-3-yl)acetic acid, (Z)-3-(5-((6-(5-(4-fluorophenyl)-4-oxo-1,4-dihydropyridine-3-carboxamido)-2-oxoindolin-3-ylidene)methyl)-2,4-dimethyl-1H-pyrrol-3-yl)propanoic acid, (Z)-5-((6-(5-(4-fluorophenyl)-4-oxo-1,4-dihydropyridine-3-carboxamido)-2-oxoindolin-3-ylidene)methyl)-4-methyl-1H-pyrrole-2-carboxylic acid, (Z)-3-(5-((6-(5-(2,4-difluorophenyl)-4-oxo-1,4-dihydropyridine-3-carboxamido)-2-oxoindolin-3-ylidene)methyl)-2,4-dimethyl-1H-pyrrol-3-yl)propanoic acid, (Z)-3-(5-((6-(5-(3,5-difluorophenyl)-4-oxo-1,4-dihydropyridine-3-carboxamido)-2-oxoindolin-3-ylidene)methyl)-2,4-dimethyl-1H-pyrrol-3-yl)propanoic acid, (Z)—N-(3-((3,5-dimethyl-4-(4-methylpiperazine-1-carbonyl)-1H-pyrrol-2-yl)methylene)-2-oxomdolin-6-yl)-5-(4-fluorophenyl)-4-oxo-1,4-dihydropyridine-3-carboxamide, (Z)—N-(3-((3,5-dimethyl-4-(2-(4-methylpiperazin-1-yl)-2-oxoethyl)-1H-pyrrol-2-yl)methylene)-2-oxoindolin-6-yl)-5-(4-fluorophenyl)-4-oxo-1,4-dihydropyridine-3-carboxamide, (Z)—N-(3-((3,5-dimethyl-4-(3-(4-methylpiperazin-1-yl)-3-oxopropyl)-1H-pyrrol-2-yl)methylene)-2-oxoindolin-6-yl)-5-(4-fluorophenyl)-4-oxo-1,4-dihydropyridine-3-carboxamide, (Z)—N-(3-((3,5-dimethyl-4-(morpholine-4-carbonyl)-1H-pyrrol-2-yl)methylene)-2-oxoindolin-6-yl)-5-(4-fluorophenyl)-4-oxo-1,4-dihydropyridine-3-carboxamide, (Z)—N-(3-((3,5-dimethyl-4-(2-morpholino-2-oxoethyl)-1H-pyrrol-2-yl)methylene)-2-oxoindolin-6-yl)-5-(4-fluorophenyl)-4-oxo-1,4-dihydropyridine-3-carboxamide, (Z)—N-(3-(3,5-dimethyl-4-(4-methylpiperazine-1-carbonyl)-1H-pyrrol-2-yl)-methylene)-2-oxoindolin-6-yl)-5-(4-methoxyphenyl)-4-oxo-1,4-dihydropyridine-3-carboxamide, (Z)—N-(3-((3,5-dimethyl-4-(morpholine-4-carbonyl)-1H-pyrrol-2-yl)-methylene)-2-oxoindolin-6-yl)-5-(4-methoxyphenyl)-4-oxo-1,4-dihydropyridine-3-carboxamide, and (Z)—N-(3-((3,5-dimethyl-4-((2-(pyrrolidin-1-yl)ethyl)carbamoyl)-1H-pyrrol-2-yl)methylene)-2-oxoindolin-6-yl)-5-(4-methoxyphenyl)-4-oxo-1,4-dihydropyridine-3-carboxamide.

In another aspect, the invention relates to a pharmaceutical composition comprising a therapeutically effective amount of a compound as aforementioned, or a salt, solvate, hydrate or prodrug thereof, and a pharmaceutically acceptable carrier or excipient.

In another aspect, the invention relates to a compound or a pharmaceutically acceptable salt, a solvate or hydrate, a prodrug, or a metabolite thereof as aforementioned for use as an anti-tumor agent for treating cancer.

Further in another aspect, the invention relates to a method of treating cancer, comprising administering to a subject in need thereof the pharmaceutical composition as aforementioned.

In one embodiment of the invention, the cancer is at least one selected from the group consisting of lung cancer, colorectal cancer, liver cancer and acute myelomonocytic leukemia.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1A:
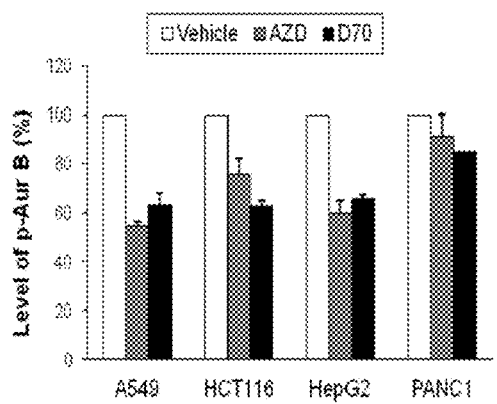
FIGS. 1A-B show the effects of the compound D70 (10 µM) on mRNA level of p-Aur B (A) and p-histone H3 (B) in A549 (lung cancer), HCT116 (colon cancer), HepG2 (liver cancer) and PANC1 (Pancreatic cancer) cells after 4 h treatment assessed by Dot blot analysis. Reference standard AZD1152-HQPA (10 μM).

The term "amino" refers to —NH$_2$. The amino group can be optionally substituted as defined herein for the term "substituted." The term "alkylamino" refers to —NR$_2$, wherein at least one R is alkyl and the second R is alkyl or hydrogen. The term "acylamino" refers to N(R)C(=O)R, wherein each R is independently hydrogen, alkyl, or aryl.

The term "acyl" group refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen atom, the group is a "formyl" group, an acyl group as the term is defined herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "alkyl" refers to a C$_1$-C$_{18}$ is hydrocarbon containing normal, secondary, tertiary or cyclic carbon atoms. Examples are methyl, ethyl, 1-propyl, 2-propyl, 1-butyl, 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (tert-butyl, —C(CH$_3$)$_3$), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl.

The alkyl can be a monovalent hydrocarbon radical, as described and exemplified above, or it can be a divalent hydrocarbon radical (i.e., alkylene).

The alkyl can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl or hydroxy. The alkyl can optionally be interrupted with one or more non-peroxide oxy (—O—), thio (—S—), amino(—N(H)—), methylene dioxy (—OCH$_2$O—), carbonyl (—C(=O)—), carboxy (—C(=O)O—), carbonyldioxy (—OC(=O)O—), carboxylato (—OC(=O)—), imino (C=NH), sulfinyl (SO) or sulfonyl (SO$_2$). Additionally, the alkyl can optionally be at least partially unsaturated, thereby providing an alkenyl.

The term "alkoxy" refers to the group alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The alkoxy can optionally be substituted with one or more halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl, or hydroxy.

The term "alkoxycarbonyl" refers to —C(=O)OR (or "COOR"), wherein R is an alkyl group as previously defined.

The terms "amide" (or "amido") refer to C- and N-amide groups, i.e., —C(O)NR$_2$, and —NRC(O)R groups, respectively. Amide groups therefore include but are not limited to carbamoyl groups (—C(O)NH$_2$) and formamide groups (—NHC(O)H).

The terms "amidine" or "amidino" refer to groups of the formula —C(NR)NR$_2$. Typically, an amidino group is —C(NH)NH$_2$.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like. The aryl can optionally be a divalent radical, thereby providing an arylene.

The aryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl aryl, heteroaryl, heterocycle, cycloalkyl, or hydroxy.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

The term "carbocycle" refers to a saturated, unsaturated or aromatic ring having 3 to 8 carbon atoms as a monocyclic, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "carboxyl" refers to —COOH.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The cycloalkyl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The cycloalkyl can optionally be at least partially unsaturated, thereby providing a cycloalkenyl. Additionally, the cycloalkyl can optionally be a divalent radical, thereby providing a cycloalkylene.

The term "an effective amount" refers to an amount sufficient to effect beneficial or desired results. An effective amount can be administered in one or more administrations, applications, or dosages. Determination of an effective amount for a given administration is well within the ordinary skill in the pharmaceutical arts.

The term "exchanged" is intended to indicate that in between two or more adjacent carbon atoms, and the hydrogen atoms to which they are attached (e.g., methyl ($CH_3$), methylene ($CH_2$), or methine (CH)), indicated in the expression using "interrupted" is inserted with a selection from the indicated group(s), provided that the each of the indicated atoms' normal valency is not exceeded, and that the interruption results in a stable compound. Such suitable indicated groups include, e.g., with one or more non-peroxide oxy (—O—), thio (—S—), amino (—N(H)—), methylene dioxy (—$OCH_2O$—), carbonyl (—C(=O)—), carboxy (—C(=O)O—), carbonyldioxy (—OC(=O)O—), carboxylato (—OC(=O)—), imino (C=NH), sulfinyl (SO) and sulfonyl ($SO_2$).

The term "halo" refers to fluoro, chloro, bromo, and iodo. The term "halogen" refers to fluorine, chlorine, bromine, and iodine. The term "haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted. The heteroaryl can optionally be a divalent radical, thereby providing a heteroarylene. Examples of heteroaryl groups include, but are not limited to, 2H-pyrrolyl, 3H-indolyl, 4H-quinolizinyl, 4H-carbazoly, acridinyl, benzo[h]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl, or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl aryl, heteroaryl, heterocycle, cycloalkyl, or hydroxy.

The term "heterocycle" or "heterocyclyl" refers to a saturated or partially unsaturated ring system, containing at least one heteroatom selected from the group oxygen, nitrogen, and sulfur, and optionally substituted with alkyl, or C(=O) $OR^b$, wherein $R^b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyraoline, 4H-pyran, chromanyl, imidazolidinyl, imidazolinyl, indolinyl, isochromanyl, isoindolinyl, morpholine, piperalinyl, piperidine, piperidyl, pyrazolone, pyrazolidinyl, pyrazolinyl, pyrrolidine, pyrroline, quinuclidine, and thiomorpholine. The heterocycle can optionally be a divalent radical, thereby providing a heterocyclene.

The heterocycle can optionally be substituted with one or more alkyl, alkenyl alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "hydrate" refers to the complex where the solvent molecule is water.

The term "imino" refers to —C=NH. The imino can optionally be substituted with one or more alkyl, alkenyl, alkoxy, aryl, heteroaryl, heterocycle, or cycloalkyl.

As used herein, the term "metabolite" refers to any compound of the Formula (A) produced in vivo or in vitro from the parent drug, or its prodrugs.

The term "oxo" refers to =O.

The term "pharmaceutically acceptable salts" refers to ionic compounds, wherein a parent non-ionic compound is modified by making acid or base salts thereof.

The term "prodrug" refers to any pharmaceutically acceptable form of compound of the Formula (A), which, upon administration to a patient provides a compound of the Formula (A). Pharmaceutically acceptable prodrugs refer to a compound that is metabolized, for example hydrolyzed or oxidized, in the host to form a compound of the Formula (A). Typical examples of prodrugs include compounds that have biologically labile protecting groups on a functional moiety of the active compound. Prodrugs include compounds that can be oxidized, reduced, animated, deaminated, hydroxylated, dehydroxylated, hydrolyzed, dehydrolyzed, alkylated, dealkylated, acylated, deacylated, phosphorylated, dephosphorylated to produce the active compound. The prodrug can be readily prepared from the compounds of Formula (A) using methods known in the art.

The term "substituted" is intended to indicate that one or more hydrogens on the atom indicated in the expression using "substituted" is replaced with a selection from the indicated group(s), provided that the indicated atom's normal valency is not exceeded, and that the substitution results in a stable compound. Suitable indicated groups include, e.g., alkyl, alkenyl, alkylidenyl, alkenylidenyl, alkoxy, halo, haloalkyl, hydroxy, hydroxyalkyl, aryl, heteroaryl heterocycle, cycloalkyl, alkanoyl, acyloxy, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyanato, sulfamoyl, sulfmamoyl, sulfino, sulfo, sulfoamino, thiosulfo, $NR^xR^y$ and/or $COOR^x$ wherein each $R^x$ and $R^y$ are independently H, alkyl, alkenyl, aryl, heteroaryl, heterocycle, cycloalkyl, or hydroxy. When a substituent is oxo (i.e., =O) or thioxo (i.e., =S) group, then two hydrogens on the atom are replaced.

A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound.

Preparation of Compounds of Formula (I), (II), (III) and (IV)

The compounds of this invention may be made by variety of methods, including standard chemistry. Compounds of formula (I), wherein Y is oxygen, Z is —NH—, V is bond, and $R^1$ is hydrogen, $R^2$ is optionally substituted aryl/heteroaryl, $R^3$ optionally substituted aryl and $R^4$ is hydrogen or fluoro, may be prepared from compounds of formula (V):

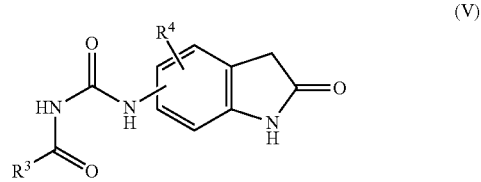

(V)

wherein, $R^3$ optionally substituted aryl and $R^4$ is hydrogen or fluoro, by treatment with an aryl/heteroaryl aldehyde compounds of formula (VI): $R^1R^2C=O$, wherein, $R^1$ is hydrogen and $R^2$ is optionally substituted aryl/heteroaryl.

Suitable conditions for process include stirring compounds of formula (V) and formula (VI) in a suitable solvent such as ethanol, at a suitable temperature, such as reflux temperature of the solvent in presence of a suitable base such as pyrrolidine, for 4-72 hrs.

Alternatively, process may be carried out under microwave irradiation (CEM, Discover), at 100° C., for 10-15 minutes.

Compounds of formula (V), wherein $R^3$ optionally substituted aryl and $R^4$ is hydrogen or fluoro, may be prepared from compounds of formula (VIII):

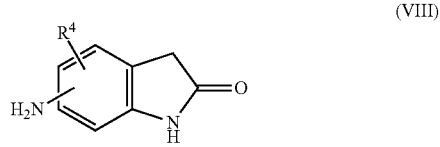

(VIII)

wherein, $R^4$ is hydrogen or fluoro, by treatment with an aryl isocyanate compounds of formula (VII): $R^3CONCO$, wherein $R^3$ optimally substituted aryl.

Suitable conditions for process include stirring compounds of formula (VIII) and formula (VII) under argon, in a suitable solvent such as acetonitrile, at a suitable temperature, such as 70-80° C. for 3-12 hrs.

Compounds of formula (VI), wherein, $R^1$ is hydrogen and $R^2$ is optionally substituted aryl/heteroaryl, are known compounds which are commercially available or can be prepared according to methods known to one skilled in art.

Compounds of formula (VIII), wherein, $R^4$ is hydrogen or fluoro, are known compounds which are commercially available or can be prepared according to methods known to one skilled in art.

Compounds of formula (VII), wherein $R^3$ optionally substituted aryl, may be prepared from compounds of formula (IX): $R^3CONH_2$, wherein $R^3$ optionally substituted aryl, by treatment with oxalyl chloride.

Suitable conditions for process include stirring compounds of formula (IX) and oxalyl chloride in a suitable solvent such as dichloromethane under argon, at a suitable temperature, such as 40° C. for 20-40 hrs.

Compounds of formula (IX), wherein $R^3$ optionally substituted aryl are known compounds which are commercially available or can be prepared according to methods known to one skilled in art.

Compounds of formula (I), wherein Y is oxygen, Z is —$CR^5R^6$—, V is —N—, and $R^1$ is hydrogen, $R^2$ is optionally substituted aryl/heteroaryl, R³ optionally substituted aryl and R⁴ is hydrogen or fluoro, R⁵ and R⁶ are hydrogen or taken together to form cyclopropane ring, may be prepared from compounds of formula (X):

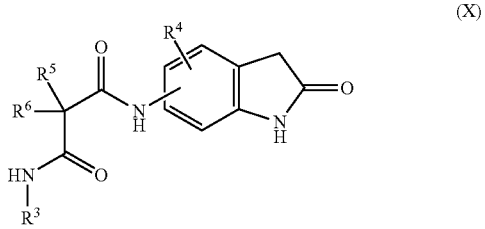

(X)

wherein, R³ optionally substituted aryl, R⁴ is hydrogen or fluoro and R⁵ and R⁶ are hydrogen or taken together to form cyclopropane ring, by treatment with an aryl/heteroaryl aldehyde compounds of formula (VI): R¹R²C=O, wherein, R¹ is hydrogen and R² is optionally substituted aryl/heteroaryl.

Suitable conditions for process include stirring compounds of formula (V) and formula (VI) in a suitable solvent such as ethanol, at a suitable temperature, such as reflux temperature of the solvent in presence of a suitable base such as pyrrolidine, for 4-72 hrs.

Alternatively, process may be carried out under microwave irradiation (CEM, Discover), at 100° C., for 10-15 minutes.

Compounds of formula (X), wherein, R³ optionally substituted aryl, R⁴ is hydrogen or fluoro and R⁵ and R⁶ are hydrogen or taken together to form cyclopropane ring, may be prepared from compounds of formula (VIII) wherein, R⁴ is hydrogen or fluoro, by treatment with compounds of formula (XI):

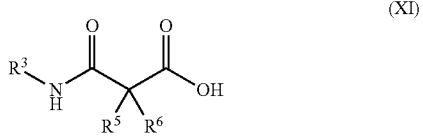

(XI)

wherein R³ optionally substituted aryl and R⁵ and R⁶ are hydrogen or taken together to form cyclopropane ring.

Suitable conditions for process include stirring compounds of formula (VIII) and formula (XI) under argon, in a suitable solvent such as mixture of dry dimethylformamide and acetonitrile (1:3) under argon, at a suitable temperature such as room temperature of the solvent in presence of coupling reagents such as O-(Benzotriazol-1-yl)-N,N,N',N'-tetramethyluronium tetrafluoroborate (TBTU) and triethylamine (TEA) for 2-4 hrs.

Compounds of formula (XI), wherein R³ optionally substituted aryl and R⁵ and R⁶ are hydrogen, may be prepared by hydrolysis of ester intermediate compound prepared from commercially available aryl amine compounds of formula (XV): R³NH₂, wherein R³ optionally substituted aryl, by treatment with commercially available ethyl 3-chloro-3-oxopropanoate (XIV).

Suitable conditions for the later process include stirring ethyl 3-chloro-3-oxopropanoate (XIV) and aryl amine compounds of formula (XV) in a suitable solvent such as dry dichloromethane under argon, at a suitable temperature, such as 0° C. to room temperature, for 4 hrs in presence of triethylamine and suitable condition for ester hydrolysis include stirring the ester intermediate in suitable solvent such as ethanol, at suitable temperature such as refluxing temperature of solvent for 1.5 hrs, in presence of 10% sodium hydroxide.

Compounds of formula (XI), wherein R³ optionally substituted aryl and R⁵ and R⁶ are taken together to form cyclopropane ring, may be prepared from commercially available aryl amine compounds of formula (XV): R³NH₂, wherein R³ optionally substituted aryl, by treatment with compounds of formula (XII):

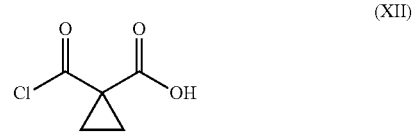

(XII)

Suitable conditions for the process include stirring compounds of formula (XII) and aryl amine compounds of formula (XV) in a suitable solvent such as dry tetrahydrofuran under argon, at a suitable temperature, such as 0° C. to room temperature, for a 4 hrs in presence of triethylamine.

Compounds of formula (XII) may be prepared from commercially available cyclopropane-1,1-dicarboxylic acid (XIII) by treatment with commercially available thionyl chloride.

Suitable conditions for the process include stirring compounds of formula (XIII) in a suitable solvent such as dry tetrahydrofuran under argon, at a suitable temperature, such as 0° C., for a 30 mins in presence of triethylamine and thionyl chloride.

Compounds of formula (II), wherein ~~~ is a single bond, Y is oxygen, Z is nitrogen, V is nitrogen, X is methane and R¹ is hydrogen, R² is optionally substituted aryl/neteroaryl, R²ᵃ is hydrogen, R²ᵇ is hydrogen, R³ optionally substituted aryl and R⁴ is hydrogen or fluoro, may be prepared from compounds of formula (XVI):

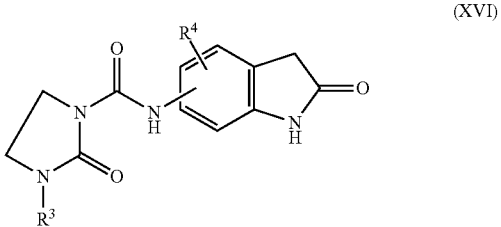

(XVI)

wherein, R³ optionally substituted aryl and R⁴ is hydrogen or fluoro, by treatment with an aryl/heteroaryl aldehyde compounds of formula (VI): R¹R²C=O, wherein, R¹ is hydrogen and R² is optionally substituted aryl/heteroaryl.

Suitable conditions for process include stirring compounds of formula (XVI) and formula (VI) in a suitable solvent such as ethanol, at a suitable temperature, such as reflux temperature of the solvent in presence of a suitable base such as pyrrolidine, for 4-72 hrs.

Alternatively, process may be carried out under microwave irradiation (CEM, Discover), at 100° C., for 10-15 minutes.

Compounds of formula (XVI), wherein R³ optionally substituted aryl and R⁴ is hydrogen or fluoro, may be prepared from compounds of formula (VIII) wherein, R⁴ is hydrogen or fluoro, by treatment with compounds of formula (XVII):

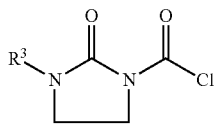

(XVII)

wherein R³ optionally substituted aryl.

Suitable conditions for process include stirring compounds of formula (VIII) and formula (XVII) under argon, in a suitable solvent such as dichloromethane under argon, at a suitable temperature, reflux temperature of the solvent for 4-12 hrs.

Compounds of formula (XVII), wherein R³ optionally substituted aryl, may be prepared from compounds of formula (XVIII):

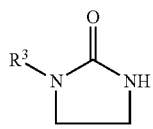

(XVIII)

wherein R³ optionally substituted aryl, by treatment with oxalyl chloride.

Suitable conditions for process include stirring compounds of formula (XVIII) and triphosgene in a suitable solvent such as tetrahydrofuran under argon, at a suitable temperature, such as 60° C. for 5-10 hrs.

Compounds of formula (XVIII), wherein R³ optionally substituted aryl are known compounds which are commercially available or can be prepared from urea compounds of formula (XIX):

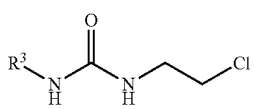

(XIX)

wherein R³ optionally substituted and by treatment with ammonium hydroxide.

Suitable conditions for process include stirring compounds of formula (XIX) in a suitable solvent such as tetrahydrofuran under argon, at a suitable temperature, such as room temperature, in presence of a suitable base such as sodium hydride, for 20-40 hrs.

Compounds of formula (XIX), wherein. R³ optionally substituted and may be prepared, from commercially available aryl amine compounds of formula (XV): R³NH₂, wherein R³ optionally substituted aryl, by treatment with commercially available 2-chloroethyl isocyanates (XX).

Suitable conditions for process include stirring compounds of formula (XV) and 2-chloroethyl isocyanates (XX) in a suitable solvent such as tetrahydrofuran under argon, at a suitable temperature, such as room temperature, for 18-36 hrs.

Compounds of formula (III), wherein Y is oxygen, R¹ is hydrogen, R² is optionally substituted aryl/heteroaryl, R³ is optionally substituted aryl and R⁴ is hydrogen or fluoro, may be prepared from compounds or formula (XXI):

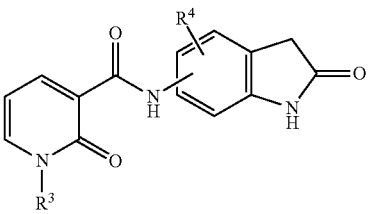

(XXI)

wherein, R³ optionally substituted aryl and R⁴ is hydrogen or fluoro, by treatment with an aryl/heteroaryl aldehyde compounds of formula (VI): R¹R²C=O, wherein, R¹ is hydrogen and R² is optionally substituted aryl/heteroaryl.

Suitable conditions for process include stirring compounds of formula (XXI) and formula (VI) in a suitable solvent such as ethanol, at a suitable temperature, such as reflux temperature of the solvent in presence of a suitable base such as pyrrolidine, for 4-72 hrs.

Alternatively, process may be carried out under microwave irradiation (CEM, Discover), at 100° C., for 10-15 minutes.

Compounds of formula (XXI), wherein R³ optionally substituted aryl and R⁴ is hydrogen or fluoro, may be prepared from compounds of formula (VIII) wherein, R⁴ is hydrogen or fluoro, by treatment with compounds of formula (XXII):

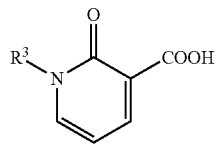

(XXII)

wherein R³ optionally substituted aryl.

Suitable conditions for process include stirring compounds of formula (VIII) and formula (XXII) under argon, in a suitable solvent such as mixture of N,N-dimethylformamide and acetonitrile, at a suitable temperature, such as room temperature in presence of a coupling reagent such as O-(benzotriazol-1-yl)-N,N,N',N'-tetramethyluronium tetrafluoroborate) and triethylamine for 4-12 hrs.

Compounds of formula (XXII), wherein R³ optionally substituted aryl, may be prepared from compounds of formula (XXIII):

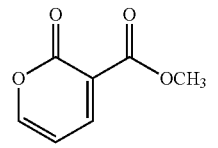

(XXIII)

by treatment with commercially available aryl amine compounds of formula (XV): R³NH₂, wherein R³ optionally substituted aryl.

Suitable conditions for process include stirring compounds of formula (XXIII) and compounds of formula (XV) in a suitable solvent such as N,N-dimethylformamide under argon, at a suitable temperature, such as room temperature for 6-12 hrs, followed by addition of 1-ethyl-3-(3-dimethylaminopropyl) carbodiimide (EDCI) and 4-Dimethylaminopyridine (DMAP) and then stirring the reaction mixture for overnight to give intermediate ester compound which further undergoes saponification.

In an alternative procedure, the compound of formula (XXII) may be prepared by reaction of 2-hydroxynicotinic acid and compounds of formula aromatic halides, where halogen is a leaving group such as bromo or iodo.

Compounds of formula (IV), wherein Y is oxygen, X is $NR^8$, $R^1$ is hydrogen, $R^2$ is optionally substituted aryl/heteroaryl, $R^3$ is optionally substituted aryl and $R^4$ is hydrogen or fluoro, may be prepared from compounds of formula (XXIV):

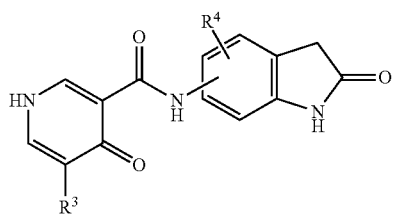

(XXIV)

wherein, $R^3$ optionally substituted aryl and $R^4$ is hydrogen or fluoro, by treatment with an aryl/heteroaryl aldehyde compounds of formula (VI): $R^1R^2C=O$, wherein, $R^1$ is hydrogen and $R^2$ is optionally substituted aryl/heteroaryl.

Suitable conditions for process include stirring compounds of formula (XXIV) and formula (VI) in a suitable solvent such as ethanol, at a suitable temperature, such as reflux temperature of the solvent in presence of a suitable base such as pyrrolidine, for 4-72 hrs.

Alternatively, process may be carried out under microwave irradiation (CEM, Discover), at 100° C., for 10-15 minutes.

Compounds of formula (XXIV), wherein $R^3$ optionally substituted aryl and $R^4$ is hydrogen or fluoro, may be prepared from compounds of formula (VIII) wherein, $R^4$ is hydrogen or fluoro, by treatment with compounds of formula (XXV):

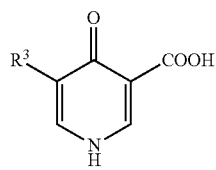

(XXV)

wherein $R^3$ optionally substituted aryl.

Suitable conditions for process include stirring compounds of formula (VIII) and formula (XXV) under argon, in a suitable solvent such as mixture of N,N-dimethylformamide and acetonitrile, at a suitable temperature, such as room temperature in presence of a coupling reagent (such as O-(benzotriazol-1-yl)-N,N,N',N'-tetramethyluronium tetrafluoroborate) and triethylamine for 4-12 hrs.

Compounds of formula (XXV), wherein $R^3$ optionally substituted aryl, may be prepared from compounds of formula (XXVI):

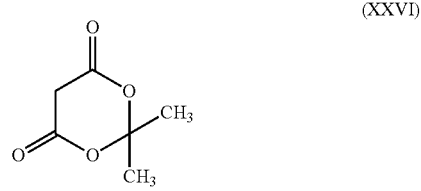

(XXVI)

by treatment with commercially available compounds of formula (XXVII): $R^3CH_2COCl$, wherein $R^3$ optionally substituted aryl.

Suitable conditions for process include stirring compounds of formula (XXVI) and compounds of formula (XXVII) in a suitable solvent such as dichloromethane (DCM) at suitable temperature such as 0° C. in presence of suitable base such as triethylamine to give intermediate compound, which on subsequent heating in suitable solvent such as ethanol to suitable temperature such as reflux temperature give β-ketoester compound. This β-ketoester compound can be cyclized by stirring it in suitable solvent such as xylene at suitable temperature such as 140° C., in presence of N,N-dimethylformamide-N,N-dimethylaniline for 3-6 hrs followed by addition of ammonium acetate in methanol and refluxing the reaction mixture for 3-6 hrs. Cyclized compound further undergoes saponification.

SCHEME 1:

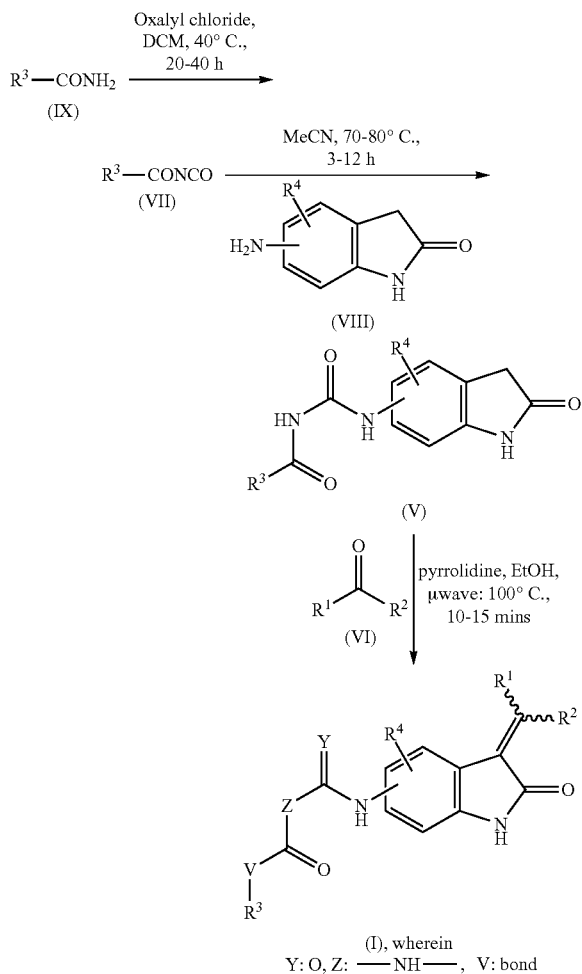

SCHEME 2:
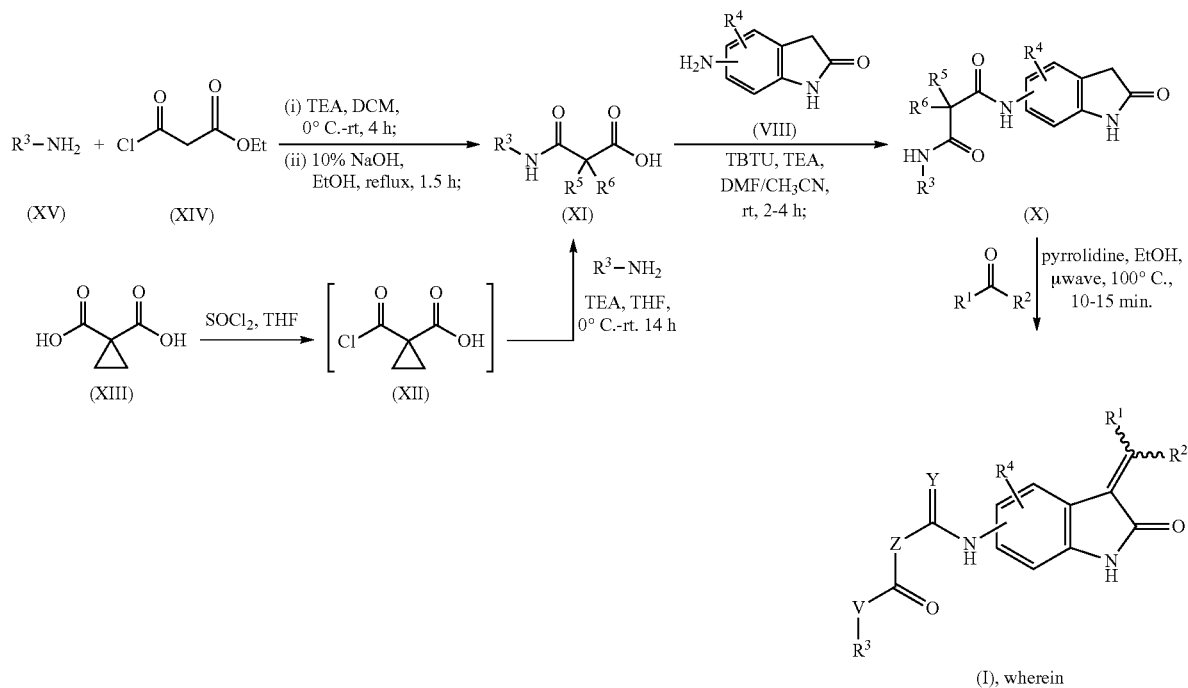
SCHEME 3:
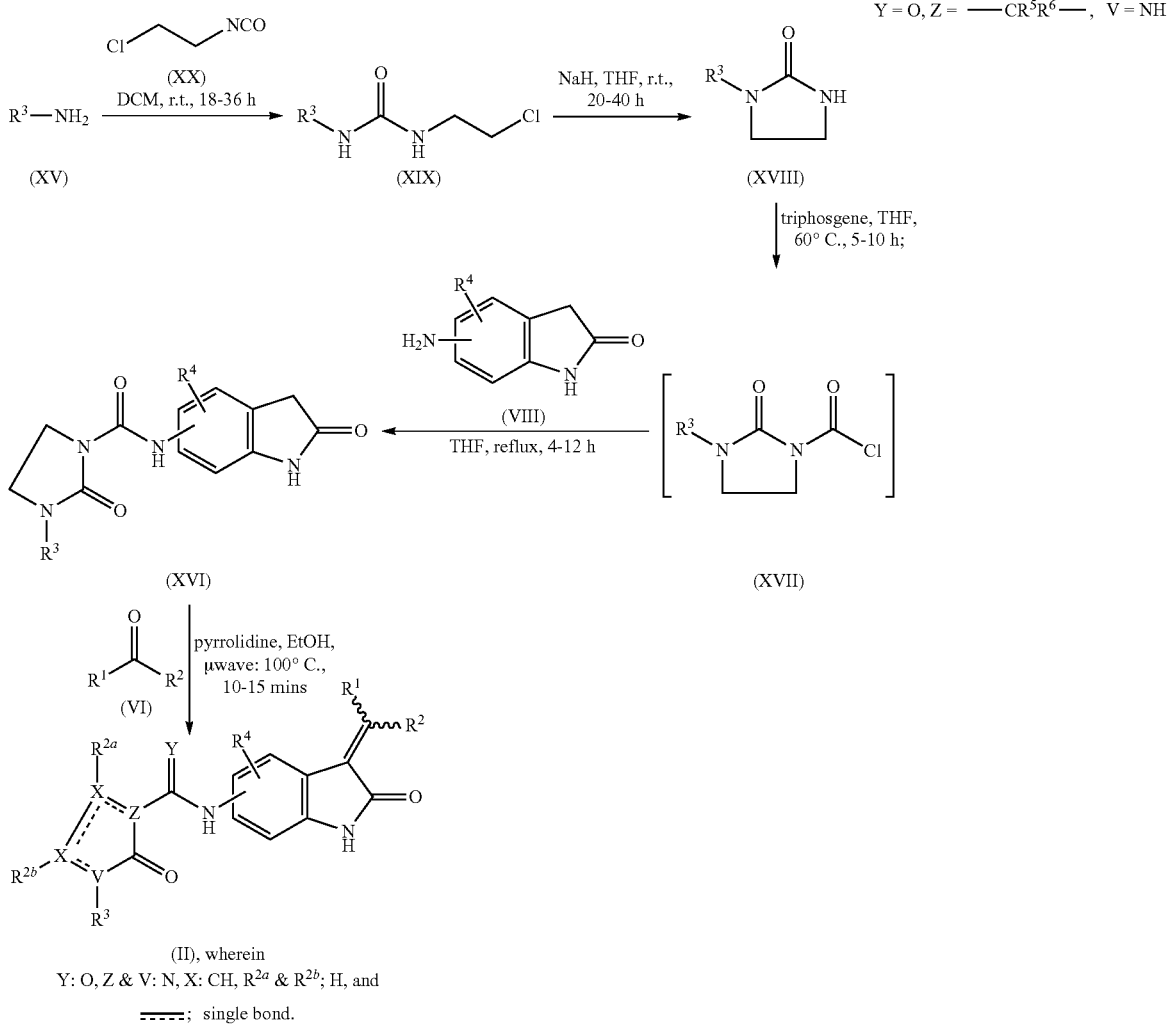

SCHEME 4:

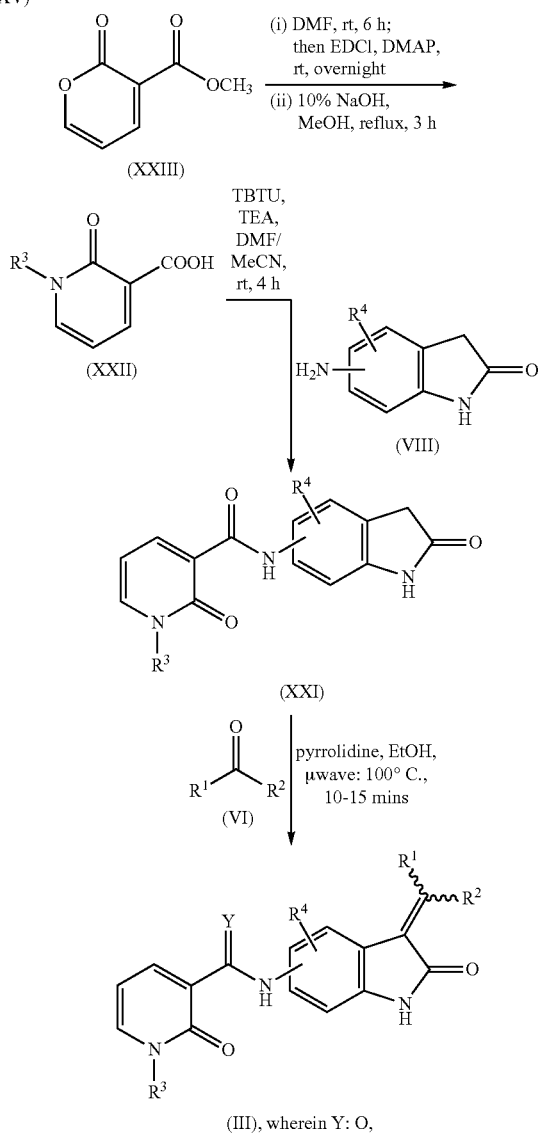

SCHEME 5:

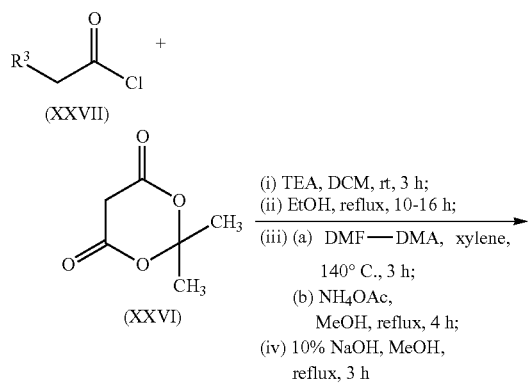

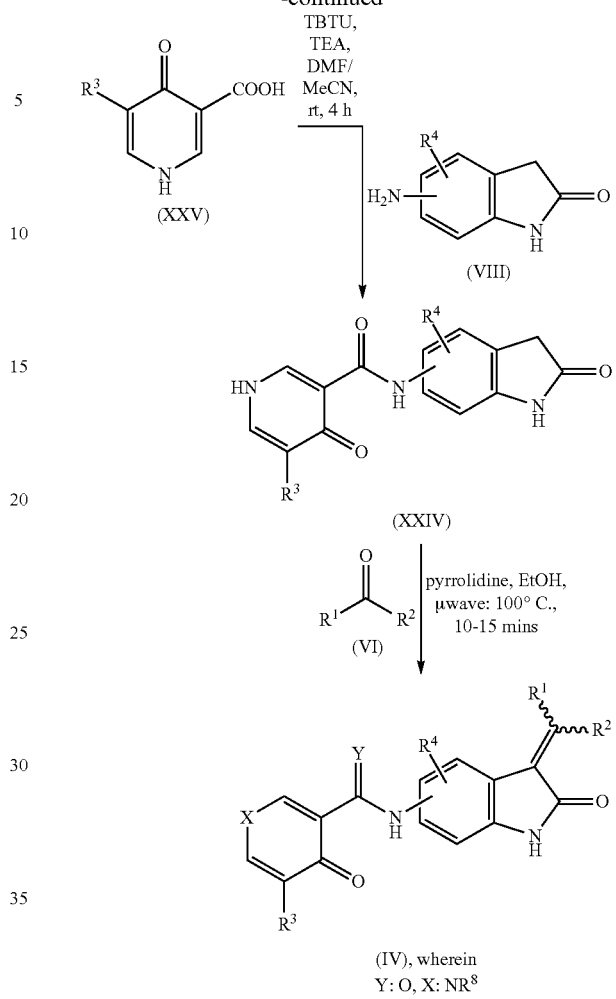

Synthesis of Compounds of Formula (VIII)

A. Synthesis of 4-aminoindolin-2-one (D3)

3-(Methylthio)-4-nitroindolin-2-one (D1)

Dichloromethane (150 mL) cooled to −78° C. under N₂ Ethyl(methylthio)acetate (2.91 gm) was added, then sulfuryl choride (1.75 mL, 21.72 mmol), and the mixture stirred for 35 min. m-Nitroaniline (3 gm) and proton sponge (4.65 gm) in dichloromethane (100 mL) were added to the above mixture for 1 hr. Resulting mixture was stirred for 2 h and triethylamine (3.01 mL) in dichloromethane (10 mL) was added dropwise, the mixture kept stirred for 1 h at the same temperature, then allowed to warm to RT. This reaction mixture was washed with H₂O. The combined aqueous layers were back-extracted with dichloromethane (100 mL). The combined organic layers were washed with brine, dried over MgSO₄ filtered and concentrated to yield ethyl-2-(2-amino-6-nitrophenyl)-2-(methylthio)-acetate (brown solid). The crude material was taken up in glacial acetic acid (200 mL) and stirred for 5 hrs. The acetic acid was removed by a rotary evaporator to yield brown tacky solid, which was washed with saturated potassium bicarbonate and brine, dried with MgSO₄, filtered and evaporated to afford the title compound D1; YD: 52.00%, ¹H NMR (DMSO-d₆) 400 MHz, δ: 1.885 (s, 3H), 4.834 (s, 1H), 7.219 (d, J=8.0 Hz, 1H), 7.503 (dd, J=8.0 & 8.0 Hz, 1H), 7.694 (d, J=8.4 Hz, 1H), 10.991 (s, 1H), MS (ESI): m/z 222.8 [M−H]−.

4-Amino-3-(methylthio)indolin-2-one (D2)

A mixture of compound D1 (1 g), stannous chloride dihydrate (5.03 g) in 36 mL of ethanol and acetic acid (EtOH:AcOH:5:1) was heated at 70° C. under argon. Reaction was monitored using TLC and terminated after 7 hrs on disappearance of the starting material. The reaction mixture was cooled, solvent evaporated to give a sticky solid, water added, then extracted with chloroform. Saturated sodium bicarbonate was added stepwise to water layer, extracted with chloroform. Organic layers were combined, washed with saturated sodium bicarbonate and brine solution, dried over $MgSO_4$, filtered and concentrated to give crude product, which was washed with toluene to give the title compound D2. YD: 95.85%. $^1H$ NMR (DMSO-$d_6$) 400 MHz. δ: 1.888 (s, 3H) 4.303 (s, 1H), 5.121 (s, 2H), 6.050 (d, J=7.6 Hz, 1H), 6.250 (d, J=8.4, 1H), 6.889 (dd, J=7.6 & 8.0 Hz, 1H), 10.231 (s, 1H). MS (ESI): m/z 217.0 [M+Na]+.

4-aminoindolin-2-one (D3)

Under $N_2$, compound D2 (0.8 g) was dissolved in ethanol (10 mL), treated with an excess of Raney nickel. The suspension was refluxed for 2 h. Analysis (TLC) showed the reaction completeness. The mixture was filtered through Celite and concentrated to give crude title compound D3. YD: 39.35%. $^1H$ NMR (DMSO-$d_6$) 400 MHz, δ: 3.152 (s, 2H), 5.011 (s, 2H), 6.052 (d, J=7.6 Hz, 1H), 6.211 (d, J=8.0, 1H), 6.831 (dd, J=7.6 & 8.0 Hz, 1H), 10.088 (s, 1H). MS (ESI): m/z 146.8 [M−H]−.

B. Synthesis of 6-aminoindolin-2-one (D4)

To 2,4-dinitrophenylacetic acid (1.2 gm) in methanol (60 mL), added Pd/C (80 mg, 10 wt %). $H_2$ gas environment was maintained with pressure using hydrogen gas balloon and solution stirred for 6 hours at RT. The catalyst was removed by filtration, over celite. The filtrate was concentrated in vacuo to give 2,4-diaminophenylacetic acid without further purification, immediately refluxed with 16 ml of 1N HCl for 6 hrs. Reaction was monitored with TLC. The solution was neutralized with 1% sodium hydroxide, extracted with three portions of ethyl acetate. The organic layers were combined, dried over anhydrous sodium sulfate or magnesium sulfate, evaporated in vacuo to get the title compound D4: YD: 67.85%: mp: 193-195° C.; $R_f$: 0.358 (EA:Hx: 7.0:3.0). $^1H$ NMR (DMSO-$d_6$) 200 MHz, δ: 3.227 (s, 2H), 5.004 (s, 2H) —$NH_2$, 6.094 (dd, J=2.2 & 6.2 Hz, 1H), 6.098 (d, J=2.0 Hz, 1H), 6.786 (d, J=8.4 Hz, 1H), 10.088 (s, 1H). MS (ESI): m/z 146.8 [M−H]−.

C. Synthesis of 7-aminoindolin-2-one (D5)

To a solution of 7-nitroindoline-2-one in methanol (1.0 gm/60 mL), added Pd/C (300 mg, 30 wt %). $H_2$ gas maintained with pressure using hydrogen gas balloon, solution stirred for 4 hours at RT. The catalyst was removed by filtration over celite. The filtrate was concentrated in vacuo to give crude product, which was washed with diethyl ether to afford compound 7-aminoindolin-2-one; YD: 76.77%; mp: 248-251° C.; $R_f$: 0.6 (CHCl$_3$:MeOH: 9.0:1.0). $^1H$ NMR (DMSO-$d_6$) 200 MHz, δ: 3.382 (s, 2H), 4.794 (s, 2H), 6.453-6.498 (m, 2H), 6.673 (t, J=8.0 Hz, 1H), 9.906 (s, 1H). MS (ESI): m/z 146.8 [M−H]−.

D. Synthesis of 6-amino-5-fluoroindolin-2-one (D7)

Methyl (5-fluoro-2,4-dinitrophenyl) acetate (D6)

Synthesis of methyl-2-(5-fluoro-2,4-dinitrophenyl)acetate: m-Fluorophenyl acetic acid (15.00 gm) was dissolved in concentrated sulfuric acid (30 mL). A solution consisting of 90% nitric acid (18 mL) and concentrated sulfuric acid (22.5 mL) was added drop wise during 1 hour while maintaining the internal temperature between 20-35° C. After the addition, the solution was stirred for an additional 20 hours at 35° C. and the resultant yellow slurry was poured onto ice and filtered to give 21 gm of an off white solid. This solid obtained (mix of nitro acids) was dissolved in methanol (250 mL). Sulfuric acid (1 mL) was added and the solution was heated at reflux for 5 hours and then cooled in an ice bath. The pH was brought to ca 5 by dropwise addition of 2.5; N sodium hydroxide. Most of the methanol was removed by rotary evaporator and remainder solution was partitioned with ethyl acetate and water. After removing the aqueous phase the organic layer was dried with anhydrous sodium sulfate or magnesium sulfate, filtered over celite and concentrated to give light brown oil comprised of the following three compounds (listed in order of increasing polarity by tlc): methyl (3-fluoro-2,6-dinitrophenyl)acetate, methyl (5-fluoro-2,4-dinitrophenyl) acetate and methyl (5-methoxy-2,4-dinitrophenyl)acetate. The compounds were separated by flash chromatography (ethyl acetate/hexane 15-50%). (1) Methyl (3-fluoro-2,6-dinitrophenyl) acetate; $^1H$ NMR (DMSO-$d_6$) 400 MHz, δ: 3.645 (s, 3H), 4.056 (s, 2H), 7.909 (dd, J=8.8 & 9.2 Hz, 1H), 8.490 (dd, J=7.6 & 8.0 Hz, 1H). MS (ESI): m/z 256.8 [M−H]−. (2) Methyl (5-fluoro-2,4-dinitrophenyl) acetate; YD; 32%, $R_f$: 0.39 (EA:Hx: 3.0:7.0). $^1H$ NMR (DMSO-$d_6$) 400 MHz, δ: 3.637 (s, 3H), 4.223 (s, 2H), 7.923 (d, J=11.6 Hz, 1H), 8.832 (d, J=6.8 Hz, 1H). ($C_9H_7FN_2O_6$.1/9$CH_3COOC_2H_5$) C, H, N. MS (ESI): m/z 256.8 [M−H]−. (3) Methyl (5-methoxy-2,4-dinitrophenyl) acetate; $^1H$ NMR (DMSO-$d_6$) 400 MHz, δ: 3.635 (s, 3H), 4.051 (s, 3H), 4.214 (s, 2H), 7.628 (s, 1H), 8.714 (s, 1H). MS (ESI); m/z 268.9 [M−H]−.

6-amino-5-fluoroindolin-2-one (D7)

Methyl (5-fluoro-2,4-dinitrophenyl)acetate (6.0 gm, 23.25 mmol) was dissolved in ethanol (200 mL) and to it added 10% Pd/C (500 mg, 10 wt %). The reaction was hydrogenated at room temperature using hydrogen gas balloon until hydrogen uptake ceased. Further the crude reaction mixture was filtered to remove the catalyst. The solvent was concentrated to leaving diamino ester as oil. The oil was taken in 1M HCl (50 mL) & heated at reflux for 1 hour. After cooling, the solution was neutralized with 2.5 M sodium hydroxide (approximately 20 mL) and extracted with three portions of ethyl acetate. The organic layers were combined, dried anhydrous sodium sulfate or magnesium sulfate and concentrated to afford a greenish brown solid (3.075 gm) of 6-amino-5-fluoroindolin-2-one. YD: 78.94%; mp: 185-187° C.; $R_f$: 0.45 (CHCl$_3$: MeOH: 9.0:1.0). $^1H$ NMR (DMSO-$d_6$) 400 MHz, δ: 3.269 (s, 2H), 5.023 (s, 2H), 6.282 (d, J=8.0 Hz, 1H), 6.837 (d, J=10.8 Hz, 1H). ($C_8H_7FN_2O$.1/7$CH_3COOC_2H_5$)C, H, N. MS (ESI): m/z 164.8 [M−H]−.

Synthesis of Compounds of Formula (IX)

4-(dimethylamino)benzamide (D8)

To 4-(dimethylamino)benzoic acid (30 mmol) in dry dichloromethane (50 mL) at 0° C. under $N_2$ was added dropwise oxalyl chloride (50 mmol) followed by dimethylformamide (2-3 drops). The ice bath removed, the reaction heated to reflux for 4-5 hrs, cooled, the solvent removed in vacuo to afford light brown oil. It was placed under reduced pressure to remove residual oxalyl chloride. The acid chloride was taken up in dry ethyl acetate (50 ml), added dropwise to an ice cold ethyl acetate (250 mL) containing concentrated ammonium hydroxide 30% (50 mL). The reaction mixture was stirred cold for 30 min and layers were separated. Ethyl acetate layer was washed twice with water (100 mL), twice with brine (75 mL), dried over anhydrous sodium sulfate or magnesium sulfate, evaporated to afford the title compound D8; YD: 59.09%; mp: 218-220° C.; $R_f$ 0.34 (EA:Hx: 7.0:3.0). $^1H$ NMR (DMSO-$d_6$) 400 MHz. δ: 2.942 (s, 6H), 6.665 (d, J=7.6 Hz, 2H), 6.906 (s, 1H), 7.612 (s, 1H), 7.725 (d, J=8.0 Hz, 2H), ($C_9H_{12}N_2O$) C, N, N. MS (ESI): m/z 165.0 [M+H]$^+$.

2-Fluoro-4-methoxybenzamide (D9)

YD: 50.30%; mp: 152-155° C. $^1H$ NMR (DMSO-$d_6$) 400 MHz, δ: 3.762 (s, 3H), 6.792-6.819 (m, 2H), 7.414 (s, 1H), 7.455 (s, 1H), 7.657 (dd, J=8.4 & 8.8 Hz, 1H). ($C_9H_{12}N_2O$) C, H, N. MS (ESI): m/z 170.0 [M+H]$^+$.

2,6-difluoro-4-methoxybenzimide (D10)

YD: 56.34%, mp: 165-168° C. $^1H$ NMR (DMSO-$d_6$) 400 MHz. δ: 3.787 (s, 3H), 6.728-6.782 (m, 2H), 7.672 (s, 1H), 7.930 (s, 1H). ($C_9H_{12}N_2O$) C, H, N. MS (ESI): m/z 188.0 [M+H]$^+$.

Synthesis of Compounds of Formula (I)

4-Methoxybenzoyl isocyanate (D11)

To 4-methoxybenzamide (2.6 mmol) in dichloromethane (10 mL) was added oxalyl chloride 98% (6.61 mmol) dropwise. The mixture was heated to reflux for 20 h. Reaction completion monitored by TLC. The solvent was removed in vacuo (40° C., 760 mmHg) to obtain title compound D11, which was immediately used without purification.

Other intermediate compounds were made by using appropriate starting materials and similar process described above.

4-Methoxy-N-(2-oxoindolin-4-ylcarbamoyl)benzamide (D12)

To 4-aminoindoline-2-one (D3) (2.8 mmol) in dry acetonitrile (10 mL) was added compound D11 (2.8 mmol). The mixture was heated to 70-80° C. for 2-3 hr. Solid precipitate of the title compound D12 was separated out, filtered, washed with acetonitrile, air dried. YD: 75.90%; mp: 276-279° C. $^1H$ NMR (DMSO-$d_6$) 200 MHz, δ: 3.450 (s, 2H), 3.838 (s, 3H), 6.609 (d, J=7.6 Hz, 1H), 7.055 (d, J=9.2 Hz, 2H), 7.172 (t, J=8.0 Hz, 1H), 7.540 (d, J=8.4 Hz, 1H), 8.054 (d, J=8.8 Hz, 2H), 10.442 (s, 1H), 10.840 (s, 1H), 10.928 (s, 1H), ($C_{17}H_{15}N_3O_4.1/2H_2O$) C, H, N. MS (ESI): m/z 324.0 [M–H]$^-$.

(Z)—N-(3-((1H-pyrrol-2-yl)methylene)-2-oxoindolin-4-ylcarbamoyl)-4-methoxybenzamide (D13)

A catalytic amount of pyrrolidine (0.001 mmol) was added to a solution of 4-methoxy-N-(2-oxoindolin-4-ylcarbamoyl) benzamide (1 mmol) and pyrrole-2-carbaldehyde (1.2 mmol) in ethanol (5 mL). The reaction was carried out using microwave (CEM, Discover) at 100° C. (200 W. Standard mode) for 15 mins. Crude product was precipitated after cooling to RT, which was collected by filtration, washed with ethanol and air dried. YD: 65.57%; mp: Charred at 290-295° C. $^1H$ NMR (DMSO-$d_6$) 200 MHz, δ: 3.859 (s, 3H), 6.342-6.363 (m, 1H), 6.722-6.731 (m, 1H), 6.748 (d, J=7.6 Hz, 1H), 7.101 (d, J=9.2 Hz, 2H), 7.160 (t, J=8.0 Hz, 1H), 7.354 (br, 1H), 7.436 (d, J=8.0 Hz, 1H), 8.043 (s, 1H), 8.126 (d, J=8.8 Hz, 2H), 10.894 (s, 1H), 11.028 (s, 2H), 13.376 (s, 1H). ($C_{22}H_{18}N_4O_4.1/2H_2O$) C, H, N. ESI-MS: m/z 400.9 [M–H]$^-$.

(Z)—N-(3-((1H-pyrrol-2-yl)methylene)-2-oxoindolin-5-ylcarbamoyl)-4-methoxybenzamide (D14)

YD: 74.37%; mp: 285-290° C. (charring). $^1H$ NMR (DMSO-$d_6$) 400 MHz, δ: 3.840 (s, 3H), 6.356 (br, 1H), 6.869 (br, 1H), 6.858 (d, J=8.4 Hz, 1H), 7.059 (d, J=8.8 Hz, 2H), 7.357 (br, 1H), 7.405 (d, J=8.4 Hz, 1H), 7.769 (s, 1H), 7.794 (br, 1H), 8.056 (d, J=8.8 Hz, 2H), 10.827 (s, 1H), 10.856 (s, 1H), 10.885 (s, 1H), 13.433 (s, 1H), ($C_{22}H_{18}N_4O_4.1/3H_2O$) C, H, N. ESI-MS: m/z 401.0 [M–H]$^-$.

(Z)—N-(3-((1H-pyrrol-2-yl)methylene-2-oxoindolin-6-ylcarbamoyl)-4-methoxybenzamide (D15)

YD: 79.78%; mp: 278-283° C. (charring). $^1H$ NMR (DMSO-$d_6$) 400 MHz, δ: 3.830 (s, 3H), 6.320-6.340 (m, 1H), 6.782-6.791 (m, 1H), 6.994 (dd, J=1.6 & 8.2 Hz, 1H), 7.046 (d, J=8.8 Hz, 2H), 7.316 (br, 1H), 7.450 (d, J=2 Hz, 1H), 7.564 (d, J=8.4 Hz, 1H), 7.629 (s, 1H), 8.043 (d, J=8.8 Hz, 2H), 10.866 (s, 1H), 10.894 (s, 1H), 11.029 (s, 1H), 13.227 (s, 1H), ($C_{22}H_{18}N_4O_4$) C, H, N. ESI-MS: m/z 401.0 [M–H]$^-$.

(Z)—N-(3-((1H-pyrrol-2-yl)methylene)-2-oxoindolin-7-ylcarbamoyl)-4-methoxybenzamide (D16)

YD: 54.16%; mp: 253-258° C. (Charring). $^1H$ NMR (DMSO-$d_6$) 400 MHz, δ: 3.845 (s, 3H), 6.361 (br, 1H), 6.857 (br, 1H), 7.005 (t, J=7.6 Hz, 1H), 7.069 (d, J=8.8 Hz, 2H), 7.165 (d J=8.0 Hz, 1H), 7.358 (br, 1H), 7.533 (d, J=8.0 Hz, 1H), 7.782 (s, 1H), 8.065 (d, J=8.8 Hz, 2H), 10.286 (s, 1H), 10.826 (s, 1H), 10.892 (s, 1H), 13.323 (s, 1H). ($C_{22}H_{18}N_4O_4.1/8H_2O$) C, H, N. ESI-MS: m/z 401.0 [M–H]$^-$.

(E)-N-(3-benzylidene-2-oxoindolin-6-ylcarbamoyl)-4-methoxybenzamide (D17)

YD: 70.82%; mp: 277-282° C. (Charring). $^1H$ NMR (DMSO-$d_6$) 400 MHz, δ: 3.834 (s, 3H), 6.826 (dd, J=1.6 & 8.4 Hz, 1H), 7.048 (d, J=8.8 Hz, 2H), 7.439-7.535 (m, 6H), 7.691 (d, J=7.2 Hz, 2H), 8.032 (d, J=8.8 Hz, 2H), 10.617 (s, 1H), 10.879 (s, 1H), 11.045 (s, 1H). ($C_{24}H_{19}N_3O_4.1/3H_2O$) C, H, N. ESI-MS: m/z 412.0 [M–H]$^-$.

(E)-N-(3-(4-chlorobenzylidene)-2-oxoindolin-6-ylcarbamoyl)-4-methoxybenz-amide (D18)

YD: 48.00%; mp: 278-283° C. (Charring). $^1H$ NMR (DMSO-$d_6$) 400 MHz, δ: 3.838 (s, 3H), 6.842 (d, J=8.4 Hz, 1H), 7.055 (d, J=8.4 Hz, 2H), 7.457-774 (m, 3H), 7.574 (d, J=8.4 Hz, 2H), 7.721 (d, J=8.0 Hz, 2H), 8.035 (d, J=8.8 Hz, 2H), 10.640 (s, 1H), 10.916 (s, 1H), 11.050 (s, 1H). ($C_{24}H_{18}ClN_3O_4.H_2O$) C, H, N. ESI-MS: m/z 445.9 [M–H]$^-$.

(E)-4-methoxy-N-(3-(4-methoxybenzylidene)-2-oxoindolin-6-yl-carbamoyl)benzamide (D19)

YD: 68.48%; mp: 274-279° C. (Charring). $^1$H NMR (DMSO-$d_6$) 400 MHz, δ: 3.811 (s, 6H), 7.055 (d, J=8.4 Hz, 2H), 7.669 (d, J=8.4 Hz, 2H), 7.585 (d, J=8.4 Hz, 1H), 6.829 (dd, J=2.0 & 8.6 Hz, 1H), 7.443 (s, 2H), 7.028 (d, J=8.8 Hz, 2H), 8.011 (d, J=8.8 Hz, 2H), 10.543 (s, 1H), 10.860 (s, 1H), 11.016 (s, 1H). ($C_{25}H_{21}N_3O_5 \cdot 1/2H_2O$) C, H, N. ESI-MS: m/z 442.0 [M–H]$^-$.

(Z)-4-methoxy-N-(2-oxo-3-(pyridin-2-ylmethylene)indolin-6-ylcarbamoyl)benzamide (D20)

YD: 73.27%; mp: 268-273° C. (Charring). $^1$H NMR (DMSO-$d_6$) 400 MHz, δ: 3.842 (s, 3H), 6.948 (dd, J=1.6 & 8.8 Hz, 1H), 7.061 (d, J=9.2 Hz, 2H), 7.425-7.444 (m, 1H), 7.455 (s, 1H), 7.481 (s, 1H), 7.831 (d, J=8.0 Hz, 1H), 7.910-7.948 (m, 1H), 8.050 (d, J=8.8 Hz, 2H), 8.873 (d, J=4.0 Hz, 1H), 8.984 (d, J=8.4 Hz, 1H), 10.630 (s, 1H), 10.922 (s, 1H), 11.108 (s, 1H). ($C_{23}H_{18}N_4O_4 \cdot 1/3H_2O$) C, H, N. ESI-MS: m/z 413.1 [M–H]$^-$.

(Z)-4-methoxy-N-(2-oxo-3-(pyridin-4-ylmethylene)indolin-6-ylcarbamoyl)benzamide (D21)

YD: 69.47%; mp: 270-275° C. (Charring), $^1$H NMR (DMSO-$d_6$) 400 MHz, δ: 3.835 (s, 3H), 6.836 (dd, J=1.6 & 8.4 Hz, 1H), 7.051 (d, J=8.8 Hz, 2H), 7.375 (d, J=8.4 Hz, 1H), 7.424 (s, 1H), 7.478 (br, 1H), 7.618 (d, J=5.6 Hz, 2H), 8.028 (d, J=8.8 Hz, 2H), 8.704 (d, J=5.6 Hz, 2H), 10.702 (s, 1H), 10.871 (s, 1H), 11.058 (s, 1H). ($C_{23}H_{18}N_4O_4 \cdot 4/3 H_2O$) C, H, N. ESI-MS: m/z 413.1 [M–H]$^-$.

(Z)-4-methoxy-N-(2-oxo-3-(thiophen-2-ylmethylene)indolin-6-ylcarbamoyl)benzamide (D22)

YD: 44.96%; mp: 262-267° C. (Charring). $^1$H NMR (DMSO-$d_6$) 400 MHz, δ: 3.847 (s, 3H), 7.011 (dd, J=2.0 & 8.4 Hz, 1H), 7.067 (d, J=8.8 Hz, 2H), 7.296 (m, 1H), 7.522 (d, J=1.6 Hz, 1H), 7.684 (s, 1H), 7.775 (d, J=3.6 Hz, 1H), 7.952 (d, J=5.2 Hz, 1H), 8.054 (d, J=8.8 Hz, 2H), 8.118 (d, J=8.4 Hz, 1H), 10.636 (s, 1H), 10.932 (s, 1H), 11.109 (s, 1H). ESI-MS: m/z 417.9 [M–H]$^-$.

(E)-N-(3-(furan-2-ylmethylene)-2-oxoindolin-6-ylcarbamoyl)-4-methoxybenzamide (D23)

YD: 89.25%; mp: 278-283° C. (charring). $^1$H NMR (DMSO-$d_6$) 400 MHz, δ: 3.838 (s, 3H), 6.775 (dd, J=2.0 & 3.2 Hz, 1H), 6.983 (dd, J=2.0 & 8.6 Hz, 1H), 7.056 (d, J=8.8 Hz, 2H), 7.194 (d, J=3.6 Hz, 1H), 7.231 (s, 1H), 7.476 (d, J=2 Hz, 1H), 8.047 (d, J=8.8 Hz, 2H), 8.121 (br, 1H), 8.293 (d, J=8.4 Hz, 1H), 10.574 (s, 1H), 10.912 (s, 1H), 11.081 (s, 1H). ($C_{22}H_{17}N_3O_5 \cdot H_2O$) C, H, N. ESI-MS: m/z 402.0 [M–H]$^-$.

(Z)—N-(3-((1H-pyrrol-2-yl)methylene)-2-oxoindolin-6-ylcarbamoyl)benzamide (D24)

YD: 78.24%, mp: 290-295° C. (Charring). $^1$H NMR (DMSO-$d_6$) 400 MHz, δ: 6.334 (br, 1H), 6.792 (br, 1H), 7.016 (dd J=1.6 & 8.4 Hz, 1H), 7.320 (br, 1H), 7.452 (br, 1H), 7.533 (t, J=7.6 Hz, 2H), 7.579 (d, J=8.4 Hz, 1H), 7.646 (m, 2H), 8.022 (d, J=7.6 Hz, 2H), 10.902 (s, 1H), 10.921 (s, 1H), 11.037 (s, 1H), 13.226 (s, 1H). ($C_{23}H_{16}N_4O_3 \cdot 1/5H_2O$) C, H, N.

(Z)—N-(3-((1H-pyrrol-2-yl)methylene)-2-oxoindolin-6-ylcarbonamoyl)-4-chlorobenzamide (D25)

YD: 81.00%; mp: 280-285° C. (Charring). $^1$H NMR (DMSO-$d_6$) 400 MHz, δ: 6.332 (d, J=2.4 Hz, 1H), 6.791 (s, 1H), 7.006 (d, J=8.4 Hz, 1H), 7.320 (s, 1H), 7.437 (s, 1H), 7.576 (d, J=8.4 Hz, 1H), 7.609 (d, J=8.8 Hz, 2H), 7.647 (s, 1H), 8.022 (d, J=8.4 Hz, 2H), 10.822 (s, 1H), 10.896 (s, 1H), 11.107 (s, 1H), 13.217 (s, 1H). ($C_{21}H_{15}ClN_4O_3$) C, H, N. ESI-MS: m/z 405.1 [M–H]$^-$.

(Z)—N-(3-((1H-pyrrol-2-yl)methylene)-2-oxoindolin-6-ylcarbamoyl)-3,4-dichlorobenzamide (D26)

YD: 73.45%; mp: 295-300° C. (Charring). $^1$H NMR (DMSO-$d_6$) 400 MHz, δ; 6.334 (br, 1H), 6.787 (br, 1H), 6.998 (d, J=8.4 Hz, 1H), 7.318 (br, 1H), 7.426 (s, 1H), 7.571 (d, J=8.4 Hz, 1H), 7.639 (br, 1H), 7.808 (d, J=8.4 Hz, 1H), 7.951 (d, J=8.4 Hz, 1H), 8.253 (s, 1H), 10.717 (s, 1H), 10.890 (s, 1H), 13.227 (s, 1H). ESI-MS: m/z 438.9 [M–H]$^-$.

(Z)—N-(3-((1H-pyrrol-2-yl)methylene)-2-oxoindolin-6-ylcarbamoyl)-4-(trifluoromethyl)benzamide (D27)

YD: 66.00%; mp: >300° C. $^1$H NMR (DMSO-$d_6$) 400 MHz, δ: 6.334 (br, 1H), 6.792 (br, 1H), 7.021 (dd, J=1.2 & 8.4 Hz, 1H), 7.323 (br, 1H), 7.446 (s, 1H), 7.582 (d, J=8.0 Hz, 1H), 7.649 (s, 1H), 7.907 (d, J=8.4 Hz 2H), 8.177 (d, J=8.4 Hz, 2H), 10.760 (s, 1H), 10.902 (s, 1H), 11.264 (s, 1H), 13.224 (s, 1H). ($C_{22}H_{15}F_3N_4O_3$) C, H, N.

(Z)—N-(3-((1H-pyrrol-2-yl)methylene)-2-oxoindolin-6-ylcarbamoyl)-4-chloro-3-(trifluoromethyl)benzamide (D28)

YD: 50.26%; mp; 280-285° C. (Charring). $^1$H NMR (DMSO-$d_6$) 400 MHz, δ: 6.320-6.340 (m, 1H), 6.789 (br, 1H), 7.007 (dd, J=1.6 & 8.0 Hz, 1H), 7.317 (br, 1H), 7.429 (d, J=1.6 Hz, 1H), 7.573 (d, J=8.4 Hz, 1H), 7.904 (d, J=8.4 Hz, 1H), 8.255 (d, J=8.4 Hz, 1H), 8.447 (s, 1H), 10.721 (s, 1H), 10.891 (s, 1H), 11.347 (s, 1H), 13.211 (s, 1H). ($C_{22}H_{14}ClF_3N_4O_3$) C, H, N. ESI-MS: m/z 472.9 [M–H]$^-$.

(Z)—N-(3-((1H-pyrrol-2-yl)methylene)-2-oxoindolin-6-ylcarbamoyl)-4-methylbenzamide (D29)

YD: 90.75%; mp: 290-295° C. (Charring). $^1$H NMR (DMSO-$d_6$) 400 MHz, δ: 2.376 (s, 3H), 6.322-6.343 (m, 1H), 6.785-6.794 (m, 1H), 7.004 (dd, J=2.0 & 8.6 Hz, 1H), 7.322 (br, 1H), 7.333 (d, J=8.4 Hz, 2H), 7.447 (d, J=1.6 Hz, 1H), 7.573 (d, J=8.0 Hz, 1H), 7.640 (s, 1H), 7.936 (d, J=8.4 Hz, 2H), 10.892 (s, 1H), 10.943 (s, 1H), 10.958 (s, 1H), 13.223 (s, 1H). ($C_{22}H_{18}N_4O_3 \cdot 1/3H_2O$) C, H, N.

(Z)—N-(3-((1H-pyrrol-2-yl)methylene)-2-oxoindolin-6-ylcarbamoyl)-3,5-dimethoxy)benzamide (D30)

YD: 72.32%; mp: 276-281° C. (Charring). $^1$H NMR (DMSO-$d_6$) 400 MHz, δ: 3.812 (s, 6H), 6.334 (br, 1H), 7.648 (s, 1H), 6.751 (s, 1H), 6.792 (br, 1H), 7.008 (dd, J=1.2 & 8.4 Hz, 1H), 7.203 (d, J=2 Hz, 2H), 7.332 (br, 1H), 7.445 (br, 1H), 7.579 (d, J=8.4 Hz, 1H), 10.897 (s, 1H), 10.914 (s, 1H), 13.220 (s, 1H). ($C_{23}H_{20}N_4O_5 \cdot 1/3H_2O$) C, H, N.

(Z)—N-(3-((1H-pyrrol-2-yl)methylene)-2-oxoindolin-6-ylcarbamoyl)-4-(dimethylamino)benzamide (D31)

YD: 80.25%; mp: 285-290° C. (Charring). $^1$H NMR (DMSO-d$_6$) 400 MHz, δ: 3.021 (s, 6H), 6.336 (d, J=2.8 Hz, 1H), 6.750 (d, J=8.8 Hz, 2H), 6.796 (br, 1H), 7.222 (d, J=8.0 Hz, 1H), 7.326 (br, 1H), 7.504 (s, 1H), 7.795 (d, J=8.0 Hz, 1H), 7.841 (d, J=8.8 Hz, 2H), 10.739 (s, 1H), 10.928 (s, 1H), 11.288 (s, 1H), 13.232 (s, 1H). (C$_{23}$H$_{21}$N$_5$O$_3$.5/4 H$_2$O) C, H, N.

(Z)-5-((6-(3-benzoylureido)-2-oxoindolin-3-ylidene)methyl)-2,4-dimethyl-1H-pyrrole-3-carboxylic acid (D32)

YD: 69.54%, mp: 270-275° C. (Charring). $^1$H NMR (DMSO-d$_6$) 400 MHz, δ: 2.474 (s, 3H), 2.517 (s, 3H), 6.999 (d, J=8.4 Hz, 1H), 7.462 (br, 1H), 7.532 (t, J=7.6 Hz, 2H), 7.578 (s, 1H), 7.645 (t, J=6.8 Hz, 1H), 7.749 (d, J=8.4 Hz, 1H), 8.018 (d, J=8.0 Hz, 2H), 10.919 (s, 1H), 10.951 (s, 1H), 11.028 (s, 1H), 13.698 (s, 1H). (C$_{24}$H$_{20}$N$_4$O$_5$.H$_2$O) C, H, N. ESI-MS: m/z 443.0 [M−H]$^−$.

(Z)-5-((6-(3-(4-chlorabenzoyl)ureido)-2-oxoindolin-3-ylidene)-methyl)-2,4-dimethyl-1H-pyrrole-3-carboxylic acid (D33)

YD: 61.98%; mp: >300° C. $^1$H NMR (DMSO-d$_6$) 400 MHz, δ: 2.473 (s, 3H), 2.516 (s, 3H), 6.994 (dd, J=1.2 & 8.6 Hz, 1H), 7.451 (br, 1H), 7.573 (s, 1H), 7.603 (d, J=8.8 Hz, 2H), 7.742 (d, J=8.4 Hz, 1H), 8.018 (d, J=8.4 Hz, 2H), 10.837 (s, 1H), 10.943 (s, 1H), 13.688 (s, 1H). (C$_{24}$H$_{19}$ClN$_4$O$_5$.1/4H$_2$O) C, H, N. ESI-MS: m/z 477.0 [M−H]$^−$.

(Z)-5-((6-(3-(3,4-dichlorobenzoyl)ureido)-2-oxoindolin-3-ylidene)methyl)-2,4-dimethyl-1H-pyrrole-3-carboxylic acid (D34)

YD: 63.85%; mp: 295-300° C. (Charring). (C$_{24}$H$_{18}$Cl$_2$N$_4$O$_5$) C, H, N. ESI-MS: m/z 510.9 [M−H]$^−$.

(Z)-2,4-dimethyl-5-((2-oxo-6-(3-(4-(trifluoromethyl)benzoyl)ureido)indolin-3-ylidene)methyl)-1H-pyrrole-3-carboxylic acid (D35)

YD: 67.35%, mp: >300° C. $^1$H NMR (DMSO-d$_6$) 400 MHz, δ: 2.477 (s, 3H) —CH$_3$, 2.519 (s, 3H) —CH$_3$, 7.012 (dd, J=1.6 & 8.2 Hz, 1H) H$_5$-indole, 7.457 (d, J=1.6 Hz, 1H) H$_7$-indole, 7.588 (s, 1H) vinyl H, 7.758 (d, J=8.4 Hz, 1H) H$_4$-indole, 7.912 (d, J=8.0 Hz, 2H) H$_{3\&5}$-benzoyl, 8.176 (d, J=8.4 Hz, 2H) H$_{2\&6}$-benzoyl, 10.757 (s, 1H) indole-6-NH, 10.952 (s, 1H) indole-1-NH, 11.257 (s, 1H) benzoyl-NH, 13.700 (s, 1H) pyrrole-1'-NR Calcd. for (C$_{25}$H$_{19}$F$_3$N$_4$O$_5$) C, 58.60; H, 3.74; N, 10.93. found C, 58.30; H, 4.03; N, 10.89, ESI-MS: m/z 511.0 [M−H]$^−$.

(Z)-5-((6-(3-(4-chloro-3-(trifluoromethyl)benzoyl)ureido)-2-oxoindolin-3-ylid-ene)methyl)-2,4-dimethyl-1H-pyrrol-3-carboxylic acid (D36)

YD: 70.56%; mp: 270-275° C. $^1$H NMR (DMSO-d$_6$) 400 MHz, δ: 2.470 (s, 3H), 2.513 (s, 3H), 6.991 (d, J=8.4 Hz, 1H), 7.443 (br, 1H), 7.569 (s, 1H), 7.742 (d, J=8.4 Hz, 1H), 7.908 (d, J=8.4 Hz, 1H), 8.253 (d, J=8.4 Hz, 1H), 8.447 (br, 1H), 10.716 (s, 1H), 10.938 (s, 1H), 11.343 (s, 1H), 13.682 (pyrrole-1'-NH). (C$_{25}$H$_{18}$ClF$_3$N$_4$O$_5$.3/4H$_2$O) C, H, N. ESI-MS: m/z 545.0 [M−H]$^−$.

(Z)-3-(5-((6-(3-(4-chloro-3-(trifluoromethyl)benzoyl)ureido)-2-oxo-indolin-3-ylidene)methyl)-2,4-dimethyl-1H-pyrrol-3-yl)propanoic acid (D37)

YD: 40.28%, M.P.: 270-275° C. (Charring). (C$_{27}$H$_{22}$ClF$_3$N$_4$O$_5$.1/4H$_2$O) C, H, N. ESI-MS: m/z 573.0 [M−H]$^−$.

(Z)-2,4-dimethyl-5-((6-(3-(4-nitrobenzoyl)ureido)-2-oxoindolin-3-ylidene)methyl)-1H-pyrrole-3-carboxylic acid (D38)

YD: 73.17%, mp: 293-298° C. (Charring). $^1$H NMR (DMSO-d$_6$) 400 MHz, δ: 2.464 (s, 3H), 2.508 (s, 3H), 6.986 (dd, J=1.6 & 8.4 Hz, 1H), 7.439 (d, J=1.6 Hz, 1H), 7.547 (s, 1H), 7.728 (d, J=8.4 Hz, 1H), 8.185 (d, J=8.8 Hz, 2H), 8.318 (d, J=8.4 Hz, 2H), 10.757 (s, 1H), 10.932 (s, 1H), 11.312 (s, 1H), 13.670 (s, 1H). (C$_{24}$H$_{19}$N$_5$O$_7$.1/3H$_2$O) C, H, N. ESI-MS: m/z 488.0 [M−H]$^−$.

(Z)-2,4-dimethyl-5-((6-(3-(4-methylbenzoyl)ureido)-2-oxoindolin-3-ylidene)-methyl)-1H-pyrrole-3-carboxylic acid (D39)

YD: 76.46%, mp: 295-300° C. (Charring). $^1$H NMR (DMSO-d$_6$) 400 MHz, δ: 2.380 (s, 3H), 2.519 (s, 3H), 6.994 (d, J=8.0 Hz, 1H), 7.337 (d, J=7.2 Hz, 2H), 7.464 (br, 1H), 7.583 (s, 1H), 7.752 (d, J=8.0 Hz, 1H), 7.935 (d, J=7.2 Hz, 2H), 10.946 (s, 2H), 12.083 (br, 1H), 13.702 (s, 1H). (C$_{25}$H$_{22}$N$_4$O$_5$.2/3H$_2$O) C, H, N. ESI-MS: m/z 457.0 [M−H]$^−$.

(Z)-3-(2,4-dimethyl-5-((6-(3-(3-methylbenzoyl)ureido)-2-oxoindolin-3-ylidene)-methyl)-1H-pyrrol-3-yl)propanoic acid (D40)

YD: 32.82%; mp: 240-245° C. (Charring). $^1$H NMR (DMSO-d$_6$) 400 MHz, δ: 2.239 (s, 3H), 2.280 (s, 3H), 2.341 (t, J=7.6 Hz, 2H), 2.377 (s, 3H), 2.632 (t J=7.6 Hz, 2H), 6.963 (d, J=8.0 Hz, 1H), 7.393-7.468 (m, 3H), 7.479 (s, 1H), 7.663 (d, J=8.0 Hz, 1H), 7.809 (d, J=7.6 Hz, 1H), 7.855 (br, 1H), 10.759 (s, 1H), 10.887 (s, 1H), 10.926 (s, 1H), 13.259 (s, 1H). (C$_{25}$H$_{22}$N$_4$O$_5$.1/3H$_2$O) C, H, N. ESI-MS: m/z 485.0 [M−H]$^−$.

(Z)-5-((6-(3-(4-methoxybenzyl)ureido)-2-oxoindolin-3-ylidene)-methyl)-2,4-di-methyl-1H-pyrrole-3-carboxylic acid (D41)

YD: 52.11%; mp>300° C., $^1$H NMR (DMSO-d$_6$) 400 MHz, δ: 2.472 (s, 3H), 2.516 (s, 3H), 3.838 (s, 3H), 6.982 (dd, J=1.6 & 8.4 Hz, 1H), 7.055 (d, J=8.8 Hz, 2H), 7.461 (d, J=1.6 Hz, 1H), 7.574 (s, 1H), 7.743 (d, J=8.4 Hz, 1H), 8.042 (d, J=8.8 Hz, 2H), 10.864 (s, 1H), 10.944 (s, 1H), 11.020 (s, 1H), 13.696 (s, 1H). (C$_{25}$H$_{22}$N$_4$C$_6$.2/3H$_2$O) C, H, N. ESI-MS: m/z 473.0 [M−H]$^−$.

(Z)-5-((6-(3-(3,5-dimethoxybenzoyl)ureido)-2-oxoindolin-3-ylidene)methyl)-2,4-dimethyl-1H-pyrrole-3-carboxylic acid (D42)

YD: 75.12%; mp>300° C. $^1$H NMR (DMSO-d$_6$) 400 MHz, δ: 2.472 (s, 3H), 2.517 (s, 3H), 3.808 (s, 6H), 6.741 (t, J=2.0 Hz, 1H), 6.992 (dd, J=2.0 & 8.6 Hz, 1H), 7.197 (d, J=2.4 Hz, 2H), 7.457 (d, J=1.6 Hz, 1H), 7.576 (s, 1H), 7.746 (d, J=8.4

Hz, 1H), 10.911 (s, 1H), 10.946 (s, 1H), 11.009 (s, 1H), 13.692 (s, 1H). ($C_{26}SH_{24}N_4O_7 \cdot H_2O$) C, H, N.

(Z)—N-(3-((3,5-dimethyl-4-phenyl-1H-pyrrol-2-yl)methylene)-2-oxoindolin-6-ylcarbamoyl)-4-methoxybenzamide (D43)

YD: 58.23%; mp: >300° C. $^1$H NMR (DMSO-$d_6$) 200 MHz, δ: 2.285 (s, 3H), 2.326 (s, 3H), 3.841 (s, 3H), 6.977 (dd, J=1.6 & 8.2 Hz, 1H), 7.062 (d, J=8.8 Hz, 2H), 7.291-7.327 (m, 3H), 7.414 (d. J=6.8 Hz, 2H), 7.467 (d, J=1.4 Hz, 1H), 7.592 (s, 1H), 7.718 (d, J=8.2 Hz, 1H), 8.050 (d, J=8.8 Hz, 2H), 10.865 (s, 2H), 11.022 (s, 1H), 13.542 (s, 1H). ($C_{30}H_{26}N_4O_4 \cdot 1/3H_2O$) C, H, N. ESI-MS: m/z 505.0 [M−H]$^-$.

(Z)—N-(3-((3,5-dimethyl-1H-pyrrol-2-yl)methylene)-2-oxoindolin-6-ylcarbamoyl)-4-methoxybenzamide (D44)

YD: 66.67%; mp 293-298° C. $^1$H NMR (DMSO-$d_6$) 400 MHz, δ: 2.280 (s, 3H), 2.302 (s, 3H), 3.841 (s, 3H), 5.975 (s, 1H), 6.960 (dd, J=1.6 & 8.4 Hz, 1H), 7.058 (d, J=9.2 Hz, 2H), 7.438 (br, 1H), 7.473 (s, 1H), 7.657 (d, J=8.0 Hz, 1H), 8.047 (d, J=8.8 Hz, 2H), 10.786 (s, 1H), 10.852 (s, 1H), 10.997 (s, 1H), 13.218 (s, 1H). ($C_{24}H_{22}N_4O_4 \cdot 1/3H_2O$) C, H, N.

(Z)-5-((6-(3-(4-methoxybenzoyl)ureido)-2-oxoindolin-3-ylidene)-methyl)-1H-pyrrole-2-carboxylic acid (D45)

YD: 58.82%, mp: 286-291° C. (Charring). $^1$H NMR (DMSO-$d_6$) 400 MHz, δ: 3.840 (s, 3H), 6.785 (s, 1H), 6.870 (s, 1H), 7.028-7.069 (m, 3H), 7.479 (s, 1H), 7.627 (d, J=8.0 Hz, 1H), 7.688 (s, 1H), 8.045 (d, J=8.8 Hz, 2H), 10.902 (s, 1H), 11.033 (s, 1H), 11.062 (s, 2H), 13.677 (s, 1H). ($C_{23}N_{18}O_4H_2O_6 \cdot H_2O$) C, H, N. ESI-MS: m/z 445.0 [M−H]$^-$.

(Z)-(2-(5-((6-(3-(4-methoxybenzoyl)ureido-2-oxoindolin-3-ylidene)methyl)-2,4-dimethyl-1H-pyrrol-3-yl)acetic acid (D46)

YD: 47.57%; mp: 240-245° C. (Charring). $^1$H NMR (DMSO-$d_6$) 200 MHz. δ: 2.214 (s, 3H), 2.265 (s, 3H), 3.285 (s, 2H), 3.836 (s, 3H), 6.956 (dd, J=1.8 & 8.2 Hz, 1H), 7.052 (d, J=9.0 Hz, 2H), 7.484 (s, 1H), 7.439 (d, J=1.6 Hz, 1H), 7.657 (d, J=8.2 Hz, 1H), 8.045 (d, J=8.8 Hz, 2H), 10.782 (s, 1H), 11.039 (s, 1H), 13.292 (s, 1H). ($C_{26}H_{24}N_4O_6 \cdot H_2O$) C, H, N. ESI-MS: m/z 487.0 [M−H]$^-$.

(Z)-3-(5-((6-(4-methoxybenzoyl)ureido)-2-oxoindolin-3-ylidene)methyl)-2,4-dimethyl-1H-pyrrol-3-yl)propanoic acid (D47)

YD: 52.22%; mp: 240-245° C. (Charring). $^1$H NMR (DMSO-$d_6$) 400 MHz, δ: 2.279 (s, 3H), 2.238 (s, 3H), 2.339 (t, J=7.6 Hz, 2H), 2.630 (t, J=7.6 Hz, 2H), 3.840 (s, 3H), 6.953 (dd, J=1.6 & 8.4 Hz, 1H), 7.058 (d, J=8.8 Hz, 2H), 7.433 (d, J=1.6 Hz, 1H), 7.475 (s, 1H), 7.658 (d, J=8.4 Hz, 1H), 8.045 (d, J=8.8 Hz, 2H), 10.758 (s, 1H), 10.990 (s, 1H), 12.169 (br, 1H), 13.256 (s, 1H). ($C_{27}H_{26}N_4O_6 \cdot 1/2H_2O$) C, H, N. ESI-MS: m/z 501.0 [M−H]$^-$.

(Z)—N-(3-((1H-pyrrol-2-yl)methylene)-5-fluoro-2-oxoindolin-6-ylcarbamoyl)-4-methoxybenzamide (D48)

YD: 67.49%, mp: >300° C. $^1$H NMR (DMSO-$d_6$) 400 MHz, δ: 3.835 (s, 3H), 6.350 (d, J=2.4 Hz, 1H), 6.784 (s, 1H), 7.049 (d, J=8.8 Hz, 2H), 7.352 (s, 1H), 7.656 (d, J=10.8 Hz, 1H), 7.705 (s, 1H), 7.878 (d, J=6.4 Hz, 1H), 8.056 (d, J=8.8 Hz, 2H), 10.862 (s, 1H), 11.033 (s, 1H), 11.401 (d, 1H, J=2.4 Hz), 13.258 (s, 1H). ($C_{22}H_{17}FN_4O_4$) C, H, N. ESI-MS: m/z 419.0 [M−H]$^-$.

(Z)-5-((5-fluoro-6-(3-(4-methoxybenzoyl)ureido-2-oxoindolin-3-ylidene)methyl)-2,4-dimethyl-1H-pyrrole-3-carboxylic acid (D49)

YD: 74.34%; mp: 290-295° C. (Charring). $^1$H NMR (DMSO-$d_6$) 400 MHz, δ: 2.451 (s, 3H), 2.477 (s, 3H), 3.806 (s, 3H), 7.014 (d, J=8.8 Hz, 2H), 7.598 (s, 1H), 7.835-7.865 (m, 2H), 8.019 (d, J=8.8 Hz, 2H), 10.868 (s, 1H), 11.003 (s, 1H), 11.358 (d, J=2.4 Hz, 1H), 13.687 (s, 1H). ($C_{25}H_{21}FN_4O_6 \cdot 4/3 H_2O$) C, H, N. ESI-MS: m/z 491.0 [M−H]$^-$.

(Z)-2-(5-((5-fluoro-6-(3-(4-methoxybenzoyl)ureido)-2-oxoindolin-3-ylidene)-methyl)-2,4-dimethyl-1H-pyrrol-3-yl)acetic acid (D50)

YD: 64.38%. mp: 292-297° C. (Charring). $^1$H NMR (DMSO-$d_6$) 400 MHz, δ: 2.231 (s, 3H), 2.271 (s, 3H), 3.355 (s, 2H), 3.840 (s, 3H), 7.056 (d, J=8.8 Hz, 2H), 7.569 (s, 1H), 7.811 (d, J=11.2 Hz, 1H), 7.849 (d, J=6.4 Hz, 1H), 8.058 (d, J=8.8 Hz, 2H), 10.747 (s, 1H), 11.027 (s, 1H), 11.359 (d, J=2.4 Hz, 1H), 13.368 (s, 1H). ($C_{26}H_{23}FN_4O_6 \cdot 1/2H_2O$) C, H, N.

(Z)-3-(5-((5-fluoro-6-(3-(4-methylbenzoyl)ureido)-2-oxoindolin-3-ylidene)-methyl)-2,4-dimethyl-1H-pyrrol-3-yl)propanoic acid (D51)

YD: 46.15%; mp: 265-270° C. $^1$H NMR (DMSO-$d_6$) 400 MHz, δ: 2.249 (s, 3H), 2.280 (s, 3H), 2.341 (t, J=7.2 Hz, 2H), 2.627 (t, J=6.4 Hz, 2H), 3.839 (s, 3H), 7.054 (d, J=8.4 Hz, 2H), 7.544 (s, 1H), 7.787-7.847 (m, 2H), 8.056 (d, J=8.4 Hz, 2H), 10.717 (s, 1H), 11.022 (s, 1H), 11.349 (s, 1H), 13.319 (s, 1H). ($C_{27}H_{25}FN_4O_6 \cdot 7/3 H_2O$) C, H, N. ESI-MS: m/z 519.0 [M−H]$^-$.

(Z)—N-(3-((1H-pyrrol-2-yl)methylene)-2-oxoindolin-6-ylcarbamoyl)-2-fluorobenzamide (D52)

YD: 77.04%; mp: 276-281° C. (Charring). $^1$H NMR (DMSO-$d_6$) 400 MHz, δ: 6.333 (br, 1H), 6.791 (br, 1H), 7.010 (d, J=8.0 Hz, 1H), 7.326-7.371 (m, 3H), 7.415 (s, 1H), 7.577 (d, J=8.0 Hz, 1H), 7.614-7.714 (m, 3H), 10.549 (s, 1H), 10.903 (s, 1H), 11.050 (s, 1H), 13.220 (s, 1H). ($C_{21}H_{15}FN_4O_3 \cdot 1/5H_2O$) C, H, N. ESI-MS: m/z 389.0 [M−H]$^-$.

(Z)-5-((6-(3-(2-fluorobenzoyl)ureido)-2-oxoindolin-3-ylidene)methyl)-2,4-dimethyl-1H-pyrrole-3-carboxylic acid (D53)

YD: 67.75%, mp: 264-269° C. (Charring), $^1$H NMR, (DMSO-$d_6$) 400 MHz, δ: 2.476 (s, 3H), 2.521 (s, 3H), 7.007 (dd, J=1.6 & 8.2 Hz, 1H), 7.313-7.373 (m, 2H), 7.426 (d, J=1.6 Hz, 1H), 7.591 (s, 1H), 7.615-7.635 (m, 1H), 7.675-7.712 (m, 1H), 7.755 (d, J=8.0 Hz, 1H), 10.554 (s, 1H), 10.957 (s, 1H), 11.045 (s, 1H), 13.701 (s, 1H), ($C_{24}H_{19}FN_4O_5 \cdot 2H_2O$) C, H, N. ESI-MS: m/z 461.0 [M−H]$^-$.

(Z)-3-(5-((6-(3-(2-fluorobenzoyl)ureido)-2-oxoindolin-3-ylidene)methyl)-2,4-dimethyl-1H-pyrrol-3-yl)propanoic acid (D54)

YD: 41.67%; mp: 267-272° C. (Charring). $^1$H NMR (DMSO-d$_6$) 400 MHz, δ: 2.240 (s, 3H), 2.282 (s, 3H), 2.342 (t, J=7.6 Hz, 2H), 2.633 (t, J=7.6 Hz, 2H), 6.976 (dd, J=2.0 & 8.2 Hz, 1H), 7.313-7.372 (m, 2H), 7.395 (d, J=2.0 Hz, 1H), 7.486 (s, 1H), 7.600-7.713 (m, 3H), 10.521 (s, 1H), 10.763 (s, 1H), 11.021 (s, 1H), 13.261 (s, 1H). (C$_{26}$H$_{23}$FN$_4$O$_5$. ⅓H$_2$O) C, H, N. ESI-MS: m/z 489.0 [M−H]$^-$.

(Z)-3-(5-((6-(3-(4-fluorobenzoyl)ureido)-2-oxoindolin-3-ylidene)methyl)-2,4-dimethyl-1H-pyrrol-3-yl)propanoic acid (D55)

YD: 44.87%; mp: >300° C. $^1$H NMR (DMSO-d$_6$) 400 MHz, δ: 2.237 (s, 3H), 2.278 (s, 3H), 2.340 (t, J=7.6 Hz, 2H), 2.630 (t, J=8.0 Hz, 2H), 6.964 (dd, J=1.6 & 8.0 Hz, 1H), 7.372 (dd, J=8.8 & 8.8 Hz, 2H), 7.421 (br, 1H), 7.476 (s, 1H), 7.661 (d, J=8.0 Hz, 1H), 8.102 (dd, J=5.2 & 5.2 Hz, 2H), 10.760 (s, 1H), 10.835 (s, 1H), 11.036 (s, 1H), 13.255 (s, 1H). ESI-MS: m/z 489.0 [M−H]$^-$.

(Z)-3-(5-((6-(3-(2,4-difluorobenzoyl)ureido]-2-oxoindolin-3-ylidene)methyl)-2,4-dimethyl-1H-pyrrol-3-yl)propanoic acid (D56)

YD: 43.33%; mp: 280-285° C. (Charring). $^1$H NMR (DMSO-d$_6$) 400 MHz, δ: 2.238 (s, 3H), 2.280 (s, 3H), 2.341 (t, J=7.6 Hz, 2H), 2.632 (t J=7.6 Hz, 2H), 6.967 (dd, J=1.6 & 8.4 Hz, 1H), 7.209-7.257 (m, 1H), 7.388 (d, J=1.6 Hz, 1H), 7.400-7.472 (m, 1H), 7.484 (s, 1H), 7.664 (d, J=8.0 Hz, 1H), 7.757-7.815 (m, 1H), 10.475 (s, 1H), 10.761 (s, 1H), 11.028 (s, 1H), 13.259 (s, 1H). (C$_{26}$H$_{22}$F$_2$N$_4$O$_5$) C, H, N. ESI-MS: m/z 507.0 [M−H]$^-$.

(Z)-5-((6-(3-(2-fluoro-4-methoxybenzoyl)ureido)-2-oxoindolin-3-ylidene)methyl)-2,4-dimethyl-1H-pyrrol-3-carboxylic acid (D57)

YD: 74.29%: mp: 295-300° C. (Charring). $^1$H NMR (DMSO-d$_6$) 400 MHz, δ: 2.471 (s, 3H), 2.517 (s, 3H), 3.837 (s, 3H), 6.892 (dd, J=2.0 & 8.8 Hz, 1H), 6.959 (dd, J=2.0 & 13.2 Hz, 1H), 6.986 (dd, J=2.0 & 8.6 Hz, 1H), 7.423 (d, J=1.6 Hz, 1H), 7.573 (s, 1H), 7.686 (dd, J=8.4 & 8.8 Hz, 1H), 7.739 (d, J=8.4 Hz, 1H), 10.652 (s, 1H), 10.716 (s, 1H), 10.942 (s, 1H), 12.072 (br, 1H), 13.692 (s, 1H). (C$_{25}$H$_{21}$FN$_4$O$_6$.5/4H$_2$O) C, H, N. ESI-MS: m/z 491.0 [M−H]$^-$.

(Z)-3-(5-((6-(3-(2-fluoro-4-methoxybenzoyl)ureido)-2-oxoindolin-3-ylidene)methyl)-2,4-dimethyl-1H-pyrrol-3-yl)propanoic acid (D58)

YD: 49.21%; mp: 255-260° C. (Charring). $^1$H NMR (DMSO-d$_6$) 400 MHz, δ: 2.237 (s, 3H), 2.279 (s, 3H), 2.339 (t, J=7.6 Hz, 2H), 2.631 (t, J=7.6 Hz, 2H), 3.839 (s, 3H), 6.895 (dd, J=2.0 & 8.6 Hz, 1H), 6.950-6.981 (m, 2H), 7.396 (d, J=1.6 Hz, 1H), 7.476 (s, 1H), 7.645-7.710 (m, 2H), 10.629 (s, 1H), 10.758 (s, 1H), 13.256 (s, 1H). (C$_{27}$H$_{25}$FN$_4$O$_6$.1/2H$_2$O) C, H, N. ESI-MS: m/z 519.0 [M−H]$^-$.

(Z)-5-((5-fluoro-(3-(2-fluoro-4-methoxybenzoyl)ureido)-2-oxoindolin-3-ylidene)methyl)-2,4-dimethyl-1H-pyrrole-3-carboxylic acid (D59)

YD: 75.89%; mp: 297-300° C. $^1$H NMR (DMSO-d$_6$) 400 MHz, δ: 2.498 (s, 3H), 2.523 (s, 3H), 3.848 (s, 3H), 6.900 (d, J=2.4 & 8.8 Hz, 1H), 6.972 (dd, J=2.4 & 12.8 Hz, 1H), 7.659 (s, 1H), 7.659 (dd, J=8.8 & 8.8 Hz, 1H), 7.839 (d, J=6.4 Hz), 7.909 (d, J=11.2 Hz), 10.928 (s, 1H), 11.029 (s, 1H), 11.036 (s, 1H), 13.734 (s, 1H). (C$_{25}$H$_{20}$F$_2$N$_4$O$_6$.1/2H$_2$O) C, H, N. ESI-MS: m/z 509.1 [M−H]$^-$.

(Z)-3-(5-((5-fluoro-6-(3-(2-fluoro-4-methoxybenzoyl)ureido)-2-oxoindolin-3-ylidene)methyl)-2,4-dimethyl-1H-pyrrol-3-yl)propanic acid (D60)

YD: 53.69%; mp: 275-280° C. (Charring). $^1$H NMR (DMSO-d$_6$) 400 MHz, δ: 2.250 (s, 3H), 2.284 (s, 3H), 2.342 (t, J=7.6 Hz, 2H), 2.630 (t, J=7.6 Hz, 2H), 3.842 (s, 3H), 6.898 (d, J=2.0 & 8.8 Hz, 1H), 6.971 (dd, J=2.4 & 13.2 Hz, 1H), 7.556 (s, 1H), 7.704 (dd, J=8.8 & 8.4 Hz, 1H), 7.798 (d, J=6.8 Hz), 7.811 (d, J=11.2 Hz), 10.736 (s, 1H), 10.983 (s, 1H), 10.990 (s, 1H), 13.325 (s, 1H), (C$_{27}$H$_{24}$F$_2$N$_4$C$_6$.2/3H$_2$O) C, H, N. ESI-MS: m/z 537.0 [M−H]$^-$.

(Z)-5-((6-(3-(2,6-difluoro-4-methoxybenzoyl)ureido)-5-fluoro-2-oxoindolin-3-ylidene)methyl)-2,4-dimethyl)-1H-pyrrole-3-carboxylic acid (D61)

YD: 50.35%, mp: >300° C. $^1$H NMR (DMSO-d$_6$) 400 MHz, δ: 2.490 (s, 3H), 2.523 (s, 3H), 3.842 (s, 3H), 6.889 (d, J=10.0 Hz, 2H), 7.674 (s, 1H), 7.793 (d, J=6.4 Hz), 7.919 (d, J=11.2 Hz), 10.702 (s, 1H), 10.928 (s, 1H), 11.501 (s, 1H), 13.739 (s, 1H). (C$_{25}$H$_{19}$F$_3$N$_4$O$_6$.1/2H$_2$O) C, H, N. ESI-MS: m/z 527.0 [M−H]$^-$.

(Z)-ethyl-5-((6-(3-(2-fluoro-4-methoxybenzoyl)ureido)-2-oxoindolin-3-ylidene)methyl)-2,4-dimethyl-1H-pyrrole-3-carboxylate (D62)

YD: 62.88%; mp: 278-283° C. (Charring). $^1$H NMR (DMSO-d$_6$) 400 MHz, δ: 1.292 (t, J=7.0 Hz, 3H), 2.476 (s, 3H), 2.525 (s, 3H), 3.842 (s, 3H), 4.206 (q, J=7.2 Hz, 2H), 6.898 (dd, J=2.2 & 8.4 Hz, 1H), 6.947-7.005 (m, 2H), 7.426 (d, J=1.6 Hz, 1H), 7.584 (s, 1H), 7.669 (dd, J=8.4 & 8.8 Hz, 1H), 7.754 (d, J=8.4 Hz, 1H), 10.657 (s, 1H), 10.729 (s, 1H), 10.966 (s, 1H), 13.751 (s, 1H).

(Z)-ethyl-3-(5-((6-(3-(2-fluoro-4-methoxybenzoyl)-2-oxoindolin-3-ylidene)methyl-2,4-dimethyl-1H-pyrrol-3-yl)propanoate (D63)

YD: 45.45%: mp: 250-255° C. (Charring). $^1$H NMR (DMSO-d$_6$) 400 MHz, δ: 1.151 (t, J=7.0 Hz, 3H), 2.233 (s, 3H), 2.274 (s, 3H), 2.421 (t, J=7.6 Hz, 2H), 2.659 (t, J=7.4 Hz, 2H), 3.842 (s, 3H), 4.030 (q, J=7.2 Hz, 2H), 6.899 (dd, J=2.0 & 8.4 Hz, 1H), 6.949-6.981 (m, 2H), 7.394 (br, 1H), 7.480 (s, 1H), 7.650-7.711 (m, 2H), 10.625 (s, 1H), 10.727 (s, 1H), 10.762 (s, 1H), 13.257 (s, 1H). ESI-MS: m/z 547.0 [M−H]$^-$.

(Z)—N-(3-((3,5-dimethyl-4-(4-methylpiperazine-1-carbonyl)-1H-pyrrol-2-yl)methylene)-2-oxoindolin-6-ylcarbamoyl)-2-fluoro-4-methoxybenzamide (D64)

YD: 34.71%, mp: 250-255° C. (Charring). $^1$H NMR (DMSO-d$_6$) 400 MHz, δ: 2.169 (s, 3H), 2.223 (br, 4H), 2.261 (s, 6H), 3.436 (br, 4H), 3.834 (s, 3H), 6.891 (dd, J=2.4 & 8.8 Hz, 1H), 6.941-6.992 (m, 2H), 7.414 (d, J=2.0 Hz, 1H), 7.520 (s, 1H), 7.682 (dd, J=8.4 & 8.8 Hz, 1H), 7.704 (d, J=8.0 Hz, 1H), 10.642 (s, 1H), 10.723 (s, 1H), 10.884 (s, 1H), 13.432 (s, 1H). ($C_{30}H_{31}FN_6O_5 \cdot 3/2H_2O$) C, H, N. ESI-MS: m/z 573.1 [M−H]⁻.

(Z)—N-(3-((3,5-dimethyl-4-(3-(4-methylpiperazin-1-yl)-3-oxopropyl)-1H-pyrrol-2-yl)methylene)-2-oxoindolin-6-ylcarbomoyl)-2-fluoro-4-methoxybenzamide (D65)

YD: 36.74%; mp: 229-234° C. (Charring). ¹H NMR (DMSO-d₆) 400 MHz, δ: 2.106 (s, 3H), 2.119-2.145 (m, 2H), 2.187-2.199 (m, 2H), 2.231 (s, 3H), 2.271 (s, 3H), 2.413 (t, J=7.6 Hz, 2H), 2.618 (t, J=7.6 Hz, 2H), 3.419 (br, 4H), 3.842 (s, 3H), 6.899 (dd, J=2.4 & 8.4 Hz, 1H), 6.949-6.986 (m, 2H), 7.414 (br, 1H), 7.482 (s, 1H), 7.651-7.711 (m, 2H), 10.626 (s, 1H), 10.757 (s, 2H), 13.269 (s, 1H). ($C_{32}H_{35}FN_6O_5 \cdot 5/4H_2O$) C, H, N. ESI-MS: m/z 601.1 [M−H]⁻.

(Z)—N-(3-((3,5-dimethyl-4-(morpholine-4-carbonyl)-1H-pyrrol-2-yl)methylene)-2-oxoindolin-6-ylcarbamoyl)-2-fluoro-4-methoxybenzamide (D66)

YD: 38.65%; mp: 273-278° C. (Charring). ¹H NMR (DMSO-d₆) 400 MHz, δ: 2.246 (s, 3H), 2.285 (s, 3H), 3.461 (br, 4H), 3.568 (br, 4H), 3.843 (s, 3H) 6.901 (dd, J=2.4 & 8.4 Hz, 1H), 6.950-7.003 (m, 2H), 7.422 (d, J=1.6 Hz, 1H), 7.533 (s, 1H), 7.669-7.726 (m, 2H), 10.652 (s, 2H), 10.898 (s, 1H), 13.454 (s, 1H). ($C_{29}H_{28}FN_5O_6 \cdot 1/2H_2O$) C, H, N. ESI-MS: m/z 560.0 [M−H]⁻.

(Z)—N-(3-(3,5-dimethyl-4-(3-morpholino-3-oxopropyl)-1H-pyrrol-2-yl)methylene)-2-oxoindolin-6-ylcarbamoyl)-2-fluoro-4-methoxybenzamide (D67)

YD: 34.21%: mp: 248-253° C. (Charring). ¹H NMR (DMSO-d₆) 400 MHz, δ: 2.237 (s, 3H), 2.278 (s, 3H), 2.422 (t, J=7.6 Hz, 2H), 2.626 (t, J=7.6 Hz, 2H), 3.340-3.495 (m, 8H), 3.844 (s, 3H), 6.905 (d, J=8.4 Hz, 1H), 6.951-6.984 (m, 2H), 7.402 (br, 1H), 7.485 (s, 1H), 7.654-7.712 (m, 2H), 10.629 (s, 1H), 10.721 (s, 1H), 10.763 (s, 1H), 13.271 (s, 1H). ($C_{31}H_{32}FN_5O_6 \cdot 2/3H_2O$) C, H, N. ESI-MS: m/z 588.1 [M−H]⁻.

(Z)—N-(2-dimethylamino)ethyl)-5-((6-(3-(2-fluoro-4-methoxybenzoyl)-ureido)-2-oxoindolin-3-ylidene)methyl)-2,4-dimethyl-1H-pyrrole-3-carboxamide (D68)

YD: 42.95%; mp: 298→300° C. ¹H NMR (DMSO-d₆) 400 MHz, δ: 2.182 (s, 6H), 2.376 (m, 5H), 2.415 (s, 3H), 3.293 (t, J=6.4 Hz, 2H), 3.842 (s, 3H), 6.899 (dd, J=2.2 & 8.8 Hz, 1H), 6.948-7.000 (m, 2H), 7.420-7.452 (m, 2H), 7.542 (s, 1H), 7.667-7.733 (m, 2H), 10.651 (s, 1H), 10.731 (s, 1H), 10.901 (s, 1H), 13.487 (s, 1H).

(Z)—N-(2-(diethylamino)ethyl)-5-((6-(3-(2-fluoro-4-methoxybenzoyl)ureido)-2-oxoindolin-3-ylidene)methyl)-2,4-dimethyl-1H-pyrrole-3-carboxamide (D69)

YD: 36.04%; mp: 275-280° C. (Charring). ¹H NMR (DMSO-d₆) 400 MHz, δ: 0.969 (t, J=7.0 Hz, 6H), 2.391 (s, 3H), 2.426 (s, 3H), 2.520-2.558 (m, 4H), 3.250-3.282 (m, 2H), 3.843 (s, 3H), 6.900 (dd, J=2.4 & 8.8 Hz, 1H), 6.950-7.001 (m, 2H), 7.376 (t, J=5.4 Hz, 1H), 7.423 (d, J=2.0 Hz, 1H), 7.551 (s, 1H), 7.690 (dd, J=8.4 & 8.8 Hz, 1H), 7.728 (d, J=8.4 Hz, 1H), 10.651 (s, 1H), 10.736 (s, 1H), 10.900 (s, 1H), 13.497 (s, 1H), ($C_{31}H_{35}FN_6O_5 \cdot 2/3H_2O$) C, H, N. ESI-MS: m/z 589.1 [M−H]⁻.

(Z)-5-((6-(3-(2-fluoro-4-methoxybenzoyl)ureido)-2-oxoindolin-3-ylidene)methyl)-2,4-dimethyl-N-(2-(pyrrolidin-1-yl)ethyl)-1H-pyrrole-3-carboxamide (D70)

YD: 49.70%: mp: 291-296° C. (Charring). ¹H NMR (DMSO-d₆) 400 MHz, δ: 1.679 (br, 4H), 2.377 (s, 3H), 2.414 (s, 3H), 2.566 (t, J=6.8 Hz, 2H), 3.841 (s, 3H), 6.898 (dd, J=2.0 & 8.8 Hz, 1H), 6.947-6.999 (m, 2H), 7.421 (d, J=2.0 Hz, 1H), 7.480 (t, J=5.6 Hz, 1H), 7.542 (s, 1H), 7.666-7.732 (m, 2H), 10.652 (s, 1H), 10.732 (s, 1H), 10.901 (s, 1H), 13.486 (s, 1H). ($C_{31}H_{33}FN_6O_5 \cdot 1/2 H_2O$) C, H, N. ESI-MS: m/z 587.1 [M−H]⁻.

D14-D70 were prepared using appropriate starling materials with a process similar to D13.

Malate salt of (Z)-5-((6-(3-(2-fluoro-4-methoxybenzoyl)ureido)-2-oxoindolin-3-ylidene)methyl)-2,4-dimethyl-N-(2-(pyrrolidin-1-yl)ethyl)-1H-pyrrole-3-carboxamide (D71)

L-Malic acid (0.25 mmol) was added to a solution of compound D70 (0.08 mmol) in ethanol (1 mL). The reaction was carried out using microwave (CEM. Discover) at 100° C. (200 W: Standard mode) for 15 mins. Crude product was recovered by evaporation of ethanol. ¹H NMR (DMSO-d₆) 400 MHz, δ: 1.816 (br, 4H), 2.402 (s, 3H), 2.439 (s, 3H), 2.945 (br, 8H), 3.431-3.477 (m, 3H), 3.909-3.943 (m, 0.5; H), 6.898 (dd, J=2.0 & 8.8 Hz, 1H), 6.948-7.004 (m, 2H), 7.426 (d, J=2.0 Hz, 1H), 7.552 (s, 1H), 7.640 (t, J=5.6 Hz, 1H), 7.667-7.738 (m, 2H), 10.665 (s, 1H), 10.747 (s, 1H), 10.911 (s, 1H), 13.527 (s, 1H).

3-((4-Fluorophenyl)amino)-3-oxopropanoic acid (D72)

The compound was prepared according to literature procedure. To a solution of 4-fluoroaniline (2.0 mL, 20.8 mmol) and TEA (3.5 mL, 25.0 mmol) in dry DCM in ice bath was added ethyl malonyl chloride (3.5 mL, 27.3 mmol) dropwise. Reaction mixture was stirred at such temperature for 4 h. Reaction mixture was quenched by saturated aqueous solution of NaHCO₃. Crude product was extracted by EA (50 mL×3). Organic layers were combined, washed by brine and dried over anhydrous MgSO₄. After removal of solvent, ethyl ester of 3-((4-fluorophenyl)amino)-3-oxopropanoic acid was obtained, which was subjected to saponification by 10% NaOH in EtOH. Reaction mixture was heated to reflux for 1.5 h. Solid obtained by acidic workup (3N HCl) was collected by filter to give the title compound. YD: 75% (for two steps). ¹H-NMR (400 MHz, DMSO-d₆) δ 12.60 (br s, 1H, COOH), 10.2 (s, 1H, NH), 7.60-7.56 (m, 2H, ArH), 7.16-7.11 (m, 2H, ArH), 3.33 (s, 2H, CH₂).

1-((4-Methoxyphenyl)carbamoyl)cyclopropanecarboxylic acid (D73)

The compound was prepared according to literature procedure. To a solution of cyclopropane-1,1-dicarboxylic acid (390.0 mg, 3.0 mmol) in dry THF (20 mL) in ice bath was added triethylamine (TEA; 0.40 mL, 3.1 mL) dropwise. The solution was stirred for 15 min and SOCl₂ (0.20 mL, 2.9 mmol) was added to it. After 15 min reaction at such temperature, a solution of p-anisidine (387.0 mg, 3.1 mmol) in THF (5 mL) was added slowly. Reaction mixture was allowed to warm to rt and stirred for additional 18 h. After that, reaction mixture was diluted by EA; unconsumed diacid was quenched by 10% NaOH (0.5 mL). Crude product was extracted by EA and washed by water and brine. Organic portions were concentrated in vacuo. Solid precipitated by addition of n-heptane was collected by filter. Prolonged drying in vacuo gave the title compound. YD: 82%; mp 133-136° C. $^1$H-NMR (400 MHz, DMSO-$d_6$) δ: 1.40 (s, 4H, 2×$CH_2$), 3.71 (s, 3H, $OCH_3$), 6.85 (d, J=8.8 Hz, 2H, ArH), 7.49 (d, J=8.8 Hz, 2H, ArH), 10.42 (s, 1H, NH). Anal. ($C_{13}H_{13}NO_4$.0.5; $H_2O$) C, H, N. MS (ESI) 233.8 (M–H)$^-$.

$N^1$-(4-Fluorophenyl)-$N^3$-(2-oxoindolin-6-yl)malonamide (D74)

6-Aminoindolin-2-one (148.0 mg, 1.0 mmol) was made to react to D72 (197.0 mg, 1.0 mmol) in the presence of TBTU (487.0 mg, 1.5 mmol) and TEA (0.42 mL, 3.0 mmol) in a mixture of dry DMF and acetonitrile (1:3, 6 mL) under rt for 3 h. Resultant solid was collected, washed by water and dried to give the title compound. YD: 65%; mp: 221° C. (Charring). $^1$H-NMR (400 MHz, DMSO-$d_6$) δ: 3.39 (s, 2H, $CH_2$), 3.43 (s, 2H, $CH_2$), 7.01 (d, J=8.4 Hz, 1H, ArH), 7.10 (d, J=8.4 Hz, 1H, ArH), 7.17-7.12 (m, 2H, ArH), 7.35 (s, 1H, ArH), 7.63-7.59 (m, 2H, ArH), 10.11 (s, 1H, NH), 10.20 (s, 1H, NH), 10.35 (s, 1H, NH). Anal. ($C_{17}H_{14}FN_3O_3$.1$H_2O$) C, H, N. MS (ESI) 325.9 (M–H)$^-$.

(Z)—$N^1$-(3-((1H-pyrrol-2-yl)methylene)-2-oxoindolin-6-yl)-$N^3$-(4-fluorophenyl)malonamide (D75)

Compound D74 (80.0 mg, 0.2 mmol) was made to react to pyrrole-2-carboxaldehyde (25.0 mg, 0.3 mmol) in the presence of cat. pyrrolidine in EtOH (3 mL). Reaction mixture was heated by a CEM microwave machine at 100° C. for 20 min. Resultant solid was collected by filter, washed by EtOH and ether, and dried to give the title compound. YD: 44%; mp: >300° C. $^1$H-NMR (DMSO-$d_6$) δ: 13.22 (s, 1H, NH), 10.87 (s, 1H, NH), 10.21 (s, 1H, NH), 10.20 (s, 1H, NH), 7.62-7.60 (m, 3H, ArH+vinyl-H), 7.54 (d, J=8 Hz, 1H, ArH), 7.45 (s, 1H, ArH), 7.31 (s, 1H, pyrrole-H), 7.17-7.13 (m, 2H, ArH), 7.09 (d, J=8 Hz, 1H, ArH), 6.77 (s, 1H, pyrrole-H), 6.33 (s, 1H, pyrrole-H), 3.46 (s, 2H, $CH_2$). Anal. ($C_{22}H_{17}FN_4O_3$.0.2$H_2O$) C, H, N.

(Z)—$N^1$-(3-((1H-pyrrol-2-yl)methylene)-2-oxoindolin-6-yl)-$N^3$-(4-methoxyphenyl)malonamide (D76)

YD: 70%; mp>300° C. $^1$H-NMR (DMSO-$d_6$) δ: 13.22 (s, 1H, NH), 10.88 (s, 1H, NH), 10.20 (s, 1H, NH), 10.02 (s, 1H, NH), 7.60 (s, 1H, vinyl-H), 7.55-7.50 (m, 3H, ArH), 7.46 (s, 1H, ArH), 7.31 (s, 1H, pyrrole-H), 7.09 (d, J=8.4 Hz, 1H, ArH), 6.88 (d, J=9.2 Hz, 2H, ArH), 6.77 (s, 1H, pyrrole-H), 6.33 (s, 1H, pyrrole-H), 3.71 (s, 3H, $OCH_3$), 3.44 (s, 2H, $CH_2$) Anal. ($C_{23}H_{20}N_4O_4$) C, H, N.

(Z)—N-(3-((1H-pyrrol-2-yl)methylene)-2-oxoindolin-6-yl)-N-(4-methoxyphenyl)cyclopropane-1,1-dicarboxamide (D77)

YD: 52%; $^1$H-NMR (DMSO-d6) δ: 13.22 (s, 1H, NH), 10.88 (s, 1H, NH), 10.19 (s, 1H, NH), 9.76 (s, 1H, NH), 7.60 (s, 1H, vinyl-H), 7.53-7.47 (m, 3H, ArH), 7.42 (s, 1H, ArH), 7.31 (s, 1H, pyrrole-H), 7.14 (dd, J=8.2, 1.6 Hz, 1H, ArH), 6.87 (d, J=9.2 Hz, 2H, ArH), 6.77 (s, 1H, pyrrole-H), 6.33 (s, 1H, pyrrole-H), 3.71 (s, 3H, $OCH_3$), 1.45 (s, 4H, 2*$CH_2$). Anal. ($C_{25}H_{22}N_4O_4$.0.2; $H_2O$) C, H, N.

D76, D77, were prepared using appropriate starting materials with procedure similar to D75.

Synthesis of Compounds of Formula (II)

1-methylimidazolidin-2-one (D78)

To 2-chloroethyl isocyanate (0.4 M) in THF was added methylamine, stirred at 22° C. under $N_2$ for 18 hours. The solvent was removed in vacuo and the presence of intermediate compound 1-(2-chloroethyl)-3-methylurea was confirmed by 1H NMR and dissolved in THF (0.4 M), and added NaH (2.4 eq.). The mixture was stirred at RT under $N_2$ for 18 h, and concentrated in vacuo. The resulting residue was purified using flash chromatography on silica gel to give the title compound D78.

3-methyl-2-oxo-N-(2-oxoindolin-6-yl)imidazolidine-1-carboxamide (D79)

bis(trichloromethyl)carbonate in tetrahydrofuran was added dropwise within 1 hour to the compound D78 in tetrahydrofuran in such a way that the internal temperature was kept at 55-60° C. The mixture was stirred for 5 h at this temperature. The formation of 3-methyl-2-oxoimidazolidine-1-carbonyl chloride was confirmed by TLC. The 6-aminoindolin-2-one (D4) was added to the mixture in situ and the mixture was refluxed for 4 h. The completion of reaction was monitored using TLC. The residue obtained after workup using saturated sodium carbonate was further purified using flash chromatography on silica gel to afford the title compound D79.

(Z)—N-(3-((1H-pyrrol-2-yl)methylene)-2-oxoindolin-6-yl)-3-methyl-2-oxoimidazolidine-1-carboxamide (D80)

A catalytic amount of pyrrolidine (0.001 mmol) was added to compound D75 (1 mmol) and pyrrole-2-carbaldehyde (1.2 mmol) in ethanol (5 mL). After addition the reaction was carried out using microwave (CEM, Discover) at 100° C. (200 W: Standard mode) for 15 mins. Crude product was precipitated after cooling to RT, collected by filtration, washed with ethanol and air dried. YD: 55.06%; mp: 267-272° C. (charring). $^1$H NMR (400 MHz, DMSO-$d_6$) δ: 2.788 (s, 3H), 3.420 (t, J=8.2 Hz, 2H), 3.766 (t, J=8.2 Hz, 2H), 6.320 (br, J=3.2 Hz, 1H), 6.767 (br, 1H), 6.879 (dd, J=1.6 & 8.4 Hz, 1H), 7.301 (br, 1H), 7.320 (br, 1H), 7.526 (d, J=8.0 Hz, 1H), 7.599 (s, 1H), 10.480 (s, 1H), 10.872 (s, 1H), 13.198 (s, 1H). ($C_{18}H_{17}N_5O_3$) C, H, N.

(Z)—N-(3-((1H-pyrrol-2-yl)methylene)-2-oxoindolin-6-yl)-3-cyclopropyl-2-oxoimidazolidine-1-carboxamide (D81)

YD: 77.46%; mp: 284-289° C. (charring). $^1$H NMR (400 MHz, DMSO-$d_6$) δ: 0.696 (d, J=5.2 Hz, 4H), 2.575 (p, J=5.2 Hz, 1H), 3.389 (t J=8.2 Hz, 2H), 3.719 (t, J=8.2 Hz, 2H), 6.310-6.331 (m, 1H), 6.762-6.771 (m, 1H), 6.886 (dd, J=1.8 & 8.4 Hz, 1H), 7.304 (br, 1H), 7.324 (d, J=2.0 Hz, 1H), 7.528 (d, J=8.0 Hz, 1H), 7.601 (s, 1H), 10.485 (s, 1H), 10.882 (s, 1H), 13.200 (s, 1H). ($C_{20}H_{19}N_5O_3$.1/5$H_2O$) C, H, N.

(Z)—N-(3-((1H-pyrrol-2-yl)methylene)-5-fluoro-2-oxoindolin-6-yl)-3-cyclopropyl-2-oxoimidazolidine-1-carboxamide (D82)

YD: 55.01%; M.P.: >300° C. $^1$H NMR (400 MHz, DMSO-d$_6$) δ: 0.687 (d, J=5.2 Hz, 4H), 2.567 (p, J=5.4 Hz, 1H), 3.725 (t, J=8.2 Hz, 2H), 6.331-6.351 (m, 1H), 6.776 (br, 1H), 7.331 (br, 1H), 7.600 (d, J=10.8 Hz, 1H), 7.662 (s, 1H), 7.780 (d, J=6.8 Hz, 1H), 10.782 (d, J=2.8 Hz, 1H), 10.868 (s, 1H), 13.233 (s, 1H), (C$_{20}$H$_{18}$FN$_5$O$_3$) C, H, N.

(Z)—N-(3-((1H-pyrrol-2-yl)methylene)-2-oxoindolin-6-yl)-2-oxo-3-phenylimidazolidine-1-carboxamide (D83)

YD: 88.95%; mp: 294-299° C. (charring). $^1$H NMR (400 MHz, DMSO-d$_6$) δ: 3.930 (s, 4H), 6.315-6.336 (m, 1H), 6.774 (br, 1H), 6.951 (dd, J=1.8 & 8.4 Hz, 1H), 7.161 (t, J=7.4 Hz, 1H), 7.307 (br, 1H), 7.373 (d, J=2.0 Hz, 1H), 7.412 (t, J=7.8 Hz, 2H), 7.553 (d, J=8.4 Hz, 1H), 7.609 (d, J=7.6 Hz, 2H), 7.619 (s, 1H), 10.441 (s, 1H), 10.907 (s, 1H), 13.208 (s, 1H). (C$_{23}$H$_{19}$N$_5$O$_3$) C, H, N.

(Z)—N-(3-((1H-pyrrol-2-yl)methylene)-2-oxoindolin-6-yl)-3-(4-chlorophenyl)-2-oxoimidazolidine-1-carboxamide (D84)

YD: 76.16%; mp: >300° C. $^1$H NMR (400 MHz, DMSO-d$_6$) δ: 3.914 (s, 4H), 6.320-6.326 (m, 1H), 6.772 (br, 1H), 6.942 (d, J=8.4 Hz, 1H), 7.305 (br, 1H), 7.365 (br, 1H), 7.462 (d, J=8.8 Hz, 2H), 7.548 (d, J=8.4 Hz, 1H), 7.615 (s, 1H), 7.615 (d, J=8.8 Hz, 2H), 10.375 (s, 1H), 10.903 (s, 1H), 13.205 (s, 1H). (C$_{23}$H$_{18}$ClN$_5$O$_3$) C, H, N.

(Z)—N-(3-((1H-pyrrol-2-yl)methylene)-2-oxoindolin-6-yl)-3-(3-chlorophenyl)-2-oxoimidazolidine-1-carboxamide (D85)

YD: 82.27%: M.P.: >300° C. $^1$H NMR (400 MHz, DMSO-d$_6$) δ: 3.922-3.925 (br, 4H), 6.320-6.335 (m, 1H), 6.772 (br, 1H), 6.967 (dd, J=2.0 & 8.4 Hz, 1H), 7.200-7.219 (m, 1H), 7.305 (br, 1H), 7.377 (d, J=1.6 Hz, 1H), 7.411-7.507 (m, 2H), 7.552 (d, J=8.0 Hz, 1H), 7.619 (s, 1H), 7.806 (br, 1H), 10.349 (s, 1H), 10.907 (s, 1H), 13.205 (s, 1H). (C$_{23}$H$_{18}$ClN$_5$O$_3$) C, H, N.

(Z)—N-(3-((1H-pyrrol-2-yl)methylene)-2-oxoindolin-6-yl)-3-(3,4-dichlorophenyl)-2-oxoimidazolidine-1-carboxamide (D86)

YD: 16.81%; mp: >300° C. $^1$H NMR (400 MHz, DMSO-d$_6$) δ: 3.921 (s, 4H), 6.320-6.334 (m, 1H), 6.768-6.773 (br, 1H), 6.967 (dd, J=1.8 & 8.2 Hz, 1H), 7.305 (br, 1H), 7.373 (d, J=2.0 Hz, 1H), 7.541-7.574 (m, 2H), 7.620 (s, 1H), 7.660 (d, J=8.8 Hz, 1H), 7.961 (d, J=2.4 Hz, 1H), 10.303 (s, 1H), 10.909 (s, 1H), 13.199 (s, 1H).

(Z)—N-(3-((1H-pyrrol-2-yl)methylene)-2-oxoindolin-6-yl)-3-(4-chloro-3-(trifluoromethyl)phenyl)-2-oxoimidazolidine-1-carboxamide (D87)

YD: 51.29%; mp: >300° C. $^1$H NMR (400 MHz, DMSO-d$_6$) δ: 3.919-3.967 (m, 4H), 6.313-6.321 (m, 1H), 6.761 (br, 1H), 6.962 (dd, J=1.8 & 8.4 Hz, 1H), 7.297 (br, 1H), 7.370 (d, J=2.0 Hz, 1H), 7.539 (d, J=8.0 Hz, 1H), 7.610 (s, 1H), 7.743 (br, 2H), 8.210 (br, 1H), 10.257 (s, 1H), 10.910 (s, 1H), 13.190 (s, 1H). (C$_{24}$H$_{17}$ClF$_3$N$_5$O$_3$) C, H, N.

(Z)—N-(3-((1H-pyrrol-2-yl)methylene)-2-oxoindolin-6-yl)-2-oxo-3-(4-(trifluoromethyl)phenyl)imidazolidine-1-carboxamide (D88)

YD: 48.44%; mp: >300° C. $^1$H NMR (400 MHz, DMSO-d$_6$) δ: 3.941-3.978 (m, 4H), 6.321-6.330 (m, 1H), 6.774 (br, 1H), 6.963 (dd, J=1.6 & 8.4 Hz, 1H), 7.309 (br, 1H), 7.377 (d, J=1.6 Hz, 1H), 7.557 (d, J=8.0 Hz, 1H), 7.623 (s, 1H), 7.767 (d, J=8.8 Hz, 2H), 7.835 (d, J=8.8 Hz, 2H), 10.350 (s, 1H), 10.908 (s, 1H), 13.206 (s, 1H). (C$_{24}$H$_{18}$F$_3$N$_5$O$_3$) C, H, N.

(Z)—N-(3-((1H-pyrrol-2-yl)methylene)-2-oxoindolin-6-yl)-3-(4-fluorophenyl)-2-oxoimidazolidine-1-carboxamide (D89)

YD: 82.14%; mp: >300° C. $^1$H NMR (400 MHz, DMSO-d$_6$) δ: 3.914 (br, 4H), 6.323 (br, 1H), 6.772 (br, 1H), 6.937 (d, J=8.4 Hz, 1H), 7.253 (t J=8.8 Hz, 1H), 7.303 (br, 1H), 7.360 (br, 1H), 7.545 (d, J=8.0 Hz, 1H), 7.612-7.636 (m, 2H), 10.401 (s, 1H), 10.901 (s, 1H), 13.200 (s, 1H). (C$_{23}$H$_{18}$FN$_5$O$_3$·1/3H$_2$O) C, H, N.

(Z)—N-(3-((1H-pyrrol-2-yl)methylene)-2-oxoindolin-6-yl)-3-(2-fluorophenyl)-2-oxoimidazolidine-1-carboxamide (D90)

$^1$H NMR (400 MHz, DMSO-d$_6$) δ: 3.878-4.010 (m, 4H), 6.318-6.338 (m, 1H), 6.778 (br, 1H), 6.223 (dd, J=1.8 & 8.4 Hz, 1H), 7.268-7.406 (m, 5H), 7.536-7.590 (m, 2H), 7.619 (s, 1H), 10.343 (s, 1H), 10.904 (s, 1H), 13.209 (s, 1H).

(Z)—N-(3-((1H-pyrrol-2-yl)methylene)-2-oxoindolin-6-yl)-3-(4-methoxyphenyl)-2-oxoimidazolidine-1-carboxamide (D91)

YD: 89.88%; mp: 294-299° C. (charring). $^1$H NMR (400 MHz, DMSO-d$_6$) δ: 3.750 (s, 3H), 3.905 (s, 4H), 6.345 (br, 1H), 6.827 (d, J=8.4 Hz, 1H), 6.856 (br, 1H), 6.982 (d, J=8.8 Hz, 2H), 7.317-7.349 (m, 2H), 7.510 (d, J=8.8 Hz, 2H), 7.755 (s, 1H), 7.768 (br, 1H), 10.299 (s, 1H), 10.830 (s, 1H), 13.320 (s, 1H), (C$_{24}$H$_{21}$N$_5$O$_4$·1/4H$_2$O) C, H, N.

(Z)—N-(3-((1H-pyrrol-2-yl)methylene)-2-oxoindolin-6-yl)-2-oxo-3-p-tolylimida-zolidine-1-carboxamide (D92)

YD: 92.89%; mp: >300° C. $^1$H NMR (400 MHz, DMSO-d$_6$) δ: 2.285 (s, 3H), 3.903 (s, 4H), 6.320-6.326 (m, 1H), 6.771 (br, 1H), 6.941 (d, J=8.0 Hz, 1H), 7.209 (d, J=8.0, 2H), 7.305 (br, 1H), 7.365 (br, 1H), 7.485 (d, J=8.4 Hz, 2H), 7.545 (d, J=8.0 Hz, 1H), 7.611 (s, 1H), 10.450 (s, 1H), 10.898 (s, 1H), 13.206 (s, 1H). (C$_{24}$H$_{21}$N$_5$O$_3$·1/3H$_2$O) C, H, N.

(Z)—N-(3-((1H-pyrrol-2-yl)methylene)-2-oxoindolin-6-yl)-3-(4-(dimethylamino)-phenyl)-2-oxoimidazolidine-1-carboxamide (D93)

YD: 83.12%; mp: 279-284° C. (charring). $^1$H NMR (400 MHz, DMSO-d$_6$) δ: 2.877 (s, 6H), 3.876 (br, 4H), 6.319-6.327 (m, 1H), 6.740-6.763 (m, 3H), 6.926 (d, J=8.0 Hz, 1H), 7.304 (br, 1H), 7.363-7.386 (m, 3H), 7.541 (d, J=8.4 Hz, 1H), 7.609 (s, 1H), 10.507 (s, 1H), 10.890 (s, 1H), 13.203 (s, 1H). (C$_{25}$H$_{24}$N$_6$O$_3$) C, H, N.

(Z)—N-(3-((1H-pyrrol-2-yl)methylene)-2-oxoindolin-6-yl)-3-(2-fluoro-4-methoxyphenyl)-2-oxoimidazolidine-1-carboxamide (D94)

$^1$H NMR (DMSO-d$_6$) 400 MHz, δ: 3.789 (s, 3H), 3.789-3.835 (m, 2H), 3.941-3.963 (m, 2H), 6.319-6.328 (m, 1H), 6.771 (br, 1H), 6.866 (dd, J=2.8 & 8.8 Hz, 1H), 6.906 (dd, J=1.6 & 8.4 Hz, 1H), 6.989 (dd, J=2.6 & 12.4 Hz, 1H), 7.308 (br, 1H), 7.343 (d, J=2.0 Hz, 1H), 7.447 (dd, J=8.4 & 8.6 Hz, 1H), 7.538 (d, J=8.0 Hz, 1H), 7.613 (s, 1H), 10.360 (s, 1H), 10.902 (s, 1H), 13.204 (s, 1H).

(Z)-5-((6-(3-(4-methoxyphenyl)-2-oxoimidazolidine-1-carboxamido)-2-oxoindolin-3-ylidene)methyl)-2,4-dimethyl-1H-pyrrole-3-carboxylic acid (D95)

YD: 86.67%: mp: 267-272° C. (charring). $^1$H NMR (DMSO-d$_6$) 400 MHz, δ: 2.458 (s, 3H), 2.505 (s, 3H), 3.746 (s, 3H), 3.887 (s, 4H), 6.914 (d, J=8.4 Hz, 1H), 6.969 (d, J=8.8 Hz, 2H), 7.361 (br, 1H), 7.481-7.529 (m, 3H), 7.701 (d, J=8.4 Hz, 1H), 10.442 (s, 1H), 10.939 (s, 1H), 13.666 (s, 1H).

(Z)-5-((6-(3-cyclopropyl-2-oxoimidazolidine-1-carboxamido)-2-oxoindolin-3-ylidene)methyl)-2,4-dimethyl-1H-pyrrole-3-carboxylic acid (D96)

YD: 62.37%: mp: >300° C. $^1$H NMR (400 MHz, DMSO-d$_6$) δ: 0.699 (d, J=5.2 Hz, 4H), 2.461 (s, 3H), 2.514 (s, 3H), 2.578 (p, J=5.4 Hz, 1H), 3.394 (J=8.2 Hz, 2H), 3.721 (t, J=8.2 Hz, 2H), 6.888 (dd, J=1.8 & 8.2 Hz, 1H), 7.328 (d, J=1.8 Hz, 1H), 7.540 (s, 1H), 7.703 (d, J=8.8 Hz, 1H), 10.485 (s, 1H), 10.926 (s, 1H), 13.670 (s, 1H).

(Z)-2-(5-((6-(3-cyclopropyl-2-oxoimidazolidine-1-carboxamido)-2-oxoindolin-3-ylidene)methyl)-2,4-dimethyl-1H-pyrrol-3-yl)acetic acid (D97)

(C$_{24}$H$_{25}$N$_5$O$_5$.2/3H$_2$O) C, H, N.

(Z)-3-(5-((6-(3-cyclopropyl-2-oxoindolin-3-ylidene)methyl)-2,4-dimethyl-1H-pyrrol-3-yl)propanoic acid (D98)

YD: 55.34%: mp: 232-237° C. (charring). $^1$H NMR (400 MHz, DMSO-d$_6$) δ: 0.692 (d, J=5.2 Hz, 4H), 2.220 (s, 3H), 2.267 (s, 3H), 2.328 (t, J=7.6 Hz, 2H), 2.556-2.639 (m, 3H), 3.385 (t, J=8.2 Hz, 2H), 3.715 (t, J=8.6 Hz, 2H), 6.855 (dd, J=2.0 & 8.4 Hz, 1H), 7.290 (d, J=2.0 Hz, 1H), 7.436 (s, 1H), 7.611 (d, J=8.4 Hz, 1H), 10.434 (s, 1H), 10.734 (s, 1H), 13.217 (s, 1H).

(Z)-5-((6-(3-(2-fluorophenyl)-2-oxoimidazolidine-1-carboxamido)-2-oxoindolin-3-ylidene)methyl)-2,4-dimethyl-1H-pyrrole-3-carboxylic acid (D99)

(C$_{26}$H$_{22}$FN$_5$O$_5$.1/2H$_2$O) C, H, N.

(Z)-5-((6-(3-(2-fluoro-4-methoxyphenyl)-2-(oxoimidazolidine-1-carboxamido)-2-oxoindolin-3-ylidene)methyl)-2,4-dimethyl-1H-pyrrole-3-carboxylic acid (D100)

(C$_{27}$H$_{24}$N$_5$O$_5$. ½H$_2$O) C, H, N.

D81-D100 were prepared using appropriate stalling materials with procedure similar to D80,

Synthesis of Compounds of Formula III

1-(4-fluorophenyl)-2-oxo-1,2-dihydropyridine-3-carboxylic acid (D101)

To a solution of methyl 2-oxo-2H-pyran-3-carboxylate (375 mg, 2.43 mmol) in dry N,N-dimethylformamide (DMF) under room temperature (rt) was added 4-fluoroaniline (0.23 mL, 2.44 mmol), and the reaction mixture was stirred for 6 hours. To the mixture was added 1-(3-dimethylaminopropyl)-3-ethylcarbodiimide hydrochloride (EDCI, 465 mg, 2.43 mmol) and 4-dimethylaminopyridine (DMAP, 75 mg, 0.61 mmol), and was stirred for additional 12 hours. Reaction mixture was dumped to water followed by ethyl acetate partition. Organic layers were combined, washed by 3N hydrochloric acid and water, and concentrated in vacuo to give crude methyl 1-(4-fluorophenyl)-2-oxo-1,2-dihydropyridine-3-carboxylate. Crude methyl ester was saponified by 10% sodium hydroxide solution (10 mL) in methanol (20 mL). Reaction mixture was heated at 65° C. for 3 hrs. Solid precipitated during acidic workup by 3N hydrochloric acid was collected by filter, washed by methanol (small amount), water and diethyl ether, dried to give an intermediate compound, 1-(4-fluorophenyl)-2-oxo-1,2-dihydropyridine-3-carboxylic acid.

1-(4-fluorophenyl)-2-oxo-N-(2-oxoindolin-4-yl)-1,2-dihydropyridine-3-carboxamide (D102)

4-aminooxindole (80 mg, 0.54 mmol) was made to react to 1-(4-fluorophenyl)-2-oxo-1,2-dihydropyridine-3-carboxylic acid (125.5 mg, 0.54 mmol) in the presence of O-(benzotriazol-1-yl)-N,N,N',N'-tetramethyluronium tetrafluoroborate (TBTU, 250 mg, 0.78 mmol) and triethylamine (TEA, 0.23 mL, 1.62 mmol) in a mixture of dry DMF and acetonitrile (1:3, 6 mL) under rt for 14 hours. Resultant solid was collected by filter, washed by methanol, water and ether, and dried to give 1-(4-fluorophenyl)-2-oxo-N-(2-oxoindolin-4-yl)-1,2-dihydropyridine-3-carboxamide: YD: 56%; mp: 293-295° C. $^1$H-NMR (400 MHz, DMSO-d$_6$): 11.77 (s, 1H), 10.41 (s, 1H), 8.58 (dd, J=7.6, 2 Hz, 1H), 8.10 (dd, J=6.6, 2 Hz, 1H), 7.77 (d, J=8.4 Hz, 1H), 7.59 (m, 2H), 7.41 (d, J=8.8 Hz, 2H), 7.17 (dd, J=8, 7.6 Hz, 1H), 6.71 (dd, 7.6, 6.6 Hz, 1H), 6.68 (d, J=7.6 Hz, 1H), 3.36 (s, 2H). (C$_{20}$H$_{14}$N$_3$O$_3$F. 0.3; H$_2$O) C, H, N.

(Z)—N-(3-((1H-pyrrol-2-yl)methylene)-2-oxoindolin-4-yl)-1-(4-fluorophenyl)-2-oxo-1,2-dihydropyridine-3-carboxamide (D103)

1-(4-fluorophenyl)-2-oxo-N-2-oxoindolin-4-yl)-1,2-dihydropyridine-3-carboxamide (92 mg, 0.25 mmol) was made to react to pyrrole-2-carboxaldehyde (35 mg, 0.37 mmol) in the presence of catalytic pyrrolidine in ethanol under reflux. The solid product was collected by suction filtration and washed with ethanol. Prolonged drying in vacuo yielded the tide compound D103: YD: 79%; mp: >300° C. $^1$H-NMR (400 MHz, DMSO-d$_6$): 13.3 (s, 1H), 11.93 (s, 1H), 10.99 (s, 1H), 8.61 (dd, J=7.6, 1.6 Hz, 1H), 8.14-8.16 (m, 2H), 7.67-7.73 (m, 3H), 7.45 (m, 2H), 7.30 (s, 1H), 7.15 (dd, J=8, 8 Hz, 1H), 6.74 (dd, J=7.6, 7.2 Hz, 1H), 6.51 (s, 1H), 6.28 (s, 1H). MS (ESI): 439 (M−H)$^−$. (C$_{25}$H$_{17}$N$_4$O$_3$F. 0.1; H$_2$O) C, H, N.

(Z)—N-(3-((1H-pyrrol-2-yl)methylene)-2-oxoindolin-5-yl)-1-(4-fluorophenyl)-2-oxo-1,2-dihydropyridine-3-carboxamide (D104)

1-(4-fluorophenyl)-2-oxo-1,2-dihydropyridine-3-carboxylic acid (75 mg, 0.32 mmol) was chlorinated by thionyl chloride (0.1 mL, 1.38 mmol) in the presence of DMF in dichloromethane (10 mL). Reaction mixture was heated to reflux for 2 h. Solvent and excess thionyl chloride was removed in vacuo. Resultant residue was made to react to 5-aminooxindole (50 mg, 0.41 mmol) in the presence of TEA (0.2 mL, 1.43 mmol) in DMF (5 mL) under RT for 1 h. Crude product extracted by ethyl acetate (EA), washed with brine (50 mL). Residue after solvent removal was made to react with pyrrole-2-carboxaldehyde (32 mg, 0.37 mmol) in the presence of catalytic pyrrolidine in ethanol under reflux for 10 h. The solid product was collected by suction filtration, washed with ethanol. Prolonged drying in vacuo yielded the title compound D104: YD: 30% (over 3 steps); mp>300° C. $^1$H-NMR (400 MHz, DMSO-$d_6$): 13.30 (s, 1H), 11.92 (s, 1H), 10.84 (s, 1H), 8.56 (dd, J=7.2, 2 Hz, 1H), 8.07 (dd, J=6.6, 2 Hz, 1H), 7.92 (d, J=1.6 Hz, 1H), 7.76 (s, 1H), 7.61-7.54 (m, 3H), 7.43 (d, J=8.4, 1.6 Hz, 2H), 7.34 (s, 1H), 6.85-6.83 (m, 2H), 6.71 (dd, J=7.2, 6.8 Hz, 1H), 6.34 (s, 1H). MS (ESI): 439 (M−H)$^−$. ($C_{25}H_{17}FN_4O_3$) C, H, N.

(Z)—N-(3-((1H-pyrrol-2-yl)methylene)-2-oxoindolin-6-yl)-2-oxo-1-phenyl-1,2-dihydropyridine-3-carboxamide (D105)

YD: 66%; mp: >300° C. $^1$H-NMR (400 MHz, DMSO-$d_6$): 13.22 (s, 1H), 12.04 (s, 1H), 10.93 (s, 1H), 8.56 (dd, J=7.8, 2.0 Hz, 1H), 8.09 (dd, J=6.8, 2.0 Hz, 1H), 7.51-7.63 (m, 8H), 7.31 (s, 1H), 7.04 (d, J=8 Hz, 1H), 6.77 (s, 1H), 6.71 (dd, J=7.8, 6.8 Hz, 1H), 6.33 (s, 1H). Ms (ESI): 421 (M−H)$^−$. ($C_{25}H_{18}N_4O_3F. H_2O$) C, H, N.

(Z)—N-(3-((1H-pyrrol-2-yl)methylene)-2-oxoindolin-6-yl)-1-(4-methoxyphenyl)-2-oxo-1,2-dihydropyridine-3-carboxamide (D106)

YD: 69%; mp: >300° C. $^1$H-NMR (400 MHz, DMSO-$d_6$): 13.22 (s, 1H), 12.09 (s, 1H), 10.93 (s, 1H), 8.54 (dd, J=7.2, 2 Hz, 1H), 8.05 (dd, J=6.8, 2 Hz, 1H), 7.63 (s, 1H), 7.62 (d, J=1.6 Hz, 1H), 7.58 (d, J=8.4 Hz, 1H), 7.43 (d, J=8.8 Hz, 2H), 7.32 (s, 1H), 7.09 (d, J=8.8 Hz, 2H), 7.04 (dd, J=8.4, 1.6 Hz, 1H), 6.78 (s, 1H), 6.68 (dd, J=7.2, 6.8 Hz, 1H), 6.32 (s, 1H), 3.83 (s, 3H). ($C_{26}H_{20}N_4O_4.0.5H_2O$) C, H, N.

(Z)—N-(3-((1H-pyrrol-2-yl)methylene)-2-oxoindolin-6-yl)-1-(4-fluorophenyl)-2-oxo-1,2-dihydropyridine-3-carboxamide (D107)

YD: 84%; mp: 295-296° C. $^1$H-NMR (400 MHz, DMSO-$d_6$): 13.23 (s, 1H), 12.01 (s, 1H), 10.93 (s, 1H), 8.56 (dd, J=7.2, 2 Hz, 1H), 8.09 (dd, J=6.8, 2 Hz, 1H), 7.64 (s, 1H), 7.55-7.62 (m, 4H), 7.39-7.43 (m, 2H), 7.32 (s, 1H), 7.04 (dd, J=8.2, 2 Hz, 1H), 6.78 (s, 1H), 6.71 (dd, J=7.2, 6.8 Hz, 1H). MS (ESI): 439 (M−H)$^−$. ($C_{25}H_{17}N_4O_3F. 0.5; H_2O$) C, H, N.

(Z)—N-(3-(1H-pyrrol-2-yl)methylene)-2-oxoindolin-6-yl)-1-(4-chlorophenyl)-2-oxo-1,2-dihydropyridine-3-carboxamide (D108)

YD: 60%; mp: >300° C. $^1$H-NMR (400 MHz, DMSO-$d_6$): 13.22 (s, 1H), 11.97 (s, 1H), 10.93 (s, 1H), 8.55 (dd, J=7.2, 2 Hz, 1H), 8.08 (dd, J=6.8, 2 Hz, 1H), 7.55-7.65 (m, 7H), 7.31 (s, 1H), 7.04 (dd, J=8.2, 1.2 Hz, 1H), 6.78 (s, 1H), 6.71 (dd, J=7.2, 6.8 Hz, 1H), 6.32 (s, 1H), ($C_{25}H_{17}N_4O_3Cl.0.8H_2O$) C, H, N.

(Z)—N-(3-((1H-pyrrol-2-yl)methylene)-2-oxoindolin-6-yl)-1-(4-chloro-(3-trifluoromethyl)phenyl)-2-oxo-1,2-dihydropyridine-3-carboxamide (D109)

YD: 81%: mp>300° C. $^1$H-NMR (400 MHz, DMSO-$d_6$): 13.20 (s, 1H), 11.88 (s, 1H), 10.93 (s, 1H), 8.57 (dd, J=7.2, 2 Hz, 1H), 8.17 (d, J=2 Hz, 1H), 8.15 (dd, J=6.8, 2 Hz, 1H), 7.96 (d, J=8.4 Hz, 1H), 7.92 (dd, J=8.4, 2 Hz, 1H), 7.64 (s, 1H), 7.62 (d, J=1.2 Hz, 1H), 7.56 (d, J=8.4 Hz, 1H), 7.32 (s, 1H), 7.05 (dd, J=8, 1.6 Hz, 1H), 6.78 (s, 1H), 6.74 (dd, J=7.2, 6.8 Hz, 1H), 6.33 (s, 1H). ($C_{26}H_{16}N_4O_3Cl_3F$) C, H, N.

(Z)—N-(3-((1H-pyrrol-2-yl)methylene)-2-oxoindolin-6-yl)-1-(3,4-dichlorophenyl)-2-oxo-1,2-dihydropyridine-3-carboxamide (D110)

YD: 88%; mp: >300° C., $^1$H-NMR (200 MHz, DMSO-$d_6$): 13.22 (s, 1H), 11.92 (s, 1H), 10.96 (s, 1H), 8.56 (dd, J=7.3, 2.0 Hz, 1H), 8.12 (dd, J=6.6, 2.0 Hz, 1H), 7.99 (d, J=2.4 Hz, 1H), 7.86 (d, J=8.6 Hz, 1H), 7.64-7.55 (m, 4H), 7.32 (s, 1H), 7.04 (dd, J=8.6, 1.6 Hz, 1H), 6.78 (s, 1H), 6.73 (dd, J=7.3, 6.6 Hz, 1H), 6.34 (s, 1H). ($C_{25}H_{26}N_4O_3Cl_2.1.4H_2O$) C, H, N.

(Z)—N-(3-((1H-pyrrol-2-yl)methylene)-2-oxoindolin-6-yl)-2-oxo-1-p-tolyl-1,2-dihydropyridine-3-carboxamide (D111)

YD: 79%; mp: >300° C. $^1$H-NMR (400 MHz, DMSO-$d_6$): 13.22 (s, 1H), 12.06 (s, 1H), 10.93 (s, 1H), 8.54 (d, J=6.8 Hz, 1H), 8.04 (d, J=6.8 Hz, 1H), 7.55-7.62 (m, 3H), 7.31-7.37 (m, 5H), 7.03 (d, J=8 Hz, 1H), 6.77 (s, 1H), 6.68 (dd, J=6.8, 6.8 Hz, 1H), 6.33 (s, 1H), 2.34 (s, 3H). MS (ESI): 437 (M+H)$^+$. ($C_{26}H_{20}N_4O_3.0.5; H_2O$) C, H, N.

(Z)—N-(3-((1H-pyrrol-2-yl)methylene)-2-oxoindolin-6-yl)-1-(4-trifluoromethyl)phenyl)-2-oxo-1-dihydropyridine-3-carboxamide (D112)

YD: 77%; mp: >300° C., $^1$H-NMR (400 MHz, DMSO-$d_6$): 13.32 (s, 1H), 11.91 (s, 1H), 10.93 (s, 1H), 8.57 (dd, J=6.8 Hz, 1H), 8.12 (d, J=6.8 Hz, 1H), 7.96 (d, J=8 Hz, 2H), 7.79 (d, J=8 Hz, 2H), 7.62 (s, 1H), 7.60 (s, 1H), 7.56 (d, J=8.4 Hz, 1H), 7.31 (s, 1H), 7.04 (d, J=8 Hz, 1H), 6.78 (s, 1H), 6.74 (dd, J=6.8, 6.8 Hz, 1H), 6.33 (s, 1H). MS (ESI): 489 (M−H)$^−$. ($C_{26}H_{17}N_4O_3F_3$) C, H, N.

(Z)—N-(3-((1H-pyrrol-2-yl)methylene)-2-oxoindolin-6-yl)-1-(3-trifluoromethyl)phenyl)-2-oxo-1,2-dihydropyridine-3-carboxamide (D113)

YD: 87%; mp: >300° C. $^1$H-NMR (400 MHz, DMSO-$d_6$): 13.22 (s, 1H), 11.93 (s, 1H), 10.93 (s, 1H), 8.57 (dd. J=7.2, 2 Hz, 1H), 8.15 (dd, J=6.8, 2 Hz, 1H), 8.03 (s, 1H), 7.80-7.92 (m, 3H), 7.63 (m, 2H), 7.56 (d, J=8 Hz, 1H), 7.32 (s, 1H), 7.04 (dd, J=8, 1.6 Hz, 1H), 6.78 (s, 1H), 6.73 (dd, J=7.2, 6.8 Hz, 1H), 6.33 (s, 1H). MS (ESI); 489 (M−H)$^−$.

(Z)—N-(3-((1H-pyrrol-2-yl)methylene)-2-oxoindolin-6-yl)-1-(3-(chlorophenyl)-2-oxo-1,2-dihydropyridine-3-carboxamide (D114)

YD: 84%; mp: >300° C. $^1$H-NMR (400 MHz, DMSO-$d_6$): 13.22 (s, 1H), 11.95 (s, 1H), 10.93 (s, 1H), 8.56 (dd, J=6.8, 2 Hz, 1H), 8.09 (dd, J=6.8, 2 Hz, 1H), 7.73 (s, 1H), 7.59-7.60 (m, 3H), 7.56 (d, J=8 Hz, 1H), 7.53-7.50 (s, 1H), 7.31 (s, 1H), 7.05 (dd, J=8, 2 Hz, 1H), 6.78 (s, 1H), 6.72 (dd, J=6.8, 6.8 Hz, 1H), 6.33 (s, 1H). ($C_{25}H_{17}N_4O_3Cl.0.3H_2O$) C, H, N.

(Z)-3-((1H-pyrrol-2-yl)methylene)-2-oxoindolin-6-yl)-1-(2-fluorophenyl)-2-oxo-1,2-dihydropyridine-3-carboxamide (D115)

YD: 54%; mp: >300° C. $^1$H-NMR (400 MHz, DMSO-$d_6$): 13.22 (s, 1H), 11.86 (s, 1H), 10.93 (s, 1H), 8.60 (dd, J=7.2, 2 Hz, 1H), 8.13 (dd, J=6.6, 2 Hz, 1H), 7.65-7.59 (m, 4H), 7.56 (d, J=8 Hz, 1H), 7.50 (m, 1H), 7.42 (dd, J=7.6, 7.6 Hz, 1H), 7.31 (s, 1H), 7.04 (d, J=8.4 Hz, 1H), 6.75 (dd, J=7.2, 6.6 Hz, 2H), 6.33 (s, 1H). MS (ESI): 439 (M–H)$^-$. ($C_{25}H_{17}N_4O_3F.0.5H_2O$) C, H, N.

(Z)—N-(3-((1H-pyrrol-2-yl)methylene)-2-oxoindolin-6-yl)-1-methyl-2-oxo-1,2-dihydropyridine-3-carboxamide (D116)

YD: 65%; mp: >300° C. $^1$H-NMR (400 MHz, DMSO-$d_6$): 13.20 (s, 1H), 12.47 (s, 1H), 10.92 (s, 1H), 8.42 (dd, J=7.2, 2.0 Hz, 1H), 8.12 (dd, J=6.8, 2.0 Hz, 1H), 7.63 (s, 1H), 7.62 (d, J=1.6 Hz, 1H), 7.57 (d, J=8.4 Hz, 1H), 7.32 (s, 1H), 7.06 (dd, J=8.4, 1.6 Hz, 1H), 6.78 (s, 1H), 6.58 (dd, J=7.2, 6.8 Hz, 1H), 6.33 (s, 1H), 3.32 (s, 3H). MS (ESI): 359 (M–H)$^-$. ($C_{20}H_{16}N_4O_3$. 0.2; $H_2O$) C, H, N.

(Z)—N-(3-((1H-pyrrol-2-yl)methylene)-2-oxoindolin-6-yl)-1-(2-hydroxyethyl)-2-oxo-1,2-dihydropyridine-3-carboxamide (D117)

YD: 87%: mp: 298° C. (charring). $^1$H-NMR (400 MHz, DMSO-$d_6$): 13.22 (s, 1H), 12.27 (s, 1H), 10.91 (s, 1H), 8.45 (dd, J=7.4, 2.0 Hz, 1H), 8.02 (dd, J=6.8, 2.0 Hz, 1H), 7.64 (s, 1H), 7.63 (d, J=1.6 Hz, 1H), 7.58 (d, J=8.2 Hz, 1H), 7.31 (s, 1H), 7.06 (dd, J=8.2, 1.6 Hz, 1H), 6.78 (s, 1H), 6.59 (dd, J=7.4, 6.8 Hz, 1H), 6.33 (s, 1H), 4.95 (t, J=5.2 Hz, 1H), 4.15 (t, J=5.2 Hz, 2H), 3.72 (q, J=5.2 Hz, 2H). MS (ESI): 389 (M–H)$^-$. ($C_{21}H_{18}N_4O_4.0.25H_2O$) C, H, N.

(Z)—N-(3-((1H-pyrol-2-yl)methylene)-2-oxoindolin-7-yl)-1-(4-fluorophenyl)-2-oxo-1,2-dihydropyridine-3-carboxamide (D118)

YD: 82%; Mp: >300° C. $^1$H-NMR (400 MHz, DMSO-$d_6$): 13.30 (s, 1H), 11.35 (s, 1H), 10.58 (s, 1H), 8.55 (dd, J=7.2, 2 Hz, 1H), 8.09 (dd, J=6.8, 2 Hz, 1H), 7.78 (s, 1H), 7.57-7.60 (m, 2H), 7.52 (d, J=7.6 Hz, 1H), 7.39-7.44 (m, 2H), 7.36 (s, 1H), 7.16 (d, J=7.6 Hz, 1H), 7.00 (dd, J=7.6, 7.6 Hz, 1H), 6.86 (s, 1H), 6.71 (dd, J=7.2, 6.8 Hz, 1H), 6.36, (s, 1H). MS (ESI): 439 (M–H)$^-$. ($C_{25}H_{17}N_4O_3F.0.3H_2O$) C, H, N.

(Z)—N-(3-((3,5-dimethyl-1H-pyrrol-2-yl)methylene)-2-oxoindolin-6-yl)-1-(4-fluorophenyl)-2-oxo-1,2-dihydropyridine-3-carboxamide (D119)

YD: 48%; mp: >300° C., $^1$H-NMR (400 MHz, DMSO-$d_6$): 13.20 (s, 1H), 11.97 (s, 1H), 10.80 (s, 1H), 8.56 (dd, J=6.8, 1.6 Hz, 1H), 8.06 (dd, J=6.8, 1.6 Hz, 1H), 7.65 (d, J=8.4 Hz, 1H), 7.61-7.57 (m, 3H), 7.46 (s, 1H), 7.41 (d, J=8.8 Hz, 2H), 7.00 (d, J=8 Hz, 1H), 6.70 (dd, J=6.8, 6.8 Hz, 1H), 5.97 (s, 1H), 2.30 (s, 3H), 2.27 (s, 3H). MS (ESI): 467 (M–H)$^-$. ($C_{27}H_{21}N_4O_3F.1H_2O$) C, H, N.

(Z)-5-((6-(1-(4-fluorophenyl)-2-oxo-1,2-dihydropyridine-3-carboxamido)-2-oxoindolin-3-ylidene)methyl)-2,4-dimethyl-1H-pyrrole-3-carboxylic acid (D120)

YD: 49%; mp: >300° C. $^1$H-NMR (400 MHz, DMSO-$d_6$): 13.70 (s, 1H), 11.99 (s, 1H), 10.96 (s, 1H), 8.54 (dd, J=7.2, 2 Hz, 1H), 8.07 (dd, J=6.8, 2 Hz, 1H), 7.71 (d, J=8.4 Hz, 1H), 7.62-7.58 (m, 3H), 7.54 (s, 1H), 7.41 (d, J=8.8 Hz, 2H), 7.00 (d, J=8 Hz, 1H), 6.69 (dd, J=7.2, 6.8 Hz, 1H), 2.51 (s, 3H), 2.46 (s, 3H). MS (ESI): 511 (M–H)$^-$. ($C_{28}H_{21}FN_4O_5.1H_2O$) C, H, N.

(Z)-2-(5-((6-(1-(4-fluorophenyl)-2-oxo-1,2-dihydropyridine-3-carboxamido)-2-oxoindolin-3-ylidene)methyl)-2,4-dimethyl-1H-pyrrol-3-yl)acetic acid (D121)

YD: 40%; mp: 275° C. (Charring). $^1$H-NMR (400 MHz, DMSO-$d_6$): 13.30 (s, 1H), 11.98 (s, 1H), 10.81 (s, 1H), 8.55 (dd, J=6.8, 2 Hz, 1H), 8.08 (dd, J=6.8, 2 Hz, 1H), 7.66-7.58 (m, 4H), 7.48 (s, 1H), 7.41 (dd, J=8.8, 8.8 Hz, 2H), 7.00 (d, J=8.4 Hz, 1H), 6.70 (dd, J=6.8, 6.8 Hz, 1H), 3.28 (s, 2H), 2.27 (s, 3H), 2.21 (s, 3H). MS (ESI): 525 (M–H)$^-$.

(Z)-3-(5-((6-(1-(4-fluorophenyl)-2-oxo-1,2-dihydropyridine-3-carboxamido)-2-oxoindolin-3-ylidene)methyl)-2,4-dimethyl-1H-pyrrol-3-yl)propanoic acid (D122)

YD: 67%; mp: >300° C. $^1$H-NMR (400 MHz, DMSO-$d_6$): 13.22 (s, 1H), 11.98 (s, 1H), 10.79 (s, 1H), 8.55 (dd, J=7.4, 2 Hz, 1H), 8.08 (dd, J=6.4, 2 Hz, 1H), 7.67-7.58 (m, 4H), 7.47 (s, 1H), 7.41 (d, J=8.8, 8.8 Hz, 2H), 7.00 (dd, J=8.2, 1.8 Hz, 1H), 6.71 (dd, J=7.4, 6.4 Hz, 1H), 2.63 (t, J=7.4 Hz, 2H), 2.34 (t, J=7.4 Hz, 2H), 2.28 (s, 3H), 2.23 (s, 3H). MS (ESI): 539 (M–H)$^-$.

(Z)-methyl-3-(5-((6-(1-(4-fluorophenyl)-2-oxo-1,2-dihydropyridine-3-carboxamido)-2-oxoindolin-3-ylidene)methyl)-2,4-dimethyl-1H-pyrrol-3-yl)propanoate (D123)

YD: 73%; mp: 266-270° C. $^1$H-NMR (400 MHz, DMSO-$d_6$): 13.25 (s, 1H), 11.97 (s, 1H), 10.79 (s, 1H), 8.55 (dd, J=7.2, 2.2 Hz, 1H), 8.07 (dd, J=6.8, 2.2 Hz, 1H), 7.65 (d, J=8 Hz, 1H), 7.61-7.58 (m, 3H), 7.46 (s, 1H), 7.41 (d, J=8.8 Hz, 2H), 6.99 (dd, J=8.4, 1.6 Hz, 1H), 6.70 (dd, J=7.2, 6.8 Hz, 1H), 3.57 (s, 3H), 2.65 (t, J=7.6 Hz, 2H), 2.43 (t, J=7.6 Hz, 2H), 2.67 (s, 3H), 2.22 (s, 3H). MS (ESI): 553 (M–H)$^-$. ($C_{31}H_{27}FN_4O_5.0.7H_2O$) C, H, N.

(Z)-2,4-dimethyl-5-((6-(1-methyl-2-oxo-1,2-dihydropyridine-3-carboxamido)-2-oxoindolin-3-ylidene)methyl)-1H-pyrrole-3-carboxylic acid (D124)

YD: 69%; mp: >300° C. $^1$H-NMR (400 MHz, DMSO-$d_6$): 13.65 (s, 1H), 12.24 (s, 1H), 10.93 (brs, 1H), 8.41 (dd, J=6.8, 1.6 Hz, 1H), 8.10 (dd, J=6.8, 1.6 Hz, 1H), 7.71 (d, J=8.4 Hz, 1H), 7.60 (d, J=1.2 Hz, 1H), 7.53 (s, 1H), 7.03 (dd, J=8, 1.6 Hz, 1H), 6.57 (dd, J=6.8, 6.8 Hz, 1H), 3.61 (s, 3H), 2.51 (s, 3H), 2.46 (s, 3H), MS (ESI): 431 (M–H)$^-$. ($C_{23}H_{20}N_4O_5.0.5H_2O$) C, H, N.

D104-D124 were prepared using appropriate starting materials with procedure similar to D103.

Synthesis of Compounds of Formula IV

4-oxo-5-phenyl-1,4-dihydropyridine-3-carboxylic acid (D125)

To a solution of Meldrum's acid (1.0 g, 7.0 mmol) and dry TEA (5 mL, 35.6 mmol) in dry dichloromethane (15 mL) was added phenylacetyl chloride (0.95 mL, 7.13 mmol) dropwise at ice bath temperature. The reaction mixture was allowed to back to RT, stirred for 3.5 h. Crude adduct of Meldrum's acid and acetyl chloride was washed by 3N hydrochloric acid and concentrated. To the residue was added ethanol (20 mL); the reaction mixture was heated to reflux for 3 h. Resultant residue was made to react to N,N-dimethylformamide dimethyl acetal (1.5 mL, 11.2 mmol) in xylenes (15 mL) at 120° C. for 4 hrs with removal of methanol and concentrated in vacuo. The residue was cyclized by ammonium acetate (1.15 g) in methanol (20 mL) at reflux for 4 hrs. Crude ethyl ester was saponificated by 10% sodium hydroxide solution (10 mL) in methanol (20 mL). Reaction mixture was heated at 65° C. for 2.5 hours. Solid precipitated during acidic workup by 3N hydrochloric acid was collected by filter, washed by methanol (small amount), water and diethyl ether, dried to give the title compound D125 (671.2 mg, 21% over four steps). $^1$H-NMR (400 MHz, DMSO-d$_6$): 13.16 (brs, 1H, NH), 8.60 (d, J=1.6 Hz, 1H, pyridone-H), 8.23 (d, J=1.6 Hz, 1H, pyridone-H), 7.65 (d, J=8 Hz, 2H, ArH), 7.50-7.41 (m, 3H, ArH).

4-oxo-N-(2-oxoindolin-5-yl)-5-phenyl-1,4-dihydropyridine-3-carboxamide (D126)

The compound D124 (142 mg, 0.66 mmol) was made to react to 6-aminiooxindole (99.5 mg, 0.67 mmol) in the presence of TBTU (169 mg, 0.53 mmol) and TEA in a mixture of dry DMF and acetonitrile (1:1, 4 mL) under rt for 10 days. The solid product was collected by suction filtration and washed by water and acetonitrile. Prolonged drying in vacuo yielded the title compound D126 (61.6 mg, 27%).

(Z)—N-(3-(1H-pyrrol-2-yl)methylene)-2-oxoindolin-6-yl)-4-oxo-5-phenyl-1,4-dihydropyridine-3-carboxamide (D127)

The compound D126 (60 mg, 0.17 mmol) was made to react with pyrrole-2-carboxaldehyde yielded the title compound 1.27. YD: 30%; mp>300° C. $^1$H-NMR (400 MHz, DMSO-d$_6$): 13.25 (s, 1H), 13.10 (s, 1H), 10.92 (s, 1H), 8.58 (s, 1H), 8.05 (s, 1H), 7.65-7.62 (m, 4H), 7.57 (d, J=8 Hz, 1H), 7.44-7.36 (m, 3H), 7.31 (s, 1H), 7.08 (dd, J=8, 1.2 Hz, 1H), 6.78 (s, 1H), 6.32 (s, 1H). MS (ESI): 421 (M−H)$^-$. (C$_{25}$H$_{18}$N$_4$O$_3$F.H$_2$O) C, H, N.

(Z)—N-(3-((1H-pyrrol-2-yl)methylene)-2-oxoindolin-6-yl)-5-(4-methoxyphenyl)-4-oxo-1,4-dihydropyridine-3-carboxamide (D128)

YD: 49%; mp>300° C. $^1$H-NMR (400 MHz, DMSO-d$_6$): 13.22 (s, 1H), 13.15 (s, 1H), 10.92 (s, 1H), 8.55 (s, 1H), 8.00 (s, 1H), 7.63-7.56 (m, 5H), 7.31 (s, 1H), 7.08 (d, J=8.4 Hz, 1H), 6.98 (d, J=8.4 Hz, 2H), 6.78 (s, 1H), 6.33 (s, 1H), 3.79 (s, 3H). MS (ESI): 451 (M−H)$^-$. (C$_{26}$H$_{20}$N$_4$O$_4$.0.5H$_2$O) C, H, N.

(Z)—N-(3-((1H-pyrrol-2-yl)methylene)-2-oxoindolin-6-yl)-5-(4-fluorophenyl)-4-oxo-1,4-dihydropyridine-3-carboxamide (D129)

YD: 31%; mp>300° C. $^1$H-NMR (400 MHz, DMSO-d$_6$): 13.22 (s, 1H), 13.07 (s, 1H), 12.60 (s, 1H), 10.92 (s, 1H), 8.58 (s, 1H), 8.07 (s, 1H), 7.70 (d, J=8.8 Hz, 2H), 7.63 (s, 1H), 7.61 (d, J=1.6 Hz, 1H), 7.57 (d, J=8.4 Hz, 1H), 7.31 (s, 1H), 7.25 (d, J=8.4 Hz, 2H), 7.08 (dd, J=8.4, 1.6 Hz, 1H), 6.78 (s, 1H), 6.33 (s, 1H). MS (ESI): 439 (M−H)$^-$. (C$_{25}$H$_{17}$N$_4$O$_3$F.0.5H$_2$O) C, H, N.

(Z)—N-(3-((1H-pyrrol-2-yl)methylene)-2-oxoindolin-6-yl)-5-(4-chlorophenyl)-4-oxo-1,4-dihydropyridine-3-carboxamide (D130)

YD: 69%; mp>300° C. $^1$H-NMR (200 MHz, DMSO-d$_6$): 13.25 (s, 1H), 13.07 (s, 1H), 12.68 (brs, 1H), 10.96 (s, 1H), 8.60 (d, J=1.2 Hz, 1H), 8.12 (d, J=1.2, 1H), 7.72 (d, J=8.4 Hz, 2H), 7.66-7.57 (m, 3H), 7.50 (d, J=8.4 Hz, 2H), 7.33 (s, 1H), 7.09 (dd, J=8, 1.7 Hz, 1H), 6.80 (s, 1H), 6.34 (s, 1H). MS (ESI): 439 (M−H)$^-$. (C$_{25}$H$_{17}$N$_4$O$_3$Cl.0.5H$_2$O) C, H, N.

(Z)—N-(3-((1H-pyrrol-2-yl)methylene)-2-oxoindolin-6-yl)-5-p-tolyl-4-oxo-1,4-dihydropyridine-3-carboxamide (D131)

YD: 41%; mp>300° C. $^1$H-NMR (400 MHz, DMSO-d$_6$): 13.22 (s, 1H), 13.13 (s, 1H), 10.91 (s, 1H), 8.57 (d, J=1.2 Hz, 1H), 8.01 (d, J=1.2 Hz, 1H), 7.64 (s, 1H), 7.60 (d, J=1.4 Hz, 1H), 7.58-7.53 (m, 3H), 7.31 (s, 1H), 7.23 (d, J=7.9 Hz, 2H), 7.07 (dd, J=7.9, 1.5 Hz, 1H), 6.78 (s, 1H), 6.33 (s, 1H), 2.33 (s, 3H). MS (ESI): 435 (M−H)$^-$. (C$_{26}$H$_{20}$N$_4$O$_3$.0.8H$_2$O) C, H, N.

(Z)—N-(3-((1H-pyrrol-2-yl)methylene)-2-oxoindolin-6-yl)-5-(3-chlorophenyl)-4-oxo-1,4-dihydropyridine-3-carboxamide (D132)

YD: 61%; mp>300° C. $^1$H-NMR (400 MHz, DMSO-d$_6$): 13.23 (s, 1H), 12.97 (s, 1H), 12.64 (br s, 1H), 10.91 (s, 1H), 8.59 (d, J=1.3 Hz, 1H), 8.13 (d, J=1.3 Hz, 1H), 7.77 (s, 1H), 7.62 (s, 2H), 7.60 (d, J=7.2 Hz, 1H), 7.57 (d, J=8.2 Hz, 1H), 7.48-7.41 (m, 2H), 7.30 (s, 1H), 7.09 (dd, J=8.2, 1.6 Hz, 1H), 6.78 (s, 1H), 6.34 (s, 1H). MS (ESI): 455 (M−H)$^-$. (C$_{25}$H$_{17}$N$_4$O$_3$Cl.0.5H$_2$O) C, H, N.

(Z)—N-(3-((1H-pyrrol-2-yl)methylene)-2-oxoindolin-6-yl)-4-oxo-5-(4-trifluoromethyl)phenyl)-1,4-dihydropyridine-3-carboxamide (D133)

mp>300° C. $^1$H-NMR (400 MHz, DMSO-d$_6$): 13.24 (s, 1H), 12.99 (s, 1H), 12.68 (brs, 1H), 10.91 (s, 1H), 8.62 (d, J=1.2 Hz, 1H), 8.18 (d, J=1.2 Hz, 1H), 7.89 (d, J=8 Hz, 2H), 7.79 (d, J=8 Hz, 2H), 7.63 (s, 1H), 7.60 (d, J=1.5 Hz, 1H), 7.57 (d, J=8.2 Hz, 1H), 7.31 (s, 1H), 7.08 (dd, J=8.2, 1.5 Hz, 1H), 6.78 (s, 1H), 6.32 (s, 1H). MS (ESI): 489 (M−H)$^-$. (C$_{26}$H$_{17}$N$_4$O$_3$F$_3$.1H$_2$O) C, H, N.

(Z)—N-(3-((1H-pyrrol-2-yl)methylene)-2-oxoindolin-6-yl)-4-oxo-5-(2-fluorophenyl)-1,4-dihydropyridine-3-carboxamide (D134)

YD: 42%; mp>300° C. $^1$H-NMR (400 MHz, DMSO-d$_6$): 13.23 (s, 1H), 12.96 (s, 1H), 10.94 (s, 1H), 8.63 (s, 1H), 8.04 (s, 1H), 7.63 (s, 1H), 7.61 (d, J=1.6 Hz, 1H), 7.56 (d, J=8.2 Hz, 1H), 7.47-7.42 (m, 2H), 7.32 (s, 1H), 7.29-7.24 (m, 2H), 7.06 (dd, J=8.2, 1.6 Hz, 1H), 6.78 (s, 1H), 6.32 (s, 1H). MS (ESI): 439 (M−H)$^-$. (C$_{25}$H$_{17}$N$_4$O$_3$F.0.3H$_2$O) C, H, N.

(Z)—N-(3-((1H-pyrrol-2-yl)methylene)-2-oxoindolin-6-yl)-4-oxo-5-(2,4-difluorophenyl)-1,4-dihydropyridine-3-carboxamide (D135)

YD: 32%; mp>300° C. 1H-NMR (400 MHz, DMSO-d$_6$): 13.20 (s, 1H), 12.91 (s, 1H), 10.92 (s, 1H), 8.62 (s, 1H), 8.05

(s, 1H), 7.63 (s, 1H), 7.61 (s, 1H), 7.58-7.49 (m, 2H), 7.31 (s, 2H), 7.19-7.13 (m, 1H), 7.05 (d, J=8 Hz, 1H), 6.78 (s, 1H), 6.33 (s, 1H). MS (ESI): 457 (M–H)⁻. ($C_{25}H_{16}F_2N_4O_3$.1.2$H_2O$) C, H, N.

(Z)—N-(3-((1H-pyrrol-2-yl)methylene)-2-oxoindolin-6-yl)-4-oxo-5-(3,5-difluorophenyl)-1,4-dihydropyridine-3-carboxamide (D136)

YD: 28%; mp>300° C.; ¹H-NMR (400 MHz, DMSO-$d_6$): 13.21 (s, 1H), 12.92 (s, 1H), 10.92 (s, 1H), 8.60 (d, J=1.2 Hz, 1H), 8.21 (d, J=1.2 Hz, 1H), 7.63 (s, 1H), 7.62 (d, J=1.8 Hz, 2H), 7.57 (d, J=8.2 Hz, 1H), 7.48 (d, J=1.8 Hz, 1H), 7.46 (d, J=1.8 Hz, 1H), 7.31 (s, 1H), 7.26-7.19 (m, 1H), 7.08 (dd, J=8.2, 1.8 Hz, 1H), 6.78 (s, 1H), 6.34 (s, 1H). MS (ESI): 457 (M–H)⁻. ($C_{25}H_{16}N_4O_3F_2$.0.6$H_2O$) C, H, N.

(Z)—N-(3-((1H-pyrrol-2-yl)methylene)-5-fluoro-2-oxoindolin-6-yl)-5-(4-fluorophenyl)-4-oxo-1,4-dihydropyridine-3-carboxamide (D137)

YD: 42%; mp>300° C., ¹H-NMR (400 MHz, DMSO-$d_6$): 13.28 (s, 1H), 13.26 (s, 1H), 12.59 (brs, 1H), 10.89 (s, 1H), 8.59 (s, 1H), 8.17 (d, J=6.4 Hz, 1H), 8.06 (s, 1H), 7.71-7.63 (m, 4H), 7.35 (s, 1H), 7.26 (d, J=8.8, 8.8 Hz, 2H), 6.78 (s, 1H), 6.36 (s, 1H). MS (ESI): 457 (M–H)⁻. ($C_{26}H_{20}N_4O_3F_2$.$H_2O$) C, H, N.

(Z)—N-(3-((1H-pyrrol-2-yl)methylene)-2-oxoindolin-6-yl)-5-(4-fluorophenyl)-1-methyl-4-oxo-1,4-dihydropyridine-3-carboxamide (D138)

YD: 81%. ¹H-NMR (400 MHz, DMSO-$d_6$): 13.22 (s, 1H), 13.06 (s, 1H), 10.91 (s, 1H), 8.63 (d, J=2.2 Hz, 1H), 8.12 (d, J=2.2 Hz, 1H), 7.71 (d, J=8.8 Hz, 2H), 7.62 (s, 1H), 7.60 (d, J=1.8 Hz), 7.56 (d, J=8.2 Hz, 1H), 7.31 (s, 1H), 7.26 (d, J=8.8 Hz, 2H), 7.07 (dd, J=8.2, 1.8 Hz, 1H), 6.78 (s, 1H), 6.33 (s, 1H), 3.90 (s, 3H). MS (ESI): 453 (M–H)⁻. ($C_{26}H_{19}N_4O_3F$.0.5$H_2O$) C, H, N.

(Z)—N-(3-((1H-pyrrol-2-yl)methylene)-2-oxoindolin-6-yl)-5-methyl-4-oxo-1,4-dihydropyridine-3-carboxamide (D139)

YD: 68%; mp: >300° C. ¹H-NMR (400 MHz, DMSO-$d_6$): 13.22 (s, 1H), 13.12 (s, 1H), 10.91 (s, 1H), 8.51 (s, 1H), 7.84 (s, 1H), 7.62 (s, 1H), 7.61 (s, 1H), 7.57 (d, J=8 Hz, 1H), 7.31 (s, 1H), 7.07 (d, J=8 Hz, 1H), 6.78 (s, 1H), 6.33 (s, 1H), 1.99 (s, 3H). MS (ESI): 359 (M–H)⁻. ($C_{20}H_{16}N_4O_3$.0.7$H_2O$) C, H, N.

(Z)—N-(3-((3,5-dimethyl-1H-pyrrol-2-yl)methylene)-2-oxoindolin-6-yl)-5-(4-fluorophenyl)-4-oxo-1,4-dihydropyridine-3-carboxamide (D140)

YD: 48%; mp: >300° C. ¹H-NMR (400 MHz, DMSO-$d_6$): 13.21 (s, 1H), 13.00 (s, 1H), 12.59 (brs, 1H), 10.80 (s, 1H), 8.58 (s, 1H), 8.07 (s, 1H), 7.71-7.66 (m, 3H), 7.62 (s, 1H), 7.48 (s, 1H), 7.25 (d, J=8.8 Hz, 2H), 7.04 (d, J=7.8 Hz, 1H), 5.98 (s, 1H), 2.29 (s, 3H), 2.28 (s, 3H), MS (ESI): 467 (M–H)⁻.

(Z)-5-((6-(5-(4-fluorophenyl)-4-oxo-1,4-dihydropyridine-3-carboxamido)-2-oxoindolin-3-ylidene)methyl)-2,4-dimethyl-1H-pyrrole-3-carboxylic acid (D141)

YD: 75%; mp: 283° C. ¹H-NMR (400 MHz, DMSO-$d_6$): 13.30 (s, 1H), 13.08 (s, 1H), 10.97 (s, 1H), 8.58 (s, 1H), 8.07 (s, 1H), 7.75 (d, J=8.4 Hz, 1H), 7.71 (d, J=8.4 Hz, 1H), 7.70 (d, J=8.8 Hz, 1H), 7.64 (s, 1H), 7.57 (s, 1H), 7.26 (d, J=8.4 Hz, 2H), 7.05 (d, J=8 Hz, 1H), 2.52 (s, 3H), 2.47 (s, 3H). MS (ESI): 5.11 (M–H)⁻.

(Z)-5-((6-(5-(4-methoxyphenyl)-4-oxo-1,4-dihydropyridine-3-carboxamido)-2-oxoindolin-3-ylidene)methyl)-2,4-dimethyl-1H-pyrrole-3-carboxylic acid (D142)

YD: 24%. ¹H-NMR (400 MHz, DMSO-$d_6$): 13.70 (s, 1H), 13.10 (s, 1H), 12.54 (s, 1H), 10.96 (s, 1H), 8.54 (dd, J=6, 1.2 Hz, 1H), 7.99 (dd, J=6, 1.2 Hz, 1H), 7.74 (d, J=8 Hz, 1H), 7.63 (d, J=1.6 Hz, 1H), 7.34 (d, J=8.4 Hz, 2H), 7.56 (s, 1H), 7.06 (dd, J=8, 1.6 Hz, 1H), 6.98 (d, J=8.4 Hz, 2H), 3.79 (s, 3H), 2.51 (s, 3H), 2.30 (s, 3H). MS (ESI): 523 (M–H)⁻. ($C_{29}H_{24}N_4O_6$.0.7$H_2O$) C, H, N.

(Z)-2,4-dimethyl-5-((6-(5-methyl-4-oxo-1,4-dihydropyridine-3-carboxamido)-2-oxoindolin-3-ylidene)methyl)-1H-pyrrole-3-carboxylic acid (D143)

YD: 56%; mp: >300° C. ¹H-NMR (400 MHz, DMSO-$d_6$): 13.68 (s, 1H), 13.11 (s, 1H), 12.24 (brs, 1H), 12.05 (brs, 1H), 10.94 (s, 1H), 8.50 (s, 1H), 7.82 (s, 1H), 7.72 (d, J=8.4 Hz, 1H), 7.61 (d, J=1.6 Hz, 1H), 7.54 (s, 1H), 7.04 (dd, J=8.4, 1.6 Hz, 1H), 2.51 (s, 3H), 2.47 (s, 3H), 1.99 (s, 3H). MS (ESI): 431 (M–H)⁻.

(Z)-2-(5-((6-(5-(4-fluorophenyl)-4-oxo-1,4-dihydropyridine-3-carboxamido)-2-oxoindolin-3-ylidene)methyl)-2,4-dimethyl-1H-pyrrol-3-yl)acetic acid (D144)

YD: 39%; mp: >300° C. ¹H-NMR (100 MHz, DMSO-$d_6$): 13.30 (s, 1H), 13.00 (s, 1H), 12.35 (brs, 1H), 10.81 (s, 1H), 8.58 (s, 1H), 8.06 (s, 1H), 7.72-7.66 (m, 3H), 7.62 (s, 1H), 7.49 (s, 1H), 7.25 (d, J=8.8 Hz, 2H), 7.04 (d, J=7.2 Hz, 1H), 3.31 (s, 2H), 2.27 (s, 3H), 2.22 (s, 3H), MS (ESI): 525 (M–H)⁻.

(Z)-3-(5-((6-(5-(4-fluorophenyl)-4-oxo-1,4-dihydropyridine-3-carboxamido)-2-oxoindolin-3-ylidene)methyl)-2,4-dimethyl-1H-pyrrol-3-yl)propanoic acid (D145)

YD: 75%; mp: >300° C. ¹H-NMR (400 MHz, DMSO-$d_6$): 13.30 (s, 1H), 12.98 (s, 1H), 12.62 (brs, 1H), 10.78 (s, 1H), 8.58 (d, J=6 Hz, 1H), 8.06 (d, J=6 Hz, 1H), 7.72-7.65 (m, 3H), 7.61 (s, 1H), 7.47 (s, 1H), 7.25 (d, J=8.8 Hz, 2H), 7.03 (d, J=8 Hz, 1H), 2.63 (t, J=7.2 Hz, 2H), 2.34 (t, J=7.2 Hz, 2H), 2.28 (s, 3H), 2.23 (s, 3H), MS (ESI): 539 (M–H)⁻.

(Z)-5-((6-(5-(4-fluorophenyl)-4-oxo-1,4-dihydropyridine-3-carboxamido)-2-oxoindolin-3-ylidene)methyl)-4-methyl-1H-pyrrole-2-carboxylic acid (D146)

YD: 56%; mp: 243° C. ¹H-NMR (400 MHz, DMSO-$d_6$): 13.70 (s, 1H), 13.10 (s, 1H), 12.67 (s, 1H), 11.02 (s, 1H), 8.58 (s, 1H), 8.06 (s, 1H), 7.78 (d, J=8 Hz, 1H), 7.62 (d, J=8.4 Hz, 2H), 7.66 (s, 1H), 7.57 (s, 1H), 7.25 (d, J=8.4 Hz, 2H), 7.07 (d, J=8 Hz, 1H), 6.70 (s, 1H), 2.31 (s, 3H). MS (ESI): 497 (M–H)⁻. ($C_{27}H_{19}FN_4O_5$.1.7$H_2O$) C, H, N.

(Z)-3-(5-((6-(5-(2,4-difluorophenyl)-4-oxo-1,4-dihydropyridine-3-carboxamido)-2-oxoindolin-3-ylidene)methyl)-2,4-dimethyl-1H-pyrrol-3-yl)propanoic acid (D147)

YD: 82%. ¹H-NMR (400 MHz, DMSO-d₆): 13.28 (s, 1H), 12.83 (s, 1H), 12.66 (s, 1H), 10.78 (s, 1H), 12.00 (br s, 1H), 8.62 (s, 1H), 8.05 (s, 1H), 7.66-7.47 (m, 4H), 7.31 (s, 1H), 7.16 (s, 1H), 7.01 (s, 1H), 2.62 (s, 2H), 2.33 (s, 2H), 2.28 (s, 3H), 2.23 (s, 3H). MS (ESI): 557 (M−H)⁻.

(Z)-3-(5-((6-(5-(3,5-difluorophenyl)-4-oxo-1,4-dihydropyridine-3-carboxamido)-2-oxoindolin-3-ylidene)methyl)-2,4-dimethyl-1H-pyrrol-3-yl)propanoic acid (D148)

YD: 68%; mp: >300° C. ¹H-NMR (400 MHz, DMSO-d₆): 13.33 (s, 1H), 12.85 (s, 1H), 12.10 (brs, 1H), 10.78 (s, 1H), 8.59 (s, 1H), 8.21 (s, 1H), 7.66 (d, J=8.4 Hz, 2H), 7.63 (s, 1H), 7.47-7.46 (m, 3H), 7.26-7.21 (m, 1H), 7.04 (d, J=8.4 Hz, 1H), 2.63 (t, J=7.2 Hz, 2H), 2.34 (t, J=7.6 Hz, 2H), 2.28 (s, 3H), 2.23 (s, 3H). MS (ESI): 557 (M−H)⁻.

(Z)—N-(3-((3,5-dimethyl-4-(4-methylpiperazine-1-carbonyl)-1H-pyrrol-2-yl)methylene)-2-oxoindolin-6-yl)-5-(4-fluorophenyl)-4-oxo-1,4-dihydropyridine-3-carboxamide (D149)

YD: 35%; mp: 283° C. (charring). ¹H-NMR (400 MHz, DMSO-d₆): 13.46 (s, 1H), 13.05 (s, 1H), 10.91 (s, 1H), 8.58 (s, 1H), 8.06 (s, 1H), 7.70 (dd, J=7.6, 7.2 Hz, 2H and 1H), 7.63 (s, 1H), 7.51 (s, 1H), 7.25 (dd, J=9.2, 8.8 Hz, 2H), 7.05 (d, J=8 Hz, 1H), 3.45 (brs, 4H), 2.27 (brs, 7H), 2.23 (s, 3H), 2.18 (s, 3H). MS (ESI): 593 (M−H)⁻. (C₃₃H₃₁FN₆O₆.0.5H₂O) C, H, N.

(Z)—N-(3-((3,5-dimethyl-4-(2-(4-methylpiperazin-1-yl)-2-oxoethyl)-1H-pyrrol-2-yl)methylene)-2-oxoindolin-6-yl)-5-(4-fluorophenyl)-4-oxo-1,4-dihydropyridine-3-carboxamide (D150)

YD: 61%; mp: >300° C. ¹H-NMR (400 MHz, DMSO-d₆): 13.28 (s, 1H), 13.00 (s, 1H), 10.78 (s, 1H), 8.57 (d, J=1.2 Hz, 1H), 8.06 (d, J=1.2 Hz, 1H), 7.71 (d, J=8.8 Hz, 1H), 7.69 (d, J=8.4 Hz, 1H), 7.65 (d, J=8.4, 1H), 7.61 (d J=1.6 Hz, 1H), 7.47 (s, 1H), 7.25 (dd, J=8.8 Hz, 1H), 7.04 (d, J=1.6 Hz, 1H), 7.02 (d, J=1.6 Hz, 1H), 3.49 (brs, 4H), 3.46 (s, 3H), 2.22 (brs, 7H), 2.17 (s, 3H), 2.16 (s, 3H). MS (ESI): 607 (M−H)⁻. (C₃₄H₃₃FN₄O₆.0.3H₂O) C, H, N.

(Z)—N-(3-((3,5-dimethyl-4-(3-(4-methylpiperazin-1-yl)-3-oxopropyl)-1H-pyrrol-2-yl)methylene)-2-oxoindolin-6-yl)-5-(4-fluorophenyl)-4-oxo-1,4-dihydropyridine-3-carboxamide (D151)

YD: 72%; mp: 250° C. ¹H-NMR (400 MHz, DMSO-d₆): 14.12 (s, 1H), 13.30 (s, 1H), 10.72 (s, 1H), 8.58 (s, 1H), 7.97 (s, 1H), 7.70 (d, J=6.4 Hz, 2H), 7.63-7.60 (m, 2H), 7.43 (s, 1H), 7.16 (d, J=8.4 Hz, 2H), 7.01 (d, J=8.4 Hz, 1H), 2.61-2.60 (m, 2H), 2.43-2.39 (m, 2H), 2.27-2.12 (m, 7H); MS (ESI): 621 (M−H)⁻.

(Z)—N-(3-((3,5-dimethyl-4-(morpholine-4-carbonyl)-1H-pyrrol-2-yl)methylene)-2-oxoindolin-6-yl)-5-(4-fluorophenyl)-4-oxo-1,4-dihydropyridine-3-carboxamide (D152)

YD: 26%. ¹H-NMR (400 MHz, DMSO-d₆): 13.45 (s, 1H), 13.05 (s, 1H), 12.60 (brs, 1H), 10.91 (s, 1H), 8.58 (d, J=1.2 Hz, 1H), 8.07 (d, J=1.2 Hz, 1H), 7.73-7.68 (m, 3H), 7.64 (d, J=1.6 Hz, 1H), 7.52 (s, 1H), 7.26 (dd, J=9.2, 8.8 Hz, 2H), 7.05 (dd, J=8.4, 1.6 Hz, 1H) 3.57 (s, 4H) 3.46 (s, 4H), 2.28 (s, 3H), 2.24 (s, 3H), MS (ESI): 580 (M−H)⁻. (C₃₂H₂₈FN₅O₅.0.5H₂O) C, H, N.

(Z)—N-(3-((3,5-dimethyl-4-(2-morpholino-2-oxoethyl)-1H-pyrrol-2-yl)methylene)-2-oxoindolin-6-yl)-5-(4-fluorophenyl)-4-oxo-1,4-dihydropyridine-3-carboxamide (D153)

YD: 55%. ¹H-NMR (400 MHz, DMSO-d₆): 13.30 (s, 1H), 13.05 (s, 1H), 10.78 (s, 1H), 8.57 (s, 1H), 8.05 (s, 1H), 7.70 (d, J=8.4 Hz, 2H), 7.65 (d, J=8.4 Hz, 1H), 7.61 (s, 1H), 7.46 (s, 1H), 7.25 (d, J=8.8 Hz, 2H), 7.03 (d, J=8.4 Hz, 1H), 3.53-3.44 (br, 10H), 2.23 (s, 3H), 2.17 (s, 3H). MS (ESI): 594 (M−H)⁻. (C₃₃H₃₀N₄O₅F.1H₂O) C, H, N.

(Z)—N-(3-((3,5-dimethyl-4-(4-methylpiperazine-1-carbonyl)-1H-pyrrol-2-yl)-methylene)-2-oxoindolin-6-yl)-5-(4-methoxyphenyl)-4-oxo-1,4-dihydropyridine-3-carboxamide (D154)

YD: 32% (for two steps); mp: 235° C. (charring). ¹H-NMR (400 MHz, DMSO-d₆): 13.54 (s, 1H), 13.12 (s, 1H), 12.50 (brs, 1H), 10.91 (s, 1H), 8.56 (s, 1H), 8.00 (s, 1H), 7.71 (d, J=8 Hz, 1H), 7.64 (d, J=1.6 Hz, 1H), 7.61 (dd. J=8.8, 8.8 Hz, 2H), 7.52 (s, 1H), 7.05 (dd, J=8, 1.6 Hz, 1H), 6.99 (dd, J=8.8, 8.8 Hz, 2H), 3.79 (s, 3H), 3.50 (brs, 4H), 2.27 (s, 7H), 2.23 (s, 3H), 2.18 (s, 3H). MS (ESI): 605 (M−H)⁻. (C₃₄H₃₄N₆O₅.2H₂O) C, H, N.

(Z)—N-(3-((3,5-dimethyl-4-(morpholine-4-carbonyl)-1H-pyrrol-2-yl)methylene)-2-oxoindolin-6-yl)-5-(4-methoxyphenyl)-4-oxo-1,4-dihydropyridine-3-carboxamide (D155)

YD: 49%; mp 205° C. (charring). ¹H-NMR (400 MHz, DMSO-d₆): 13.45 (s, 1H), 13.10 (s, 1H), 12.50 (brs, 1H), 10.91 (s, 1H), 8.55 (s, 1H), 8.00 (s, 1H), 7.72 (d, J=8 Hz, 1H), 7.64 (s, 1H), 7.60 (d, J=8.8 Hz, 2H), 7.52 (s, 1H), 7.05 (dd, J=8.4, 1.6 Hz, 1H), 6.99 (d, J=8.8 Hz, 2H), 3.79 (s, 3H), 3.57 (s, 4H), 3.46 (s, 4H), 2.28 (s, 3H), 2.24 (s, 3H). MS (ESI): 592 (M−H)⁻. (C₃₃H₃₁N₅O₆.2.2H₂O) C, H, N.

(Z)—N-(3-((3,5-dimethyl-4-((2-(pyrrolidin-1-yl)ethyl)carbamoyl)-1H-pyrrol-2-yl)methylene)-2-oxoindolin-6-yl)-5-(4-methoxyphenyl)-4-oxo-1,4-dihydropyridine-3-carboxamide (D156)

YD: 27% (for two steps); mp: >300° C. ¹H-NMR (400 MHz, DMSO-d₆): 13.50 (s, 1H), 13.20 (s, 1H), 10.91 (s, 1H), 8.55 (s, 1H), 8.00 (s, 1H), 7.72 (d, J=8 Hz, 1H), 7.64 (s, 1H), 7.60 (d, J=8.4 Hz, 2H), 7.53 (s, 1H), 7.48 (d, J=5.6 Hz, 1H), 7.05 (dd, J=7.6, 1.6 Hz, 1H), 6.98 (d, J=8.8 Hz, 2H), 3.79 (s, 3H), 3.34 (t, J=7.2, 6.4 Hz, 2H), 2.64 (t, J=6.8, 6.4 Hz, 2H), 2.57 (s, 4H), 2.37 (s, 3H), 2.33 (s, 3H), 1.69 (s, 4H); MS (ESI): 619 (M−H)⁻. (C₃₆H₄₀N₆O₅.1.1H₂O) C, H, N.

D128-D156 were prepared using appropriate starting materials with procedure similar to D127.

Compounds of formula (I)-(IV) were evaluated for abilities in inhibiting protein kinases aurora B and FLT-3 activity using radioisotope-based P81 filter-binding assay (Table 1). The IC₅₀ values were averaged from two independent dose-response curves with the variation was generally <30; The numbers in parentheses are the mean values (n=2) for percent inhibition of enzyme catalytic activity after treatment with compound at 1.0 μM. Dual inhibitors of aurora B and FLT-3 kinases have potential for the improvement in efficacy and reducing the susceptibility to resistance in FLT-3 mutated acute myeloid leukemia. D49, D50, D51, D52, D90 and D94 showed selective inhibition of aurora B over FLT-3 and other aurora kinases with selectivity index (SI) of more than 150 fold (SI=$IC_{50}$ for FLT-3 or other aurora kinases/$IC_{50}$ for aurora B kinase).

TABLE 1

| Cpd. No. | Enzyme assay $IC_{50}$ (nM) | | Cpd. No. | Enzyme assay $IC_{50}^a$ (nM) | |
|---|---|---|---|---|---|
| | Aur B | FLT-3 | | Aur B | FLT-3 |
| D13 | (11.2) | 58.2 | D85 | 14.3 | 1787.5 |
| D14 | (39.3) | 201.1 | D86 | 145.3 | 500.6 |
| D15 | 14.9 | 333.9 | D87 | 1037.5 | 569.1 |
| D16 | (7.3) | (6.9) | D88 | 824.0 | 498.4 |
| D17 | (61.2) | (34.4) | D89 | 37.9 | 74.1 |
| D18 | (12.8) | (6.1) | D90 | 1.8 | >10000.0 |
| D19 | (55.9) | (43.2) | D91 | (25.3) | (26.0) |
| D20 | (28.7) | >1000.00 | D92 | 19.3 | 223.3 |
| D21 | (7.0) | (3.6) | D93 | 24.2 | 1224.1 |
| D22 | 21.5 | >1000.00 | D94 | 4.4 | >10000.0 |
| D23 | (44.0) | (15.4) | D95 | 3.7 | 39.4 |
| D24 | 5.3 | >10,000.0 | D96 | 3.5 | 216.5 |
| D25 | 6.5 | 675.8 | D97 | 2.7 | 113.5 |
| D26 | 7.7 | >1000.0 | D98 | 3.2 | 119.3 |
| D27 | 40.9 | >1000.0 | D103 | >1000 | >1000 |
| D28 | 15.0 | 384.8 | D104 | >1000 | >1000 |
| D29 | 18.4 | >1000.0 | D105 | 87.4 | 48.4 |
| D30 | 29.8 | >1000.0 | D106 | 209.3 | >1000 |
| D31 | 158.7 | 133.5 | D107 | 791.1 | 8.6 |
| D32 | 2.1 | 904.5 | D108 | >1000 | 26.3 |
| D33 | 3.1 | 506.5 | D109 | >1000 | 77.4 |
| D34 | 2.1 | 54.2 | D110 | >1000 | 59.9 |
| D35 | 3.1 | 230.6 | D111 | 209.4 | 37.5 |
| D36 | 10.7 | 51.6 | D112 | >1000 | 136.9 |
| D37 | 1.6 | 2.4 | D113 | 688.9 | 134.1 |
| D38 | 1.2 | >1000.0 | D114 | 250.6 | 91.2 |
| D39 | 2.5 | 264.9 | D115 | 137.6 | 534.8 |
| D40 | 1.9 | 6.1 | D116 | 102.2 | 510.0 |
| D41 | 1.9 | 179.8 | D117 | 32.5 | 612.3 |
| D42 | 2.1 | 115.3 | D118 | >1000 | >1000 |
| D43 | (12.4) | >1000.0 | D119 | >1000 | 8.1 |
| D44 | 55.5 | >1000.0 | D120 | 10.7 | 8.1 |
| D45 | (20.9) | (10.0) | D121 | 5.0 | 7.3 |
| D46 | 1.8 | 31.7 | D122 | 5.5 | 3.5 |
| D47 | 1.2 | 2.7 | D123 | 237.6 | 45.2 |
| D48 | 35.1 | >10,000.0 | D124 | 14.3 | 4.2 |
| D49 | 1.5 | 908.9 | D127 | 38.8 | 27.7 |
| D50 | 1.0 | >1000.0 | D128 | 10.2 | 24.9 |
| D51 | 3.0 | >1000.0 | D129 | 127.6 | 38.1 |
| D52 | 6.5 | >1000.0 | D130 | 53.8 | 7.6 |
| D53 | 3.7 | 508.4 | D131 | 63.2 | 74.7 |
| D54 | 1.5 | 12.4 | D132 | 161.4 | 148.4 |
| D55 | 1.8 | 45.7 | D133 | 348.0 | 100.3 |
| D56 | 2.1 | 2.7 | D134 | 25.5 | 100.1 |
| D57 | 2.3 | 111.1 | D135 | 64.5 | 50.1 |
| D58 | 1.3 | 10.0 | D136 | 123.3 | >1000 |
| D59 | 3.0 | 405.5 | D137 | 236.7 | 37.9 |
| D60 | 1.5 | 16.3 | D138 | 94.6 | >1000 |
| D61 | 2.1 | 379.5 | D139 | 29.2 | 64.2 |
| D62 | 1722.0 | 2983.0 | D140 | 178.6 | 86.6 |
| D63 | 217.9 | 3839.5 | D141 | 3.5 | 2.9 |
| D64 | 30.6 | 57.1 | D142 | 4.5 | 24.6 |
| D65 | 18.4 | 41.4 | D143 | 3.7 | 193.6 |
| D66 | 16.8 | 79.5 | D144 | 2.3 | 1.3 |
| D67 | 16.4 | 106.0 | D145 | 3.4 | 1.6 |
| D68 | 10.5 | 16.2 | D146 | >1000 | >1000 |

TABLE 1-continued

| Cpd. No. | Enzyme assay $IC_{50}$ (nM) | | Cpd. No. | Enzyme assay $IC_{50}^a$ (nM) | |
|---|---|---|---|---|---|
| | Aur B | FLT-3 | | Aur B | FLT-3 |
| D69 | 7.6 | 4.4 | D147 | 6.2 | 2.9 |
| D70 | 0.4 | 0.5 | D148 | 6.7 | 50.4 |
| D75 | 25.0 | $ND^d$ | D149 | 70.5 | 1.4 |
| D76 | 29.6 | ND | D150 | 91.6 | 10.3 |
| D77 | 347.0 | ND | D151 | 107.1 | 4.8 |
| D80 | 1095.5 | 70.6 | D152 | 2.9 | 753.1 |
| D81 | 19.9 | 1803.0 | D153 | 73.9 | 2.7 |
| D82 | 10.7 | 3330.0 | D154 | 134.8 | 1.2 |
| D83 | 17.3 | 359.3 | D155 | 42.8 | 34.9 |
| D84 | >10000.0 | 854.4 | D156 | 19.2 | 11.6 |

These compounds exhibited anti-proliferation activities on A549 human lung carcinoma cells (Table 2). HCT116 human colorectal carcinoma cells (Table 3), HepG2 human hepatocellular carcinoma cells (Table 4), and MV4-11 human acute myelomonocytic leukemia cells (Table 5). Cells were treated with the test compound and the concentration required for 50% growth inhibition ($IC_{50}$) determined by sulfomodamine B (SRB) colorimetric assay.

Figure 1B:
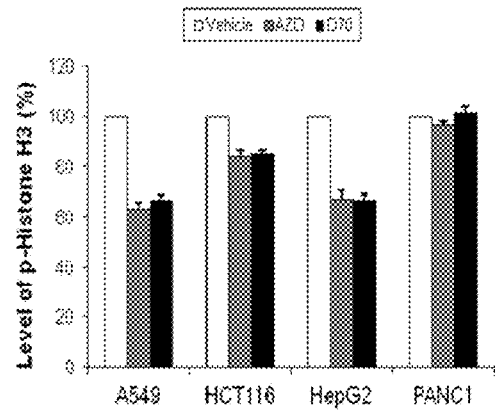
Figure 2:
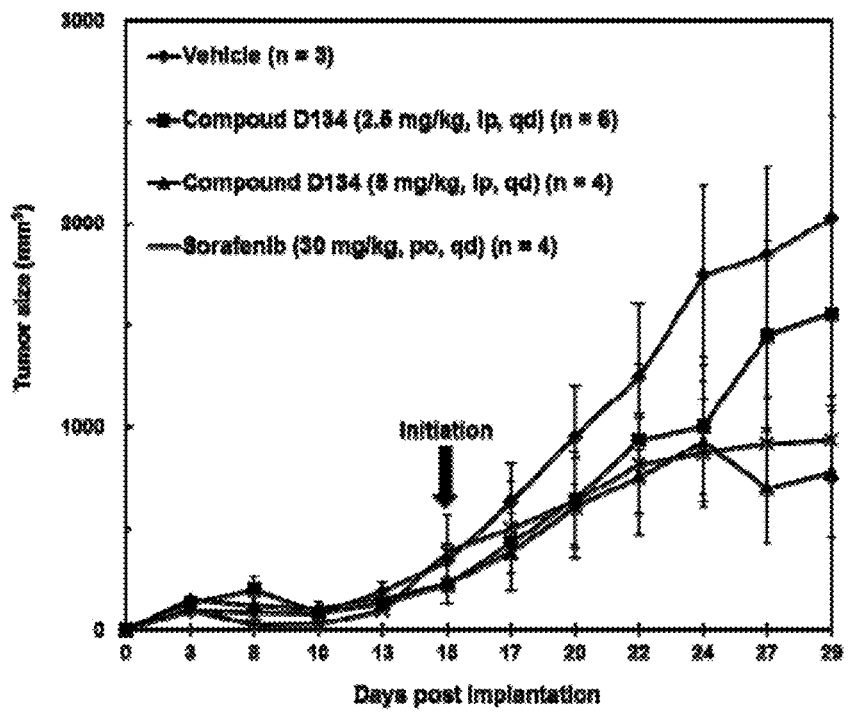
FIG. 2 shows the compound D134 suppressed the tumor size in mice.

FIGS. 1A-B show the effect of D70 on mRNA level of p-Aur B and p-histone H3 in various cancer cell lines after 4 h treatment assessed by Dot blot analysis. AZD1152-HQPA (10 μM) was used as a reference. FIG. 2 shows in vivo efficacy of a compound D134 determined using established xenografts of Huh7 cancer cell line in female SCID mice.

TABLE 2

| Cpd. No. | $IC_{50}$ (μM, mean ± S.D.) |
|---|---|
| D14 | 0.73 ± 0.02 |
| D16 | 0.99 ± 0.08 |
| D39 | 0.77 ± 0.11 |
| D41 | 0.48 ± 0.05 |
| D53 | 0.63 ± 0.08 |
| D54 | 0.11 ± 0.01 |
| D55 | 0.08 ± 0.01 |
| D56 | 0.10 ± 0.01 |
| D68 | 0.47 ± 0.01 |
| D69 | 0.46 ± 0.07 |
| D70 | 0.56 ± 0.05 |
| D75 | 0.69 ± 0.05 |
| D97 | 0.83 ± 0.04 |
| D107 | 0.70 ± 0.20 |
| D127 | 0.49 ± 0.03 |
| D128 | 0.62 ± 0.06 |
| D129 | 0.45 ± 0.07 |
| D130 | <0.1 |
| D131 | 0.52 ± 0.03 |
| D132 | 0.50 ± 0.01 |
| D133 | 0.45 ± 0.08 |
| D134 | 0.46 ± 0.06 |
| D135 | 0.59 ± 0.09 |
| D136 | 0.60 ± 0.00 |
| D149 | 0.55 ± 0.05 |
| D150 | 0.57 ± 0.04 |
| D151 | 0.66 ± 0.07 |

TABLE 3

| Cpd. No. | IC$_{50}$ (µM, mean ± S.D.) |
| --- | --- |
| D54 | 0.97 ± 0.21 |
| D55 | 0.45 ± 0.02 |
| D56 | 0.32 ± 0.07 |
| D68 | 0.87 ± 0.06 |
| D69 | 0.91 ± 0.01 |
| D70 | 0.85 ± 0.08 |
| D110 | 0.85 ± 0.13 |
| D128 | 0.63 ± 0.09 |
| D130 | 0.57 ± 0.04 |
| D131 | 0.56 ± 0.03 |
| D132 | 0.63 ± 0.03 |
| D133 | 0.65 ± 0.04 |
| D134 | 0.73 ± 0.09 |
| D135 | 0.78 ± 0.10 |
| D136 | 0.60 ± 0.00 |

TABLE 4

| Cpd. No. | IC$_{50}$ (µM, mean ± S.D.) |
| --- | --- |
| D14 | 0.64 ± 0.01 |
| D15 | 0.96 ± 0.03 |
| D16 | 0.84 ± 0.01 |
| D24 | 0.89 ± 0.03 |
| D25 | 0.94 ± 0.03 |
| D26 | 0.63 ± 0.04 |
| D27 | 0.86 ± 0.02 |
| D29 | 0.93 ± 0.01 |
| D30 | 0.86 ± 0.02 |
| D31 | 0.63 ± 0.02 |
| D33 | 0.65 ± 0.05 |
| D36 | 0.12 ± 0.07 |
| D37 | 0.09 ± 0.04 |
| D39 | 0.63 ± 0.21 |
| D41 | 0.73 ± 0.13 |
| D53 | 0.85 ± 0.11 |
| D54 | 0.47 ± 0.10 |
| D55 | 0.21 ± 0.02 |
| D56 | 0.13 ± 0.06 |
| D68 | 0.74 ± 0.07 |
| D69 | 0.88 ± 0.04 |
| D70 | 0.68 ± 0.03 |
| D97 | 0.87 ± 0.05 |
| D107 | 0.90 ± 0.20 |
| D110 | 0.82 ± 0.03 |
| D128 | 0.81 ± 0.04 |
| D130 | 0.67 ± 0.05 |
| D131 | 0.71 ± 0.07 |
| D132 | 0.55 ± 0.03 |
| D133 | 0.73 ± 0.03 |
| D134 | 0.60 ± 0.07 |
| D135 | 0.56 ± 0.16 |
| D136 | 0.60 ± 0.00 |
| D140 | 0.56 ± 0.02 |
| D149 | 0.65 ± 0.11 |
| D150 | 0.70 ± 0.07 |
| D151 | 0.88 ± 0.13 |

TABLE 5

| Cpd. No. | IC$_{50}$ (nM) |
| --- | --- |
| D14 | 0.07 |
| D15 | 6.13 |
| D25 | 6.14 |
| D26 | 1.13 |
| D28 | 0.79 |
| D39 | 7.21 |
| D53 | 8.07 |
| D105 | 0.13 |
| D106 | 12.58 |
| D107 | 0.02 |
| D108 | 0.88 |
| D109 | 7.19 |
| D110 | 2.40 |
| D111 | 3.42 |
| D112 | 2.09 |
| D113 | 2.78 |
| D114 | 1.55 |
| D115 | 6.69 |
| D119 | 1.39 |
| D120 | 0.23 |
| D121 | 3.03 |
| D122 | 15.76 |
| D123 | 1.56 |
| D127 | 7.18 |
| D128 | 25.03 |
| D129 | 1.83 |
| D130 | 4.38 |
| D131 | 18.44 |
| D132 | 9.10 |
| D133 | 5.90 |
| D134 | 13.17 |
| D135 | 4.25 |
| D137 | 0.97 |
| D138 | 17.77 |
| D140 | 12.80 |
| D141 | 0.81 |
| D142 | 6.69 |
| D144 | 22.80 |
| D145 | 9.45 |
| D149 | 0.05 |
| D150 | 0.10 |
| D151 | 0.34 |
| D155 | 1.96 |
| D156 | 2.57 |

A compound of Formula A:

TABLE 6

Formula A

| Compound Number Chemical Name | Structure | Substituents of Formula A |
|---|---|---|
| D13 (Z)-N-(3-((1H-pyrrol-2-yl)methylene)-2-oxoindolin-4-ylcarbamoyl)-4-methoxybenzamide | 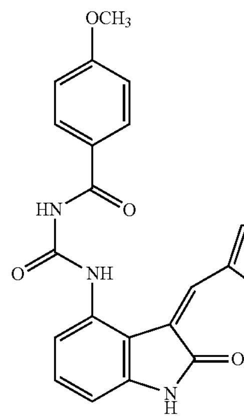 | $R^a$ = hydrogen $R^b$ = 1H-pyrrol-2-yl $R^c$ = $N^3$-(4-methoxybenzoyl) ureido $R^d$ = hydrogen $R^e$ = hydrogen $R^f$ = hydrogen |
| D14 (Z)-N-(3-((1H-pyrrol-2-yl)methylene)-2-oxoindolin-5-ylcarbamoyl)-4-methoxybenzamide | 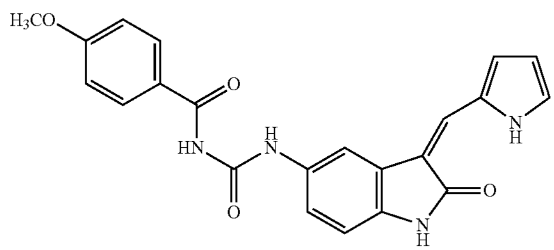 [SMILES: COc1ccc(C(=O)NC(=O)Nc2ccc3c(c2)/C(=C/c2ccc[nH]2)C(=O)N3)cc1] | $R^a$ = hydrogen $R^b$ = 1H-pyrrol-2-yl $R^c$ = hydrogen $R^d$ = $N^3$-(4-methoxybenzoyl) uredio $R^e$ = hydrogen $R^f$ = hydrogen |
| D15 (Z)-N-(3-((1H-pyrrol-2-yl)methylene)-2-oxoindolin-6-ylcarbamoyl)-4-methoxybenzamide | 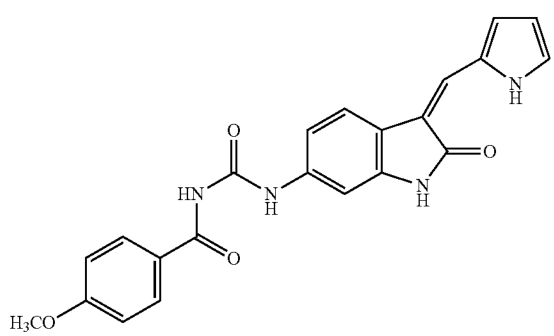 [SMILES: COc1ccc(C(=O)NC(=O)Nc2ccc3c(c2)NC(=O)/C3=C\c2ccc[nH]2)cc1] | $R^a$ = hydrogen $R^b$ = 1H-pyrrol-2-yl $R^c$ = hydrogen $R^d$ = hydrogen $R^e$ = $N^3$-(4-methoxybenzoyl) uredio $R^f$ = hydrogen |

TABLE 6-continued

Formula A

| Compound Number Chemical Name | Structure | Substituents of Formula A |
|---|---|---|
| D16 (Z)-N-(3-((1H-pyrrol-2-yl)methylene)-2-oxoindolin-7-ylcarbamoyl)-4-methoxybenzamide | 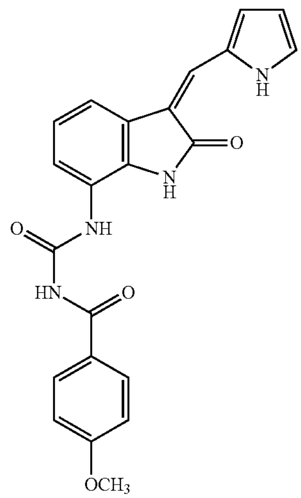 [SMILES: COc1ccc(C(=O)NC(=O)Nc2cccc3c2NC(=O)/C3=C\c2ccc[nH]2)cc1] | $R^a$ = hydrogen $R^b$ = 1H-pyrrol-2-yl $R^c$ = hydrogen $R^d$ = hydrogen $R^e$ = hydrogen $R^f$ = $N^3$-(4-methoxybenzoyl) uredio |
| D17 (E)-N-(3-benzylidene-2-oxoindolin-6-ylcarbamoyl)-4-methoxybenzamide | 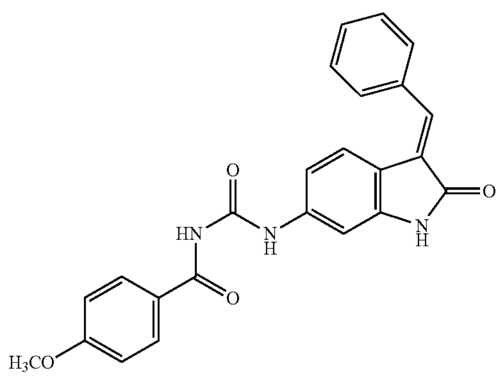 [SMILES: COc1ccc(C(=O)NC(=O)Nc2ccc3c(c2)NC(=O)/C3=C/c2ccccc2)cc1] | $R^a$ = phenyl $R^b$ = hydrogen $R^c$ = hydrogen $R^d$ = hydrogen $R^e$ = $N^3$-(4-methoxybenzoyl) uredio $R^f$ = hydrogen |
| D18 (E)-N-(3-(4-chlorobenzylidene)-2-oxoindolin-6-ylcarbamoyl)-4-methoxybenzamide | 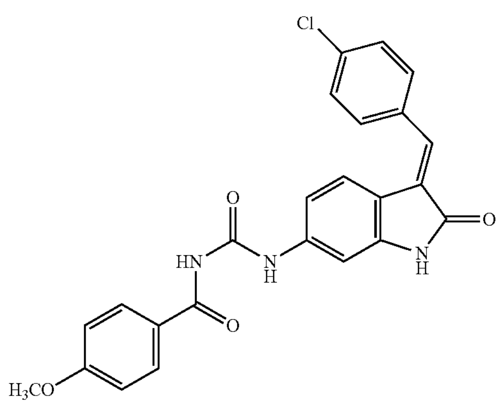 [SMILES: COc1ccc(C(=O)NC(=O)Nc2ccc3c(c2)NC(=O)/C3=C/c2ccc(Cl)cc2)cc1] | $R^a$ = 4-chlorophenyl $R^b$ = hydrogen $R^c$ = hydrogen $R^d$ = hydrogen $R^e$ = $N^3$-(4-methoxybenzoyl) uredio $R^f$ = hydrogen |

TABLE 6-continued

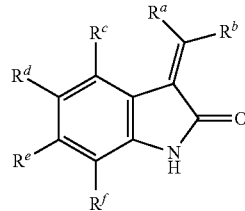

Formula A

| Compound Number Chemical Name | Structure | Substituents of Formula A |
|---|---|---|
| D19 (E)-4-methoxy-N-(3-(4-methoxybenzylidene)-2-oxoindolin-6-yl-carbamoyl)benzamide | 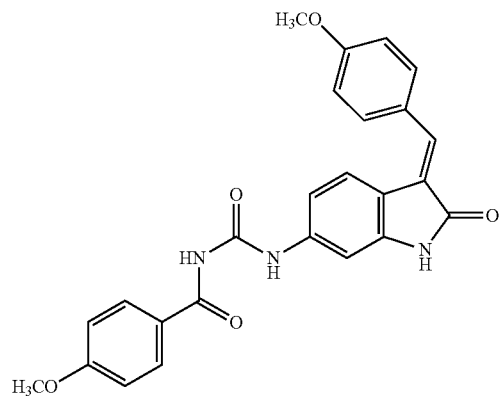 [SMILES: COc1ccc(/C=C2/C(=O)Nc3cc(NC(=O)NC(=O)c4ccc(OC)cc4)ccc32)cc1] | $R^a$ = 4-methoxyphenyl<br>$R^b$ = hydrogen<br>$R^c$ = hydrogen<br>$R^d$ = hydrogen<br>$R^e$ = $N^3$-(4-methoxybenzoyl)uredio<br>$R^f$ = hydrogen |
| D20 (Z)-4-methoxy-N-(2-oxo-3-(pyridin-2-ylmethylene)indolin-6-ylcarbamoyl)benzamide | 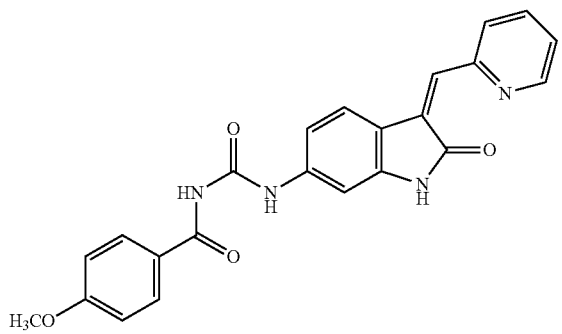 [SMILES: COc1ccc(C(=O)NC(=O)Nc2ccc3c(c2)NC(=O)/C3=C\c2ccccn2)cc1] | $R^a$ = hydrogen<br>$R^b$ = pyrid-2-yl<br>$R^c$ = hydrogen<br>$R^d$ = hydrogen<br>$R^e$ = $N^3$-(4-methoxybenzoyl)uredio<br>$R^f$ = hydrogen |
| D21 (Z)-4-methoxy-N-(2-oxo-3-(pyridin-4-ylmethylene)indolin-6-ylcarbamoyl)benzamide | 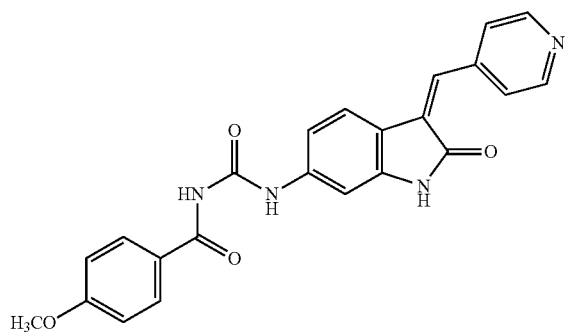 [SMILES: COc1ccc(C(=O)NC(=O)Nc2ccc3c(c2)NC(=O)/C3=C\c2ccncc2)cc1] | $R^a$ = hydrogen<br>$R^b$ = pyrid-4-yl<br>$R^c$ = hydrogen<br>$R^d$ = hydrogen<br>$R^e$ = $N^3$-(4-methoxybenzoyl)uredio<br>$R^f$ = hydrogen |

TABLE 6-continued

Formula A

| Compound Number Chemical Name | Structure | Substituents of Formula A |
|---|---|---|
| D22 (Z)-4-methoxy-N-(2-oxo-3-(thiophen-2-ylmethylene)indolin-6-ylcarbamoyl)benzamide | | $R^a$ = hydrogen $R^b$ = thiophen-2-yl $R^c$ = hydrogen $R^d$ = hydrogen $R^e$ = $N^3$-(4-methoxybenzoyl) uredio $R^f$ = hydrogen |
| D23 (E)-N-(3-(furan-2-ylmethylene)-2-oxoindolin-6-ylcarbamoyl)-4-methoxybenzamide | | $R^a$ = hydrogen $R^b$ = furan-2-yl $R^c$ = hydrogen $R^d$ = hydrogen $R^e$ = $N^3$-(4-methoxybenzoyl) uredio $R^f$ = hydrogen |
| D24 (Z)-N-(3-((1H-pyrrol-2-yl)methylene)-2-oxoindolin-6-ylcarbamoyl)benzamide | | $R^a$ = hydrogen $R^b$ = 1H-pyrrol-2-yl $R^c$ = hydrogen $R^d$ = hydrogen $R^e$ = $N^3$-benzoyluredio $R^f$ = hydrogen |
| D25 (Z)-N-(3-((1H-pyrrol-2-yl)methylene)-2-oxoindolin-6-ylcarbamoyl)-4-chlorobenzamide | | $R^a$ = hydrogen $R^b$ = 1H-pyrrol-2-yl $R^c$ = hydrogen $R^d$ = hydrogen $R^e$ = $N^3$-(4-chlorobenzoyl) uredio $R^f$ = hydrogen |

TABLE 6-continued

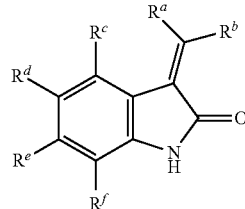

Formula A

| Compound Number Chemical Name | Structure | Substituents of Formula A |
|---|---|---|
| D26<br>(Z)-N-(3-((1H-pyrrol-2-yl)methylene)-2-oxoindolin-6-ylcarbamoyl)-3,4-dichlorobenzamide | | $R^a$ = hydrogen<br>$R^b$ = 1H-pyrrol-2-yl<br>$R^c$ = hydrogen<br>$R^d$ = hydrogen<br>$R^e$ = $N^3$-(3,4-dichlorobenzoyl) uredio<br>$R^f$ = hydrogen |
| D27<br>(Z)-N-(3-((1H-pyrrol-2-yl)methylene)-2-oxoindolin-6-ylcarbamoyl)-4-(trifluoromethyl)-benzamide | | $R^a$ = hydrogen<br>$R^b$ = 1H-pyrrol-2-yl<br>$R^c$ = hydrogen<br>$R^d$ = hydrogen<br>$R^e$ = $N^3$-(4-trifluoromethylbenzoyl) uredio<br>$R^f$ = hydrogen |
| D28<br>(Z)-N-(3-((1H-pyrrol-2-yl)methylene)-2-oxoindolin-6-ylcarbamoyl)-4-chloro-3-(trifluoromethyl)-benzamide | | $R^a$ = hydrogen<br>$R^b$ = 1H-pyrrol-2-yl<br>$R^c$ = hydrogen<br>$R^d$ = hydrogen<br>$R^e$ = $N^3$-(3-trifluoromethyl-4-chlorobenzoyl) uredio<br>$R^f$ = hydrogen |
| D29<br>(Z)-N-(3-((1H-pyrrol-2-yl)methylene)-2-oxoindolin-6-ylcarbamoyl)-4-methylbenzamide | | $R^a$ = hydrogen<br>$R^b$ = 1H-pyrrol-2-yl<br>$R^c$ = hydrogen<br>$R^d$ = hydrogen<br>$R^e$ = $N^3$-(4-methylbenzoyl) uredio<br>$R^f$ = hydrogen |

TABLE 6-continued

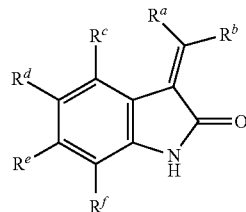

Formula A

| Compound Number Chemical Name | Structure | Substituents of Formula A |
|---|---|---|
| D30 (Z)-N-(3-((1H-pyrrol-2-yl)methylene)-2-oxoindolin-6-ylcarbamoyl)-3,5-dimethoxybenzamide | 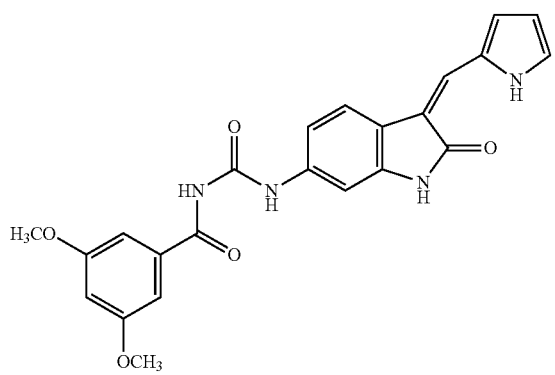 [SMILES: COc1cc(OC)cc(C(=O)NC(=O)Nc2ccc3c(c2)NC(=O)/C3=C\c2ccc[nH]2)c1] | $R^a$ = hydrogen<br>$R^b$ = 1H-pyrrol-2-yl<br>$R^c$ = hydrogen<br>$R^d$ = hydrogen<br>$R^e$ = $N^3$-(3,5-dimethoxybenzoyl) uredio<br>$R^f$ = hydrogen |
| D31 (Z)-N-(3-((1H-pyrrol-2-yl)methylene)-2-oxoindolin-6-ylcarbamoyl)-4-(dimethylamino)-benzamide | 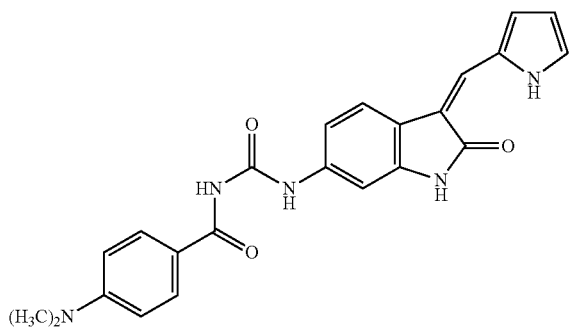 | $R^a$ = hydrogen<br>$R^b$ = 1H-pyrrol-2-yl<br>$R^c$ = hydrogen<br>$R^d$ = hydrogen<br>$R^e$ = $N^3$-((4-dimethylamino-benzoyl) uredio<br>$R^f$ = hydrogen |
| D32 (Z)-5-((6-(3-benzoylureido)-2-oxoindolin-3-ylidene)methyl-2,4-dimethyl-1H-pyrrole-3-carboxylic acid | 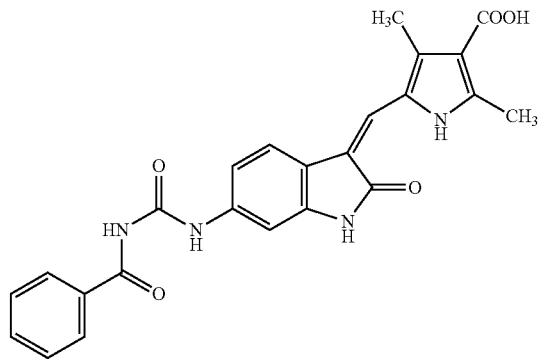 [SMILES: Cc1[nH]c(/C=C2\C(=O)Nc3cc(NC(=O)NC(=O)c4ccccc4)ccc32)c(C)c1C(=O)O] | $R^a$ = hydrogen<br>$R^b$ = 3,5-dimethyl-4-carboxy-1H-pyrrol-2-yl<br>$R^c$ = hydrogen<br>$R^d$ = hydrogen<br>$R^e$ = $N^3$-benzoyluredio<br>$R^f$ = hydrogen |

TABLE 6-continued

Formula A

| Compound Number Chemical Name | Structure | Substituents of Formula A |
|---|---|---|
| D33 (Z)-5-((6-(3-(4-chlorobenzoyl)ureido)-2-oxoindolin-3-ylidene)-methyl)-2,4-dimethyl-1H-pyrrole-3-carboxylic acid | | $R^a$ = hydrogen $R^b$ = 3,5-dimethyl-4-carboxy-1H-pyrrol-2-yl $R^c$ = hydrogen $R^d$ = hydrogen $R^e$ = $N^3$-(4-chlorobenzoyl)uredio $R^f$ = hydrogen |
| D34 (Z)-5-((6-(3-(3,4-dichlorobenzoyl)ureido)-2-oxoindolin-2-ylidene)methyl)-2,4-dimethyl-1H-pyrrole-3-carboxylic acid | | $R^a$ = hydrogen $R^b$ = 3,5-dimethyl-4-carboxy-1H-pyrrol-2-yl $R^c$ = hydrogen $R^d$ = hydrogen $R^e$ = $N^3$-(3,4-dichlorobenzoyl)uredio $R^f$ = hydrogen |
| D35 (Z)-2,4-dimethyl-5-((2-oxo-6-(3-(4-(trifluoromethyl)benzoyl)ureido)indolin-3-ylidene)methyl)-1H-pyrrole-3-carboxylic acid | | $R^a$ = hydrogen $R^b$ = 3,5-dimethyl-4-carboxy-1H-pyrrol-2-yl $R^c$ = hydrogen $R^d$ = hydrogen $R^e$ = $N^3$-(4-trifluoromethyl-benzoyl)uredio $R^f$ = hydrogen |

TABLE 6-continued

Formula A

| Compound Number Chemical Name | Structure | Substituents of Formula A |
|---|---|---|
| D36 (Z)-5-(((6-(3-(4-chloro-3-(trifluoromethyl)benzoyl)ureido)-2-oxoindolin-3-ylidene) methyl)-2,4-dimethyl-1H-pyrrole-3-carboxylic acid | | $R^a$ = hydrogen<br>$R^b$ = 3,5-dimethyl-4-carboxy-1H-pyrrol-2-yl<br>$R^c$ = hydrogen<br>$R^d$ = hydrogen<br>$R^e$ = $N^3$-(3-trifluoromethyl-4-chlorobenzoyl) uredio<br>$R^f$ = hydrogen |
| D37 (Z)-3-(5-((6-(3-(4-chloro-3-(trifluoromethyl)benzoyl) ureido)-2-oxo-indolin-3-ylidene)methyl)-2,4-dimethyl-1H-pyrrol-3-yl)propanoic acid | 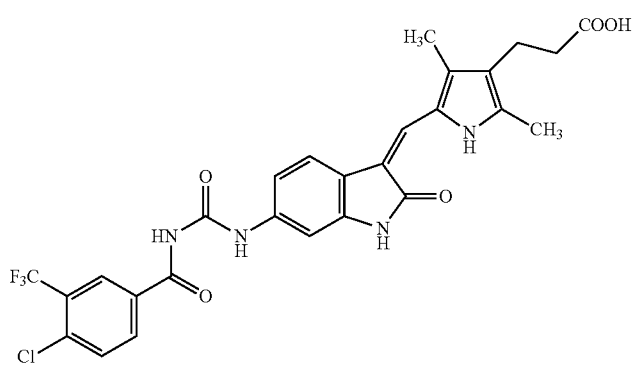 [SMILES: Cc1[nH]c(/C=C2\C(=O)Nc3cc(NC(=O)NC(=O)c4ccc(Cl)c(C(F)(F)F)c4)ccc32)c(C)c1CCC(=O)O] | $R^a$ = hydrogen<br>$R^b$ = 3,5-dimethyl-4-(2-carboxyethyl)-1H-pyrrol-2-yl<br>$R^c$ = hydrogen<br>$R^d$ = hydrogen<br>$R^e$ = $N^3$-(3-trifluoromethyl-4-chlorobenzoyl) uredio<br>$R^f$ = hydrogen |
| D38 (Z)-2,4-dimethyl-5-((6-(3-(4-nitrobenzoyl)ureido)-2-oxoindolin-3-ylidene)methyl)-1H-pyrrole-3-carboxylic acid | 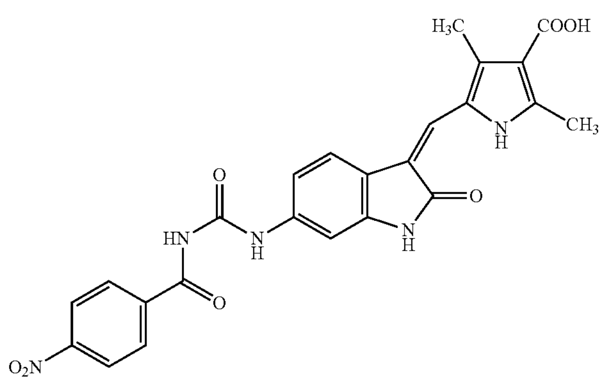 [SMILES: Cc1[nH]c(/C=C2\C(=O)Nc3cc(NC(=O)NC(=O)c4ccc([N+](=O)[O-])cc4)ccc32)c(C)c1C(=O)O] | $R^a$ = hydrogen<br>$R^b$ = 3,5-dimethyl-4-carboxy-1H-pyrrol-2-yl<br>$R^c$ = hydrogen<br>$R^d$ = hydrogen<br>$R^e$ = $N^3$-(4-nitrobenzoyl)uredio<br>$R^f$ = hydrogen |

TABLE 6-continued

Formula A

| Compound Number Chemical Name | Structure | Substituents of Formula A |
|---|---|---|
| D39<br>(Z)-2,4-dimethyl-5-((6-(3-(4-methylbenzoyl)ureido)-2-oxoindolin-3-ylidene)-methyl)-1H-pyrrole-3-carboxylic acid | | $R^a$ = hydrogen<br>$R^b$ = 3,5-dimethyl-4-carboxy-1H-pyrrol-2-yl<br>$R^c$ = hydrogen<br>$R^d$ = hydrogen<br>$R^e$ = $N^3$-(4-methylbenzoyl) uredio<br>$R^f$ = hydrogen |
| D40<br>(Z)-3-(2,4-dimethyl-5-((6-(3-(3-methylbenzoyl)ureido)-2-oxoindolin-3-ylidene)-methyl)-1H-pyrrol-3-yl)propanoic acid | | $R^a$ = hydrogen<br>$R^b$ = 3,5-dimethyl-4-(2-carboxyethyl)-1H-pyrrol-2-yl<br>$R^c$ = hydrogen<br>$R^d$ = hydrogen<br>$R^e$ = $N^3$-(3-methylbenzoyl) uredio<br>$R^f$ = hydrogen |
| D41<br>(Z)-5-((6-(3-(4-methoxybenzoyl)ureido)-2-oxoindolin-3-ylidene)-methyl)-2,4-di-methyl-1H-pyrrole-3-carboxylic acid | | $R^a$ = hydrogen<br>$R^b$ = 3,5-dimethyl-4-carboxy-1H-pyrrol-2-yl<br>$R^c$ = hydrogen<br>$R^d$ = hydrogen<br>$R^e$ = $N^3$-(4-methoxybenzoyl) uredio<br>$R^f$ = hydrogen |

TABLE 6-continued

Formula A

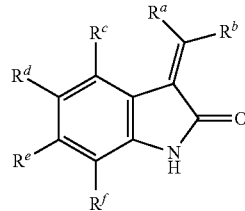

| Compound Number Chemical Name | Structure | Substituents of Formula A |
|---|---|---|
| D42 (Z)-5-((6-(3-(3,5-dimethoxybenzoyl)-ureido)-2-oxoinidolin-3-ylidene)methyl)-2,4-dimethyl-1H-pyrrole-3-carboxylic acid | 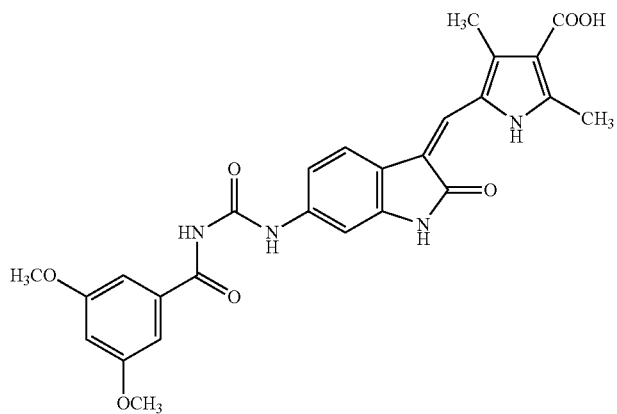 [SMILES: COc1cc(OC)cc(C(=O)NC(=O)Nc2ccc3c(c2)NC(=O)/C3=C\c2[nH]c(C)c(C(=O)O)c2C)c1] | $R^a$ = hydrogen $R^b$ = 3,5-dimethyl-4-carboxy-1H-pyrrol-2-yl $R^c$ = hydrogen $R^d$ = hydrogen $R^e$ = $N^3$-(3,5-dimethoxybenzoyl)uredio $R^f$ = hydrogen |
| D43 (Z)-N-(3-((3,5-dimethyl-4-phenyl-1H-pyrrol-2-yl)methylene)-2-oxoindolin-6-ylcarbamoyl)-4-methoxybenzamide | 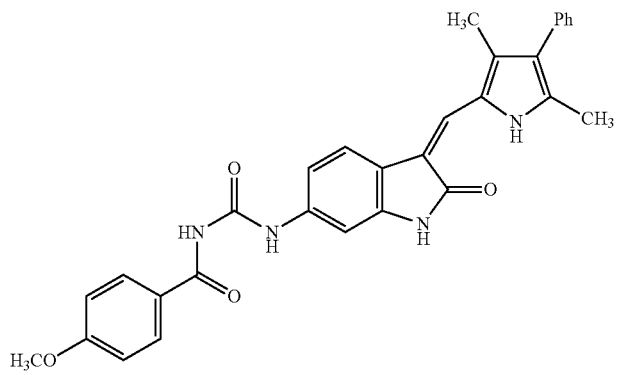 [SMILES: COc1ccc(C(=O)NC(=O)Nc2ccc3c(c2)NC(=O)/C3=C\c2[nH]c(C)c(-c3ccccc3)c2C)cc1] | $R^a$ = hydrogen $R^b$ = 3,5-dimethyl-4-phenyl-1H-pyrrol-2-yl $R^c$ = hydrogen $R^d$ = hydrogen $R^e$ = $N^3$-(4-methoxybenzoyl)uredio $R^f$ = hydrogen |
| D44 (Z)-N-(3-((3,5-dimethyl-1H-pyrrol-2-yl)methylene)-2-oxoindolin-6-ylcarbamoyl)-4-methoxybenzamide | 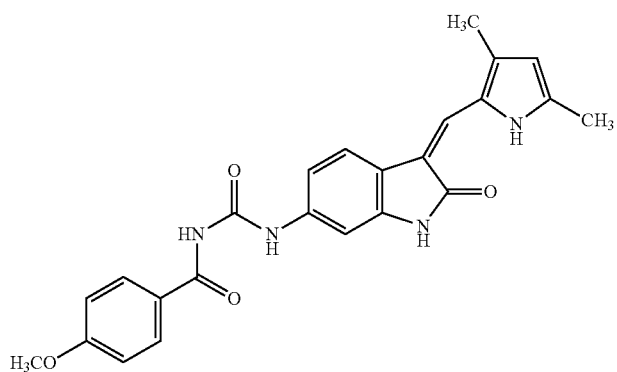 [SMILES: COc1ccc(C(=O)NC(=O)Nc2ccc3c(c2)NC(=O)/C3=C\c2[nH]c(C)cc2C)cc1] | $R^a$ = hydrogen $R^b$ = 3,5-dimethyl-1H-pyrrol-2-yl $R^c$ = hydrogen $R^d$ = hydrogen $R^e$ = $N^3$-(4-methoxybenzoyl)uredio $R^f$ = hydrogen |

TABLE 6-continued

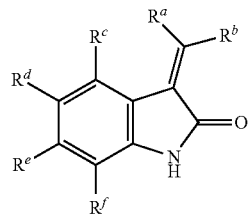

Formula A

| Compound Number Chemical Name | Structure | Substituents of Formula A |
|---|---|---|
| D45 (Z)-5-((6-(3-(4-methoxybenzoyl)ureido)-2-oxoindolin-3-ylidene)methyl)-1H-pyrrole-2-carboxylic acid | 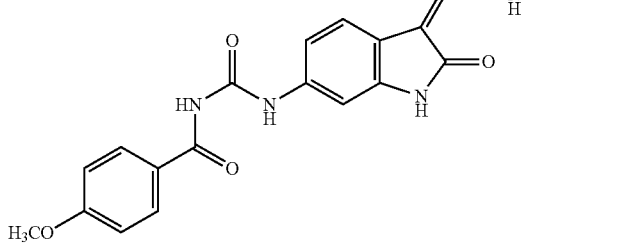 | $R^a$ = hydrogen $R^b$ = 5-carboxy-1H-pyrrol-2-yl $R^c$ = hydrogen $R^d$ = hydrogen $R^e$ = $N^3$-(4-methoxybenzoyl)uredio $R^f$ = hydrogen |
| D46 (Z)-2-(5-((6-(3-(4-methoxybenzoyl)ureido)-2-oxoindolin-3-ylidene)methyl)-2,4-dimethyl-1H-pyrrol-3-yl)acetic acid | 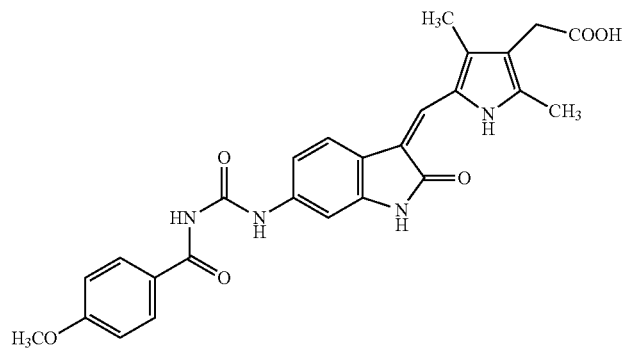 [SMILES: COc1ccc(C(=O)NC(=O)Nc2ccc3c(c2)NC(=O)/C3=C\c2[nH]c(C)c(CC(=O)O)c2C)cc1] | $R^a$ = hydrogen $R^b$ = 3,5-dimethyl-4-carboxymethyl-1H-pyrrol-2-yl $R^c$ = hydrogen $R^d$ = hydrogen $R^e$ = $N^3$-(4-methoxybenzoyl)uredio $R^f$ = hydrogen |
| D47 (Z)-3-(5-((6-(3-(4-methoxybenzoyl)ureido)-2-oxoindolin-3-ylidene)methyl)-2,4-dimethyl-1H-pyrrol-3-yl)propanoic acid | 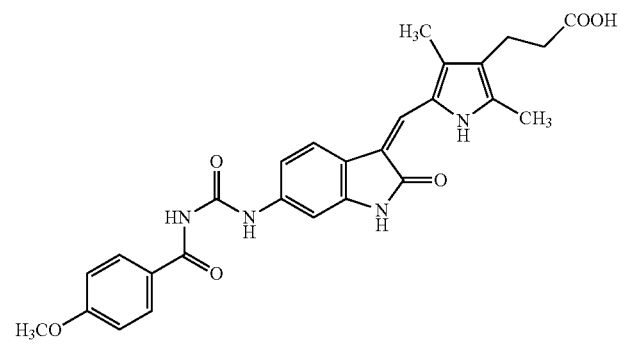 [SMILES: COc1ccc(C(=O)NC(=O)Nc2ccc3c(c2)NC(=O)/C3=C\c2[nH]c(C)c(CCC(=O)O)c2C)cc1] | $R^a$ = hydrogen $R^b$ = 3,5-dimethyl-4-(2-carboxyethyl)-1H-pyrrol-2-yl $R^c$ = hydrogen $R^d$ = hydrogen $R^e$ = $N^3$-(4-methoxybenzoyl)uredio $R^f$ = hydrogen |

TABLE 6-continued

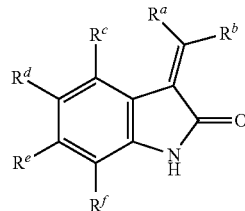

Formula A

| Compound Number<br>Chemical Name | Structure | Substituents of<br>Formula A |
|---|---|---|
| D48<br>(Z)-N-(3-((1H-pyrrol-2-yl)methylene)-5-fluoro-2-oxoindolin-6-ylcarbamoyl)-4-methoxybenzamide | | $R^a$ = hydrogen<br>$R^b$ = 1H-pyrrol-2-yl<br>$R^c$ = hydrogen<br>$R^d$ = fluoro<br>$R^e$ = $N^3$-(4-methoxybenzoyl)uredio<br>$R^f$ = hydrogen |
| D49<br>(Z)-5-((5-fluoro-6-(3-(4-methoxybenzoyl)ureido)-2-oxoindolin-3-ylidene)methyl)-2,4-dimethyl-1H-pyrrole-3-carboxylic acid | | $R^a$ = hydrogen<br>$R^b$ = 3,5-dimethyl-4-carboxy-1H-pyrrol-2-yl<br>$R^c$ = hydrogen<br>$R^d$ = fluoro<br>$R^e$ = $N^3$-(4-methoxybenzoyl)uredio<br>$R^f/R^f$ = hydrogen |
| D50<br>(Z)-2-(5-((5-fluoro-6-(3-(4-methoxybenzoyl)ureido)-2-oxoindolin-3-ylidene)-methyl)-2,4-dimethyl-1H-pyrrol-3-yl)acetic acid | | $R^a$ = hydrogen<br>$R^b$ = 3,5-dimethyl-4-carboxymethyl-1H-pyrrol-2-yl<br>$R^c$ = hydrogen<br>$R^d$ = fluoro<br>$R^e$ = $N^3$-(4-methoxybenzoyl)uredio<br>$R^f$ = hydrogen |

TABLE 6-continued

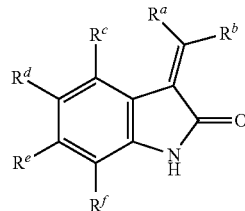

Formula A

| Compound Number Chemical Name | Structure | Substituents of Formula A |
|---|---|---|
| D51 (Z)-3-(5-((5-fluoro-6-(3-(4-methoxybenzoyl)ureido)-2-oxoindolin-3-ylidene)-methyl)-2,4-dimethyl-1H-pyrrol-3-yl)propanoic acid | 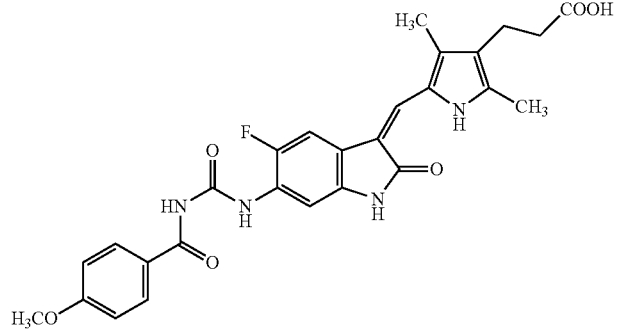 [SMILES: COc1ccc(C(=O)NC(=O)Nc2cc3c(cc2F)/C(=C/c2[nH]c(C)c(CCC(=O)O)c2C)C(=O)N3)cc1] | $R^a$ = hydrogen $R^b$ = 3,5-dimethyl-4-(2-carboxyethyl)-1H-pyrrol-2-yl $R^c$ = hydrogen $R^d$ = fluoro $R^e$ = $N^3$-(4-methoxybenzoyl)uredio $R^f$ = hydrogen |
| D52 (Z)-N-(3-((1H-pyrrol-2-yl)methylene)-2-oxoindolin-6-ylcarbamoyl)-2-fluorobenzamide | 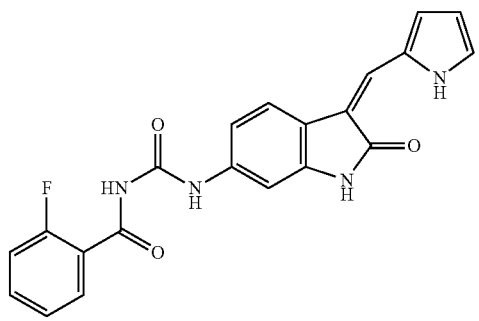 [SMILES: O=C(NC(=O)c1ccccc1F)Nc1ccc2c(c1)NC(=O)/C2=C\c1ccc[nH]1] | $R^a$ = hydrogen $R^b$ = 1H-pyrrol-2-yl $R^c$ = hydrogen $R^d$ = hydrogen $R^e$ = $N^3$-(2-fluorobenzoyl)uredio $R^f$ = hydrogen |
| D53 (Z)-5-((6-(3-(2-fluorobenzoyl)ureido)-2-oxoindolin-3-ylidene)methyl)-2,4-dimethyl-1H-pyrrole-3-carboxylic acid | 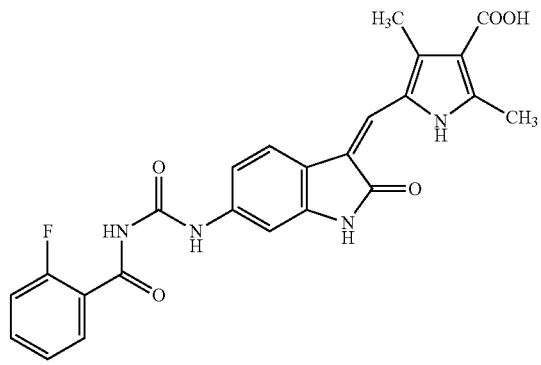 [SMILES: Cc1[nH]c(/C=C2\C(=O)Nc3cc(NC(=O)NC(=O)c4ccccc4F)ccc32)c(C)c1C(=O)O] | $R^a$ = hydrogen $R^b$ = 3,5-dimethyl-4-carboxy-1H-pyrrol-2-yl $R^c$ = hydrogen $R^d$ = hydrogen $R^e$ = $N^3$-(2-fluoro benzoyl)uredio $R^f$ = hydrogen |

TABLE 6-continued

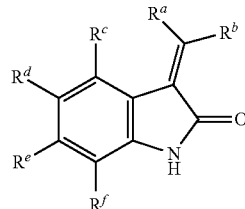
Formula A

| Compound Number Chemical Name | Structure | Substituents of Formula A |
|---|---|---|
| D54 (Z)-3-(5-((6-(3-(2-fluorobenzoyl)ureido)-2-oxoindolin-3-ylidene)methyl)-2,4-dimethyl-1H-pyrrol-3-yl)propanoic acid | 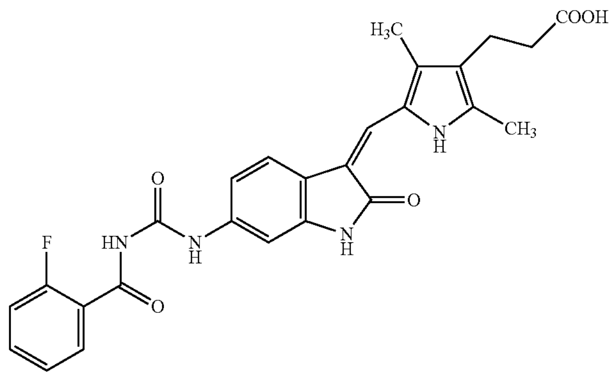 [SMILES: Cc1[nH]c(/C=C2\C(=O)Nc3cc(NC(=O)NC(=O)c4ccccc4F)ccc32)c(C)c1CCC(=O)O] | $R^a$ = hydrogen $R^b$ = 3,5-dimethyl-4-(2-carboxyethyl)-1H-pyrrol-2-yl $R^c$ = hydrogen $R^d$ = hydrogen $R^e$ = $N^3$-(2-fluoro benzoyl)uredio $R^f$ = hydrogen |
| D55 (Z)-3-(5-((6-(3-(4-fluorobenzoyl)ureido)-2-oxoindolin-3-ylidene)methyl)-2,4-dimethyl-1H-pyrrol-3-yl)propanoic acid | 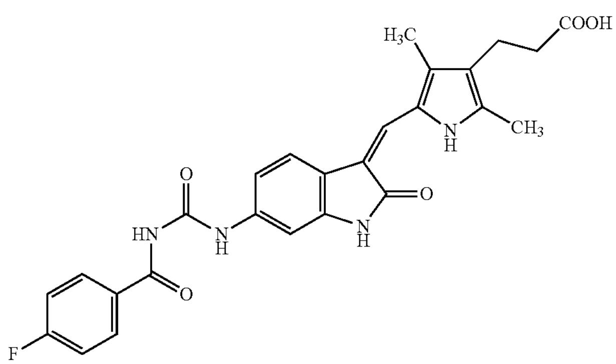 [SMILES: Cc1[nH]c(/C=C2\C(=O)Nc3cc(NC(=O)NC(=O)c4ccc(F)cc4)ccc32)c(C)c1CCC(=O)O] | $R^a$ = hydrogen $R^b$ = 3,5-dimethyl-4-(2-carboxyethyl)-1H-pyrrol-2-yl $R^c$ = hydrogen $R^d$ = hydrogen $R^e$ = $N^3$-(4-fluoro-benzoyl)uredio $R^f$ = hydrogen |
| D56 (Z)-3-(5-((6-(3-(2,4-difluorobenzoyl)ureido]-2-oxoindolin-3-ylidene)methyl)-2,4-dimethyl-1H-pyrrol-3-yl)propanoic acid | 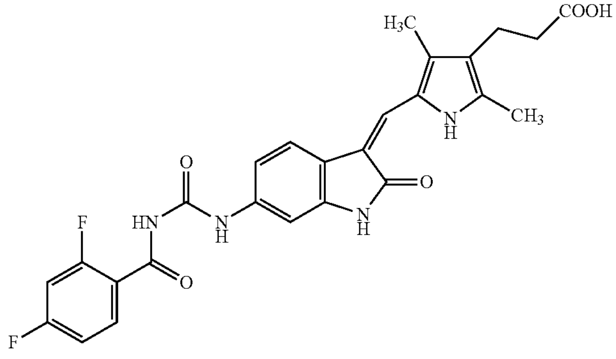 [SMILES: Cc1[nH]c(/C=C2\C(=O)Nc3cc(NC(=O)NC(=O)c4ccc(F)cc4F)ccc32)c(C)c1CCC(=O)O] | $R^a$ = hydrogen $R^b$ = 3,5-dimethyl-4-(2-carboxyethyl)-1H-pyrrol-2-yl $R^c$ = hydrogen $R^d$ = hydrogen $R^e$ = $N^3$-(2,4-difluoro benzoyl)uredio $R^f$ = hydrogen |

TABLE 6-continued

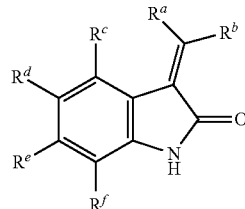
Formula A

| Compound Number Chemical Name | Structure | Substituents of Formula A |
|---|---|---|
| D57 (Z)-5-((6-(3-(2-fluoro-4-methoxybenzoyl)ureido)-2-oxoindolin-3-ylidene)methyl)-2,4-dimethyl-1H-pyrrole-3-carboxylic acid | 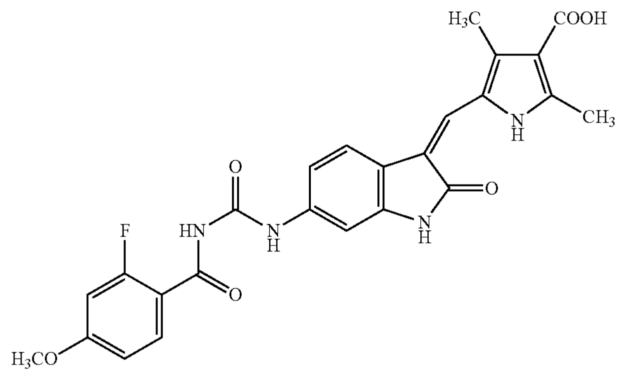 [SMILES: COc1ccc(C(=O)NC(=O)Nc2ccc3c(c2)NC(=O)/C3=C\c2[nH]c(C)c(C(=O)O)c2C)c(F)c1] | $R^a$ = hydrogen $R^b$ = 3,5-dimethyl-4-carboxy-1H-pyrrol-2-yl $R^c$ = hydrogen $R^d$ = hydrogen $R^e$ = $N^3$-(2-fluoro-4-methoxybenzoyl)uredio $R^f$ = hydrogen |
| D58 (Z)-3-(5-((6-(3-(2-fluoro-4-methoxybenzoyl)ureido)-2-oxoindolin-3-ylidene)methyl)-2,4-dimethyl-1H-pyrrol-3-yl)propanoic acid | 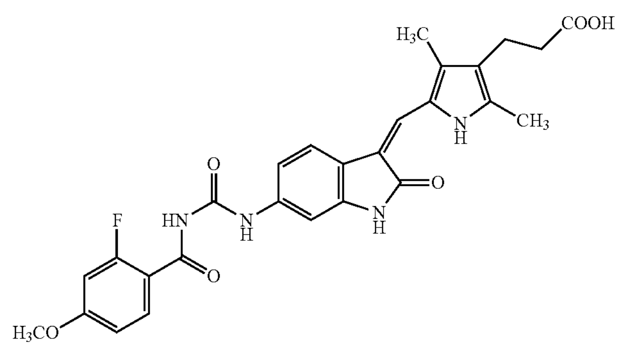 [SMILES: COc1ccc(C(=O)NC(=O)Nc2ccc3c(c2)NC(=O)/C3=C\c2[nH]c(C)c(CCC(=O)O)c2C)c(F)c1] | $R^a$ = hydrogen $R^b$ = 3,5-dimethyl-4-(2-carboxyethyl)-1H-pyrrol-2-yl $R^c$ = hydrogen $R^d$ = hydrogen $R^e$ = $N^3$-(2-fluoro-4-methoxybenzoyl)uredio $R^f$ = hydrogen |
| D59 (Z)-5-((5-fluoro-6-(3-(2-fluoro-4-methoxybenzoyl)ureido)-2-oxoindolin-3-ylidene)methyl)-2,4-dimethyl-1H-pyrrole-3-carboxylic acid | 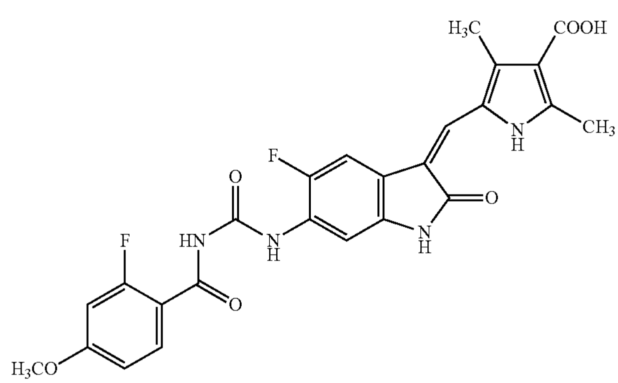 [SMILES: COc1ccc(C(=O)NC(=O)Nc2cc3c(cc2F)/C(=C/c2[nH]c(C)c(C(=O)O)c2C)C(=O)N3)c(F)c1] | $R^a$ = hydrogen $R^b$ = 3,5-dimethyl-4-carboxy-1H-pyrrol-2-yl $R^c$ = hydrogen $R^d$ = fluoro $R^e$ = $N^3$-(2-fluoro-4-methoxybenzoyl)uredio $R^f$ = hydrogen |

TABLE 6-continued

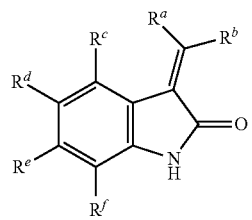

Formula A

| Compound Number<br>Chemical Name | Structure | Substituents of<br>Formula A |
|---|---|---|
| D60<br>(Z)-3-(5-((5-fluoro-6-(3-(2-fluoro-4-methoxybenzoyl)ureido)-2-oxoindolin-3-ylidene)methyl)-2,4-dimethyl-1H-pyrrol-3-yl)propanoic acid | | $R^a$ = hydrogen<br>$R^b$ = 3,5-dimethyl-4-(2-carboxyethyl)-1H-pyrrol-2-yl<br>$R^c$ = hydrogen<br>$R^d$ = fluoro<br>$R^e$ = $N^3$-(2-fluoro-4-methoxybenzoyl)uredio<br>$R^f$ = hydrogen |
| D61<br>(Z)-5-((6-(3-(2,6-difluoro-4-methoxybenzoyl)ureido)-5-fluoro-2-oxoindolin-3-ylidene)methyl)-2,4-dimethyl-1H-pyrrole-3-carboxylic acid | | $R^a$ = hydrogen<br>$R^b$ = 3,5-dimethyl-4-carboxy-1H-pyrrol-2-yl<br>$R^c$ = hydrogen<br>$R^d$ = fluoro<br>$R^e$ = $N^3$-(2,6-difluoro-4-methoxybenzoyl)uredio<br>$R^f$ = hydrogen |
| D62<br>(Z)-ethyl-5-((6-(3-(2-fluoro-4-methoxybenzoyl)ureido)-2-oxoindolin-3-ylidene)methyl)-2,4-dimethyl-1H-pyrrole-3-carboxylate | | $R^a$ = hydrogen<br>$R^b$ = 3,5-dimethyl-4-ethoxycarbonyl-1H-pyrrol-2-yl<br>$R^c$ = hydrogen<br>$R^d$ = hydrogen<br>$R^e$ = $N^3$-(2,6-difluoro-4-methoxybenzoyl)uredio<br>$R^f$ = hydrogen |

TABLE 6-continued

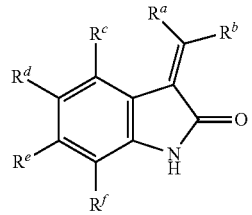

Formula A

| Compound Number Chemical Name | Structure | Substituents of Formula A |
|---|---|---|
| D63<br>(Z)-ethyl-3-(5-((6-(3-(2-fluoro-4-methoxybenzoyl)ureido)-2-oxoindolin-3-ylidene)methyl)-2,4-dimethyl-1H-pyrrol-3-yl)propanoate | | $R^a$ = hydrogen<br>$R^b$ = 3,5-dimethyl-4-(3-ethoxy-3-oxopropyl)-1H-pyrrol-2-yl<br>$R^c$ = hydrogen<br>$R^d$ = hydrogen<br>$R^e$ = $N^3$-(2-fluoro-4-methoxybenzoyl)uredio<br>$R^f$ = hydrogen |
| D64<br>(Z)-N-(3-((3,5-dimethyl-4-(4-methylpiperazine-1-carbonyl)-1H-pyrrol-2-yl)methylene)-2-oxoindolin-6-ylcarbamoyl)-2-fluoro-4-methoxybenzamide | | $R^a$ = hydrogen<br>$R^b$ = 3,5-dimethyl-4-(4-methylpiperazine-1-carbonyl)-1H-pyrrol-2-yl<br>$R^c$ = hydrogen<br>$R^d$ = hydrogen<br>$R^e$ = $N^3$-(2-fluoro-4-methoxybenzoyl)uredio<br>$R^f$ = hydrogen |
| D65<br>(Z)-N-(3-((3,5-dimethyl-4-(3-(4-methylpiperazin-1-yl)-3-oxopropyl)-1H-pyrrol-2-yl)methylene)-2-oxoindolin-6-ylcarbamoyl)-2-fluoro-4-methoxybenzamide | | $R^a$ = hydrogen<br>$R^b$ = 3,5-dimethyl-4-(3-(4-methylpiperazino-3-oxopropyl))-1H-pyrrol-2-yl<br>$R^c$ = hydrogen<br>$R^d$ = hydrogen<br>$R^e$ = $N^3$-(2-fluoro-4-methoxybenzoyl)uredio<br>$R^f$ = hydrogen |
| D66<br>(Z)-N-(3-((3,5-dimethyl-4-(morpholine-4-carbonyl)-1H-pyrrol-2-yl)methylene)-2-oxoindolin-6-ylcarbamoyl)-2-fluoro-4-methoxybenzamide | | $R^a$ = hydrogen<br>$R^b$ = 3,5-dimethyl-4-(morpholine-1-carbonyl)-1H-pyrrol-2-yl<br>$R^c$ = hydrogen<br>$R^d$ = hydrogen<br>$R^e$ = $N^3$-(2-fluoro-4-methoxybenzoyl)uredio<br>$R^f$ = hydrogen |

TABLE 6-continued

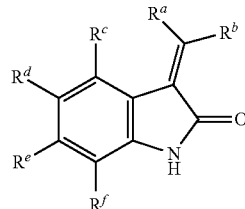

Formula A

| Compound Number Chemical Name | Structure | Substituents of Formula A |
|---|---|---|
| D67<br>(Z)-N-(3-((3,5-dimethyl-4-(3-morpholino-3-oxopropyl)-1H-pyrrol-2-yl)methylene)-2-oxoindolin-6-ylcarbamoyl)-2-fluoro-4-methoxybenzamide | | $R^a$ = hydrogen<br>$R^b$ = 3,5-dimethyl-4-(3-morpholino-3-oxopropyl)-1H-pyrrol-2-yl<br>$R^c$ = hydrogen<br>$R^d$ = hydrogen<br>$R^e$ = $N^3$-(2-fluoro-4-methoxybenzoyl) uredio<br>$R^f$ = hydrogen |
| D68<br>(Z)-N-(2-(dimethylamino)ethyl)-5-((6-(3-(2-fluoro-4-methoxybenzoyl)-ureido)-2-oxoindolin-3-ylidene)methyl)-2,4-dimethyl-1H-pyrrole-3-carboxamide | | $R^a$ = hydrogen<br>$R^b$ = 3,5-dimethyl-4-([2-(dimethylamino)ethyl]carbamoyl)-1H-pyrrol-2-yl<br>$R^c$ = hydrogen<br>$R^d$ = hydrogen<br>$R^e$ = $N^3$-(2-fluoro-4-methoxybenzoyl) uredio<br>$R^f$ = hydrogen |
| D69<br>(Z)-N-(2-(diethylamino)ethyl)-5-((6-(3-(2-fluoro-4-methoxybenzoyl)ureido)-2-oxoindolin-3-ylidene)methyl)-2,4-dimethyl-1H-pyrrole-3-carboxamide | | $R^a$ = hydrogen<br>$R^b$ = 3,5-dimethyl-4-([2-(diethylamino)ethyl] carbamoyl)-1H-pyrrol-2-yl<br>$R^c$ = hydrogen<br>$R^d$ = hydrogen<br>$R^e$ = $N^3$-(2-fluoro-4-methoxybenzoyl) uredio<br>$R^f$ = hydrogen |

TABLE 6-continued

Formula A

| Compound Number Chemical Name | Structure | Substituents of Formula A |
|---|---|---|
| D70 (Z)-5-((6-(3-(2-fluoro-4-methoxybenzoyl)ureido)-2-oxoindolin-3-ylidene)methyl)-2,4-dimethyl-N-(2-(pyrrolidin-1-yl)ethyl)-1H-pyrrole-3-carboxamide | | $R^a$ = hydrogen<br>$R^b$ = 3,5-dimethyl-4-([2-(pyrrolidin-1-yl)ethyl]carbamoyl)-1H-pyrrol-2-yl<br>$R^c$ = hydrogen<br>$R^d$ = hydrogen<br>$R^e$ = $N^3$-(2-fluoro-4-methoxybenzoyl) uredio<br>$R^f$ = hydrogen |
| D71 Malic acid salt of (Z)-5-((6-(3-(2-fluoro-4-methoxybenzoyl)ureido)-2-oxoindolin-3-ylidene)methyl)-2,4-dimethyl-N-(2-(pyrrolidin-1-yl)ethyl)-1H-pyrrole-3-carboxamide | | $R^a$ = hydrogen<br>$R^b$ = 3,5-dimethyl-4-([2-(pyrrolidin-1-yl)ethyl]carbamoyl)-1H-pyrrol-2-yl<br>$R^c$ = hydrogen<br>$R^d$ = hydrogen<br>$R^e$ = $N^3$-(2-fluoro-4-methoxybenzoyl) uredio<br>$R^f$ = hydrogen<br>Malic acid salt |
| D75 (Z)-$N^1$-(3-((1H-pyrrol-2-yl)methylene)-2-oxoindolin-6-yl)-$N^3$-(4-fluorophenyl)malonamide | | $R^a$ = hydrogen<br>$R^b$ = 1H-pyrrol-2-yl<br>$R^c$ = hydrogen<br>$R^d$ = hydrogen<br>$R^e$ = 2-[(4-fluorophenyl) carbomyl]acetamido<br>$R^f$ = hydrogen |
| D76 (Z)-$N^1$-(3-((1H-pyrrol-2-yl)methylene)-2-oxoindolin-6-yl)-$N^3$-(4-methoxyphenyl)malonamide | | $R^a$ = hydrogen<br>$R^b$ = 1H-pyrrol-2-yl<br>$R^c$ = hydrogen<br>$R^d$ = hydrogen<br>$R^e$ = 2-[(4-methoxyphenyl) carbomyl]acetamido<br>$R^f$ = hydrogen |

TABLE 6-continued

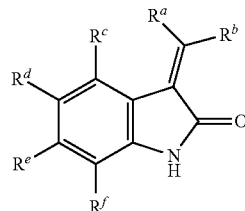

Formula A

| Compound Number Chemical Name | Structure | Substituents of Formula A |
|---|---|---|
| D77 (Z)-N-(3-((1H-pyrrol-2-yl)methylene)-2-oxoindolin-6-yl)-N-(4-methoxyphenyl)cyclopropane-1,1-dicarboxamide | 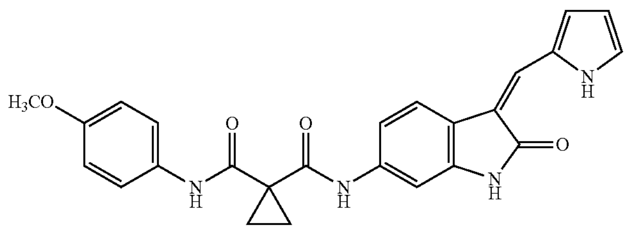 [SMILES: COc1ccc(NC(=O)C2(C(=O)Nc3ccc4c(c3)NC(=O)/C4=C\c3ccc[nH]3)CC2)cc1] | $R^a$ = hydrogen $R^b$ = 1H-pyrrol-2-yl $R^c$ = hydrogen $R^d$ = hydrogen $R^e$ = 1-{(4-methoxyphenyl) carbamoyl] cyclopropane amido} $R^f$ = hydrogen |
| D80 (Z)-N-(3-((1H-pyrrol-2-yl)methylene)-2-oxoindolin-6-yl)-3-methyl-2-oxoimidazolidine-1-carboxamide | 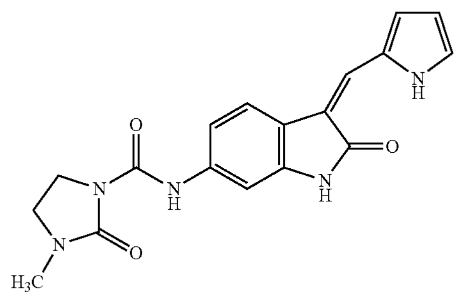 [SMILES: CN1CCN(C(=O)Nc2ccc3c(c2)NC(=O)/C3=C\c2ccc[nH]2)C1=O] | $R^a$ = hydrogen $R^b$ = 1H-pyrrol-2-yl $R^c$ = hydrogen $R^d$ = hydrogen $R^e$ = 3-methyl-2-oxoimidazolidine-1-carbonylamino $R^f$ = hydrogen |
| D81 (Z)-N-(3-((1H-pyrrol-2-yl)methylene)-2-oxoindolin-6-yl)-3-cyclopropyl-2-oxoimidazolidine-1-carboxamide | 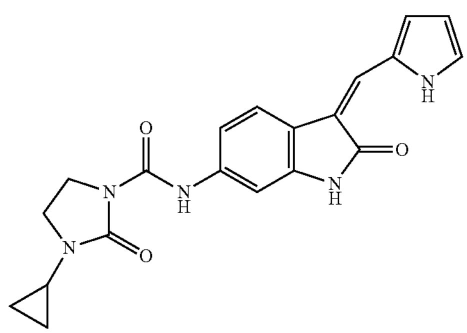 [SMILES: O=C1Nc2cc(NC(=O)N3CCN(C4CC4)C3=O)ccc2/C1=C/c1ccc[nH]1] | $R^a$ = hydrogen $R^b$ = 1H-pyrrol-2-yl $R^c$ = hydrogen $R^d$ = hydrogen $R^e$ = 3-cyclopropyl-2-oxoimidazolidine-1-carbonylamino $R^f$ = hydrogen |
| D82 (Z)-N-(3-((1H-pyrrol-2-yl)methylene)-5-fluoro-2-oxoindolin-6-yl)-3-cyclopropyl-2-oxoimidazolidine-1-carboxamide | 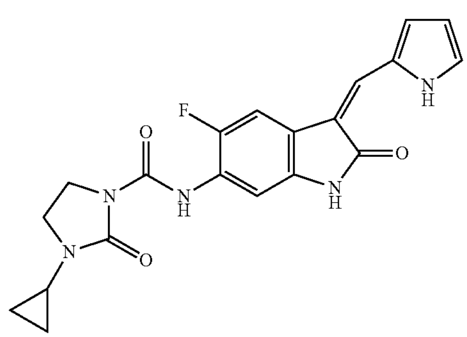 [SMILES: O=C1Nc2cc(NC(=O)N3CCN(C4CC4)C3=O)c(F)cc2/C1=C/c1ccc[nH]1] | $R^a$ = hydrogen $R^b$ = 1H-pyrrol-2-yl $R^c$ = hydrogen $R^d$ = fluoro $R^e$ = 3-cyclopropyl-2-oxoimidazolidine-1-carbonylamino $R^f$ = hydrogen |

TABLE 6-continued

Formula A

| Compound Number Chemical Name | Structure | Substituents of Formula A |
|---|---|---|
| D83 (Z)-N-(3-((1H-pyrrol-2-yl)methylene)-2-oxoindolin-6-yl)-2-oxo-3-phenylimidazolidine-1-carboxamide | 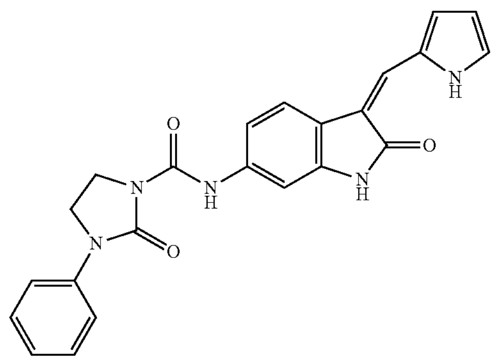 [SMILES: O=C1Nc2cc(NC(=O)N3CCN(c4ccccc4)C3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 3-phenyl-2-oxoimidazolidine-1-carbonylamino<br>$R^f$ = hydrogen |
| D84 (Z)-N-(3-((1H-pyrrol-2-yl)methylene)-2-oxoindolin-6-yl)-3-(4-chlorophenyl)-2-oxoimidazolidine-1-carboxamide | 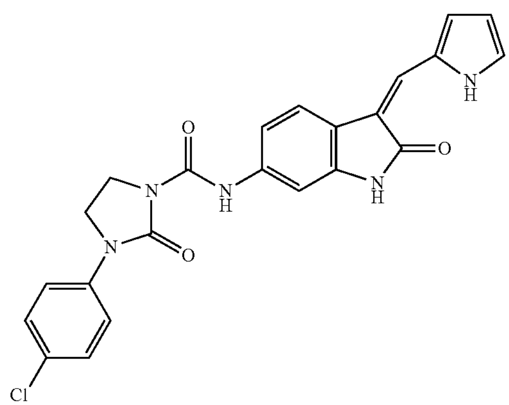 [SMILES: O=C1Nc2cc(NC(=O)N3CCN(c4ccc(Cl)cc4)C3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 3-(4-chlorophenyl)-2-oxoimidazolidine-1-carbonylamino<br>$R^f$ = hydrogen |
| D85 (Z)-N-(3-((1H-pyrrol-2-yl)methylene)-2-oxoindolin-6-yl)-3-(3-chlorophenyl)-2-oxoimidazolidine-1-carboxamide | 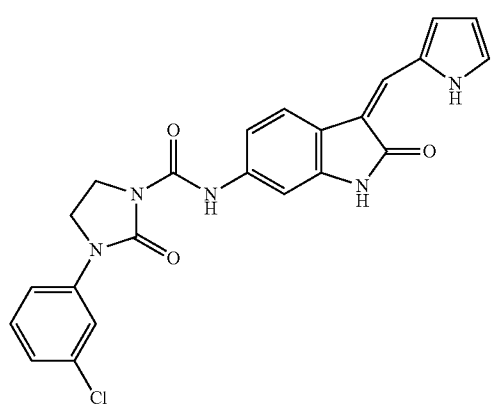 [SMILES: O=C1Nc2cc(NC(=O)N3CCN(c4cccc(Cl)c4)C3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 3-(3-chlorophenyl)-2-oxoimidazolidine-1-carbonylamino<br>$R^f$ = hydrogen |

TABLE 6-continued

Formula A

| Compound Number Chemical Name | Structure | Substituents of Formula A |
|---|---|---|
| D86<br>(Z)-N-(3-((1H-pyrrol-2-yl)methylene)-2-oxoindolin-6-yl)-3-(3,4-dichlorophenyl)-2-oxoimidazolidine-1-carboxamide | | $R^a$ = hydrogen<br>$R^b$ = 1H-pyrrol-2-yl<br>$R^c$ = hydrogen<br>$R^d$ = hydrogen<br>$R^e$ = 3-(3,4-dichlorophenyl)-2-oxoimidazolidine-1-carbonylamino<br>$R^f$ = hydrogen |
| D87<br>(Z)-N-(3-((1H-pyrrol-2-yl)methylene)-2-oxoindolin-6-yl)-3-(4-chloro-3-(trifluoromethyl)phenyl)-2-oxoimidazolidine-1-carboxamide | | $R^a$ = hydrogen<br>$R^b$ = 1H-pyrrol-2-yl<br>$R^c$ = hydrogen<br>$R^d$ = hydrogen<br>$R^e$ = 3-(3-trifluoromethyl-4-chlorophenyl)-2-oxoimidazolidine-1-carbonylamino<br>$R^f$ = hydrogen |
| D88<br>(Z)-N-(3-((1H-pyrrol-2-yl)methylene)-2-oxoindolin-6-yl)-2-oxo-3-(4-(trifluoromethyl)phenyl)imidazolidine-1-carboxamide | | $R^a$ = hydrogen<br>$R^b$ = 1H-pyrrol-2-yl<br>$R^c$ = hydrogen<br>$R^d$ = hydrogen<br>$R^e$ = 3-(4-trifluoromethyl-phenyl)-2-oxoimidazolidine-1-carbonylamino<br>$R^f$ = hydrogen |

TABLE 6-continued

Formula A

| Compound Number Chemical Name | Structure | Substituents of Formula A |
|---|---|---|
| D89 (Z)-N-(3-((1H-pyrrol-2-yl)methylene)-2-oxoindolin-6-yl)-3-(4-fluorophenyl)-2-oxoimidazolidine-1-carboxamide | 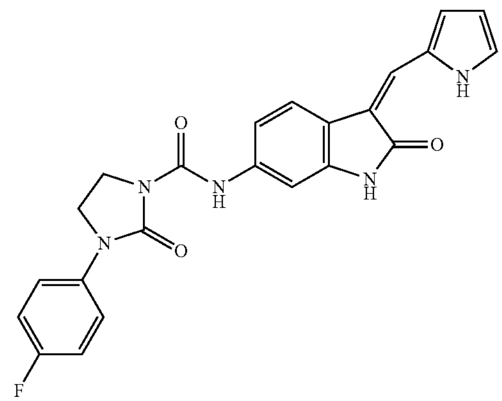 [SMILES: O=C1Nc2cc(NC(=O)N3CCN(c4ccc(F)cc4)C3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 3-(4-fluorophenyl)-2-oxoimidazolidine-1-carbonylamino<br>$R^f$ = hydrogen |
| D90 (Z)-N-(3-((1H-pyrrol-2-yl)methylene)-2-oxoindolin-6-yl)-3-(2-fluorophenyl)-2-oxoimidazolidine-1-carboxamide | 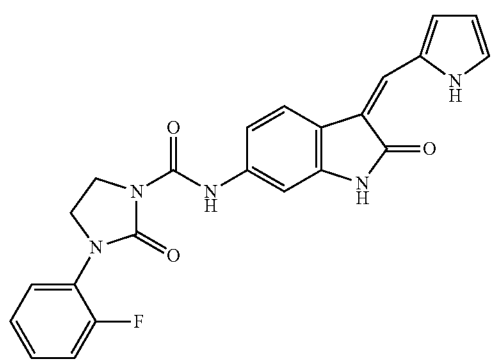 [SMILES: O=C1Nc2cc(NC(=O)N3CCN(c4ccccc4F)C3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 3-(2-fluorophenyl)-2-oxoimidazolidine-1-carbonylamino<br>$R^f$ = hydrogen |
| D91 (Z)-N-(3-((1H-pyrrol-2-yl)methylene)-2-oxoindolin-6-yl)-3-(4-methoxyphenyl)-2-oxoimidazolidine-1-carboxamide | 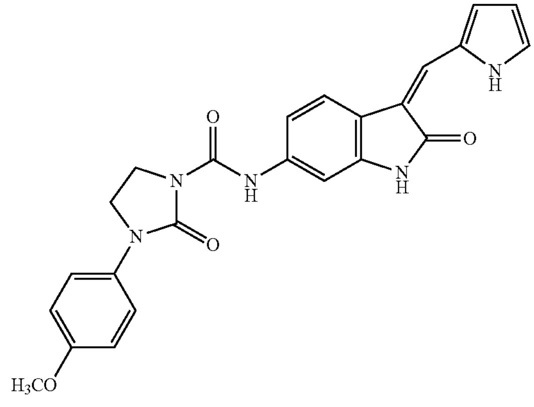 [SMILES: COc1ccc(N2CCN(C(=O)Nc3ccc4c(c3)NC(=O)/C4=C\c3ccc[nH]3)C2=O)cc1] | $R^a$ = hydrogen<br>$R^b$ = 1H-pyrrol-2-yl<br>$R^c$ = hydrogen<br>$R^d$ = hydrogen<br>$R^e$ = 3-(4-methoxyphenyl)-2-oxoimidazolidine-1-carbonylamino<br>$R^f$ = hydrogen |

TABLE 6-continued

Formula A

| Compound Number Chemical Name | Structure | Substituents of Formula A |
|---|---|---|
| D92<br>(Z)-N-(3-((1H-pyrrol-2-yl)methylene)-2-oxoindolin-6-yl)-2-oxo-3-p-tolylimidazolidine-1-carboxamide | 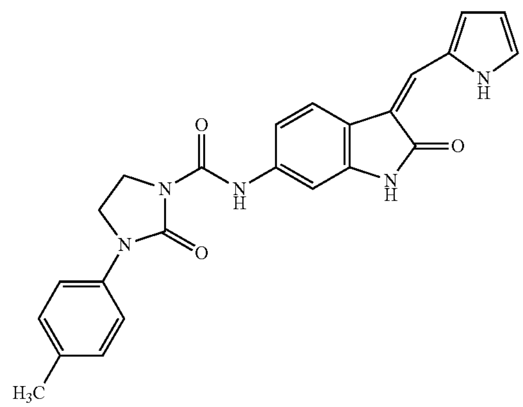 [SMILES: Cc1ccc(N2CCN(C(=O)Nc3ccc4c(c3)NC(=O)/C4=C\c3ccc[nH]3)C2=O)cc1] | $R^a$ = hydrogen<br>$R^b$ = 1H-pyrrol-2-yl<br>$R^c$ = hydrogen<br>$R^d$ = hydrogen<br>$R^e$ = 3-(4-methylphenyl)-2-oxoimidazolidine-1-carbonylamino<br>$R^f$ = hydrogen |
| D93<br>(Z)-N-(3-((1H-pyrrol-2-yl)methylene)-2-oxoindolin-6-yl)-3-(4-(dimethylamino)phenyl)-2-oxoimidazolidine-1-carboxamide | | $R^a$ = hydrogen<br>$R^b$ = 1H-pyrrol-2-yl<br>$R^c$ = hydrogen<br>$R^d$ = hydrogen<br>$R^e$ = 3-(4-dimethylaminophenyl)-2-oxoimidazolidine-1-carbonylamino<br>$R^f$ = hydrogen |
| D94<br>(Z)-N-(3-((1H-pyrrol-2-yl)methylene)-2-oxoindolin-6-yl)-3-(2-fluoro-4-methoxyphenyl)-2-oxoimidazolidine-1-carboxamide | 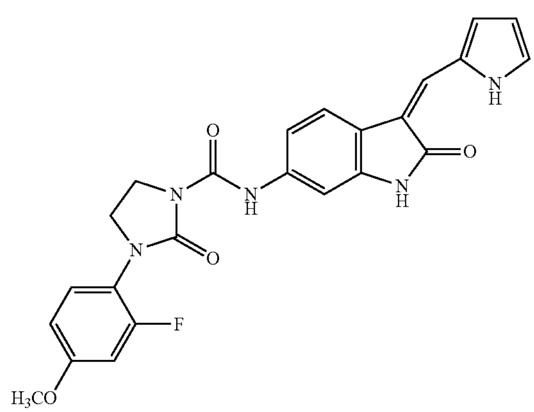 [SMILES: COc1ccc(N2CCN(C(=O)Nc3ccc4c(c3)NC(=O)/C4=C\c3ccc[nH]3)C2=O)c(F)c1] | $R^a$ = hydrogen<br>$R^b$ = 1H-pyrrol-2-yl<br>$R^c$ = hydrogen<br>$R^d$ = hydrogen<br>$R^e$ = 3-(2-fluoro-4-methoxyphenyl)-2-oxoimidazolidine-1-carbonylamino<br>$R^f$ = hydrogen |

TABLE 6-continued

Formula A

| Compound Number Chemical Name | Structure | Substituents of Formula A |
|---|---|---|
| D95<br>(Z)-5-((6-(3-(4-methoxyphenyl)-2-oxoimidazolidine-1-carboxamido)-2-oxoindolin-3-ylidene)methyl)-2,4-dimethyl-1H-pyrrole-3-carboxylic acid | 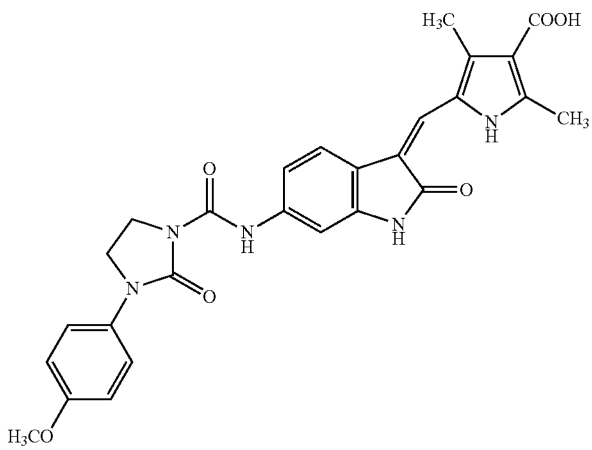 [SMILES: COc1ccc(N2CCN(C(=O)Nc3ccc4c(c3)NC(=O)/C4=C\c3[nH]c(C)c(C(=O)O)c3C)C2=O)cc1] | $R^a$ = hydrogen<br>$R^b$ = 3,5-dimethyl-4-carboxy-1H-pyrrol-2-yl<br>$R^c$ = hydrogen<br>$R^d$ = hydrogen<br>$R^e$ = 3-(4-methoxyphenyl)-2-oxoimidazolidine-1-carbonylamino<br>$R^f$ = hydrogen |
| D96<br>(Z)-5-((6-(3-cyclopropyl-2-oxoimidazolidine-1-carboxamido)-2-oxoindolin-3-ylidene)methyl)-2,4-dimethyl-1H-pyrrole-3-carboxylic acid | 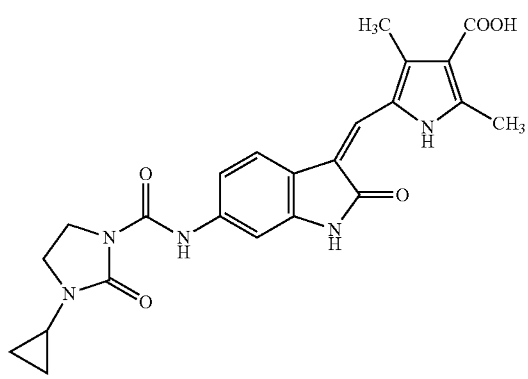 [SMILES: Cc1[nH]c(/C=C2\C(=O)Nc3cc(NC(=O)N4CCN(C5CC5)C4=O)ccc32)c(C)c1C(=O)O] | $R^a$ = hydrogen<br>$R^b$ = 3,5-dimethyl-4-carboxy-1H-pyrrol-2-yl<br>$R^c$ = hydrogen<br>$R^d$ = hydrogen<br>$R^e$ = 3-cyclopropyl-2-oxoimidazolidine-1-carbonylamino<br>$R^f$ = hydrogen |
| D97<br>(Z)-2-(5-((6-(3-cyclopropyl-1-2-oxoimidazolidine-1-carboxamido)-2-oxoindolin-3-ylidene)methyl)-2,4-dimethyl-1H-pyrrol-3-yl)acetic acid | 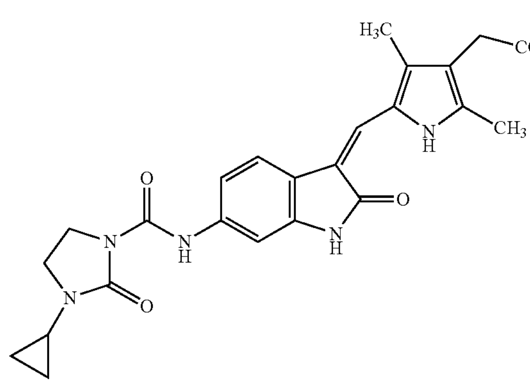 | $R^a$ = hydrogen<br>$R^b$ = 3,5-dimethyl-4-carboxymethyl-1H-pyrrol-2-yl<br>$R^c$ = hydrogen<br>$R^d$ = hydrogen<br>$R^e$ = 3-cyclopropyl-2-oxoimidazolidine-1-carbonylamino<br>$R^f$ = hydrogen |

TABLE 6-continued

Formula A

| Compound Number Chemical Name | Structure | Substituents of Formula A |
|---|---|---|
| D98<br>(Z)-3-(5-((6-(3-cyclopropyl-2-oxoimidazolidine-1-carboxamido)-2-oxoindolin-3-ylidene)methyl)-2,4-dimethyl-1H-pyrrol-3-yl)propanoic acid | 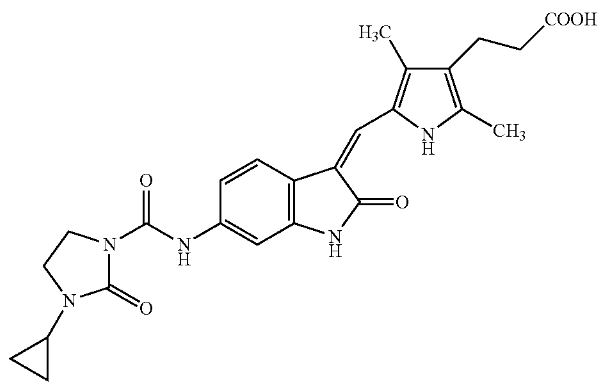 [SMILES: Cc1[nH]c(/C=C2\C(=O)Nc3cc(NC(=O)N4CCN(C5CC5)C4=O)ccc32)c(C)c1CCC(=O)O] | $R^a$ = hydrogen<br>$R^b$ = 3,5-dimethyl-4-(2-carboxyethyl)-1H-pyrrol-2-yl<br>$R^c$ = hydrogen<br>$R^d$ = hydrogen<br>$R^e$ = 3-cyclopropyl-2-oxoimidazolidine-1-carbonylamino<br>$R^f$ = hydrogen |
| D99<br>(Z)-5-((6-(3-(2-fluorophenyl)-2-oxoimidazolidine-1-carboxamido)-2-oxoindolin-3-ylidene)methyl)-2,4-dimethyl-1H-pyrrole-3-carboxylic acid | 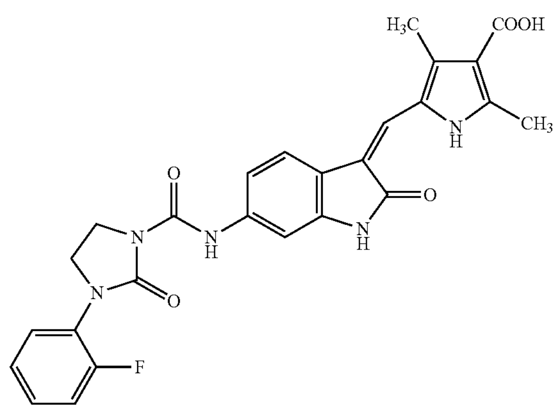 [SMILES: Cc1[nH]c(/C=C2\C(=O)Nc3cc(NC(=O)N4CCN(c5ccccc5F)C4=O)ccc32)c(C)c1C(=O)O] | $R^a$ = hydrogen<br>$R^b$ = 3,5-dimethyl-4-carboxy-1H-pyrrol-2-yl<br>$R^c$ = hydrogen<br>$R^d$ = hydrogen<br>$R^e$ = 3-(2-fluorophenyl)-2-oxoimidazolidine-1-carbonylamino<br>$R^f$ = hydrogen |
| D100<br>(Z)-5-((6-(3-(2-fluoro-4-methoxyphenyl)-2-oxoimidazolidine-1-carboxamido)-2-oxoindolin-3-ylidene)methyl)-2,4-dimethyl-1H-pyrrole-3-carboxylic acid | 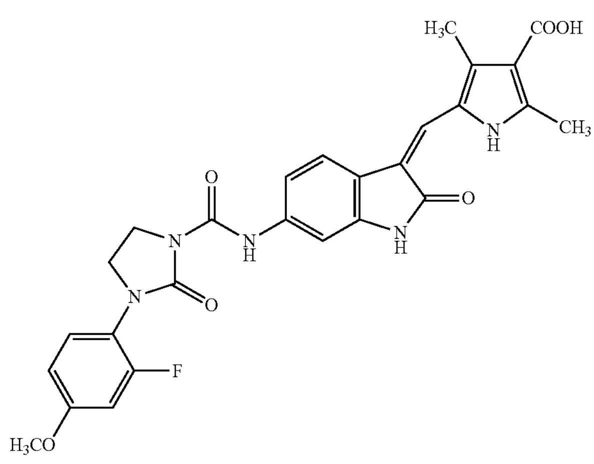 [SMILES: COc1ccc(N2CCN(C(=O)Nc3ccc4c(c3)NC(=O)/C4=C\c3[nH]c(C)c(C(=O)O)c3C)C2=O)c(F)c1] | $R^a$ = hydrogen<br>$R^b$ = 3,5-dimethyl-4-carboxy-1H-pyrrol-2-yl<br>$R^c$ = hydrogen<br>$R^d$ = hydrogen<br>$R^e$ = 3-(2-fluoro-4-methoxyphenyl)-2-oxoimidazolidine-1-carbonylamino<br>$R^f$ = hydrogen |

TABLE 6-continued

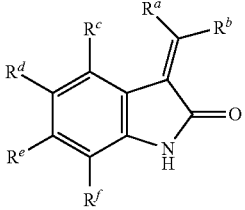

Formula A

| Compound Number Chemical Name | Structure | Substituents of Formula A |
|---|---|---|
| D103 (Z)-N-(3-((1H-pyrrol-2-yl)methylene)-2-oxoindolin-4-yl)-1-(4-fluorophenyl)-2-oxo-1,2-dihydropyridine-3-carboxamide | 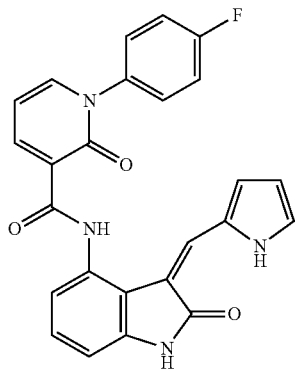 [SMILES: O=C1Nc2cccc(NC(=O)c3cccn(-c4ccc(F)cc4)c3=O)c2/C1=C/c1ccc[nH]1] | $R^a$ = hydrogen<br>$R^b$ = 1H-pyrrol-2-yl<br>$R^c$ = 1-(4-fluorophenyl)-2-oxopyridine-3-amido<br>$R^d$ = hydrogen<br>$R^e$ = hydrogen<br>$R^f$ = hydrogen |
| D104 (Z)-N-(3-((1H-pyrrol-2-yl)methylene)-2-oxoindolin-5-yl)-1-(4-fluorophenyl)-2-oxo-1,2-dihydropyridine-3-carboxamide | 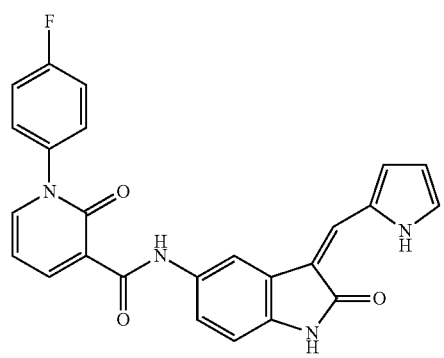 [SMILES: O=C1Nc2ccc(NC(=O)c3cccn(-c4ccc(F)cc4)c3=O)cc2/C1=C/c1ccc[nH]1] | $R^a$ = hydrogen<br>$R^b$ = 1H-pyrrol-2-yl<br>$R^c$ = hydrogen<br>$R^d$ = 1-(4-fluorophenyl)-2-oxopyridine-3-amido<br>$R^e$ = hydrogen<br>$R^f$ = hydrogen |
| D105 (Z)-N-(3-((1H-pyrrol-2-yl)methylene)-2-oxoindolin-6-yl)-2-oxo-1-phenyl-1,2-dihydropyridine-3-carboxamide | 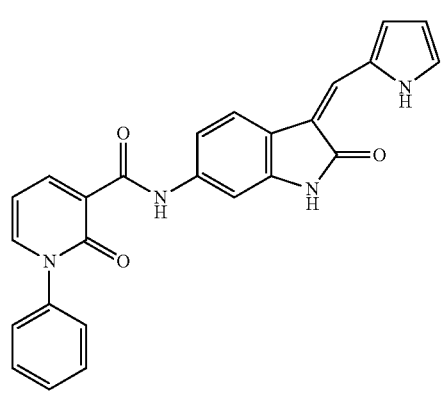 [SMILES: O=C1Nc2cc(NC(=O)c3cccn(-c4ccccc4)c3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 1-phenyl-2-oxopyridine-3-amido<br>$R^f$ = hydrogen |

TABLE 6-continued

Formula A

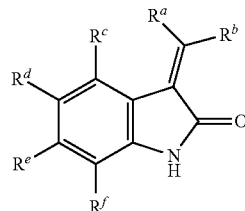

| Compound Number Chemical Name | Structure | Substituents of Formula A |
|---|---|---|
| D106 (Z)-N-(3-((1H-pyrrol-2-yl)methylene)-2-oxoindolin-6-yl)-1-(4-methoxyphenyl)-2-oxo-1,2-dihydropyridine-3-carboxamide | 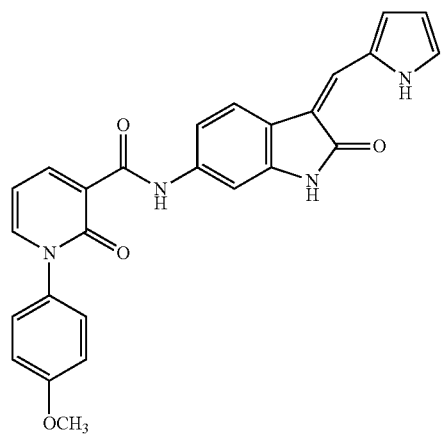 [SMILES: COc1ccc(-n2cccc(C(=O)Nc3ccc4c(c3)NC(=O)/C4=C\c3ccc[nH]3)c2=O)cc1] | $R^a$ = hydrogen $R^b$ = 1H-pyrrol-2-yl $R^c$ = hydrogen $R^d$ = hydrogen $R^e$ = 1-(4-methoxyphenyl)-2-oxopyridine-3-amido $R^f$ = hydrogen |
| D107 (Z)-N-(3-((1H-pyrrol-2-yl)methylene)-2-oxoindolin-6-yl)-1-(4-fluorophenyl)-2-oxo-1,2-dihydropyridine-3-carboxamide | 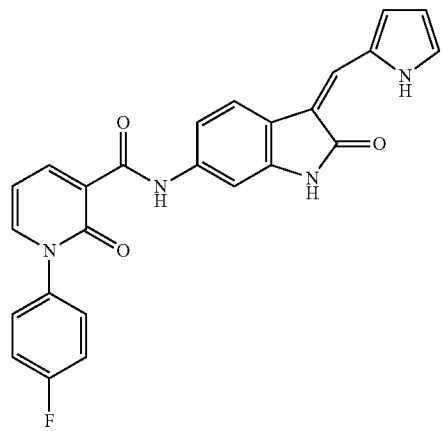 [SMILES: O=C1Nc2cc(NC(=O)c3cccn(-c4ccc(F)cc4)c3=O)ccc2/C1=C/c1ccc[nH]1] | $R^a$ = hydrogen $R^b$ = 1H-pyrrol-2-yl $R^c$ = hydrogen $R^d$ = hydrogen $R^e$ = 1-(4-fluorophenyl)-2-oxopyridine-3-amido $R^f$ = hydrogen |
| D108 (Z)-N-(3-((1H-pyrrol-2-yl)methylene)-2-oxoindolin-6-yl)-1-(4-chlorophenyl)-2-oxo-1,2-dihydropyridine-3-carboxamide | 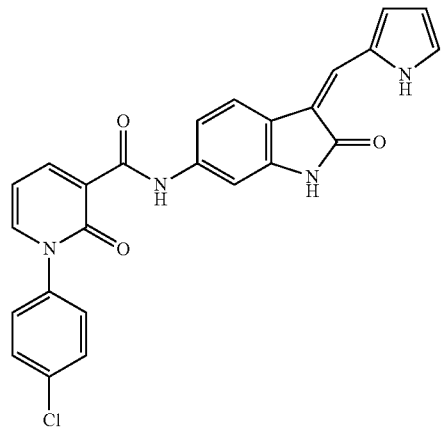 [SMILES: O=C1Nc2cc(NC(=O)c3cccn(-c4ccc(Cl)cc4)c3=O)ccc2/C1=C/c1ccc[nH]1] | $R^a$ = hydrogen $R^b$ = 1H-pyrrol-2-yl $R^c$ = hydrogen $R^d$ = hydrogen $R^e$ = 1-(4-chlorophenyl)-2-oxopyridine-3-amido $R^f$ = hydrogen |

TABLE 6-continued

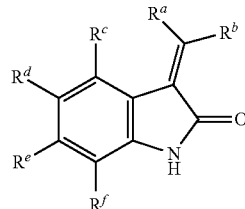

Formula A

| Compound Number Chemical Name | Structure | Substituents of Formula A |
|---|---|---|
| D109 (Z)-N-(3-((1H-pyrrol-2-yl)methylene)-2-oxoindolin-6-yl)-1-(4-chloro-(3-trifluoromethyl)phenyl)-2-oxo-1,2-dihydropyridine-3-carboxamide | 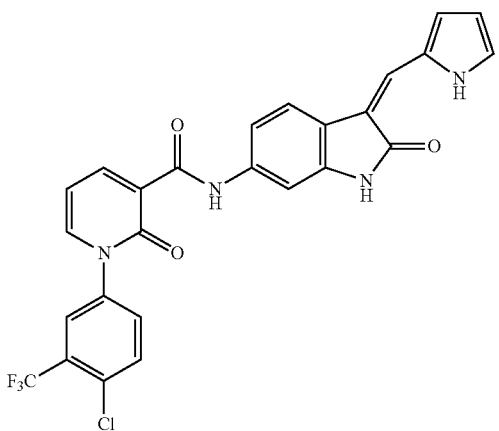 [SMILES: O=C1Nc2cc(NC(=O)c3cccn(-c4ccc(Cl)c(C(F)(F)F)c4)c3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 1-(3-trifluoromethyl-4-chlorophenyl)-2-oxopyridine-3-amido<br>$R^f$ = hydrogen |
| D110 (Z)-N-(3-((1H-pyrrol-2-yl)methylene)-2-oxoindolin-6-yl)-1-(3,4-dichlorophenyl)-2-oxo-1,2-dihydropyridine-3-carboxamide | 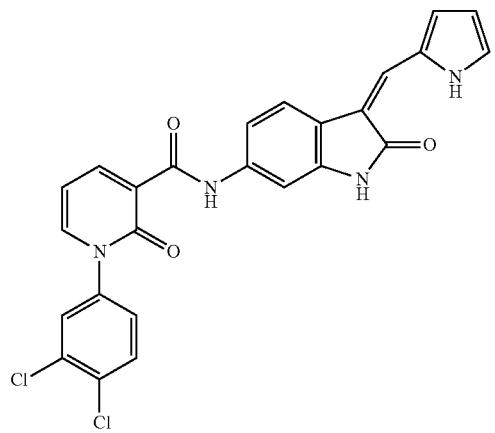 [SMILES: O=C1Nc2cc(NC(=O)c3cccn(-c4ccc(Cl)c(Cl)c4)c3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 1-(3,4-dichlorophenyl)-2-oxopyridine-3-amido<br>$R^f$ = hydrogen |
| D111 (Z)-N-(3-((1H-pyrrol-2-yl)methylene)-2-oxoindolin-6-yl)-2-oxo-1-(p-tolyl)-1,2-dihydropyridine-3-carboxamide | 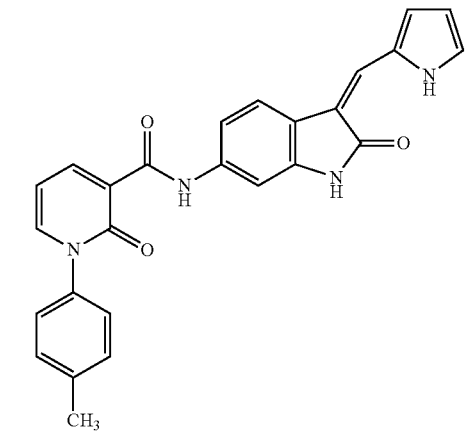 [SMILES: O=C1Nc2cc(NC(=O)c3cccn(-c4ccc(C(F)(F)F)cc4)c3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 1-(4-methylphenyl)-2-oxopyridine-3-amido<br>$R^f$ = hydrogen |

TABLE 6-continued

Formula A

| Compound Number Chemical Name | Structure | Substituents of Formula A |
|---|---|---|
| D112<br>(Z)-N-(3-((1H-pyrrol-2-yl)methylene)-2-oxoindolin-6-yl)-1-(4-(trifluoromethyl)phenyl)-2-oxo-1,2-dihydropyridine-3-carboxamide | | $R^a$ = hydrogen<br>$R^b$ = 1H-pyrrol-2-yl<br>$R^c$ = hydrogen<br>$R^d$ = hydrogen<br>$R^e$ = 1-(4-trifluoromethyl-phenyl)-2-oxopyridine-3-amido<br>$R^f$ = hydrogen |
| D113<br>(Z)-N-(3-((1H-pyrrol-2-yl)methylene)-2-oxoindolin-6-yl)-1-(3-(trifluoromethyl)phenyl-2-oxo-1,2-dihydropyridine-3-carboxamide | | $R^a$ = hydrogen<br>$R^b$ = 1H-pyrrol-2-yl<br>$R^c$ = hydrogen<br>$R^d$ = hydrogen<br>$R^e$ = 1-(3-trifluoromethyl-phenyl)-2-oxopyridine-3-amido<br>$R^f$ = hydrogen |
| D114<br>(Z)-N-(3-((1H-pyrrol-2-yl)methylene)-2-oxoindolin-6-yl)-1-(3-chlorophenyl)-2-oxo-1,2-dihydropyridine-3-carboxamide | | $R^a$ = hydrogen<br>$R^b$ = 1H-pyrrol-2-yl<br>$R^c$ = hydrogen<br>$R^d$ = hydrogen<br>$R^e$ = 1-(3-chlorophenyl)-2-oxopyridine-3-amido<br>$R^f$ = hydrogen |

TABLE 6-continued

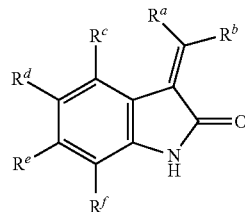

Formula A

| Compound Number Chemical Name | Structure | Substituents of Formula A |
|---|---|---|
| D115 (Z)-N-(3-((1H-pyrrol-2-yl)methylene)-2-oxoindolin-6-yl)-1-(2-fluorophenyl)-2-oxo-1,2-dihydropyridine-3-carboxamide | 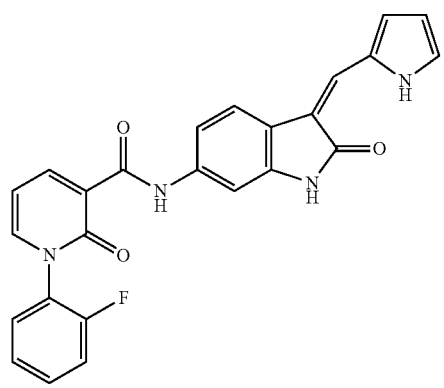 [SMILES: O=C1Nc2cc(NC(=O)c3cccn(-c4ccccc4F)c3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 1-(2-fluorophenyl)-2-oxopyridine-3-amido<br>$R^f$ = hydrogen |
| D116 (Z)-N-(3-((1H-pyrrol-2-yl)methylene)-2-oxoindolin-6-yl)-1-methyl-2-oxo-1,2-dihydropyridine-3-carboxamide | 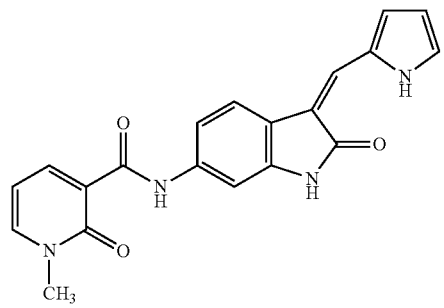 [SMILES: Cn1cccc(C(=O)Nc2ccc3c(c2)NC(=O)/C3=C\c2ccc[nH]2)c1=O] | $R^a$ = hydrogen<br>$R^b$ = 1H-pyrrol-2-yl<br>$R^c$ = hydrogen<br>$R^d$ = hydrogen<br>$R^e$ = 1-methyl-2-oxopyridine-3-amido<br>$R^f$ = hydrogen |
| D117 (Z)-N-(3-((1H-pyrrol-2-yl)methylene)-2-oxoindolin-6-yl)-1-(2-hydroxyethyl)-2-oxo-1,2-dihydropyridine-3-carboxamide | 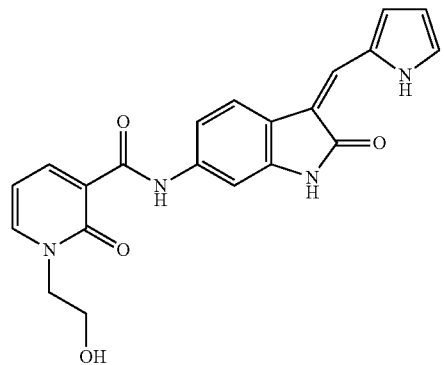 [SMILES: O=C1Nc2cc(NC(=O)c3cccn(CCO)c3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 1-(2-hydroxyethyl)-2-oxopyridine-3-amido<br>$R^f$ = hydrogen |

TABLE 6-continued

Formula A

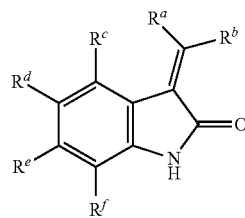

| Compound Number Chemical Name | Structure | Substituents of Formula A |
|---|---|---|
| D118 (Z)-N-(3-((1H-pyrrol-2-yl)methylene)-2-oxoindolin-7-yl)-1-(4-fluorophenyl)-2-oxo-1,2-dihydropyridine-3-carboxamide | 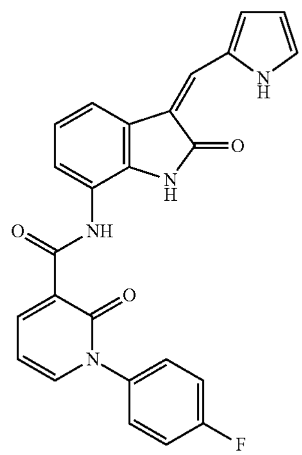 [SMILES: O=C1Nc2c(NC(=O)c3cccn(-c4ccc(F)cc4)c3=O)cccc2/C1=C/c1ccc[nH]1] | $R^a$ = hydrogen $R^b$ = 1H-pyrrol-2-yl $R^c$ = hydrogen $R^d$ = hydrogen $R^e$ = hydrogen $R^f$ = 1-(4-fluorophenyl)-2-oxopyridine-3-amido |
| D119 (Z)-N-(3-((3,5-dimethyl-1H-pyrrol-2-yl)methylene)-2-oxoindolin-6-yl)-1-(4-fluorophenyl)-2-oxo-1,2-dihydropyridine-3-carboxamide | 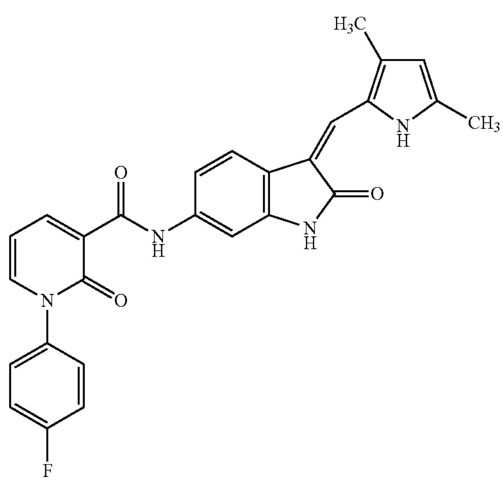 [SMILES: Cc1cc(C)c(/C=C2\C(=O)Nc3cc(NC(=O)c4cccn(-c5ccc(F)cc5)c4=O)ccc32)[nH]1] | $R^a$ = hydrogen $R^b$ = 3,5-dimethyl-1H-pyrrol-2-yl $R^c$ = hydrogen $R^d$ = hydrogen $R^e$ = 1-(4-fluorophenyl)-2-oxopyridine-3-amido $R^f$ = hydrogen |

TABLE 6-continued

Formula A

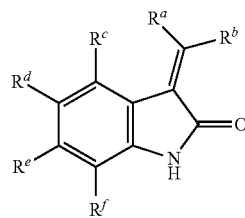

| Compound Number<br>Chemical Name | Structure | Substituents of<br>Formula A |
|---|---|---|
| D120<br>(Z)-5-((6-(1-(4-fluorophenyl)-2-oxo-1,2-dihydropyridine-3-carboxamido)-2-oxoindolin-3-ylidene)methyl)-2,4-dimethyl-1H-pyrrole-3-carboxylic acid | 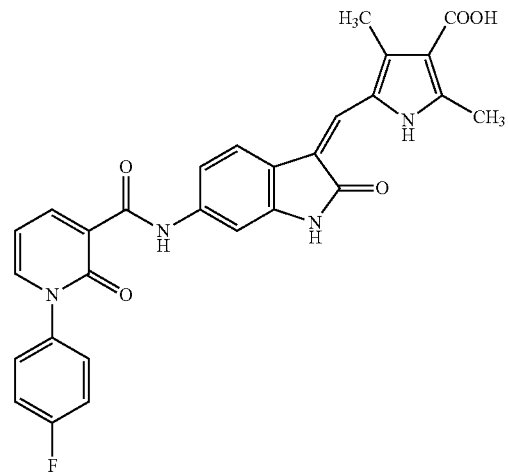 [SMILES: Cc1[nH]c(/C=C2\C(=O)Nc3cc(NC(=O)c4cccn(-c5ccc(F)cc5)c4=O)ccc32)c(C)c1C(=O)O] | $R^a$ = hydrogen<br>$R^b$ = 3,5-dimethyl-4-carboxy-1H-pyrrol-2-yl<br>$R^c$ = hydrogen<br>$R^d$ = hydrogen<br>$R^e$ = 1-(4-fluorophenyl)-2-oxopyridine-3-amido<br>$R^f$ = hydrogen |
| D121<br>(Z)-2-(5-((6-(1-(4-fluorophenyl)-2-oxo-1,2-dihydropyridine-3-carboxamido)-2-oxoindolin-3-ylidene)methyl)-2,4-dimethyl-1H-pyrrol-3-yl)acetic acid | 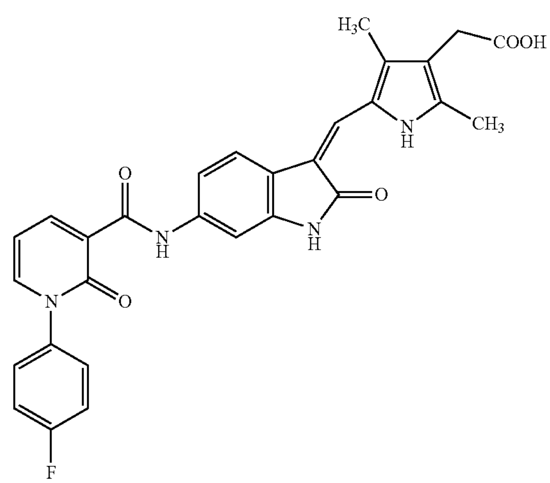 [SMILES: Cc1[nH]c(/C=C2\C(=O)Nc3cc(NC(=O)c4cccn(-c5ccc(F)cc5)c4=O)ccc32)c(C)c1CC(=O)O] | $R^a$ = hydrogen<br>$R^b$ = 3,5-dimethyl-4-carboxymethyl-1H-pyrrol-2-yl<br>$R^c$ = hydrogen<br>$R^d$ = hydrogen<br>$R^e$ = 1-(4-fluorophenyl)-2-oxopyridine-3-amido<br>$R^f$ = hydrogen |

TABLE 6-continued

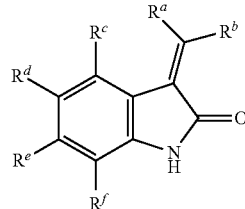

Formula A

| Compound Number Chemical Name | Structure | Substituents of Formula A |
|---|---|---|
| D122 (Z)-3-(5-((6-(1-(4-fluorophenyl)-2-oxo-1,2-dihydropyridine-3-carboxamido)-2-oxoindolin-3-ylidene)methyl)-2,4-dimethyl-1H-pyrrol-3-yl)propanoic acid | 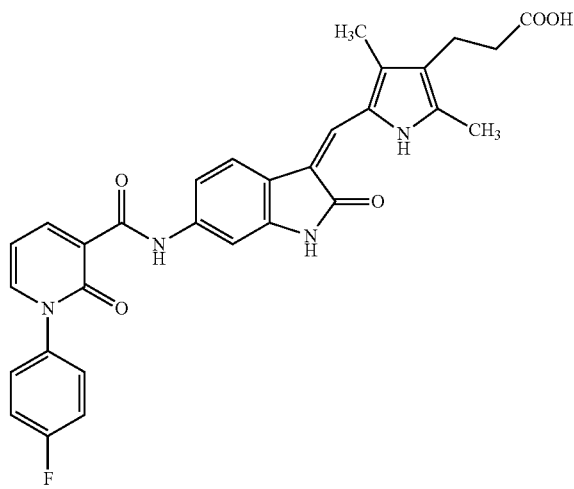 [SMILES: Cc1[nH]c(/C=C2\C(=O)Nc3cc(NC(=O)c4cccn(-c5ccc(F)cc5)c4=O)ccc32)c(C)c1CCC(=O)O] | $R^a$ = hydrogen $R^b$ = 3,5-dimethyl-4-(2-carboxyethyl)-1H-pyrrol-2-yl $R^c$ = hydrogen $R^d$ = hydrogen $R^e$ = 1-(4-fluorophenyl)-2-oxopyridine-3-amido $R^f$ = hydrogen |
| D123 (Z)-methyl-3-(5-((6-(1-(4-fluorophenyl)-2-oxo-1,2-dihydropyridine-3-carboxamido)-2-oxoindolin-3-ylidene)methyl)-2,4-dimethyl-1H-pyrrol-3-yl)propanoate | 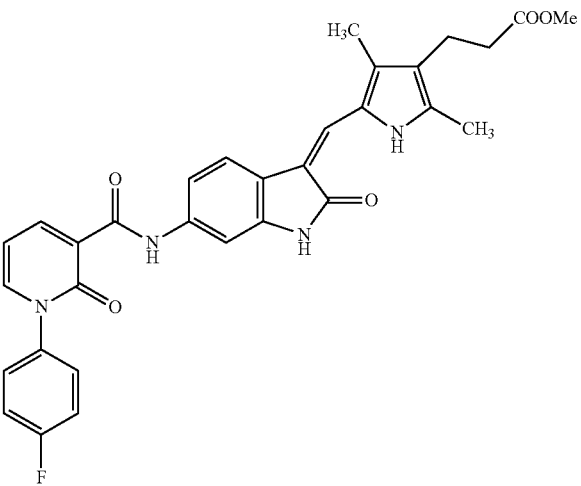 [SMILES: COC(=O)CCc1c(C)[nH]c(/C=C2\C(=O)Nc3cc(NC(=O)c4cccn(-c5ccc(F)cc5)c4=O)ccc32)c1C] | $R^a$ = hydrogen $R^b$ = 3,5-dimethyl-4-(3-methoxy-3-oxopropyl)-1H-pyrrol-2-yl $R^c$ = hydrogen $R^d$ = hydrogen $R^e$ = 1-(4-fluorophenyl)-2-oxopyridine-3-amido $R^f$ = hydrogen |
| D124 (Z)-2,4-dimethyl-5-((6-(1-methyl-2-oxo-1,2-dihydropyridine-3-carboxamido)-2-oxoindolin-3-ylidene)methyl)-1H-pyrrole-3-carboxylic acid | 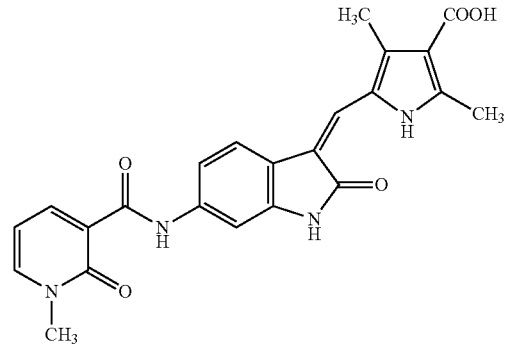 [SMILES: Cc1[nH]c(/C=C2\C(=O)Nc3cc(NC(=O)c4cccn(C)c4=O)ccc32)c(C)c1C(=O)O] | $R^a$ = hydrogen $R^b$ = 3,5-dimethyl-4-carboxy-1H-pyrrol-2-yl $R^c$ = hydrogen $R^d$ = hydrogen $R^e$ = 1-methyl-2-oxopyridine-3-amido $R^f$ = hydrogen |

TABLE 6-continued

Formula A

| Compound Number Chemical Name | Structure | Substituents of Formula A |
|---|---|---|
| D127 (Z)-N-(3-((1H-pyrrol-2-yl)methylene)-2-oxoindolin-6-yl)-4-oxo-5-phenyl-1,4-dihydropyridine-3-carboxamide | 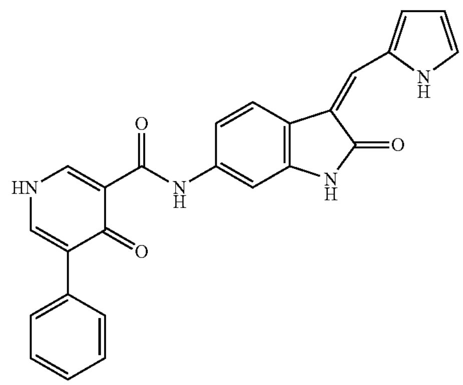 [SMILES: O=C1Nc2cc(NC(=O)c3c[nH]cc(-c4ccccc4)c3=O)ccc2/C1=C/c1ccc[nH]1] | $R^a$ = hydrogen $R^b$ = 1H-pyrrol-2-yl $R^c$ = hydrogen $R^d$ = hydrogen $R^e$ = 5-phenyl-4-oxopyridine-3-amido $R^f$ = hydrogen |
| D128 (Z)-N-(3-((1H-pyrrol-2-yl)methylene)-2-oxoindolin-6-yl)-5-(4-methoxyphenyl)-4-oxo-1,4-dihydropyridine-3-carboxamide | 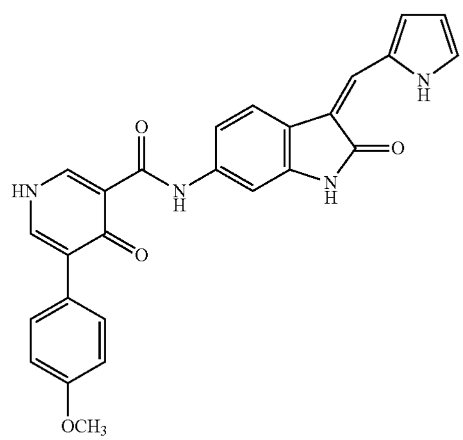 [SMILES: COc1ccc(-c2c[nH]cc(C(=O)Nc3ccc4c(c3)NC(=O)/C4=C\c3ccc[nH]3)c2=O)cc1] | $R^a$ = hydrogen $R^b$ = 1H-pyrrol-2-yl $R^c$ = hydrogen $R^d$ = hydrogen $R^e$ = 5-(4-methoxyphenyl)-4-oxopyridine-3-amido $R^f$ = hydrogen |
| D129 (Z)-N-(3-((1H-pyrrol-2-yl)methylene)-2-oxoindolin-6-yl)-5-(4-fluorophenyl)-4-oxo-1,4-dihydropyridine-3-carboxamide | 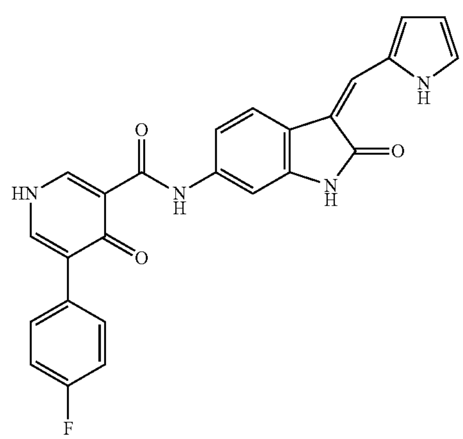 [SMILES: O=C1Nc2cc(NC(=O)c3c[nH]cc(-c4ccc(F)cc4)c3=O)ccc2/C1=C/c1ccc[nH]1] | $R^a$ = hydrogen $R^b$ = 1H-pyrrol-2-yl $R^c$ = hydrogen $R^d$ = hydrogen $R^e$ = 5-(4-fluorophenyl)-4-oxopyridine-3-amido $R^f$ = hydrogen |

TABLE 6-continued

Formula A

| Compound Number Chemical Name | Structure | Substituents of Formula A |
|---|---|---|
| D130 (Z)-N-(3-((1H-pyrrol-2-yl)methylene)-2-oxoindolin-6-yl)-5-(4-chlorophenyl)-4-oxo-1,4-dihydropyridine-3-carboxamide | | $R^a$ = hydrogen $R^b$ = 1H-pyrrol-2-yl $R^c$ = hydrogen $R^d$ = hydrogen $R^e$ = 5-(4-chlorophenyl)-4-oxopyridine-3-amido $R^f$ = hydrogen |
| D131 (Z)-N-(3-((1H-pyrrol-2-yl)methylene)-2-oxoindolin-6-yl)-5-p-tolyl-4-oxo-1,4-dihydropyridine-3-carboxamide | | $R^a$ = hydrogen $R^b$ = 1H-pyrrol-2-yl $R^c$ = hydrogen $R^d$ = hydrogen $R^e$ = 5-(4-methylphenyl)-4-oxopyridine-3-amido $R^f$ = hydrogen |
| D132 (Z)-N-(3-((1H-pyrrol-2-yl)methylene)-2-oxoindolin-6-yl)-5-(3-chlorophenyl)-4-oxo-1,4-dihydropyridine-3-carboxamide | | $R^a$ = hydrogen $R^b$ = 1H-pyrrol-2-yl $R^c$ = hydrogen $R^d$ = hydrogen $R^e$ = 5-(3-chlorophenyl)-4-oxopyridine-3-amido $R^f$ = hydrogen |

TABLE 6-continued

Formula A

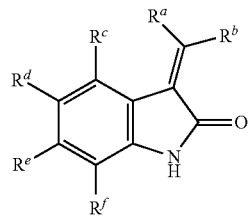

| Compound Number Chemical Name | Structure | Substituents of Formula A |
|---|---|---|
| D133 (Z)-N-(3-((1H-pyrrol-2-yl)methylene)-2-oxoindolin-6-yl)-4-oxo-5-(4-(trifluoromethyl)phenyl)-1,4-dihydropyridine-3-carboxamide | 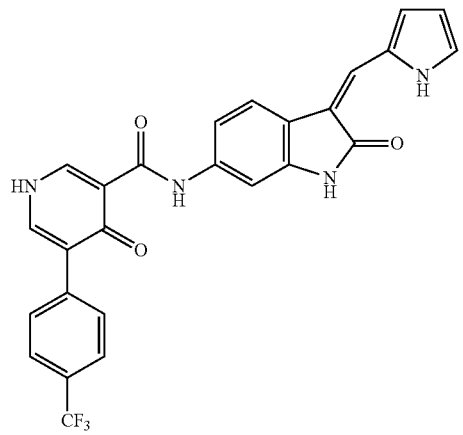 [SMILES: O=C1Nc2cc(NC(=O)c3c[nH]cc(-c4ccc(C(F)(F)F)cc4)c3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 5-(4-trifluoromethyl-phenyl)-4-oxopyridine-3-amido<br>$R^f$ = hydrogen |
| D134 (Z)-N-(3-((1H-pyrrol-2-yl)methylene)-2-oxoindolin-6-yl)-4-oxo-5-(2-fluorophenyl)-1,4-dihydropyridine-3-carboxamide | 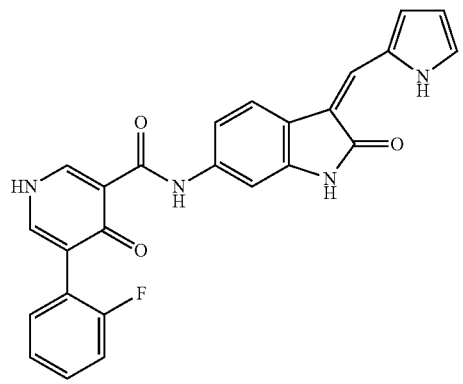 [SMILES: O=C1Nc2cc(NC(=O)c3c[nH]cc(-c4ccccc4F)c3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 5-(2-fluorophenyl)-4-oxopyridine-3-amido<br>$R^f$ = hydrogen |
| D135 (Z)-N-(3-((1H-pyrrol-2-yl)methylene)-2-oxoindolin-6-yl)-4-oxo-5-(2,4-difluorophenyl)-1,4-dihydropyridine-3-carboxamide | 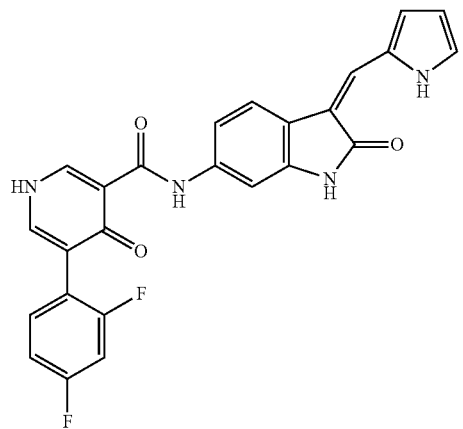 [SMILES: O=C1Nc2cc(NC(=O)c3c[nH]cc(-c4ccc(F)cc4F)c3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 5-(2,4-difluorophenyl)-4-oxopyridine-3-amido<br>$R^f$ = hydrogen |

TABLE 6-continued

Formula A

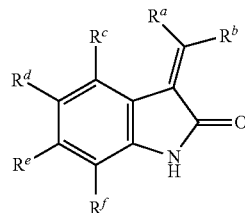

| Compound Number Chemical Name | Structure | Substituents of Formula A |
|---|---|---|
| D136<br>(Z)-N-(3-((1H-pyrrol-2-yl)methylene)-2-oxoindolin-6-yl)-4-oxo-5-(3,5-difluorophenyl)-1,4-dihydropyridine-3-carboxamide | 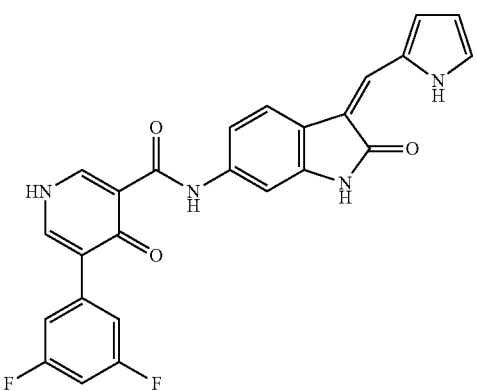 [SMILES: O=C1Nc2cc(NC(=O)c3c[nH]cc(-c4cc(F)cc(F)c4)c3=O)ccc2/C1=C/c1ccc[nH]1] | $R^a$ = hydrogen<br>$R^b$ = 1H-pyrrol-2-yl<br>$R^c$ = hydrogen<br>$R^d$ = hydrogen<br>$R^e$ = 5-(3,5-difluorophenyl)-4-oxopyridine-3-amido<br>$R^f$ = hydrogen |
| D137<br>(Z)-N-(3-((1H-pyrrol-2-yl)methylene)-5-fluoro-2-oxoindolin-6-yl)-5-(4-fluorophenyl)-4-oxo-1,4-dihydropyridine-3-carboxamide | 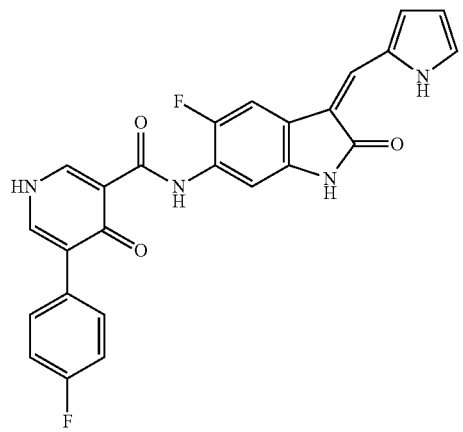 [SMILES: O=C1Nc2cc(NC(=O)c3c[nH]cc(-c4ccc(F)cc4)c3=O)c(F)cc2/C1=C/c1ccc[nH]1] | $R^a$ = hydrogen<br>$R^b$ = 1H-pyrrol-2-yl<br>$R^c$ = hydrogen<br>$R^d$ = fluoro<br>$R^e$ = 5-(4-fluorophenyl)-4-oxopyridine-3-amido<br>$R^f$ = hydrogen |
| D138<br>(Z)-N-(3-((1H-pyrrol-2-yl)methylene)-2-oxoindolin-6-yl)-5-(4-fluorophenyl)-1-methyl-4-oxo-1,4-dihydropyridine-3-carboxamide | 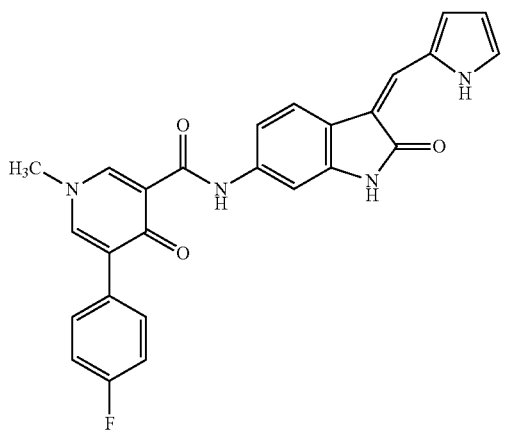 [SMILES: Cn1cc(C(=O)Nc2ccc3c(c2)NC(=O)/C3=C\c2ccc[nH]2)c(=O)c(-c2ccc(F)cc2)c1] | $R^a$ = hydrogen<br>$R^b$ = 1H-pyrrol-2-yl<br>$R^c$ = hydrogen<br>$R^d$ = hydrogen<br>$R^e$ = 1-methyl-5-(4-fluorophenyl)-4-oxopyridine-3-amido<br>$R^f$ = hydrogen |

TABLE 6-continued

Formula A

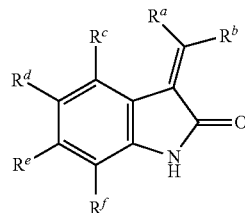

| Compound Number<br>Chemical Name | Structure | Substituents of<br>Formula A |
|---|---|---|
| D139<br>(Z)-N-(3-((1H-pyrrol-2-yl)methylene)-2-oxoindolin-6-yl)-5-methyl-4-oxo-1,4-dihydropyridine-3-carboxamide | | $R^a$ = hydrogen<br>$R^b$ = 1H-pyrrol-2-yl<br>$R^c$ = hydrogen<br>$R^d$ = hydrogen<br>$R^e$ = 5-methyl-4-oxopyridine-3-amido<br>$R^f$ = hydrogen |
| D140<br>(Z)-N-(3-((3,5-dimethyl-1H-pyrrol-2-yl)methylene)-2-oxoindolin-6-yl)-5-(4-fluorophenyl)-4-oxo-1,4-dihydropyridine-3-carboxamide | | $R^a$ = hydrogen<br>$R^b$ = 3,5-dimethyl-1H-pyrrol-2-yl<br>$R^c$ = hydrogen<br>$R^d$ = hydrogen<br>$R^e$ = 5-(4-fluorophenyl)-4-oxopyridine-3-amido<br>$R^f$ = hydrogen |
| D141<br>(Z)-5-((6-(5-(4-fluorophenyl)-4-oxo-1,4-dihydropyridine-3-carboxamido)-2-oxoindolin-3-ylidene)methyl)-2,4-dimethyl-1H-pyrrole-3-carboxylic acid | | $R^a$ = hydrogen<br>$R^b$ = 3,5-dimethyl-4-carboxy-1H-pyrrol-2-yl<br>$R^c$ = hydrogen<br>$R^d$ = hydrogen<br>$R^e$ = 5-(4-fluorophenyl)-4-oxopyridine-3-amido<br>$R^f$ = hydrogen |

TABLE 6-continued

Formula A

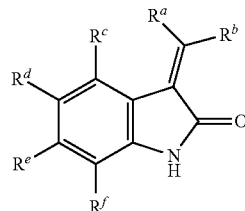

| Compound Number Chemical Name | Structure | Substituents of Formula A |
|---|---|---|
| D142 (Z)-5-((6-(5-(4-methoxyphenyl)-4-oxo-1,4-dihydropyridine-3-carboxamido)-2-oxoindolin-3-ylidene)methyl)-2,4-dimethyl-1H-pyrrole-3-carboxylic acid | 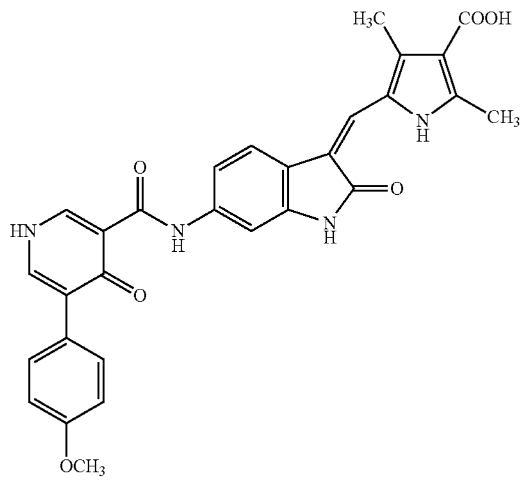 [SMILES: COc1ccc(-c2c[nH]cc(C(=O)Nc3ccc4c(c3)NC(=O)/C4=C\c3[nH]c(C)c(C(=O)O)c3C)c2=O)cc1] | $R^a$ = hydrogen $R^b$ = 3,5-dimethyl-4-carboxy-1H-pyrrol-2-yl $R^c$ = hydrogen $R^d$ = hydrogen $R^e$ = 5-(4-methoxyphenyl)-4-oxopyridine-3-amido $R^f$ = hydrogen |
| D143 (Z)-2,4-dimethyl-5-((6-(5-methyl-4-oxo-1,4-dihydropyridine-3-carboxamido)-2-oxoindolin-3-ylidene)methyl)-1H-pyrrole-3-carboxylic acid | 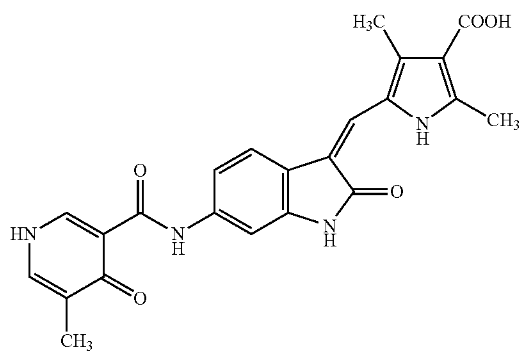 [SMILES: Cc1[nH]c(/C=C2\C(=O)Nc3cc(NC(=O)c4c[nH]cc(C)c4=O)ccc32)c(C)c1C(=O)O] | $R^a$ = hydrogen $R^b$ = 3,5-dimethyl-4-carboxy-1H-pyrrol-2-yl $R^c$ = hydrogen $R^d$ = hydrogen $R^e$ = 5-methyl-4-oxopyridine-3-amido $R^f$ = hydrogen |
| D144 (Z)-2-(5-((6-(5-(4-fluorophenyl)-4-oxo-1,4-dihydropyridine-3-carboxamido)-2-oxoindolin-3-ylidene)methyl)-2,4-dimethyl-1H-pyrrol-3-yl)acetic acid | 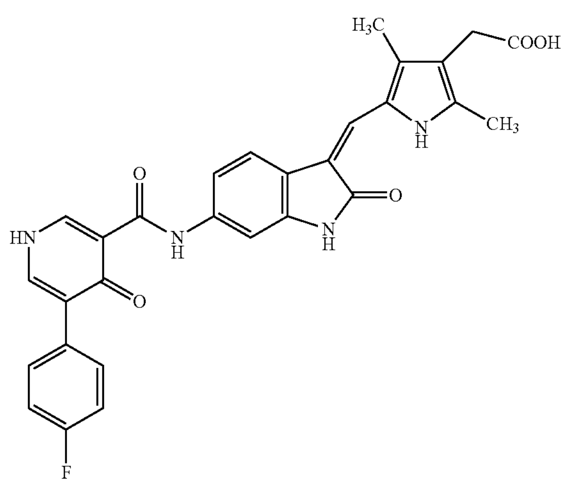 [SMILES: Cc1[nH]c(/C=C2\C(=O)Nc3cc(NC(=O)c4c[nH]cc(-c5ccc(F)cc5)c4=O)ccc32)c(C)c1CC(=O)O] | $R^a$ = hydrogen $R^b$ = 3,5-dimethyl-4-carboxymethyl-1H-pyrrol-2-yl $R^c$ = hydrogen $R^d$ = hydrogen $R^e$ = 5-(4-fluorophenyl)-4-oxopyridine-3-amido $R^f$ = hydrogen |

TABLE 6-continued

Formula A

| Compound Number Chemical Name | Structure | Substituents of Formula A |
|---|---|---|
| D145 (Z)-3-(5-((6-(5-(4-fluorophenyl)-4-oxo-1,4-dihydropyridine-3-carboxamido)-2-oxoindolin-3-ylidene)methyl)-2,4-dimethyl-1H-pyrrol-3-yl)propanoic acid | 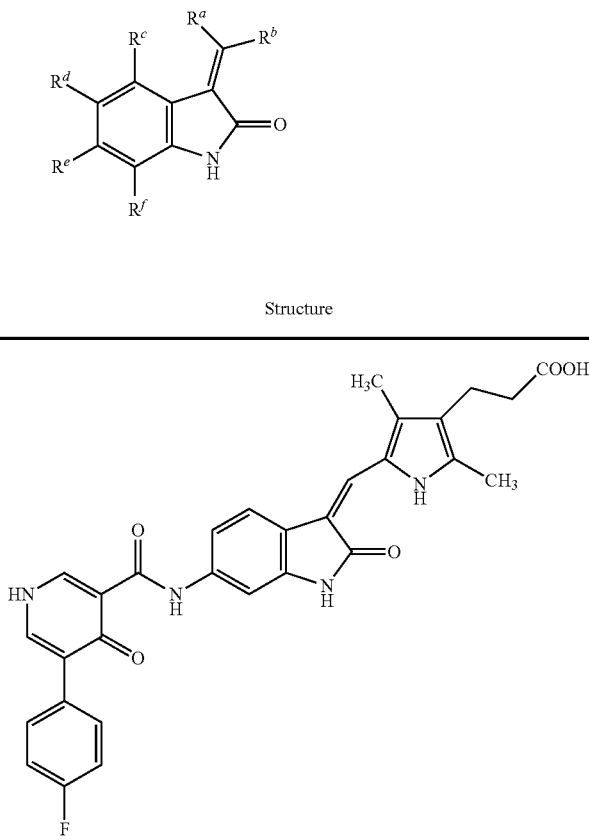 | $R^a$ = hydrogen<br>$R^b$ = 3,5-dimethyl-4-(2-carboxyethyl)-1H-pyrrol-2-yl<br>$R^c$ = hydrogen<br>$R^d$ = hydrogen<br>$R^e$ = 5-(4-fluorophenyl)-4-oxopyridine-3-amido<br>$R^f$ = hydrogen |
| D146 (Z)-5-((6-(5-(4-fluorophenyl)-4-oxo-1,4-dihydropyridine-3-carboxamido)-2-oxoindolin-3-ylidene)methyl)-4-methyl-1H-pyrrole-2-carboxylic acid | 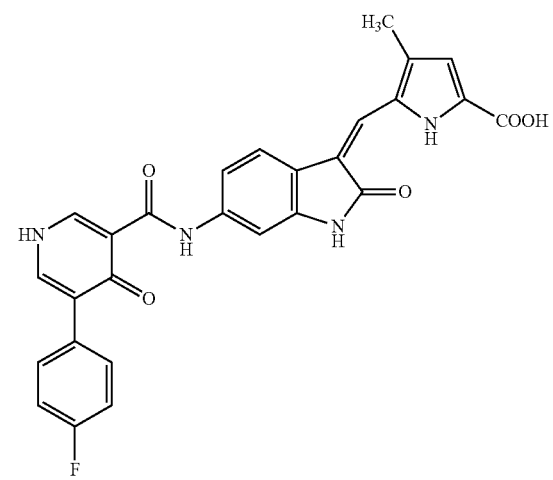 [SMILES: Cc1cc(C(=O)O)[nH]c1/C=C1\C(=O)Nc2cc(NC(=O)c3c[nH]cc(-c4ccc(F)cc4)c3=O)ccc21] | $R^a$ = hydrogen<br>$R^b$ = 3-methyl-5-carboxy-1H-pyrrol-2-yl<br>$R^c$ = hydrogen<br>$R^d$ = hydrogen<br>$R^e$ = 5-(4-fluorophenyl)-4-oxopyridine-3-amido<br>$R^f$ = hydrogen |

TABLE 6-continued

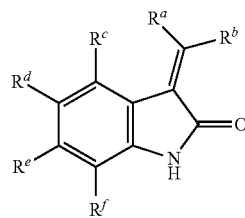

Formula A

| Compound Number Chemical Name | Structure | Substituents of Formula A |
|---|---|---|
| D147<br>(Z)-3-(5-((6-(5-(2,4-difluorophenyl)-4-oxo-1,4-dihydropyridine-3-carboxamido)-2-oxoindolin-3-ylidene)methyl)-2,4-dimethyl-1H-pyrrol-3-yl)propanoic acid | | $R^a$ = hydrogen<br>$R^b$ = 3,5-dimethyl-4-(2-carboxyethyl)-1H-pyrrol-2-yl<br>$R^c$ = hydrogen<br>$R^d$ = hydrogen<br>$R^e$ = 5-(2,4-difluorophenyl)-4-oxopyridine-3-amido<br>$R^f$ = hydrogen |
| D148<br>(Z)-3-(5-((6-(5-(3,5-difluorophenyl)-4-oxo-1,4-dihydropyridine-3-carboxamido)-2-oxoindolin-3-ylidene)methyl)-2,4-dimethyl-1H-pyrrol-3-yl)propanoic acid | | $R^a$ = hydrogen<br>$R^b$ = 3,5-dimethyl-4-(2-carboxyethyl)-1H-pyrrol-2-yl<br>$R^c$ = hydrogen<br>$R^d$ = hydrogen<br>$R^e$ = 5-(3,5-difluorophenyl)-4-oxopyridine-3-amido<br>$R^f$ = hydrogen |

Formula A

| Compound Number Chemical Name | Structure | Substituents of Formula A |
|---|---|---|
| D149<br>(Z)-N-(3-((3,5-dimethyl-4-(4-methylpiperazine-1-carbonyl)-1H-pyrrol-2-yl)methylene)-2-oxoindolin-6-yl)-5-(4-fluorophenyl)-4-oxo-1,4-dihydropyridine-3-carboxamide | 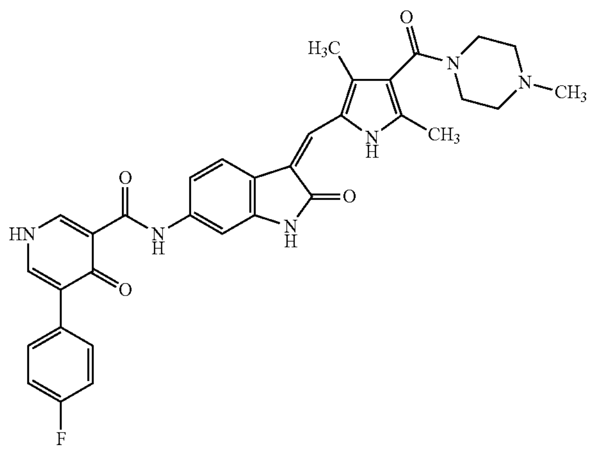 [SMILES: Cc1[nH]c(/C=C2\C(=O)Nc3cc(NC(=O)c4c[nH]cc(-c5ccc(F)cc5)c4=O)ccc32)c(C)c1C(=O)N1CCN(C)CC1] | $R^a$ = hydrogen<br>$R^b$ = 3,5-dimethyl-4-(4-methylpiperazine-1-carbonyl)-1H-pyrrol-2-yl<br>$R^c$ = hydrogen<br>$R^d$ = hydrogen<br>$R^e$ = 5-(4-fluorophenyl)-4-oxopyridine-3-amido<br>$R^f$ = hydrogen |
| D150<br>(Z)-N-(3-((3,5-dimethyl-4-(2-(4-methylpiperazin-1-yl)-2-oxoethyl)-1H-pyrrol-2-yl)methylene)-2-oxoindolin-6-yl)-5-(4-fluorophenyl)-4-oxo-1,4-dihydropyridine-3-carboxamide | 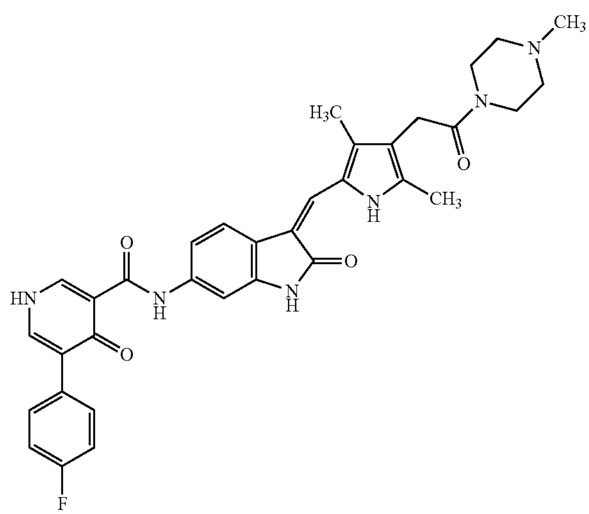 [SMILES: Cc1[nH]c(/C=C2\C(=O)Nc3cc(NC(=O)c4c[nH]cc(-c5ccc(F)cc5)c4=O)ccc32)c(C)c1CC(=O)N1CCN(C)CC1] | $R^a$ = hydrogen<br>$R^b$ = 3,5-dimethyl-4-(3-(4-methylpiperazino-2-oxoethyl))-1H-pyrrol-2-yl<br>$R^c$ = hydrogen<br>$R^d$ = hydrogen<br>$R^e$ = 5-(4-fluorophenyl)-4-oxopyridine-3-amido<br>$R^f$ = hydrogen |

TABLE 6-continued

Formula A

| Compound Number Chemical Name | Structure | Substituents of Formula A |
|---|---|---|
| D151 (Z)-N-(3-((3,5-dimethyl-4-(3-(4-methylpiperazin-1-yl)-3-oxopropyl)-1H-pyrrol-2-yl)methylene)-2-oxoindolin-6-yl)-5-(4-fluorophenyl)-4-oxo-1,4-dihydropyridine-3-carboxamide | 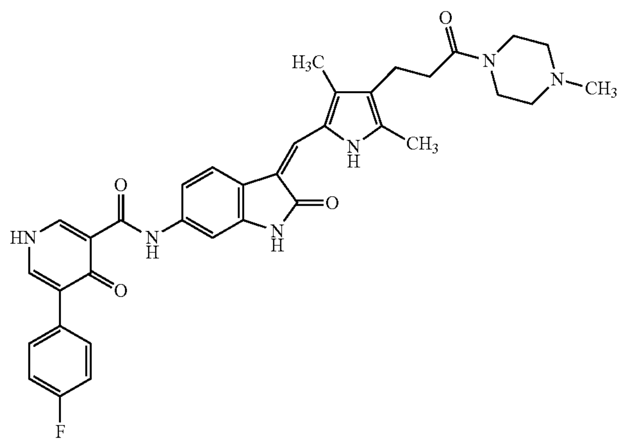 [SMILES: Cc1[nH]c(/C=C2\C(=O)Nc3cc(NC(=O)c4c[nH]cc(-c5ccc(F)cc5)c4=O)ccc32)c(C)c1CCC(=O)N1CCN(C)CC1] | $R^a$ = hydrogen<br>$R^b$ = 3,5-dimethyl-4-(3-(4-methylpiperazino-3-oxopropyl))-1H-pyrrol-2-yl<br>$R^c$ = hydrogen<br>$R^d$ = hydrogen<br>$R^e$ = 5-(4-fluorophenyl)-4-oxopyridine-3-amido<br>$R^f$ = hydrogen |
| D152 (Z)-N-(3-((3,5-dimethyl-4-(morpholine-4-carbonyl)-1H-pyrrol-2-yl)methylene)-2-oxoindolin-6-yl)-5-(4-fluorophenyl)-4-oxo-1,4-dihydropyridine-3-carboxamide | 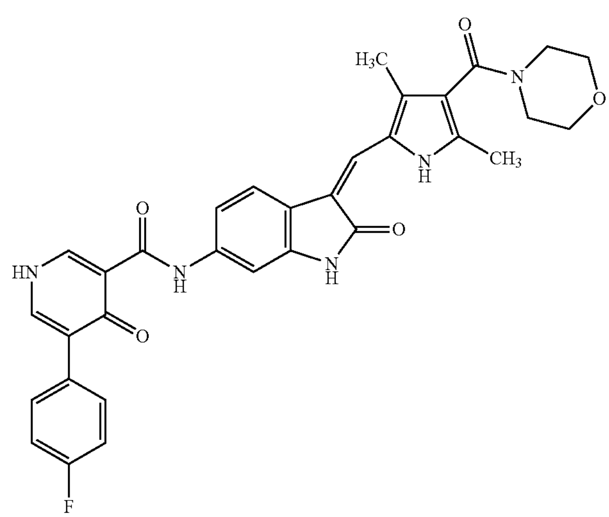 [SMILES: Cc1[nH]c(/C=C2\C(=O)Nc3cc(NC(=O)c4c[nH]cc(-c5ccc(F)cc5)c4=O)ccc32)c(C)c1C(=O)N1CCOCC1] | $R^a$ = hydrogen<br>$R^b$ = 3,5-dimethyl-4-(morpholine-1-carbonyl)-1H-pyrrol-2-yl<br>$R^c$ = hydrogen<br>$R^d$ = hydrogen<br>$R^e$ = 5-(4-fluorophenyl)-4-oxopyridine-3-amido<br>$R^f$ = hydrogen |

TABLE 6-continued

Formula A

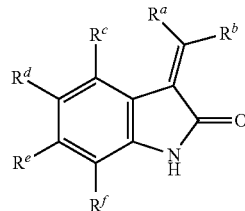

| Compound Number Chemical Name | Structure | Substituents of Formula A |
|---|---|---|
| D153 (Z)-N-(3-((3,5-dimethyl-4-(2-morpholino-2-oxoethyl)-1H-pyrrol-2-yl)methylene)-2-oxoindolin-6-yl)-5-(4-fluorophenyl)-4-oxo-1,4-dihydropyridine-3-carboxamide | 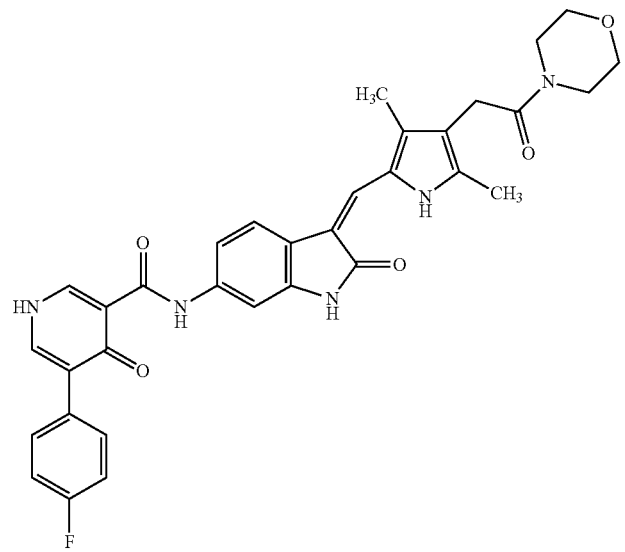 [SMILES: Cc1[nH]c(/C=C2\C(=O)Nc3cc(NC(=O)c4c[nH]cc(-c5ccc(F)cc5)c4=O)ccc32)c(C)c1CC(=O)N1CCOCC1] | $R^a$ = hydrogen<br>$R^b$ = 3,5-dimethyl-4-(3-morpholino-2-oxoethyl)-1H-pyrrol-2-yl<br>$R^c$ = hydrogen<br>$R^d$ = hydrogen<br>$R^e$ = 5-(4-fluorophenyl)-4-oxopyridine-3-amido<br>$R^f$ = hydrogen |
| D154 (Z)-N-(3-((3,5-dimethyl-4-(4-methylpiperazine-1-carbonyl)-1H-pyrrol-2-yl)-methylene)-2-oxoindolin-6-yl)-5-(4-methoxyphenyl)-4-oxo-1,4-dihydropyridine-3-carboxamide | 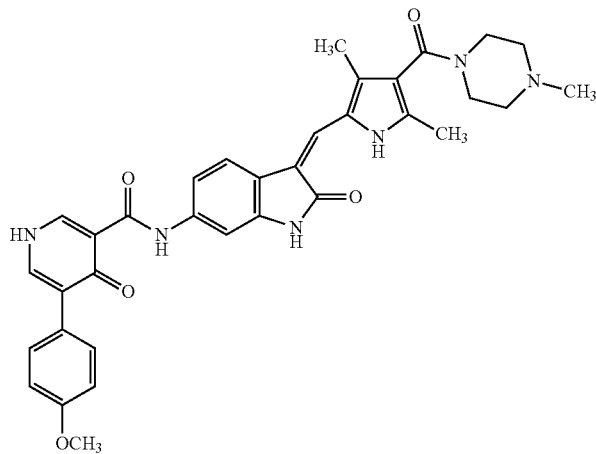 [SMILES: COc1ccc(-c2c[nH]cc(C(=O)Nc3ccc4c(c3)NC(=O)/C4=C\c3[nH]c(C)c(C(=O)N4CCN(C)CC4)c3C)c2=O)cc1] | $R^a$ = hydrogen<br>$R^b$ = 3,5-dimethyl-4-(4-methylpiperazine-1-carbonyl)-1H-pyrrol-2-yl<br>$R^c$ = hydrogen<br>$R^d$ = hydrogen<br>$R^e$ = 5-(4-methoxyphenyl)-4-oxopyridine-3-amido<br>$R^f$ = hydrogen |

TABLE 6-continued

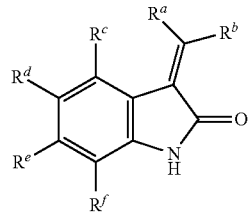

Formula A

| Compound Number Chemical Name | Structure | Substituents of Formula A |
|---|---|---|
| D155<br>(Z)-N-(3-((3,5-dimethyl-4-(morpholine-4-carbonyl)-1H-pyrrol-2-yl)methylene)-2-oxoindolin-6-yl)-5-(4-methoxyphenyl)-4-oxo-1,4-dihydropyridine-3-carboxamide | | $R^a$ = hydrogen<br>$R^b$ = 3,5-dimethyl-4-(morpholine-1-carbonyl)-1H-pyrrol-2-yl<br>$R^c$ = hydrogen<br>$R^d$ = hydrogen<br>$R^e$ = 5-(4-methoxyphenyl)-4-oxopyridine-3-amido<br>$R^f$ = hydrogen |
| D156<br>(Z)-N-(3-((3,5-dimethyl-4-((2-(pyrrolidin-1-yl)ethyl)carbamoyl)-1H-pyrrol-2-yl)methylene)-2-oxoindolin-6-yl)-5-(4-methoxyphenyl)-4-oxo-1,4-dihydropyridine-3-carboxamide | | $R^a$ = hydrogen<br>$R^b$ = 3,5-dimethyl-4-([2-(pyrrolidin-1-yl)ethyl]carbomyl)-1H-pyrrol-2-yl<br>$R^c$ = hydrogen<br>$R^d$ = hydrogen<br>$R^e$ = 5-(4-methoxyphenyl)-4-oxopyridine-3-amido<br>$R^f$ = hydrogen |

What is claimed is:
1. A compound of Formula A:

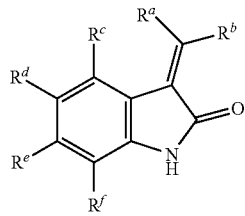

Formula A or a pharmaceutically acceptable salt thereof, wherein
$R^a$ is hydrogen;
$R^b$ is pyrrolyl or substituted pyrrolyl;
$R^c$ is hydrogen;
$R^d$ is hydrogen, halogen, or $(C_1-C_6)$alkoxybenzoylureido;
$R^e$ is benzoylureido, halobenzoylureido, halo$(C_1-C_6)$alkoxybenzoylureido, $(C_1-C_6)$alkoxybenzoylureido, $(C_1-C_6)$alkylaminobenzoylureido, $(C_1-C_6)$alkylbenzoylureido, nitrobenzoylureido, $(C_1-C_6)$haloalkylbenzoylureido, $(C_1-C_6)$haloalkylhalobenzoylureido, halo$(C_6-C_{18})$arylcarbomylacetamido, $(C_1-C_6)$alkoxy$(C_6-C_{18})$arylcarbomylacetamido, $(C_1-C_6)$alkoxy$(C_6-C_{18})$arylcarbamoyl$(C_3-C_6)$cycloalkylamido, halo$(C_6-C_{18})$aryl$(C_3-C_{18})$heteroarylcarbonylamino, $(C_3-C_6)$cycloalkyl$(C_3-C_{18})$heteroarylcarbonylamino, $(C_1-C_6)$alkylamino$(C_6-C_{18})$aryl$(C_3-C_{18})$heteroarylcarbonylamino, halo$(C_1-C_6)$alkoxy$(C_6-C_{18})$aryl$(C_6-C_{18})$heteroarylcarbonylamino, $(C_1-C_6)$alkoxy$(C_6-C_{18})$aryl$(C_3-C_{18})$heteroarylcarbonylamino, $(C_1-C_6)$alkyl$(C_3-C_{18})$heteroarylcarbonylamino, aryl$(C_3-C_{18})$heteroarylcarbonylamino, $(C_1-C_6)$haloalkylhalo$(C_6-C_{18})$aryl$(C_3-C_6)$heterocyclylcarbonylamino, $(C_1-C_6)$haloalkyl$(C_6-C_{18})$aryl$(C_3-C_{18})$heteroarylcarbonylamino, halo$(C_6-C_{18})$aryl$(C_3-C_{18})$heteroarylamido, $(C_1-C_6)$oxyalkyl$(C_3-C_6)$heterocyclylamido, $(C_1-C_6)$alkoxy$(C_1-C_6)$alkyl$(C_3-C_{18})$heteroarylamido, $(C_6-C_{18})$aryl$(C_3-C_{18})$heteroarylamido, $(C_1-C_6)$alkyl$(C_6-C_{18})$aryl$(C_3-C_{18})$heteroarylamido, $(C_1-C_6)$haloalkyl$(C_6-C_{18})$aryl$(C_3-C_{18})$heteroarylamido, $(C_1-C_6)$alkyl$(C_3-C_{18})$heteroarylamido, or $(C_1-C_6)$alkoxy$(C_6-C_{18})$aryl$(C_3-C_{18})$heteroarylamido; and
$R^f$ is hydrogen, or $(C_1-C_6)$alkoxybenzoylureido;
wherein acetamido, amido, amino, benzoylureido, carbamoyl, $(C_1-C_6)$alkyl, $(C_1-C_6)$alkylamino, $(C_1-C_6)$alkoxy, $(C_6-C_{18})$aryl, $(C_1-C_6)$carboxyalkyl, $(C_3-C_6)$cycloalkyl, $(C_3-C_{18})$heteroaryl, $(C_3-C_6)$heterocyclylcarbonyl, or $(C_1-C_6)$oxyalkyl are each independently optionally substituted on carbon or nitrogen with one or more alkyl, hydroxyalkyl, arylalkyl, heteroarylalkyl, aryl, heterocyclyl, oxo, hydroxy, halogen, nitro, alkoxy, or trifluoromethyl.

2. The compound of claim 1, wherein
$R^d$ is hydrogen, fluoro, or $N^3$-(4-methoxybenzoyl)ureido;
$R^e$ is $N^3$-benzoylureido, $N^3$-(4-chlorobenzoyl)ureido, $N^3$-(3,4-dichlorobenzoyl)ureido, $N^3$-(2,4-difluorobenzoyl)ureido, $N^3$-(2,6-difluoro-4-methoxybenzoyl)ureido, $N^3$-(2,6-difluoro-4-methoxybenzoyl)ureido, $N^3$-(3,5-dimethoxybenzoyl)ureido, $N^3$-((4-dimethylaminobenzoyl)ureido, $N^3$-(2-fluorobenzoyl)ureido, $N^3$-(4-fluorobenzoyl)ureido, $N^3$-(2-fluoro-4-methoxybenzoyl)ureido, $N^3$-(3-methylbenzoyl)ureido, $N^3$-(4-methylbenzoyl)ureido, $N^3$-(4-methoxybenzoyl)ureido, $N^3$-(4-nitrobenzoyl)ureido, $N^3$-(4-trifluoromethylbenzoyl)ureido, $N^3$-(3-trifluoromethyl-4-chlorobenzoyl)ureido, 2-[(4-fluorophenyl)carbomyl]acetamido, 2-[(4-methoxyphenyl)carbomyl]acetamido, 1-{(4-methoxyphenyl)carbamoyl]cyclopropaneamido}, 3-(4-chlorophenyl)-2-oxoimidazolidine-1-carbonylamino, 3-(3-chlorophenyl)-2-oxoimidazolidine-1-carbonylamino, 3-cyclopropyl-2-oxoimidazolidine-1-carbonylamino, 3-(3,4-dichlorophenyl)-2-oxoimidazolidine-1-carbonylamino, 3-(4-dimethylaminophenyl)-2-oxoimidazolidine-1-carbonylamino, 3-(2-fluorophenyl)-2-oxoimidazolidine-1-carbonylamino, 3-(4-fluorophenyl)-2-oxoimidazolidine-1-carbonylamino, 3-(2-fluoro-4-methoxyphenyl)-2-oxoimidazolidine-1-carbonylamino, 3-(4-methoxyphenyl)-2-oxoimidazolidine-1-carbonylamino, 3-(4-methylphenyl)-2-oxoimidazolidine-1-carbonylamino, 3-methyl-2-oxoimidazolidine-1-carbonyl]amino, 3-phenyl-2-oxoimidazolidine-1-carbonylamino, 3-(3-trifluoromethyl-4-chlorophenyl)-2-oxoimidazolidine-1-carbonylamino, 3-(4-trifluoromethylphenyl)-2-oxoimidazolidine-1-carbonylamino, 1-(4-chlorophenyl)-2-oxopyridine-3-amido, 1-(3-chlorophenyl)-2-oxopyridine-3-amido, 1-(3,4-dichlorophenyl)-2-oxopyridine-3-amido, 1-(2-fluorophenyl)-2-oxopyridine-3-amido, 1-(4-fluorophenyl)-2-oxopyridine-3-amido, 1-(2-hydroxyethyl)-2-oxopyridine-3-amido, 1-(4-methoxyphenyl)-2-oxopyridine-3-amido, 1-methyl-2-oxopyridine-3-amido, 1-(4-methyl phenyl)-2-oxopyridine-3-amido, 1-phenyl-2-oxopyridine-3-amido, 1-(3-trifluoromethyl-4-chlorophenyl)-2-oxopyridine-3-amido, 1-(3-trifluoromethylphenyl)-2-oxopyridine-3-amido, 1-(4-trifluoromethylphenyl)-2-oxopyridine-3-amido, S-(3-chlorophenyl)-4-oxopyridine-3-amido, 5-(4-chlorophenyl)-4-oxopyridine-3-amido, 5-(2,4-difluorophenyl)-4-oxopyridine-3-amido, 5-(3,5-difluorophenyl)-4-oxopyridine-3-amido; 5-(2-fluorophenyl)-4-oxopyridine-3-amido, 5-(4-fluorophenyl)-4-oxopyridine-3-amido, 1-methyl-5-(4-fluorophenyl)-4-oxopyridine-3-amido, 5-methyl-4-oxopyridine-3-amido, 5-(4-methylphenyl)-4-oxopyridine-3-amido, 5-(4-methoxyphenyl)-4-oxopyridine-3-amido, 5-phenyl-4-oxopyridine-3-amido, or 5-(4-trifluoromethylphenyl)-4-oxopyridine-3-amido; and
$R^f$ is hydrogen, or $N^3$-(4-methoxybenzoyl)ureido.

3. The compound of claim 2, wherein
$R^e$ is $N^3$-benzoylureido, $N^3$-(4-chlorobenzoyl)ureido, $N^3$-(3,4-dichlorobenzoyl)ureido, $N^3$-(2,4-difluorobenzoyl)ureido, $N^3$-(2,6-difluoro-4-methoxybenzoyl)ureido, $N^3$-(2,6-difluoro-4-methoxybenzol)ureido, $N^3$-(3,5-dimethoxybenzoyl)ureido, $N^3$-((4-dimethylaminobenzoyl)ureido, $N^3$-(2-fluorobenzoyl)ureido, $N^3$-(4-fluorobenzoyl)ureido, $N^3$-(2-fluoro-4-methoxybenzoyl)ureido, $N^3$-(3-methylbenzoyl)ureido, $N^3$-(4-methylbenzoyl)ureido, $N^3$-(4-methoxybenzoyl)ureido, $N^3$-(4-nitrobenzoyl)ureido, $N^3$-(4-trifluoromethylbenzoyl)ureido, or $N^3$-(3-trifluoromethyl-4-chlorobenzoyl)ureido.

4. The compound of claim 2, wherein
$R^d$ and $R^f$ are each independently hydrogen;
$R^b$ is 1H-pyrrol-2-yl; and R$^c$ is 2-[(4-methoxyphenyl)carbomyl]acetamido or 1-{(4-methoxyphenyl)carbamoyl]cyclopropaneamido}.

5. The compound of claim 2, wherein
R$^d$ and R$^f$ are each independently hydrogen;
R$^b$ is 1H-pyrrol-2-yl, 3,5-dimethyl-4-carboxy-1H-pyrrol-2-yl, 3,5-dimethyl-4-carboxymethyl-1H-pyrrol-2-yl, or 3,5-dimethyl-4-(2-carboxyethyl)-1H-pyrrol-2-yl; and
R$^e$ is 3-methyl-2-oxoimidazolidine-1-carbonylamino, 3-cyclopropyl-2-oxoimidazolidine-1-carbonylamino, 3-phenyl-2-oxoimidazolidine-1-carbonylamino, 3-(4-chlorophenyl)-2-oxoimidazolidine-1-carbonylamino, 3-(3-chlorophenyl)-2-oxoimidazolidine-1-carbonylamino, 3-(3,4-dichlorophenyl)-2-oxoimidazolidine-1-carbonylamino, 3-(3-trifluoromethyl-4-chlorophenyl)-2-oxoimidazolidine-1-carbonylamino, 3-(4-trifluoromethylphenyl)-2-oxoimidazolidine-1-carbonylamino, 3-(4-fluorophenyl)-2-oxoimidazolidine-1-carbonylamino, 3-(2-fluorophenyl)-2-oxoimidazolidine-1-carbonylamino, 3-(4-methoxyphenyl)-2-oxoimidazolidine-1-carbonylamino, 3-(4-methylphenyl)-2-oxoimidazolidine-1-carbonylamino, 3-(4-dimethylaminophenyl)-2-oxoimidazolidine-1-carbonylamino, 3-(2-fluoro-4-methoxyphenyl)-2-oxoimidazolidine-1-carbonylamino, 3-(4-methoxyphenyl)-2-oxoimidazolidine-1-carbonylamino, 3-cyclopropyl-2-oxoimidazolidine-1-carbonylamino, 3-(2-fluorophenyl)-2-oxoimidazolidine-1-carbonylamino, or 3-(2-fluoro-4-methoxyphenyl)-2-oxoimidazolidine-1-carbonylamino.

6. The compound of claim 2, wherein
R$^a$, R$^c$, R$^d$ and R$^f$ are each independently hydrogen;
R$^b$ is 1H-pyrrol-2-yl, 3,5-dimethyl-1H-pyrrol-2-yl, 3,5-dimethyl-4-carboxy-1H-pyrrol-2-yl, 3,5-dimethyl-4-carboxymethyl-1H-pyrrol-2-yl, 3,5-dimethyl-4-(2-carboxyethyl)-1H-pyrrol-2-yl, 3-methyl-5-carboxy-1H-pyrrol-2-yl, 3,5-dimethyl-4-(4-methylpiperazino-1-carbonyl)-1H-pyrrol-2-yl, 3,5-dimethyl-4-(3-(4-methylpiperazino-2-oxoethyl))-1H-pyrrol-2-yl, 3,5-dimethyl-4-(3-(4-methylpiperazino-3-oxopropyl))-1H-pyrrol-2-yl, 3,5-dimethyl-4-(morpholine-1-carbonyl)-1H-pyrrol-2-yl, 3,5-dimethyl-4-(3-morpholino-2-oxoethyl)-1H-pyrrol-2-yl, 3,5-dimethyl-4-(4-methylpiperazino-1-carbonyl)-1H-pyrrol-2-yl, or 3,5-dimethyl-4-([2-(pyrrolidin-1-yl)ethyl]carbomyl)-1H-pyrrol-2-yl; and
R$^e$ is 5-methyl-4-oxopyridine-3-amido, 5-phenyl-4-oxopyridine-3-amido, 5-(4-methoxyphenyl)-4-oxopyridine-3-amido, 5-(4-fluorophenyl)-4-oxopyridine-3-amido, 5-(4-chlorophenyl)-4-oxopyridine-3-amido, 5-(4-methylphenyl)-4-oxopyridine-3-amido, 5-(3-chlorophenyl)-4-oxopyridine-3-amido, 5-(4-trifluoromethylphenyl)-4-oxopyridine-3-amido, 5-(2-fluorophenyl)-4-oxopyridine-3-amido, 5-(2,4-difluorophenyl)-4-oxopyridine-3-amido, 5-(3,5-difluorophenyl)-4-oxopyridine-3-amido, or 1-methyl-5-(4-fluorophenyl)-4-oxopyridine-3-amido.

7. The compound of claim 1, wherein the compound is selected from the group consisting of
(Z)—N-(3-((1H-pyrrol-2-yl)methylene)-2-oxoindolin-6-ylcarbamoyl)-4-methoxybenzamide,
(Z)—N-(3-((1H-pyrrol-2-yl)methylene)-2-oxoindoline-6-ylcarbamoyl)benzamide,
(Z)—N-(3-((1H-pyrrol-2-yl)methylene)-2-oxoindolin-6-ylcarbamoyl)-4-chlorobenzamide,
(Z)—N-(3-((1H-pyrrol-2-yl)methylene)-2-oxoindolin-6-ylcarbamoyl)-3,4-dichlorobenzamide,
(Z)—N-(3-((1H-pyrrol-2-yl)methylene)-2-oxoindolin-6-ylcarbamoyl)-4-(trifluoromethyl)-benzamide,
(Z)—N-(3-((1H-pyrrol-2-yl)methylene)-2-oxoindolin-6-ylcarbamoyl)-4-chloro-3-(trifluoromethyl)-benzamide,
(Z)—N-(3-((1H-pyrrol-2-yl)methylene)-2-oxoindolin-6-ylcarbamoyl)-4-methylbenzamide,
(Z)—N-(3-(1H-pyrrol-2-yl)methylene)-2-oxoindolin-6-ylcarbamoyl)-3,5-dimethoxybenzamide,
(Z)—N-(3-((1H-pyrrol-2-yl)methylene)-2-oxoindolin-6-ylcarbamoyl)-4-(dimethylamino)-benzamide,
(Z)-5-((6-(3-benzoyl ureido)-2-oxoindolin-3-ylidene)methyl)-2,4-dimethyl-1H-pyrrole-3-carboxylic acid,
(Z)-5-((6-(3-(4-chlorobenzoyl)ureido)-2-oxoindolin-3-ylidene)-methyl)-2,4-dimethyl-1H-pyrrole-3-carboxylic acid,
(Z)-5-((6-(3-(3,4-dichlorobenzoyl)ureido)-2-oxoindolin-3-ylidene)methyl)-2,4-dimethyl-1H-pyrrole-3-carboxylic acid,
(Z)-2,4-dimethyl-5-((2-oxo-6-(3-(4-(trifluoromethyl)benzoyl)ureido)indolin-3-ylidene)methyl)-1H-pyrrole-3-carboxylic acid,
(Z)-5-((6-(3-(4-chloro-3-(trifluoromethyl)benzoyl)ureido)-2-oxoindolin-3-ylid-ene)methyl)-2,4-dimethyl-1H-pyrrole-3-carboxylic acid,
(Z)-3-(5-((6-(3-(4-chloro-3-(trifluoromethyl)benzoyl)ureido)-2-oxo-indolin-3-yl-idene)methyl)-2,4-dimethyl-1H-pyrrol-3-yl)propanoic acid,
(Z)-2,4-dimethyl-5-((6-(3-(4-nitrobenzoyl)ureido)-2-oxoindolin-3-ylidene)methyl)-1H-pyrrole-3-carboxylic acid,
(Z)-2,4-dimethyl-5-((6-(3-(4-methylbenzoyl)ureido)-2-oxoindolin-3-ylidene)-methyl)-1H-pyrrole-3-carboxylic acid,
(Z)-3-(2,4-dimethyl-5-((6-(3-(3-methylbenzoyl)ureido)-2-oxoindoline-3-ylidene)-methyl)-1H-pyrrol-3-yl)propanoic acid,
(Z)-5-((6-(3-(4-methoxybenzoyl)ureido)-2-oxoindolin-3-ylidene)-methyl)-2,4-di-methyl-1H-pyrrole-3-carboxylic acid,
(Z)-5-((6-(3-(3,5-dimethoxybenzoyl)-ureido)-2-oxoindolin-3-ylidene)methyl)-2,4-dimethyl-1H-pyrrole-3-carboxylic acid,
(Z)—N-(3-((3,5-dimethyl-4-phenyl-1H-pyrrol-2-yl)methylene)-2-oxoindolin-6-ylcarbamoyl)-4-methoxybenzamide,
(Z)—N-(3-((3,5-dimethyl-1H-pyrrol-2-yl)methylene)-2-oxoindolin-6-ylcarbamoyl)-4-methoxybenzamide,
(Z)-5-((6-(3-(4-methoxybenzoyl)ureido)-2-oxoindolin-3-ylidene)methyl)-1H-pyrrole-2-carboxylic acid,
(Z)-2-(5-((6-(3-(4-methoxybenzoyl)ureido)-2-oxoindolin-3-ylidene)methyl)-2,4-dimethyl-1H-pyrrol-3-yl)acetic acid,
(Z)-3-(5-((6-(3-(4-methoxybenzoyl)ureido)-2-oxoindolin-3-ylidene)methyl)-2,4-dimethyl-1H-pyrrol-3-yl)propanoic acid,
(Z)—N-(3-((1H-pyrrol-2-yl)methylene)-5-fluoro-2-oxoindolin-6-ylcarbamoyl)-4-methoxybenzamide,
(Z)-5-((5-fluoro-6-(3-methoxybenzol)ureido-2-oxoindolin-3-ylidene)methy)-2,4-dimethyl-1H-pyrrole-3-carboxylic acid,
(Z)-2-(5-((5-fluoro-6-(3-(4-methoxybenzol)ureido)-2-oxoindolin-3-ylidene)-methyl)-2,4-dimethyl-1H-pyrrol-3-yl)acetic acid,
(Z)-3-(5-((5-fluoro-6-(3-(4-methoxybenzoyl)ureido)-2-oxoindolin-3-ylidene)-methyl)-2,4-dimethyl-1H-pyrrol-3-yl)propanoic acid, (Z)—N-(3-((1H-pyrrol-2-yl)methylene)-2-oxoindolin-6-ylcarbamoyl)-2-fluorobenzamide,
(Z)-5-((6-(3-(2-fluorobenzoyl)ureido)-2-oxoindolin-3-ylidene)methyl)-2,4-dimethyl-1H-pyrrole-3-carboxylic acid,
(Z)-3-(5-((6-(3-(2-fluorobenzoyl)ureido)-2-oxoindolin-3-ylidene)methyl)-2,4-dimethyl-1H-pyrrol-3-yl)propanoic acid,
(Z)-3-(5-((6-(3-(4-fluorobenzoyl)ureido)-2-oxoindolin-3-ylidene)methyl)-2,4-dimethyl-1H-pyrrol-3-yl)propanoic acid,
(Z)-3-(5-((6-(3-(2,4-difluorobenzoyl)ureido]-2-oxoindolin-3-ylidene)methyl)-2,4-dimethyl-1H-pyrrol-3-yl)propanoic acid,
(Z)-5-((6-(3-(2-fluoro-4-methoxybenzoyl)ureido)-2-oxoindolin-3-ylidene)methyl)-2,4-dimethyl-1H-pyrrole-3-carboxylic acid,
(Z)-3-(5-((6-(3-(2-fluoro-4-methoxybenzoyl)ureido)-2-oxoindolin-3-ylidene)methyl)-2,4-dimethyl-1H-pyrrol-3-yl)propanoic acid,
(Z)-5-(5-fluoro-6-(3-(2-fluoro-4-methoxybenzoyl)ureido)-2-oxoindolin-3-ylidene)methyl)-2,4-dimethyl-1H-pyrrole-3-carboxylic acid,
(Z)-3-(5-((5-fluoro-6-(3-(2-fluoro-4-methoxybenzoyl)ureido)-2-oxoindolin-3-ylidene)methyl)-2,4-dimethyl-1H-pyrrol-3-yl)propanoic acid,
(Z)-5-((6-(3-(2,6-difluoro-4-methoxybenzoyl)ureido)-5-fluoro-2-oxoindolin-3-ylidene)methyl)-2,4-dimethyl-1H-pyrrole-3-carboxylic acid,
(Z)-ethyl-5-((6-(3-(2-fluoro-4-methoxybenzoyl)ureido)-2-oxoindolin-3-ylidene)methyl)-2,4-dimethyl-1H-pyrrole-3-carboxylate,
(Z)-ethyl-3-(5-((6-(3-(2-fluoro-4-methoxybenzoyl)ureido)-2-oxoindolin-3-ylidene)methyl)-2,4-dimethyl-1H-pyrrol-3-yl)propanoate,
(Z)—N-(3-((3,5-dimethyl-4-(4-methylpiperazine-1-carbonyl)-1H-pyrrol-2-yl)methylene)-2-oxoindolin-6-ylcarbamoyl)-2-fluoro-4-methoxybenzamide,
(Z)—N-(3-((3,5-dimethyl-4-(3-(4-methylpiperazin-1H-yl)-3-oxopropyl)-1H-pyrrol-2-yl)methylene)-2-oxoindolin-6-ylcarbamoyl)-2-fluoro-4-methoxybenzamide,
(Z)—N-(3-((3,5-dimethyl-4-(morpholine-4-carbonyl)-1H-pyrrol-2-yl)methylene)-2-oxoindolin-6-ylcarbamoyl)-2-fluoro-4-methoxybenzamide,
(Z)—N-(3-((3,5-dimethyl-4-(3-morpholino-3-oxopropyl)-1H-pyrrol-2-yl)methylene)-2-oxoindolin-6-ylcarbamoyl)-2-fluoro-4-methoxybenzamide,
(Z)—N-(2-(dimethylamino)ethyl)-5-((6-(3-(2-fluoro-4-methoxybenzoyl)-ureido)-2-oxoindolin-3-ylidene)methyl)-2,4-dimethyl-1H-pyrrole-3-carboxamide,
(Z)—N-(2-(diethylamino)ethyl)-5-((6-(3-(2-fluoro-4-methoxybenzoyl)ureido)-2-oxoindolin-3-ylidene)methyl)-2,4-dimethyl-1H-pyrrole-3-carboxamide,
(Z)-5-((6-(3-(2-fluoro-4-methoxybenzoyl)ureido)-2-oxoindolin-3-ylidene)methyl)-2,4-dimethyl-N-(2-(pyrrolidin-1-yl)ethyl)-1H-pyrrole-3-carboxamide, and
malic acid salt of (Z)-5-((6-(3-(2-fluoro-4-methoxybenzoyl)ureido)-2-oxoindolin-3-ylidene)methyl)-2,4-dimethyl-N-(2-(pyrrolidin-1-yl)ethyl)-1H-pyrrole-3-carboxamide.

8. The compound of claim 2, wherein the compound is selected from the group consisting of
(Z)—N$^1$-(3-((1H-pyrrol-2-yl)methylene)-2-oxoindolin-6-yl)-N$^3$-(4-fluorophenyl)malonamide,
(Z)—N$^1$-(3-(H-pyrrol-2-yl)methylene)-2-oxoindolin-6-yl)-N$^3$-(4-methoxyphenyl)malonamide, and
(Z)—N-(3-((1H-pyrrol-2-yl)methylene)-2-oxoindolin-6-yl)-N-(4-methoxyphenyl)cyclopropane-1,1-dicarboxamide.

9. The compound of claim 2, wherein the compound is selected from the group consisting of
(Z)—N-(3-((1H-pyrrol-2-yl)methylene)-2-oxoindolin-6-yl)-3-methyl-2-oxoimidazolidine-1-carboxamide,
(Z)—N-(3-((1H-pyrrol-2-yl)methylene)-2-oxoindolin-6-yl)-3-cyclopropyl-2-oxoimidazolidine-1-carboxamide,
(Z)—N-(3-((1H-pyrrol-2-yl)methylene)-5-fluoro-2-oxoindolin-6-yl)-3-cyclopropyl-2-oxoimidazolidine-1-carboxamide,
(Z)—N-(3-((1H-pyrrol-2-yl)methylene)-2-oxoindolin-6-yl)-2-oxo-3-phenylimidazolidine-1H-carboxamide,
(Z)—N-(3-((1H-pyrrol-2-yl)methylene)-2-oxoindolin-6-yl)-3-(4-chlorophenyl)-2-oxoimidazolidine-1-carboxamide,
(Z)—N-(3-((1H-pyrrol-2-yl)methylene)-2-oxoindolin-6-yl)-3-(3-chlorophenyl)-2-oxoimidazolidine-1-carboxamide,
(Z)—N-(3-((1H-pyrrol-2-yl)methylene)-2-oxoindolin-6-yl)-3-(3,4-dichlorophenyl)-2-oxoimidazolidine-1-carboxamide,
(Z)—N-(3-((1H-pyrrol-2-yl)methylene)-2-oxoindolin-6-yl)-3-(4-chloro-3-(trifluoro-methyl)phenyl)-2-oxoimidazolidine-1-carboxamide,
(Z)—N-(3-((1H-pyrrol-2-yl)methylene)-2-oxoindolin-6-yl)-2-oxo-3-(4-(trifluoro-methyl)phenyl)imidazolidine-1-carboxamide,
(Z)—N-(3-((1H-pyrrol-2-yl)methylene)-2-oxoindolin-6-yl)-3-(4-fluorophenyl)-2-oxoimidazolidine-1-carboxamide,
(Z)—N-(3-((1H-pyrrol-2-yl)methylene)-2-oxoindolin-6-yl)-3-(2-fluorophenyl)-2-oxoimidazolidine-1-carboxamide,
(Z)—N-(3-((1H-pyrrol-2-yl)methylene)-2-oxoindolin-6-yl)-3-(4-methoxyphenyl)-2-oxoimidazolidine-1-carboxamide,
(Z)—N-(3-((1H-pyrrol-2-yl)methylene)-2-oxoindolin-6-yl)-2-oxo-3-p-tolylimida-zolidine-1-carboxamide,
(Z)—N-(3-((1H-pyrrol-2-yl)methylene)-2-oxoindolin-6-yl)-3-(4-dimethylamino)-phenyl)-2-oxoimidazolidine-1-carboxamide,
(Z)—N-(3-((1H-pyrrol-2-yl)methylene)-2-oxoindolin-6-yl)-3-(2-fluoro-4-methoxyphenyl)-2-oxoimidazolidine-1-carboxamide,
(Z)-5-((6-(3-(4-methoxyphenyl)-2-oxoimidazolidine-1-carboxamido)-2-oxoindolin-3-ylidene)methyl)-2,4-dimethyl-1H-pyrrole-3-carboxylic acid,
(Z)-5-((6-(3-cyclopropyl-2-oxoimidazolidine-1-carboxamido)-2-oxoindolin-3-ylidene)methyl)-2,4-dimethyl-1H-pyrrole-3-carboxylic acid,
(Z)-2-(5-((6-(3-cyclopropyl-2-oxoimidazolidine-1-carboxamido)-2-oxoindolin-3-ylidene)methyl)-2,4-dimethyl-1H-pyrrol-3-yl)acetic acid,
(Z)-3-(5-((6-(3-cyclopropyl-2-oxoimidazolidine-1-carboxamido)-2-oxoindolin-3-ylidene)methyl)-2,4-dimethyl-1H-pyrrol-3-yl)propanoic acid,
(Z)-5-((6-(3-(2-fluorophenyl)-2-oxoimidazolidine-1-carboxamido)-2-oxoindolin-3-ylidene)methyl)-2,4-dimethyl-1H-pyrrol-3-carboxylic acid, and
(Z)-5-((6-(3-(2-fluoro-4-methoxyphenyl)-2-oxoimidazolidine-1-carboxamido)-2-oxoindolin-3-ylidene)methyl)-2,4-dimethyl-1H-pyrrole-3-carboxylic acid.

10. The compound of claim 2, wherein the compound is selected from the group consisting of (Z)—N-(3-((1H-pyrrol-2-yl)methylene)-2-oxoindolin-6-yl)-2-oxo-1-phenyl-1,2-dihydropyridine-3-carboxamide,
(Z)—N-(3-((1H-pyrrol-2-yl)methylene)-2-oxoindolin-6-yl)-1-(4-methoxyphenyl)-2-oxo-1,2-dihydropyridine-3-carboxamide,
(Z)—N-(3-((1H-pyrrol-2-yl)methylene)-2-oxoindolin-6-yl)-1-(4-fluorophenyl)-2-oxo-1,2-dihydropyridine-3-carboxamide,
(Z)—N-(3-((1H-pyrrol-2-yl)methylene)-2-oxoindolin-6-yl)-1-(4-chlorophenyl)-2-oxo-1,2-dihydropyridine-3-carboxamide,
(Z)—N-3-((1H-pyrrol-2-yl)methylene)-2-oxoindolin-6-yl)-1-(4-chloro-(3-trifluoromethyl)phenyl)-2-oxo-1,2-dihydropyridine-3-carboxamide,
(Z)—N-(3-(1H-pyrrol-2-yl)methylene)-2-oxoindolin-6-yl)-1-(3,4-dichlorophenyl)-2-oxo-1,2-dihydropyridine-3-carboxamide,
(Z)—N-(3-((1H-pyrrol-2-yl)methylene)-2-oxoindolin-6-yl)-2-oxo-1-(p-tolyl)-1,2-dihydropyridine-3-carboxamide,
(Z)—N-(3-((1H-pyrrol-2-yl)methylene)-2-oxoindolin-6-yl)-1-(4-(trifluoromethyl)phenyl)-2-oxo-1,2-dihydropyridine-3-carboxamide,
(Z)—N-(3-((1H-pyrrol-2-yl)methylene)-2-oxoindolin-6-yl)-1-(3-(trifluoromethyl)phenyl-2-oxo-1,2-dihydropyridine-3-carboxamide,
(Z)—N-(3-((1H-pyrrol-2-yl)methylene)-2-oxoindolin-6-yl)-1-(3-chlorophenyl)-2-oxo-1,2-dihydropyridine-3-carboxamide,
(Z)—N-(3-((1H-pyrrol-2-yl)methylene)-2-oxoindolin-6-yl)-1-(2-fluorophenyl)-2-oxo-1,2-dihydropyridine-3-carboxamide,
(Z)—N-(3-((1H-pyrrol-2-yl)methylene)-2-oxoindolin-6-yl)-1-methyl-2-oxo-1,2-dihydropyridine-3-carboxamide,
(Z)—N-(3-((1H-pyrrol-2-yl)methylene)-2-oxoindolin-6-yl)-1-(2-hydroxyethyl)-2-oxo-1,2-dihydropyridine-3-carboxamide,
(Z)—N-(3-((3,5-dimethyl-1H-pyrrol-2-yl)methylene)-2-oxoindolin-6-yl)-1-(4-fluorophenyl)-2-oxo-1,2-dihydropyridine-3-carboxamide,
(Z)-5-((6-(1-(4-fluorophenyl)-2-oxo-1,2-dihydropyridine-3-carboxamido)-2-oxoindolin-3-ylidene)methyl)-2,4-dimethyl-1H-pyrrole-3-carboxylic acid,
(Z)-2-(5-((6-(1-(4-fluorophenyl)-2-oxo-1,2-dihydropyridine-3-carboxamido)-2-oxoindolin-3-ylidene)methyl)-2,4-dimethyl-1H-pyrrol-3-yl)acetic acid,
(Z)-3-(5-((6-(1-(4-fluorophenyl)-2-oxo-1,2-dihydropyridine-3-carboxamido)-2-oxoindolin-3-ylidene)methyl)-2,4-dimethyl-1H-pyrrol-3-yl)propanoic acid,
(Z)-methyl-3-(5-((6-(1-(4-fluorophenyl)-2-oxo-1,2-dihydropyridine-3-carboxamido)-2-oxoindolin-3-ylidene)methyl)-2,4-dimethyl-1H-pyrrol-3-yl)propanoate, and
(Z)-2,4-dimethyl-5-((6-(1-methyl-2-oxo-1,2-dihydropyridine-3-carboxamido)-2-oxoindolin-3-ylidene)methyl)-1H-pyrrole-3-carboxylic acid.

11. The compound of claim 2, wherein the compound is selected from the group consisting of
(Z)—N-(3-((1H-pyrrol-2-yl)methylene)-2-oxoindolin-6-yl)-4-oxo-5-phenyl-1,4-dihydropyridine-3-carboxamide,
(Z)—N-(3-((1H-pyrrol-2-yl)methylene)-2-oxoindolin-6-yl)-5-(4-methoxyphenyl)-4-oxo-1,4-dihydropyridine-3-carboxamide,
(Z)—N-(3-((1H-pyrrol-2-yl)methylene)-2-oxoindolin-6-yl)-5-(4-fluorophenyl)-4-oxo-1,4-dihydropyridine-3-carboxamide,
(Z)—N-(3-((1H-pyrrol-2-yl)methylene)-2-oxoindolin-6-yl)-5-(4-chlorophenyl)-4-oxo-1,4-dihydropyridine-3-carboxamide,
(Z)—N-(3-((1H-pyrrol-2-yl)methylene)-2-oxoindolin-6-yl)-5-p-tolyl-4-oxo-1,4-dihydropyridine-3-carboxamide,
(Z)—N-(3-((1H-pyrrol-2-yl)methylene)-2-oxoindolin-6-yl)-5-(3-chlorophenyl)-4-oxo-1,4-dihydropyridine-3-carboxamide,
(Z)—N-(3-((1H-pyrrol-2-yl)methylene)-2-oxoindolin-6-yl)-4-oxo-5-(4-(trifluoro-methyl)phenyl)-*1,4-dihydropyridine-3-carboxamide,
(Z)—N-(3-((1H-pyrrol-2-yl)methylene)-2-oxoindolin-6-yl)-4-oxo-5-(2-fluorophenyl)-1,4-dihydropyridine-3-carboxamide,
(Z)—N-3-(1H-pyrrol-2-yl)methylene)-2-oxoindolin-6-yl)-4-oxo-5-(2,4-difluorophenyl)-1,4-dihydropyridine-3-carboxamide,
(Z)—N-(3-((1H-pyrrol-2-yl)methylene)-2-oxoindolin-6-yl)-4-oxo-5-(3,5-difluorophenyl)-1,4-dihydropyridine-3-carboxamide,
(Z)—N-(3-((1H-pyrrol-2-yl)methylene)-5-fluoro-2-oxoindolin-6-yl)-5-(4-fluorophenyl)-4-oxo-1,4-dihydropyridine-3-carboxamide,
(Z)—N-3-((1H-pyrrol-2-yl)methylene)-2-oxoindolin-6-yl)-5-(4-fluorophenyl)-1-methyl-4-oxo-1,4-dihydropyridine-3-carboxamide,
(Z)—N-(3-((1H-pyrrol-2-yl)methylene)-2-oxoindolin-6-yl)-5-methyl-4-oxo-1,4-dihydropyridine-3-carboxamide,
(Z)—N-(3-((3,5-dimethyl-1H-pyrrol-2-yl)methylene)-2-oxoindolin-6-yl)-5-(4-fluorophenyl)-4-oxo-1,4-dihydropyridine-3-carboxamide,
(Z)-5-((6-(5-(4-fluorophenyl)-4-oxo-1,4-dihydropyridine-3-carboxamido)-2-oxoindolin-3-ylidene)methyl)-2,4-dimethyl-1H-pyrrole-3-carboxylic acid,
(Z)-5-((6-(5-(4-methoxyphenyl)-4-oxo-1,4-dihydropyridine-3-carboxamido)-2-oxoindolin-3-ylidene)methyl)-2,4-dimethyl-1H-pyrrole-3-carboxylic acid,
(Z)-2,4-dimethyl-5-((6-(5-methyl-4-oxo-1,4-dihydropyridine-3-carboxamido)-2-oxoindolin-3-ylidene)methyl)-1H-pyrrole-3-carboxylic acid,
(Z)-2-(5-((6-(5-(4-fluorophenyl)-4-oxo-1,4-dihydropyridine-3-carboxamido)-2-oxoindolin-3-ylidene)methyl)-2,4-dimethyl-1H-pyrrol-3-yl)acetic acid,
(Z)-3-(5-((6-(5-(4-fluorophenyl)-4-oxo-1,4-dihydropyridine-3-carboxamido)-2-oxoindolin-3-ylidene)methyl)-2,4-dimethyl-1H-pyrrol-3-yl)propanoic acid,
(Z)-5-((6-(5-(4-fluorophenyl)-4-oxo-1,4-dihydropyridine-3-carboxamido)-2-oxoindolin-3-ylidene)methyl)-4-methyl-1H-pyrrole-2-carboxylic acid,
(Z)-3-(5-((6-(5-(2,4-difluorophenyl)-4-oxo-1,4-dihydropyridine-3-carboxamido)-2-oxoindolin-3-ylidene)methyl)-2,4-dimethyl-1H-pyrrol-3-yl)propanoic acid,
(Z)-3-(5-((6-(5-(3,5-difluorophenyl)-4-oxo-1,4-dihydropyridine-3-carboxamido)-2-oxoindolin-3-ylidene)methyl)-2,4-dimethyl-1H-pyrrol-3-yl)propanoic acid,
(Z)—N-(3-((3,5-dimethyl-4-(4-methylpiperazine-1-carbonyl)-1H-pyrrol-2-yl)methylene)-2-oxoindolin-6-yl)-5-(4-fluorophenyl)-4-oxo-1,4-dihydropyridine-3-carboxamide, (Z)—N-(3-((3,5-dimethyl-4-(2-(4-methylpiperazin-1-yl)-2-oxoethyl)-1H-pyrrol-2-yl)methylene)-2-oxoindolin-6-yl)-5-(4-fluorophenyl)-4-oxo-1,4-dihydropyridine-3-carboxamide, (Z)—N-(3-((3,5-dimethyl-4-(3-(4-methylpiperazin-1]-yl)-3-oxopropyl)-1H-pyrrol-2-yl)methylene)-2-oxoindolin-6-yl)-5-(4-fluorophenyl)-4-oxo-1,4-dihydropyridine-3-carboxamide, (Z)—N-(3-((3,5-dimethyl-4-(morpholine-4-carbonyl)-1H-pyrrol-2-yl)methylene)-2-oxoindolin-6-yl)-5-(4-fluorophenyl)-4-oxo-1,4-dihydropyridine-3-carboxamide, (Z)—N-(3-((3,5-dimethyl-4-(2-morpholino-2-oxoethyl)-1H-pyrrol-2-yl)methylene)-2-oxoindolin-6-yl)-5-(4-fluorophenyl)-4-oxo-1,4-dihydropyridine-3-carboxamide, (Z)—N-(3-((3,5-dimethyl-4-(4-methylpiperazine-1-carbonyl)-1H-pyrrol-2-yl)-methylene)-2-oxoindolin-6-yl)-5-(4-methoxyphenyl)-4-oxo-1,4-dihydropyridine-3-carboxamide, (Z)—N-(3-((3,5-dimethyl-4-(morpholine-4-carbonyl)-1H-pyrrol-2-yl)-methylene)-2-oxoindolin-6-yl)-5-(4-methoxyphenyl)-4-oxo-1,4-dihydropyridine-3-carboxamide, and (Z)—N-(3-((3,5-dimethyl-4-((2-(pyrrolidin-1-yl)ethyl)carbamoyl)-1H-pyrrol-2-yl)methylene)-2-oxoindolin-6-yl)-5-(4-methoxyphenyl)-4-oxo-1,4-dihydropyridine-3-carboxamide.

12. A pharmaceutical composition comprising a therapeutically effective amount of the compound of claim 1, or a salt thereof, and a pharmaceutically acceptable carrier or excipient.

13. A method of treating cancer, comprising administering to a subject in need thereof the pharmaceutical composition of claim 12, wherein the cancer is at least one selected from the group consisting of lung cancer, colorectal cancer, liver cancer and acute myelomonocytic leukemia.

14. A pharmaceutical composition comprising a therapeutically effective amount of the compound of claim 7, or a salt thereof, and a pharmaceutically acceptable carrier or excipient.

15. A pharmaceutical composition comprising a therapeutically effective amount of the compound of claim 8, or a salt thereof, and a pharmaceutically acceptable carrier or excipient.

16. A pharmaceutical composition comprising a therapeutically effective amount of the compound of claim 9, or a salt thereof, and a pharmaceutically acceptable carrier or excipient.

17. A compound of Formula A:

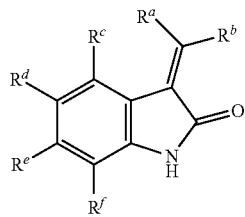

Formula A or a pharmaceutically acceptable salt thereof, wherein
$R^a$ is hydrogen;
$R^b$ is pyrrolyl or substituted pyrrolyl;
$R^c$ is hydrogen;
$R^d$ is hydrogen, halogen, or $(C_1$-$C_6)$alkoxybenzoylureido;
$R^e$ is hydrogen, benzoylureido, halobenzoylureido, halo$(C_1$-$C_6)$alkoxybenzoylureido, $(C_1$-$C_6)$alkoxybenzoylureido, $(C_1$-$C_6)$alkylaminobenzoylureido, $(C_1$-$C_6)$alkylbenzoylureido, nitrobenzoylureido, $(C_1$-$C_6)$haloalkylbenzoylureido, $(C_1$-$C_6)$haloalkylhalobenzoylureido, halo$(C_6$-$C_{18})$arylcarbomylacetamido, $(C_1$-$C_6)$alkoxy$(C_6$-$C_{18})$arylcarbomylacetamido, $(C_1$-$C_6)$alkoxy$(C_6$-$C_{18})$arylcarbamoyl$(C_3$-$C_6)$cycloalkylamido, halo$(C_6$-$C_{18})$aryl$(C_3$-$C_{18})$heteroarylcarbonylamino, $(C_3$-$C_6)$cycloalkyl$(C_3$-$C_{18})$heteroarylcarbonylamino, $(C_1$-$C_6)$alkylamino$(C_6$-$C_{18})$aryl$(C_3$-$C_{18})$heteroarylcarbonylamino, halo$(C_1$-$C_6)$alkoxy$(C_6$-$C_{18})$aryl$(C_3$-$C_{18})$heteroarylcarbonylamino, $(C_1$-$C_6)$alkoxy$(C_6$-$C_{18})$aryl$(C_3$-$C_{18})$heteroarylcarbonylamino, $(C_1$-$C_6)$alkyl$(C_3$-$C_{18})$heteroarylcarbonylamino, aryl$(C_3$-$C_{18})$heteroarylcarbonylamino, $(C_1$-$C_6)$haloalkylhalo$(C_6$-$C_{18})$aryl$(C_3$-$C_6)$heterocyclylcarbonylamino, $(C_1$-$C_6)$haloalkyl$(C_6$-$C_{18})$aryl$(C_3$-$C_{18})$heteroarylcarbonylamino, halo$(C_6$-$C_{18})$aryl$(C_3$-$C_{18})$heteroarylamido, $(C_1$-$C_6)$oxyalkyl$(C_1$-$C_6)$heterocyclylamido, $(C_1$-$C_6)$alkoxy$(C_1$-$C_6)$alkyl$(C_3$-$C_{18})$heteroarylamido, $(C_6$-$C_{18})$aryl$(C_3$-$C_{18})$heteroarylamido, $(C_1$-$C_6)$alkyl$(C_6$-$C_{18})$aryl$(C_3$-$C_{18})$heteroarylamido, $(C_1$-$C_6)$haloalkyl$(C_6$-$C_{18})$aryl$(C_3$-$C_{18})$heteroarylamido, $(C_1$-$C_6)$alkyl$(C_3$-$C_{18})$heteroarylamido, or $(C_1$-$C_6)$alkoxy$(C_6$-$C_{18})$aryl$(C_3$-$C_{18})$heteroarylamido; and
$R^f$ is $(C_1$-$C_6)$alkoxybenzoylureido;
wherein acetamido, amido, amino, benzoylureido, carbamoyl, $(C_1$-$C_6)$alkyl, $(C_1$-$C_6)$alkylamino, $(C_1$-$C_6)$alkoxy, $(C_6$-$C_{18})$aryl, $(C_1$-$C_6)$carboxyalkyl, $(C_3$-$C_6)$cycloalkyl, $(C_3$-$C_{18})$heteroaryl, $(C_3$-$C_6)$heterocyclylcarbonyl, or $(C_1$-$C_6)$oxyalkyl are each independently optionally substituted on carbon or nitrogen with one or more alkyl, hydroxyalkyl, arylalkyl, heteroarylalkyl, aryl, heterocyclyl, oxo, hydroxy, halogen, nitro, alkoxy, or trifluoromethyl.

18. A compound of Formula A:

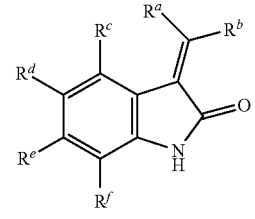

Formula A or a pharmaceutically acceptable salt thereof, wherein
$R^a$ is hydrogen;
$R^b$ is pyrrolyl or substituted pyrrolyl;
$R^c$ is hydrogen;
$R^d$ is $(C_1$-$C_6)$alkoxybenzoylureido;
$R^e$ is hydrogen, benzoylureido, halobenzoylureido, halo$(C_1$-$C_6)$alkoxybenzoylureido $(C_1$-$C_6)$alkoxybenzoylureido, $(C_1$-$C_6)$alkylaminobenzoylureido, $(C_1$-$C_6)$alkylbenzoylureido, nitrobenzoylureido, $(C_1$-$C_6)$haloalkylbenzoylureido, $(C_1$-$C_6)$haloalkylhalobenzoylureido, halo$(C_6$-$C_{18})$arylcarbomylacetamido, $(C_1$-$C_6)$alkoxy$((C_6$-$C_{18})$ arylcarbomylacetamido, $(C_1-C_6)$alkoxy$(C_6-C_{18})$ arylcarbamoyl$(C_3-C_6)$cycloalkylamido, halo$(C_6-C_{18})$aryl$(C_3-C_{18})$heteroarylcarbonylamino, $(C_3-C_6)$cycloalkyl$(C_3-C_{18})$heteroarylcarbonylamino, $(C_1-C_6)$alkylamino$(C_6-C_{18})$aryl$(C_3-C_{18})$heteroarylcarbonylamino, halo$(C_1-C_6)$alkoxy$(C_6-C_{18})$aryl$(C_3-C_{18})$heteroarylcarbonylamino, $(C_1-C_6)$alkoxy$(C_6-C_{18})$aryl$(C_3-C_{18})$heteroarylcarbonylamino, $(C_1-C_6)$alkyl$(C_3-C_{18})$heteroarylcarbonylamino, aryl$(C_3-C_{18})$heteroarylcarbonylamino, $(C_1-C_6)$haloalkylhalo$(C_6-C_{18})$aryl$(C_3-C_6)$heterocyclylcarbonylamino, $(C_1-C_6)$haloalkyl$(C_6-C_{18})$aryl$(C_3-C_{18})$heteroarylcarbonylamino, halo$(C_6-C_{18})$aryl$(C_3-C_{18})$heteroarylamido, $(C_1-C_6)$oxyalkyl$(C_3-C_6)$heterocyclylamido, $(C_1-C_6)$alkoxy$(C_1-C_6)$alkyl$(C_3-C_{18})$heteroarylamido, $(C_6-C_{18})$aryl$(C_3-C_{18})$heteroarylamido, $(C_1-C_6)$alkyl$(C_6-C_{18})$aryl$(C_3-C_{18})$heteroarylamido, $(C_1-C_6)$haloalkyl$(C_6-C_{18})$aryl$(C_3-C_{18})$heteroarylamido, $(C_1-C_6)$alkyl$(C_3-C_{18})$heteroarylamido, or $(C_1-C_6)$alkoxy$(C_6-C_{18})$aryl$(C_3-C_{18})$heteroarylamido; and $R^f$ is hydrogen, or $(C_1-C_6)$alkoxybenzoylureido;

wherein acetamido, amido, amino, benzoylureido, carbamoyl, $(C_1-C_6)$alkyl, $(C_1-C_6)$alkylamino, $(C_1-C_6)$alkoxy, $(C_6-C_{18})$aryl, $(C_1-C_6)$carboxyalkyl, $(C_3-C_6)$cycloalkyl, $(C_3-C_{18})$heteroaryl, $(C_3-C_6)$heterocyclylcarbonyl, or $(C_1-C_6)$oxyalkyl are each independently optionally substituted on carbon or nitrogen with one or more alkyl, hydroxyalkyl, arylalkyl, heteroarylalkyl, aryl, heterocyclyl, oxo, hydroxy, halogen, nitro, alkoxy, or trifluoromethyl.

\* \* \* \* \*